US011369936B2

(12) United States Patent
Ciccia et al.

(10) Patent No.: US 11,369,936 B2
(45) Date of Patent: Jun. 28, 2022

(54) VERSATILE METHOD FOR THE DETECTION OF MARKER-FREE PRECISION GENOME EDITING AND GENETIC VARIATION

(71) Applicant: THE TRUSTEES OF COLUMBIA UNIVERSITY IN THE CITY OF NEW YORK, New York, NY (US)

(72) Inventors: Alberto Ciccia, New York, NY (US); Pierre Billon, New York, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 0 days.

(21) Appl. No.: 17/192,836

(22) Filed: Mar. 4, 2021

(65) Prior Publication Data
US 2021/0283567 A1    Sep. 16, 2021

Related U.S. Application Data

(60) Provisional application No. 62/985,746, filed on Mar. 5, 2020.

(51) Int. Cl.
C40B 40/06 (2006.01)
B01J 19/00 (2006.01)
C12Q 1/686 (2018.01)
C40B 60/14 (2006.01)

(52) U.S. Cl.
CPC .......... *B01J 19/0046* (2013.01); *C12Q 1/686* (2013.01); *C40B 40/06* (2013.01); *C40B 60/14* (2013.01); *B01J 2219/00315* (2013.01); *B01J 2219/00369* (2013.01); *B01J 2219/00378* (2013.01); *B01J 2219/00387* (2013.01); *B01J 2219/00504* (2013.01)

(58) Field of Classification Search
None
See application file for complete search history.

(56) References Cited

U.S. PATENT DOCUMENTS

2016/0208319 A1    7/2016 Berman et al.
2016/0273023 A1    9/2016 Jouvenot et al.

FOREIGN PATENT DOCUMENTS

CN    104894255    9/2015
WO    2017/091811    11/2016

OTHER PUBLICATIONS

Shen, et al. "Predictable and precise template-free CRISPR editing of pathogenic variants," Nature 563, 646-651 (2018).
Song, et al. "Adenine base editing in an adult mouse model of tyrosinaemia," Nat Biomed Eng 4, 125-130 (2020).
Tan, et al. "A Class of Environmental and Endogenous Toxins Induces BRCA2 Haploinsufficiency and Genome Instability," Cell 169, 1105-1118 e1115 (2017).
Tschaharganeh, et al. "p53-dependent Nestin regulation links tumor suppression to cellular plasticity in liver cancer," Cell 158, 579-592 (2014).
Tzoneva, et al. "Clonal evolution mechanisms in NT5C2 mutant-relapsed acute lymphoblastic leukaemia," Nature 553, 511-514 (2018).
Tzoneva, et al. "Activating mutations in the NT5C2 nucleotidase gene drive chemotherapy resistance in relapsed ALL," Nat Med 19, 368-371 (2013).
Van Overbeek, et al. "DNA Repair Profiling Reveals Nonrandom Outcomes at Cas9-Mediated Breaks," Mol Cell 63, 633-646 (2016).
Villiger, et al. "Treatment of a metabolic liver disease by in vivo genome base editing in adult mice," Nat Med 24, 1519-1525 (2018).
Wang, et al. "Enhanced base editing by co-expression of free uracil DNA glycosylase inhibitor," Cell Res 27, 1289-1292 (2017).
Yeh, et al. "In vivo base editing of post-mitotic sensory cells," Nature communications 9, 2184 (2018).
Yin, et al. "Therapeutic genome editing by combined viral and non-viral delivery of CRISPR system components in vivo," Nature biotechnology 34, 328-333 (2016).
Yin, et al. "Genome editing with Cas9 in adult mice corrects a disease mutation and phenotype," Nature biotechnology 32, 551-553 (2014).
Zafra, et al. "Optimized base editors enable efficient editing in cells, organoids and mice," Nature biotechnology 36, 888-893 (2018).
Zhang, et al. "Non-invasive prenatal sequencing for multiple Mendelian monogenic disorders using circulating cell-free fetal DNA," Nat Med 25, 439-447(2019).
Wang, et al. "CRISPR/Cas9 in Genome Editing and Beyond," Annu Rev Biochem. Jun. 2016; 85: pp. 227-264.
Falabella, et al. "Single-Step qPCR and dPCR Detection of Diverse CRISPR-Cas9 Gene Editing Events In Vivo," G3 (Bethesda). Oct. 2017; 7(10): pp. 3533-3542.
Hendel, et al. "Quantifying on- and off-target genome editing," Trends Biotechnol. Feb. 2015; 33(2): pp. 132-140.
Findlay, et al. "A Digital PCR-Based Method for Efficient and Highly Specific Screening of Genome Edited Cells," PLoS One vol. 11 / Issue 4 e0153901 Apr. 2016.
Miyaoka, et al. "Systematic quantification of HDR and NHEJ reveals effects of locus, nuclease, and cell type on genome-editing," Scientific Reports vol. 6 23549 Mar. 2016.
Jayavaradhan, et al. "A Versatile Tool for the Quantification of CRISPR/Cas9-Induced Genome Editing Events in Human Hematopoietic Cell Lines and Hematopoietic Stem/Progenitor Cells," Journal of Molecular Biology doi: 10.1016/j.jmb.2018.05.005 May 2018.
St Martin, et al. "A fluorescent reporter for quantification and enrichment of DNA editing by APOBEC-Cas9 or cleavage by Cas9 in living cells," Nucleic Acids Research doi: 10.1093/nar/gky332 May 2018.

(Continued)

Primary Examiner — Christopher M Gross
(74) Attorney, Agent, or Firm — Bryan Cave Leighton Paisner LLP

(57) ABSTRACT

The present disclosure provides, inter alia, specially designed DNA adaptors and methods of preparing the same. Methods and kits for carrying out and detecting marker-free precision genome editing and genetic variation using such adaptors are also provided.

20 Claims, 70 Drawing Sheets
Specification includes a Sequence Listing.

(56) References Cited

OTHER PUBLICATIONS

Labun, et al. "Accurate analysis of genuine CRISPR editing events with ampliCan," BioRxiv doi: 10.1101/249474 Feb. 2018.
Hendel, et al. "Quantifying genome-editing outcomes at endogenous loci with SMRT sequencing," Cell Reports vol. 7 / Issue 1 pp. 293-305 Apr. 2014.
Miyaoka, et al. "Detection and Quantification of HDR and NHEJ Induced by Genome Editing at Endogenous Gene Loci Using Droplet Digital PCR," Methods in Molecular Biology vol. 1768 pp. 349-362 May 2018.
Giannoukos, et al. "UDiTaS™, a genome editing detection method for indels and genome rearrangements," BMC Genomics vol. 19 / Issue 1 212 Mar. 2018.
Harayama and Riezman "Detection of genome-edited mutant clones by a simple competition-based PCR method," PLoS One vol. 12 / Issue 6 e0179165 Jun. 2017.
Fujita, et al. "Detection of genome-edited cells by oligoribonucleotide interference-PCR," DNA Research doi: 10.1093/dnares/dsy012 Apr. 2018.
Editas Medicine Demonstrates First Achievement of In Vivo Editing in Non-human Primate Retinas, GlobeNewswire May 13, 2017.
Allen, et al. "Predicting the mutations generated by repair of Cas9-induced double-strand breaks," Nature biotechnology (2018).
Anzalone, et al. "Search-and-replace genome editing without double-strand breaks or donor DNA," Nature (2019).
Apostolou and Fostira "Hereditary breast cancer: the era of new susceptibility genes," Biomed Res Int 2013, 747318 (2013).
Barbieri, et al. "Precise Editing at DNA Replication Forks Enables Multiplex Genome Engineering in Eukaryotes," Cell 171, 1453-1467 e1413, (2017).
Bath, et al. "Many type IIs restriction endonucleases interact with two recognition sites before cleaving DNA," J Biol Chem 277, 4024-4033, (2002).
Bhagwat, et al. "Improved targeting of JAK2 leads to increased therapeutic efficacy in myeloproliferative neoplasms," Blood 123, 2075-2083 (2014).
Bhojwani and Pui "Relapsed childhood acute lymphoblastic leukaemia," Lancet Oncol 14, e205-217 (2013).
Billing, et al. "The BRCT Domains of the BRCA1 and BARD1 Tumor Suppressors Differentially Regulate Homology-Directed Repairand Stalled Fork Protection," Mol Cell 72, 127-139 e128 (2018).
Billon, et al. "CRISPR-Mediated Base Editing Enables Efficient Disruption of Eukaryotic Genes through Induction of STOP Codons," Mol Cell 67, 1068-1079 e1064 (2017).
Brinkman, et al. "Easy quantitative assessment of genome editing by sequence trace decomposition," Nucleic Acids Res 42, e168 (2014).
Brinkman, et al. "Easy quantification of template-directed CRISPR/Cas9 editing," Nucleic Acids Res 46, e58 (2018).
Canny, et al. "Inhibition of 53BP1 favors homology-dependent DNA repair and increases CRISPR-Cas9 genomeediting efficiency," Nat Biotechnol 36, 95-102 (2018).
Ceccaldi, et al. "The Fanconi anaemia pathway: new players and new functions," Nat Rev Mol Cell Biol 17, 337-349 (2016).
Chadwick, et al. "In Vivo Base Editing of PCSK9 (Proprotein Convertase Subtilisin/Kexin Type 9) as a Therapeutic Alternative to Genome Editing," Arterioscler Thromb Vase Biol 37, 1741-1747 (2017).
Clement, et al. "CRISPResso2 provides accurate and rapid genome editing sequence analysis," Nature biotechnology 37, 224-226 (2019).
Cong, et al. "Multiplex genome engineering using CRISPR/Cas systems," Science 339, 819-823 (2013).
Dieck and Ferrando "Genetics and mechanisms of NT5C2-driven chemotherapy resistance in relapsed ALL," Blood (2019).
Dow, L.E. "Modeling Disease In Vivo With CRISPR/Cas9," Trends Mol Med 21, 609-621 (2015).
Farzadfard and Lu "Emerging applications for DNA writers and molecular recorders," Science 361, 870-875 (2018).
Findlay, et al. "Accurate classification of BRCA1 variants with saturation genome editing," Nature (2018).
Gao, et al. "Treatment of autosomal dominant hearing loss by in vivo delivery of genome editing agents," Nature 553, 217-221 (2018).
Gaudelli, et al. "Programmable base editing of A*T to G*C in genomic DNA without DNA cleavage," Nature (2017).
Germini, et al. "A Comparison of Techniques to Evaluate the Effectiveness of Genome Editing," Trends Biotechnol 36, 147-159 (2018).
Guo, et al. "High-throughput creation and functional profiling of DNA sequence variant libraries using CRISPR-Cas9 in yeast," Nat Biotechnol 36, 540-546 (2018).
Inaba, et al. "Acute lymphoblastic leukaemia," Lancet 381, 1943-1955.
Jasin and Haber "The democratization of gene editing: Insights from site-specific cleavage and double-strand break repair," DNA Repair (Amst) 44, 6-16 (2016).
Kluesner, et al. "EditR: A Method to Quantify Base Editing from Sanger Sequencing," CRISPR J 1, 239-250 (2018).
Komor, et al. "Programmable editing of a target base in genomic DNA without double-stranded DNA cleavage," Nature 533, 420-424 (2016).
Komor, et al. "Improved base excision repair inhibition and bacteriophage Mu Gam protein yields C:G-to-T:A base editors with higher efficiency and product purity," Sci Adv 3, eaao4774 (2017).
Leenay, et al. "Large dataset enables prediction of repair after CRISPR-Cas9 editing in primary T cells," Nature biotechnology 37, 1034-1037 (2019).
Lek, et al. "Analysis of protein-coding genetic variation in 60,706 humans," Nature 536, 285-291 (2016).
Levine, et al. "Activating mutation in the tyrosine kinase JAK2 in polycythemia vera, essential thrombocythemia, and myeloid metaplasia with myelofibrosis," Cancer Cell 7, 387-397 (2005).
Levy, et al. "Cytosine and adenine base editing of the brain, liver, retina, heart and skeletal muscle of mice via adeno-associated viruses," Nat Biomed Eng 4, 97-110 (2020).
Lindsay, et al. "CrispRVariants charts the mutation spectrum of genome engineering experiments," Nat Biotechnol 34, 701-702 (2016).
Liu, et al. "Efficient generation of mouse models of human diseases via ABE- and BE-mediated base editing," Nat Commun 9, 2338 (2018).
Lundin, et al. "Endonuclease specificity and sequence dependence of type IIS restriction enzymes," PLoS One 10, e0117059 (2015).
Mali, et al. "RNA-guided human genome engineering via Cas9," Science 339, 823-826 (2013).
Mashal, et al. "Detection of mutations by cleavage of DNA heteroduplexes with bacteriophage resolvases," Nat Genet 9, 177-183 (1995).
McClellan and King "Genetic heterogeneity in human disease," Cell 141, 210-217 (2010).
Mullally, et al. "Physiological Jak2V617F expression causes a lethal myeloproliferative neoplasm with differential effects on hematopoietic stem and progenitor cells," Cancer Cell 17, 584-596 (2010).
Oshima, et al. "Mutational landscape, clonal evolution patterns, and role of RAS mutations in relapsed acute Tymphoblastic leukemia," Proc Natl Acad Sci USA 113, 11306-11311 (2016).
Pathania, et al. "BRCA1 haploinsufficiency for replication stress suppression in primary cells," Nature communications 5, 5496 (2014).
Paulsen, et al. "Ectopic expression of RAD52 and dn53BP1 improves homology-directed repair during CRISPR-Cas9 genome editing," Nat Biomed Eng 1, 878-888 (2017).
Pinello, et al. "Analyzing CRISPR genome-editing experiments with CRISPResso," Nature biotechnology 34, 695-697 (2016).
Qiu, et al. "Mutation detection using Surveyor nuclease," Biotechniques 36, 702-707 (2004).
Ran, et al. "Genome engineering using the CRISPR-Cas9 system," Nature protocols 8, 2281-2308 (2013).
Rees and Liu "Base editing: precision chemistry on the genome and transcriptome of living cells," Nat Rev Genet 19, 770-788 (2018).

(56) References Cited

OTHER PUBLICATIONS

Roy, et al. "Multiplexed precision genome editing with trackable genomic barcodes in yeast," Nat Biotechnol 36, 512-520 (2018).
Ryu, et al. "Adenine base editing in mouse embryos and an adult mouse model of Duchenne muscular dystrophy," Nature biotechnology 36, 536-539 (2018).
Shakya, et al. "BRCA1 tumor suppression depends on BRCT phosphoprotein binding, but not its E3 ligase activity," Science 334, 525-528 (2011).

Figure 1C

WT adaptor (CG)
STOP adaptor (CA)
Non-specific adaptor (TT)

WT adaptor (GG)
STOP adaptor (AG)
Non-specific adaptor (TT)

Figure 18A

VERSATILE METHOD FOR THE DETECTION OF MARKER-FREE PRECISION GENOME EDITING AND GENETIC VARIATION

CROSS REFERENCE TO RELATED APPLICATIONS

The present application claims benefit of U.S. Provisional Patent Application Ser. No. 62/985,746, filed on Mar. 5, 2020, which application is incorporated by reference herein in its entirety.

GOVERNMENT FUNDING

This invention was made with government support under grant no. GM117064, awarded by the National Institutes of Health. The government has certain rights in the invention.

FIELD OF DISCLOSURE

The present disclosure provides, inter alia, specially designed DNA adaptors and various methods and kits for carrying out and detecting marker-free precision genome editing and genetic variation using such adaptors.

INCORPORATION BY REFERENCE OF SEQUENCE LISTING

This application contains references to amino acids and/or nucleic acid sequences that have been filed as sequence listing text file "1035795-000704-seq.txt", file size of 63 KB, created on Apr. 8, 2021. The aforementioned sequence listing is hereby incorporated by reference in its entirety pursuant to 37 C.F.R. § 1.52(e)(5).

BACKGROUND OF THE DISCLOSURE

Precision genome editing allows the modeling and correction of desired genomic variants containing insertions or deletions of specific nucleotide sequences or changes in single DNA bases (Anzalone et al., 2019; Barbieri et al., 2017; Cong et al., 2013; Dow, 2015; Guo et al., 2018; Liu et al., 2018; Mali et al., 2013; Roy et al., 2018). Precision genome editing can be obtained by CRISPR-dependent homology-directed repair (HDR) of Cas9-induced DNA double-strand breaks (DSBs) (Jasin and Haber, 2016) or result from the use of alternative DSB-free methods, such as CRISPR-dependent base editing, which utilizes cytidine or adenosine deaminases fused to a nickase Cas9 (nCas9) mutant to generate base transitions (Gaudelli et al., 2017; Komor et al., 2016), and prime editing, which employs a reverse transcriptase-nCas9 fusion and a template prime editing guide RNA (pegRNA) to install into the genome a large variety of genomic changes, including transversions, transitions, small insertions and deletions (Anzalone et al., 2019).

Genome editing has been facilitated by the development of accessible and cost-effective methods for the detection of small insertions and deletions (indels) resulting from the repair of Cas9-induced DSBs, such as the T7E1 and Surveyor nuclease assays (Mashal et al., 1995; Qiu et al., 2004; Ran et al., 2013). However, since these methods do not determine the identity of DNA bases, they are ill-suited for the detection of genomic changes introduced by precision genome editing (Germini et al., 2018). Precision genome editing events can be detected by the addition of genomic markers by CRISPR-dependent HDR or prime editing, such as silent mutations that create or disrupt restriction sites, or selectable reporters encoding for antibiotic resistance or fluorescent proteins. However, the use of genomic markers entails an elaborate experimental design that is unique for each targeted site, thus complicating the insertion of the desired genetic modifications. In addition, genomic markers can cause unintended perturbations of coding or non-coding genomic elements. Moreover, marker-based detection methods are not compatible with CRISPR-dependent base editing strategies, which induce single DNA base changes (Rees and Liu, 2018). Alternatively, methods that employ Sanger sequencing or next-generation sequencing (NGS) enable the detection of precise genomic changes without the use of genomic markers (Brinkman et al., 2014; Pinello et al., 2016). However, Sanger sequencing-based approaches suffer from low sensitivity and precision due to variable quality of the sequencing reactions and background signals that often affect the sequencing reads (Brinkman et al., 2014; Brinkman et al., 2018). While NGS-based detection strategies are highly sensitive (Clement et al., 2019; Lindsay et al., 2016; Pinello et al., 2016), they remain expensive and time-consuming, which limits their value for the development of mutant cell lines and animal models and for applications that require a rapid turnaround time, such as the identification of pathogenic variants in certain clinical settings. Therefore, a simple, efficient, inexpensive and rapid method that enables quantitative detection of genetic variants in complex biological systems is needed. This disclosure is directed to meeting these and other needs.

SUMMARY OF THE DISCLOSURE

Genome editing technologies have transformed our ability to engineer desired genomic changes within living systems. However, detecting precise genomic modifications often requires sophisticated, expensive and time-consuming experimental approaches. The present disclosure provides DTECT (Dinucleotide signaTurE CapTure), a rapid and versatile detection method that relies on the capture of targeted dinucleotide signatures resulting from the digestion of genomic DNA amplicons by the type IIS restriction enzyme AcuI. DTECT enables the accurate quantification of marker-free precision genome editing events introduced by CRISPR-dependent homology-directed repair, base editing or prime editing in various biological systems, such as mammalian cell lines, organoids and tissues. Furthermore, DTECT allows the identification of oncogenic mutations in cancer mouse models, patient-derived xenografts and human cancer patient samples; it also allows the identification of genetic modifications incurred in various infectious diseases. Ultimately, DTECT enables the capture of signatures in nucleic acids from any organism including, e.g., viruses such as SARS-CoV-2. The ease, speed and cost efficiency by which DTECT identifies genomic signatures should facilitate the generation of marker-free cellular and animal models of human disease and expedite the detection of human pathogenic variants.

Accordingly, one embodiment of the present disclosure is a DNA adaptor comprising: (a) one strand with sequence of 5'-CTGGGGCACGGGTAAGAAGCATTCTGTCTCTC-TTCTAAGAATTCGAGCTCGGTACC CG-3' (SEQ ID NO: 230); and (b) one complementary strand with sequence of 5'-CGGGTACCGAGCTCGAATTCTTAGAAGAGAG-ACAGAATGCTTCTTACCCGTGCCC CAGNN-3' with "N" corresponding to A, T, G or C (SEQ ID NOs: 231-246).

Another embodiment of the present disclosure is a method of preparing a DNA adaptor disclosed herein, comprising: (a) synthesizing one constant oligonucleotide with sequence of 5'-CTGGGGCACGGGTAAGAAGCATTCTGTCTC-TCTTCTAAGAATTCGAGCTCGGTACC CG-3' (SEQ ID NO: 230); (b) synthesizing one complementary oligonucleotide with sequence of 5'-CGGGTACCGAGCTCGAAT-TCTTAGAAGAGAGACAGAATGCTTCTTACCCGTG-CCC CAGNN-3' with "N" corresponding to A, T, G or C (SEQ ID NOs: 231-246); (c) mixing the constant and complementary oligonucleotides; and (d) annealing the mixture to obtain the DNA adaptor.

Another embodiment of the present disclosure is a library of DNA adaptors prepared by methods disclosed herein, the library comprises 16 DNA adaptors, wherein each DNA adaptor has a different "NN".

Another embodiment of the present disclosure is a method for detecting a genetic modification, comprising the steps of: (a) amplifying a genomic locus of interest using a specially designed Type IIS restriction enzyme-tagging primer, comprising: (i) extracting genomic DNA from a biological sample of interest; (ii) synthesizing the Type IIS restriction enzyme-tagging primer based on the genomic locus of interest; (iii) amplifying the genomic locus of interest using the Type IIS restriction enzyme-tagging primer and a reverse primer; and (iv) purifying a Type IIS restriction enzyme-tagged genomic amplicon; (b) digesting the Type IIS restriction enzyme-tagged genomic amplicon with the Type IIS restriction enzyme; (c) isolating the smaller DNA fragment containing a genomic signature of interest exposed in a 3' single-stranded overhang; (d) capturing the genomic signature of interest, comprising: (i) preparing the library of DNA adaptors disclosed herein; (ii) incubating the isolated smaller DNA fragment containing the 3' overhang signature with the library of DNA adaptors and performing a ligation; and (iii) obtaining a ligated product; and (e) amplifying the ligated product to detect the presence of the genetic modification.

A further embodiment of the present disclosure is a kit for detecting a genetic modification of interest, comprising a specially designed Type IIS restriction enzyme-tagging primer disclosed herein, and a library of DNA adaptors disclosed herein, packaged together with instructions for its use.

Another embodiment of the present disclosure is a method for detecting a genetic modification, comprising the steps of: (a) amplifying a genomic locus of interest using a specially designed AcuI-tagging primer, comprising: (i) extracting DNA of interest; (ii) synthesizing the AcuI-tagging primer based on the genomic locus of interest; (iii) amplifying the genomic locus of interest using the AcuI-tagging primer and a reverse primer; and (iv) purifying an AcuI-tagged genomic amplicon; (b) digesting the AcuI-tagged genomic amplicon with restriction enzyme AcuI; (c) isolating the smaller DNA fragment containing a genomic signature of interest produced by AcuI-digestion; (d) capturing the genomic signature of interest, comprising: (i) preparing the library of DNA adaptors disclosed herein; (ii) incubating the isolated smaller DNA fragment with the library of DNA adaptors and performing a ligation; and (iii) obtaining a ligated product; and (e) amplifying the ligated product to detect the presence of the genetic modification.

An additional embodiment of the present disclosure is a kit for detecting a genetic modification, comprising a specially designed AcuI-tagging primer and a library of DNA adaptors disclosed herein, packaged together with instructions for its use.

Another embodiment of the present disclosure is a method for quantifying a genomic variant in a biological system, comprising the steps of: (a) obtaining a sample from the biological system; (b) amplifying a genomic locus of interest using a specially designed AcuI-tagging primer, comprising: (i) extracting DNA of interest; (ii) synthesizing the AcuI-tagging primer based on the genomic locus of interest; (iii) amplifying the genomic locus of interest using the AcuI-tagging primer and a reverse primer; and (iv) purifying an AcuI-tagged genomic amplicon; (c) digesting the AcuI-tagged genomic amplicon with restriction enzyme AcuI; (d) isolating the smaller DNA fragment containing a genomic signature of interest produced by the AcuI-digestion; (e) capturing the genomic signature of interest, comprising: (i) preparing the library of DNA adaptors disclosed herein; (ii) incubating the isolated smaller DNA fragment with the library of DNA adaptors and performing a ligation; and (iii) obtaining a ligated product; and (f) quantifying the genomic variant and determining its relative abundance.

Still another embodiment of the present disclosure is a method for identifying and quantifying an oncogenic mutation of interest in a biological sample, comprising the steps of: (a) obtaining a biological sample; (b) amplifying a genomic locus of interest using a specially designed AcuI-tagging primer, comprising: (i) extracting DNA of interest; (ii) synthesizing the AcuI-tagging primer based on the genomic locus of interest; (iii) amplifying the genomic locus of interest using the AcuI-tagging primer and a reverse primer; and (iv) purifying an AcuI-tagged genomic amplicon; (c) digesting the AcuI-tagged genomic amplicon with restriction enzyme AcuI; (d) isolating the smaller DNA fragment containing a genomic signature of interest produced by the AcuI-digestion; (e) capturing the genomic signature of interest, comprising: (i) preparing the library of DNA adaptors disclosed herein; (ii) incubating the isolated smaller DNA fragment with the library of DNA adaptors and performing a ligation; and (iii) obtaining a ligated product; (f) amplifying the ligated product to identify the presence of the oncogenic mutation of interest; and (g) quantifying the oncogenic mutation of interest, if present, and determining its frequency.

A further embodiment of the present disclosure is a process for marker-free detection of a precision genome editing event comprising carrying out Dinucleotide signaTurE CapTure (DTECT) on a nucleic acid sequence of interest.

Still another embodiment of the present disclosure is a method for detecting a virus variant of interest, comprising the steps of: (a) obtaining a nucleic acid of the virus variant of interest from a biological sample; and (b) if the nucleic acid is DNA, carrying out Dinucleotide signaTurE CapTure (DTECT) to detect the variant of interest; or (c) if the nucleic acid is RNA, coverting it to DNA by reverse transcription PCR (RT-PCR) and then carrying out DTECT to detect the variant of interest.

BRIEF DESCRIPTION OF THE DRAWINGS

FIGS. 1A-1C show the identification of targeted dinucleotide signatures using DTECT.

FIG. 1A is a schematic representation of DTECT. The targeted genomic locus containing a hypothetical targeted dinucleotide (N=A, C, G or T; green) is PCR-amplified using a forward AcuI-tagging primer juxtaposed to the targeted dinucleotide and a locus-specific DNA primer (AcuI-tagging primer design and PCR, steps I and II). The AcuI-tagging primer (60 nt) is constituted of DNA sequences complementary to the genomic locus (purple) interrupted by a hairpin containing an AcuI recognition site (green), and a non-complementary DNA sequence (blue). The locus-specific reverse primer (red) is located at a distance >100 bp from the targeted dinucleotide. The obtained PCR product is subsequently cleaved by the AcuI restriction enzyme in a position adjacent to the targeted dinucleotide, resulting in the generation of two DNA fragments of 60 bp and >100 bp (AcuI digestion, step III). The 60 bp fragment containing the exposed signature of the targeted dinucleotide is then isolated using SPRI beads with higher affinity towards >100 bp DNA products (Small fragment isolation, step IV). The 60 bp fragment is then ligated to DNA adaptors containing 3'-overhangs of two bases complementary (specific) or not (non-specific) to the dinucleotide signature (Adaptor ligation, step V). The ligated product is then subjected to PCR amplification for analytical or quantitative detection (Detection PCR, step VI). The approximate time required for each step is indicated.

FIG. 1B shows the schematics of the DTECT adaptor library. Control (green) and mutant (purple) dinucleotide signatures (left panel) are detected using a library of 16 unique adaptors (middle panel). The library contains adaptors with dinucleotides complementary to the control (green) or mutant (purple) signature, as well as non-specific adaptors (blue) (right panel).

FIG. 1C shows the schematics of the positive and negative controls used in DTECT experiments to identify signatures of interest (e.g., mutant allele) in allele populations. In genomic DNA samples containing only the WT dinucleotide signature, the adaptor complementary to the WT dinucleotide signature (green) serves as a positive control, while the adaptor complementary to the mutant signature of interest (purple) and a non-specific adaptor (blue) are used as negative controls. In genomic DNA samples containing a mixture of the WT and the mutant dinucleotide signature, the adaptor complementary to the WT dinucleotide signature (green) is used as a positive control and a non-specific adaptor (blue) serves as a negative control. The adaptor complementary to the mutant dinucleotide signature (purple) is used to detect the presence of the variant of interest and quantify its frequency.

FIG. 2A shows the design of AcuI-tagging primers that allow the capture of two dinucleotide signatures (CC and TT; blue) on opposite DNA strands.

FIG. 2B shows the PCR amplification (22 cycles) of the AcuI-digested DNA products containing the CC and TT signatures shown in FIG. 2A, which have been captured using GG or AA adaptors.

FIG. 2C shows the PCR amplification (22 cycles) of DNA fragments captured as in FIG. 2B with or without dephosphorylation of the AcuI-digested products by the shrimp alkaline phosphatase (rSAP).

FIG. 2D shows the PCR amplification (22 cycles) of DNA fragments captured as in FIG. 2B in the absence or presence of AcuI, DNA adaptors (GG adaptor for signature CC; AA adaptor for signature TT) or T4 DNA ligase.

FIG. 2E shows the schematic representation of the AcuI-tagging primer design for detecting four possible dinucleotide signatures (#1-4) containing the same targeted base (C:G, red) in the PIK3R1 gene.

FIG. 2F shows the detection of the four dinucleotide signatures shown in FIG. 2E by DTECT (18 PCR cycles) using specific (green) and non-specific (blue) adaptors.

FIG. 2G shows the quantification by DTECT of the relative abundance of SMARCAL1, SPRTN and PIK3R1 WT (green) and STOP (purple) dinucleotide signatures in mixtures of WT and STOP alleles at predefined ratios. Graphs (left) represent the correlation between the frequency of WT and STOP variants determined by DTECT and the expected frequency of the same variants in the mixed populations for each of the above 3 genes. Error bars represent the s.d. of independent experiments (n=2). Pearson correlation (r) was determined by comparing expected and DTECT-based frequency. Comparison of the mean frequency of STOP and WT signatures determined by DTECT and their expected frequency is shown in the right panel (n=3 independent genes, SMARCAL1, SPRTN and PIK3R1).

FIG. 2H shows the representation of the AcuI-tagging primers used to detect the WT and STOP alleles of the PIK3R1 gene. The targeted dinucleotides are shown in blue, the edited base is indicated with an asterisk and part of the AcuI-tagging primer sequence is shown in purple.

FIG. 2I shows the PCR amplification (25 cycles) of WT and STOP PIK3R1 alleles (arrow) captured using DTECT from WT:STOP allele mixtures (i.e., 100:0 and 99:1). An adaptor (CG) specific for the WT allele is used as a positive control and a non-specific adaptor (TT) is used as a negative control. An adaptor that captures the STOP PIK3R1 allele (CA) serves as an additional negative control in the reaction containing only the WT allele. Background non-specific PCR products are indicated with an asterisk.

FIG. 2J shows the fold change variation in the frequency of capture of each of the 16 dinucleotide signatures relative to the mean dinucleotide capture frequency. Oligonucleotides containing distinct dinucleotide signatures are captured using specific adaptors. The fraction of captured material is then quantified by qPCR and normalized to the mean value obtained from the capture of all 16 dinucleotide signatures. Error bars indicate the s.d. of 4 independent experiments. Dots represent individual data point.

FIG. 2K shows the fold change variation in the frequency of capture of dinucleotide signatures with 1 A/T+1 C/G, 2 NT or 2 C/G bases relative to the mean dinucleotide capture frequency, determined as described in FIG. 2J. Error bars represent the s.d. of 8 mean values for dinucleotides with 1 NT+1 C/G and 4 mean values for dinucleotides with 2 NT and 2 C/G, as determined in FIG. 2J.

FIG. 3A shows the schematics of the protocol used to identify genomic changes introduced by CRISPR-dependent HDR, base editing or prime editing. In HDR experiments (blue), HEK293T cells were transfected with Cas9 and sgRNA targeting a gene of interest with or without donor DNA molecules. In base editing experiments (red), HEK293T cells were transfected with BE3 base editors with either control or base editing sgRNAs. Base editing experiments were also conducted in cells stably expressing FNLS-BE3. In prime editing experiments (grey), HEK293T cells were transfected with PE2 with or without pegRNA. Genomic DNA was then extracted from cell populations and subjected to DTECT using adaptors specific for WT (green) or edited (purple) variants.

FIG. 3B shows the identification by DTECT of WT and HDR-edited (R209fs*6) TP53 alleles (top), WT and base-edited (Q223*) FANCD2 alleles (middle), and WT and prime-edited (CTT_ins) HEK3 alleles (bottom). Adaptors specific for the WT (CT, CA, CG; green) or edited (TT, TA;

purple) signatures were utilized in DTECT experiments. Captured samples were subjected to analytical (left; 21 cycles) or quantitative PCR (right). In the HDR experiment, cells were transfected with Cas9, sgRNA and an ssODN specific for the TP53 locus with or without the HDR stimulatory factor i53. The ssODN was omitted in control reactions. In the base editing experiment, cells were transfected with BE3 and sgRNA to induce Q223* in FANCD2. In prime editing experiments, cells were transfected with PE2 and pegRNA to introduce a CTT insertion in the HEK3 locus.

Figure 3A:
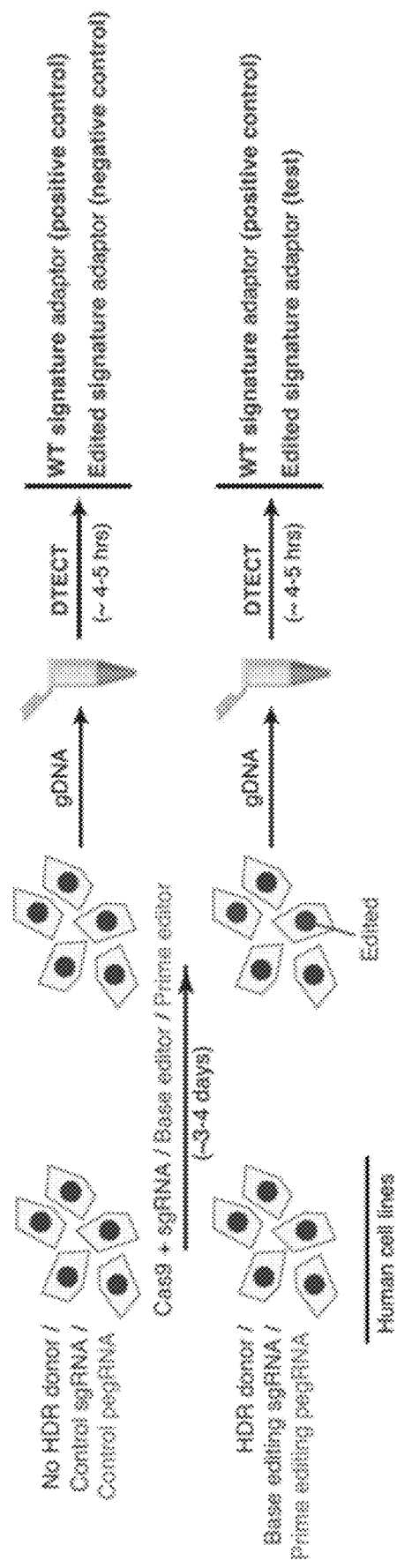
FIGS. 3A-3E show the detection and quantification of precision genome editing by CRISPR-mediated HDR, base editing and prime editing using DTECT.
Figure 3B:
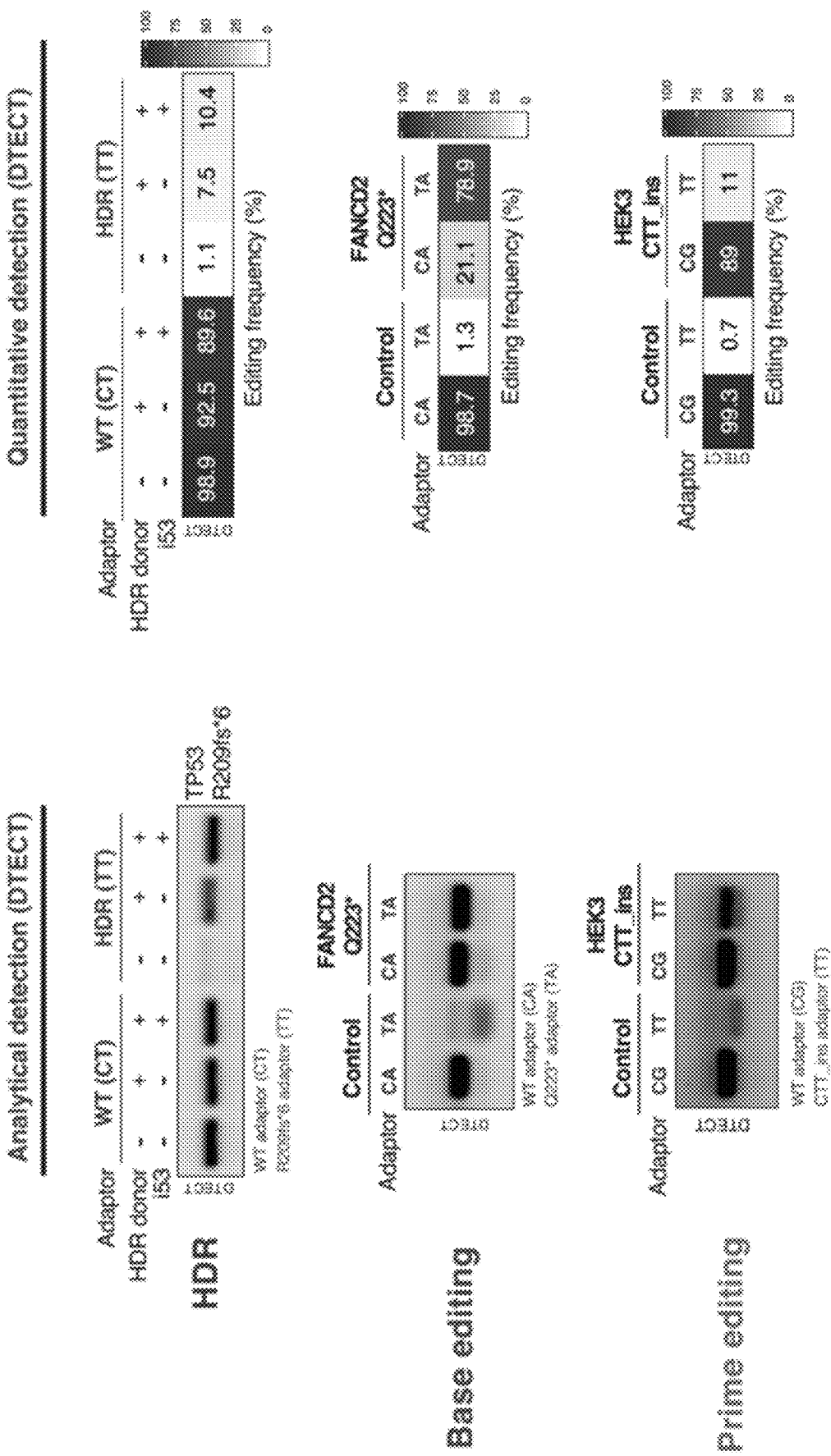
Figure 3C:
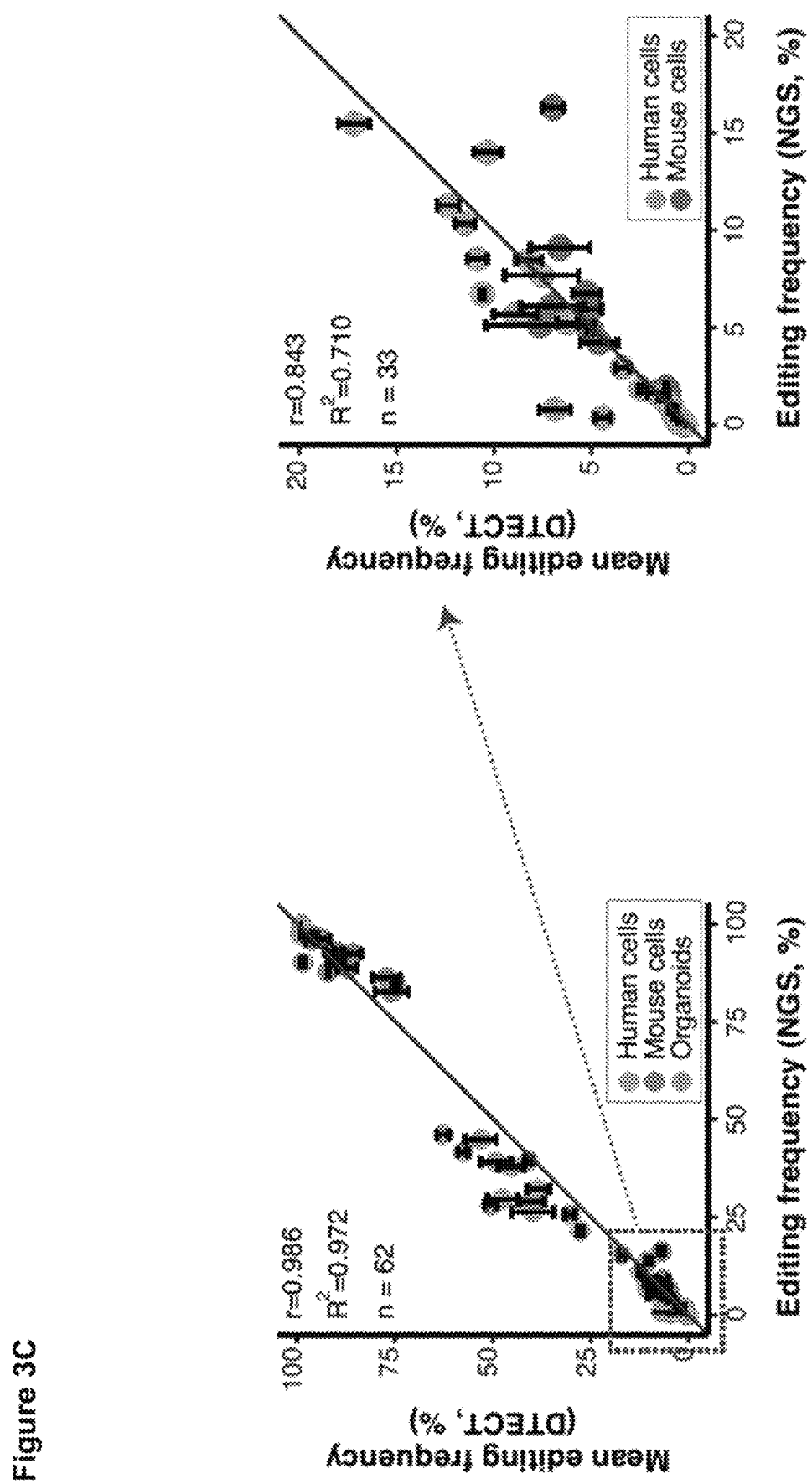

FIG. 3C provides the graphical representation of the correlation of DTECT- and NGS-based estimations of the frequency of genetic variants introduced by precision genome editing in human and mouse cells, and mouse intestinal organoids (n=62). Data points in the dashed box (frequency <20%) of the left panel are shown enlarged on the right panel (n=33). Error bars indicate the s.e.m. of 2-5 independent replicates. The source of the edited sample is indicated by distinct colors.

Figure 3D:
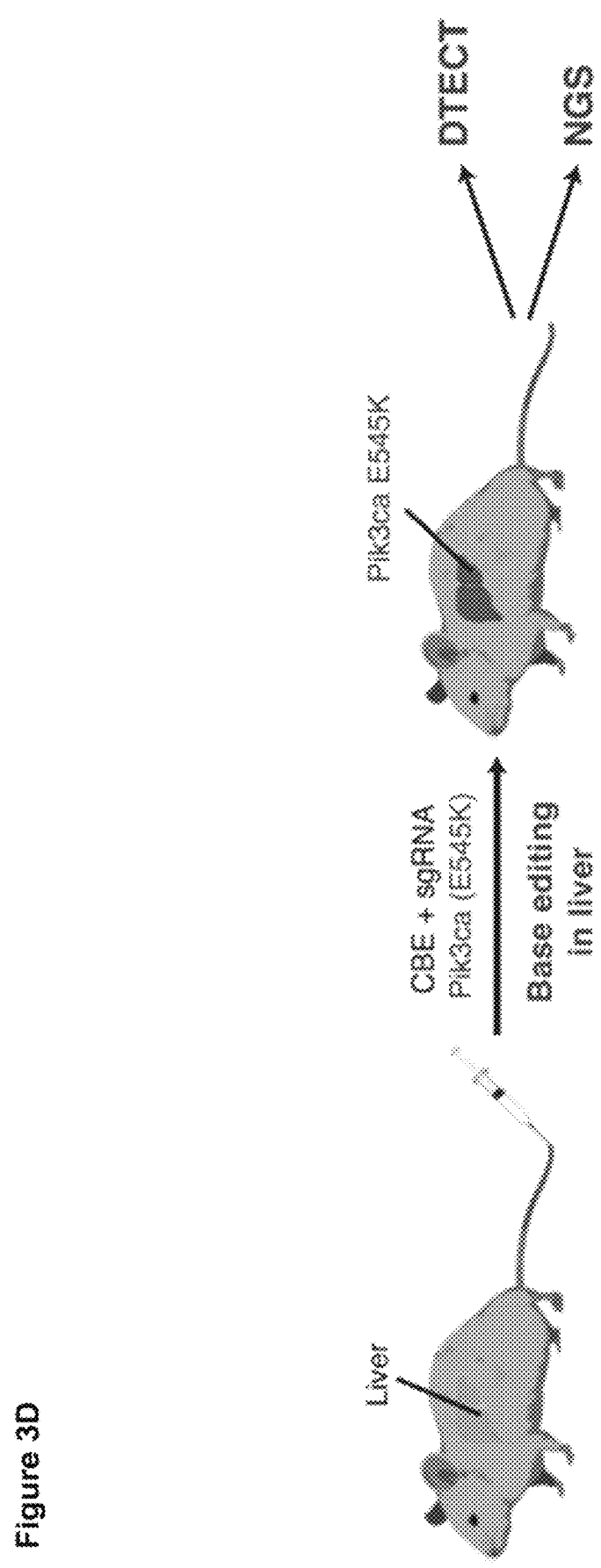

FIG. 3D shows the schematic representation of the experiments conducted to measure the efficiency of precision genome editing in vivo using DTECT. Editing of the mouse liver was performed by hydrodynamic injection of the cytidine base editor (CBE) FNLS-BE3 and an sgRNA to introduce the Pik3ca E545K variant. DTECT (red) and NGS (green) were used to determine the efficiency of editing in the mouse liver sample.

Figure 3E:
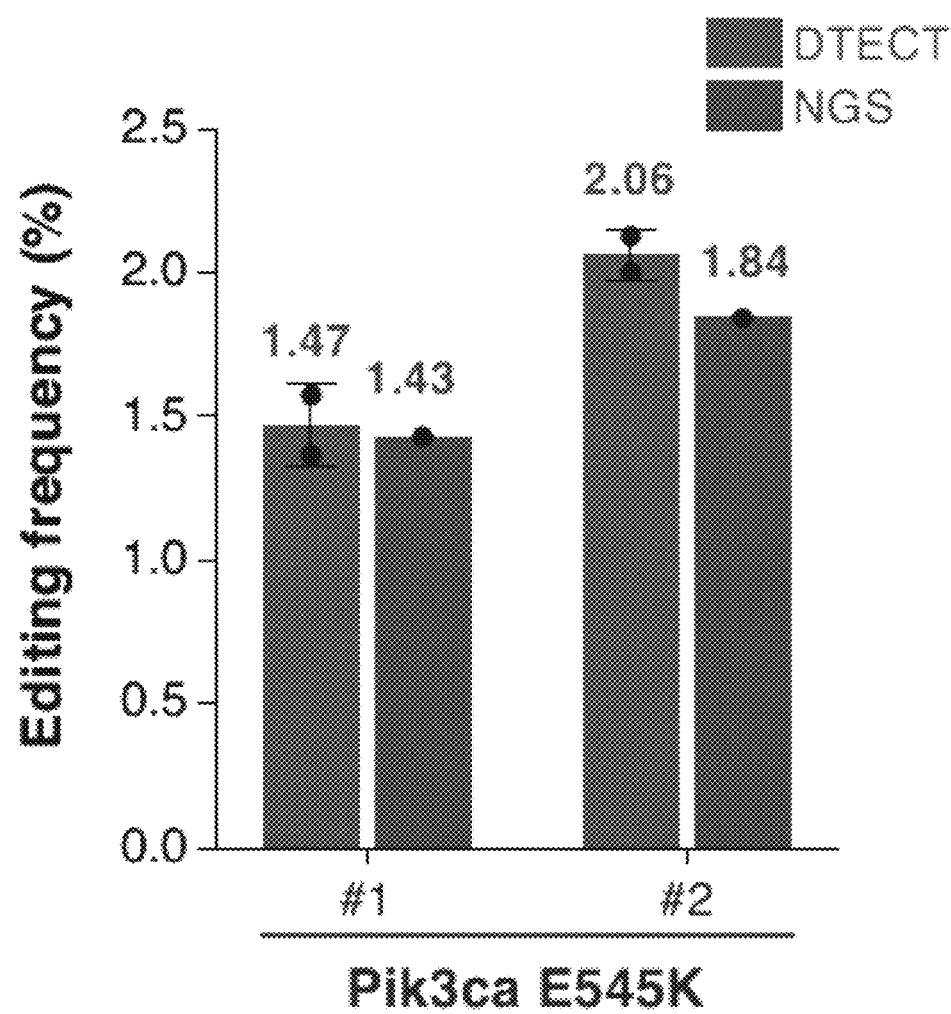

FIG. 3E shows the quantification by DTECT (red) and NGS (green) of the Pik3ca E545K variant introduced by CRISPR-mediated base editing in the mouse liver, as shown in FIG. 3D. Error bars indicate the s.d. of 2 independent experiments. Dots represent individual data point.

Figure 4A:
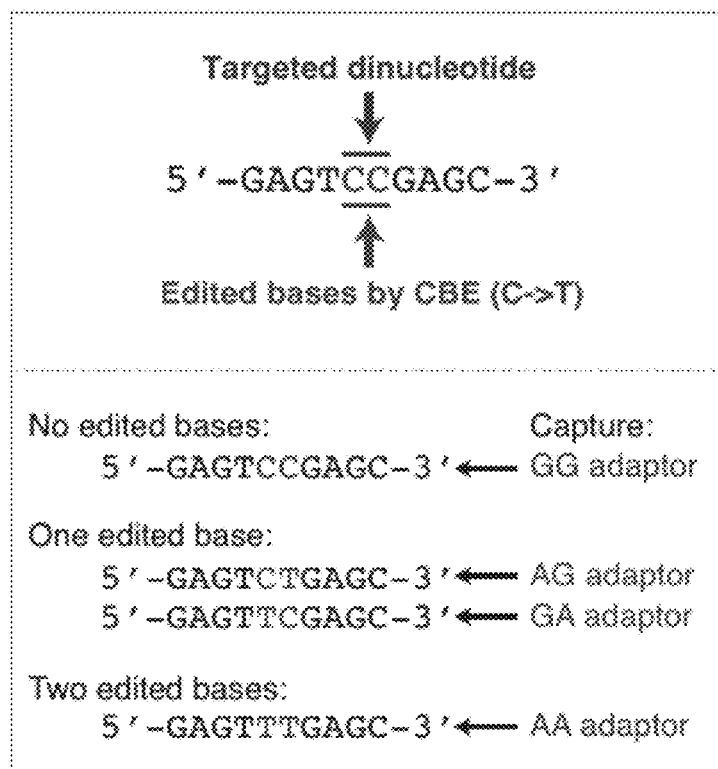
Figure 4A:
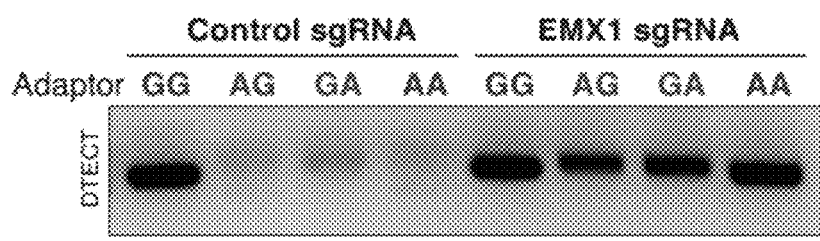
Figure 4B:
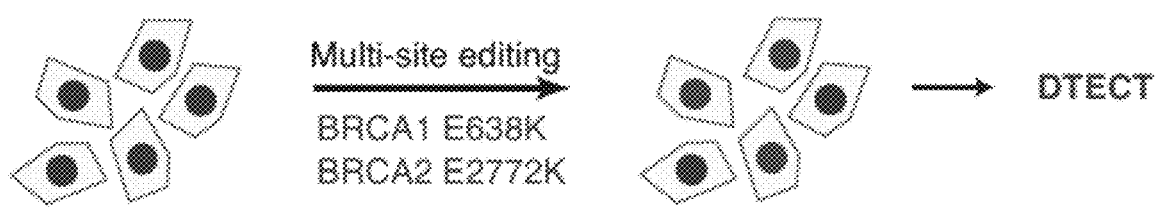
Figure 4C:
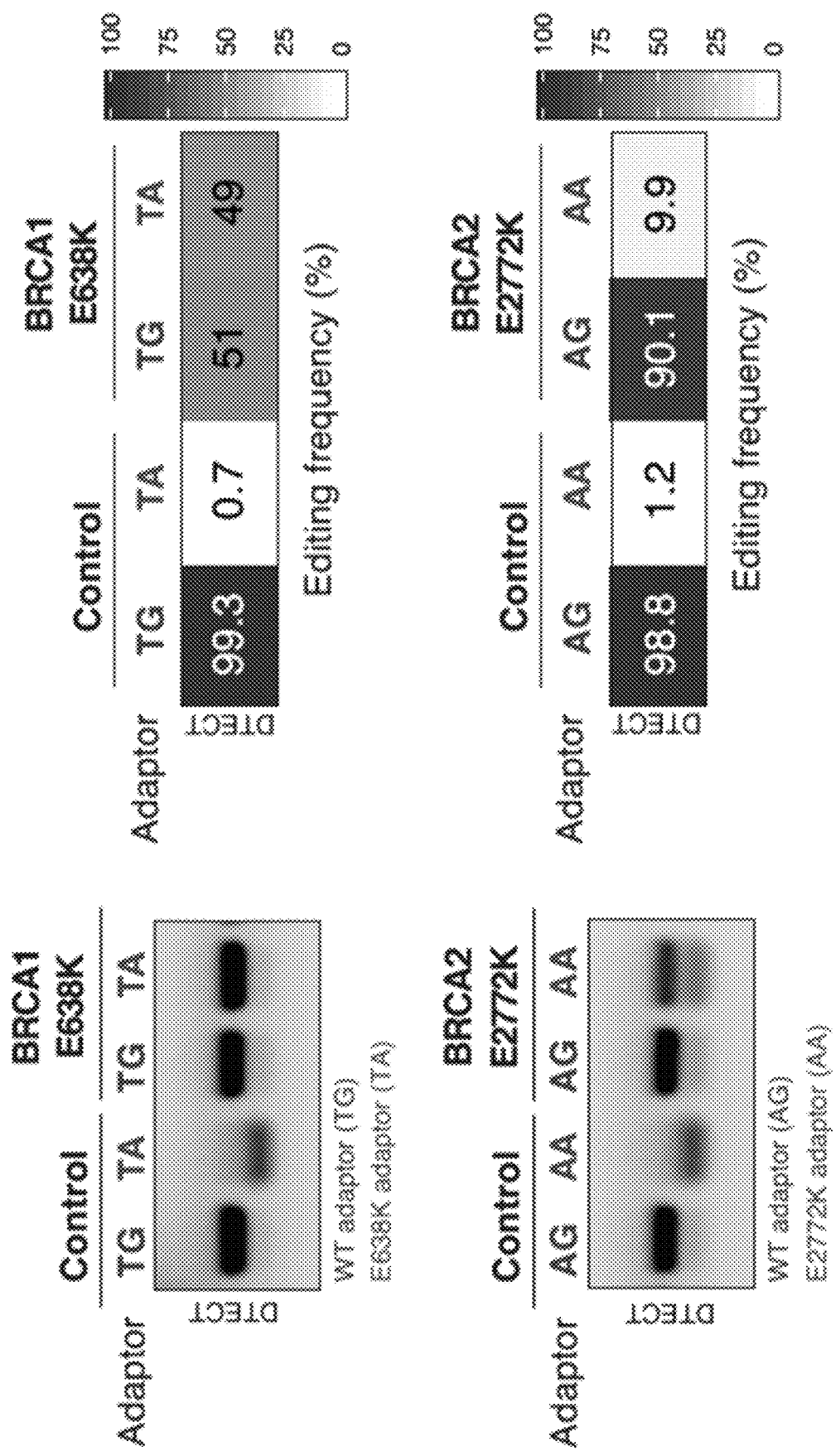

FIGS. 4A-4C show the identification of multiple genome editing events in a single locus or distinct loci by DTECT.

FIG. 4A shows the detection by PCR (21 cycles) of allelic mixtures induced by CRISPR-mediated base editing events occurring at a CC sequence (green) in the EMX1 gene. The sequences of the EMX1 alleles resulting from four possible C→T base transitions (CC, CT, TC, TT) induced by CRISPR-mediated base editing and the adaptors to capture them (GG, AG, GA, AA) are shown. In these experiments HEK293T cells constitutively expressing the cytidine base editor (CBE) FNLS-BE3 were transfected with sgRNA targeting the EMX1 locus.

FIG. 4B shows the schematics of the experiments conducted to detect multiple simultaneously induced variants using DTECT. HEK293T cells constitutively expressing the base editor FNLS-BE3 were transfected with two sgRNAs to introduce simultaneously the BRCA1 E638K and the BRCA2 E2772K mutations by CRISPR-mediated base editing.

FIG. 4C shows the detection of multiple precision genome editing events introduced by CRISPR-mediated base editing in HEK293T cell populations, as illustrated in FIG. 4B. WT and edited BRCA1 and BRCA2 alleles captured using adaptors specific for the WT (TG, AG; green) or edited (TA, AA; purple) alleles were subjected to analytical (left; 21 cycles) or quantitative PCR (right).

FIGS. 5A-5J show the DTECT-mediated identification of clinically relevant BRCA1/2 mutations generated by precision genome editing and genotyping of cell lines and animal models carrying BRCA1 or BARD1 mutations.

Figure 5A:
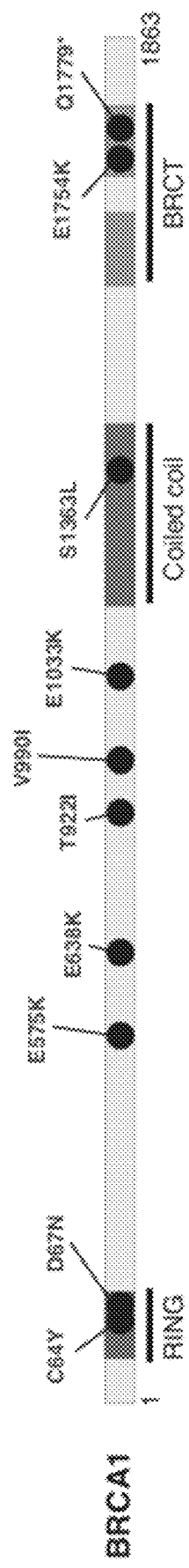

FIG. 5A shows the schematic representation of the human BRCA1 protein. BRCA1 domains and ClinVar BRCA1 mutations generated in this study are indicated.

Figure 5B:
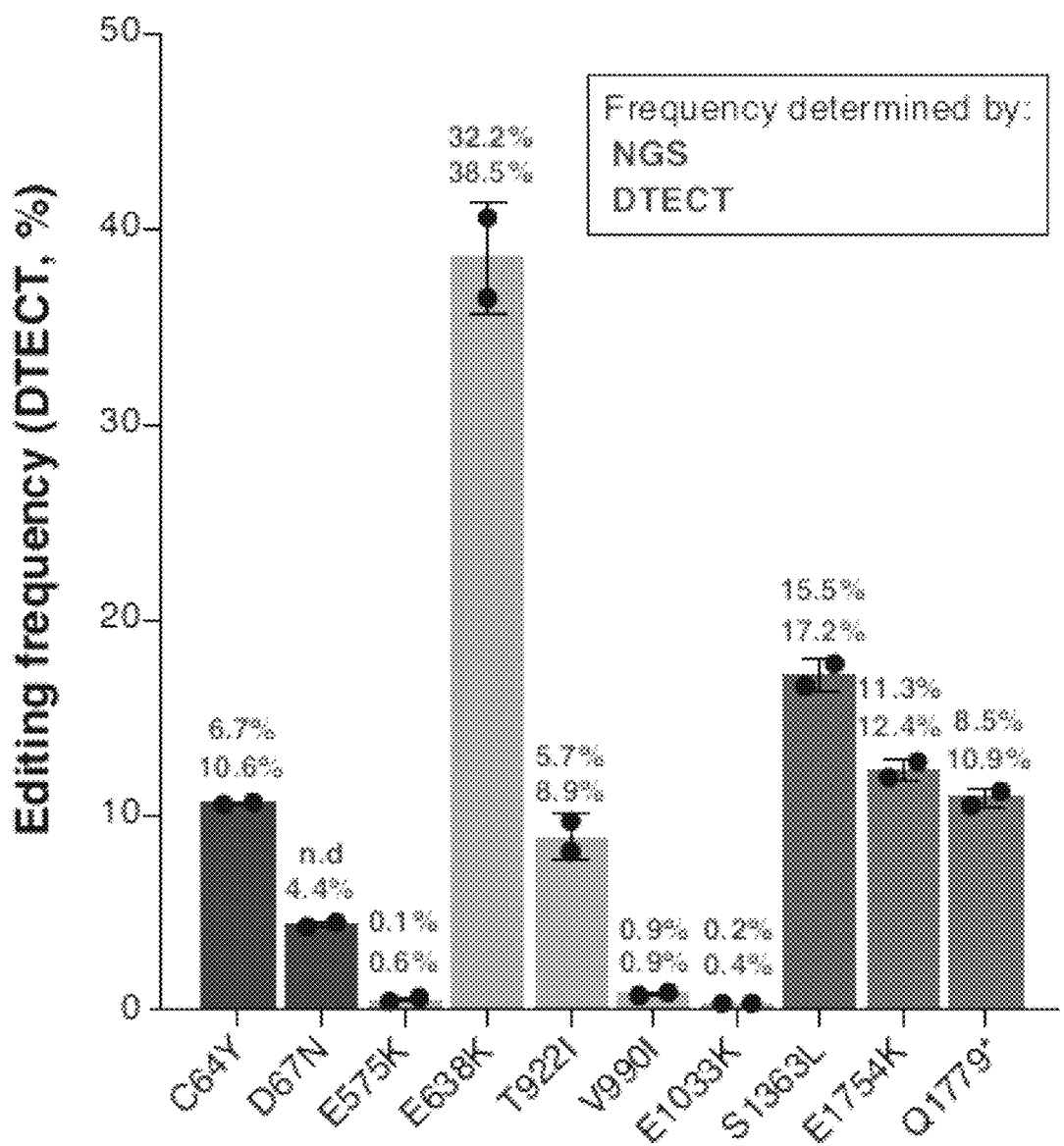

FIG. 5B shows the quantification using DTECT (red) and NGS (green) of the editing efficiency by which 10 BRCA1 mutations are introduced into HEK293T cells by CRISPR-mediated base editing. Experiments were conducted in cells expressing the base editor FNLS-BE3 upon transfection of sgRNAs to introduce the indicated mutations. Histograms show the mean frequency of the indicated variants estimated by DTECT and error bars represent the s.d. from 2 independent DTECT assays for the same AcuI-tagged amplicon. n.d.: not determined, due to sequencing failure.

Figure 5C:
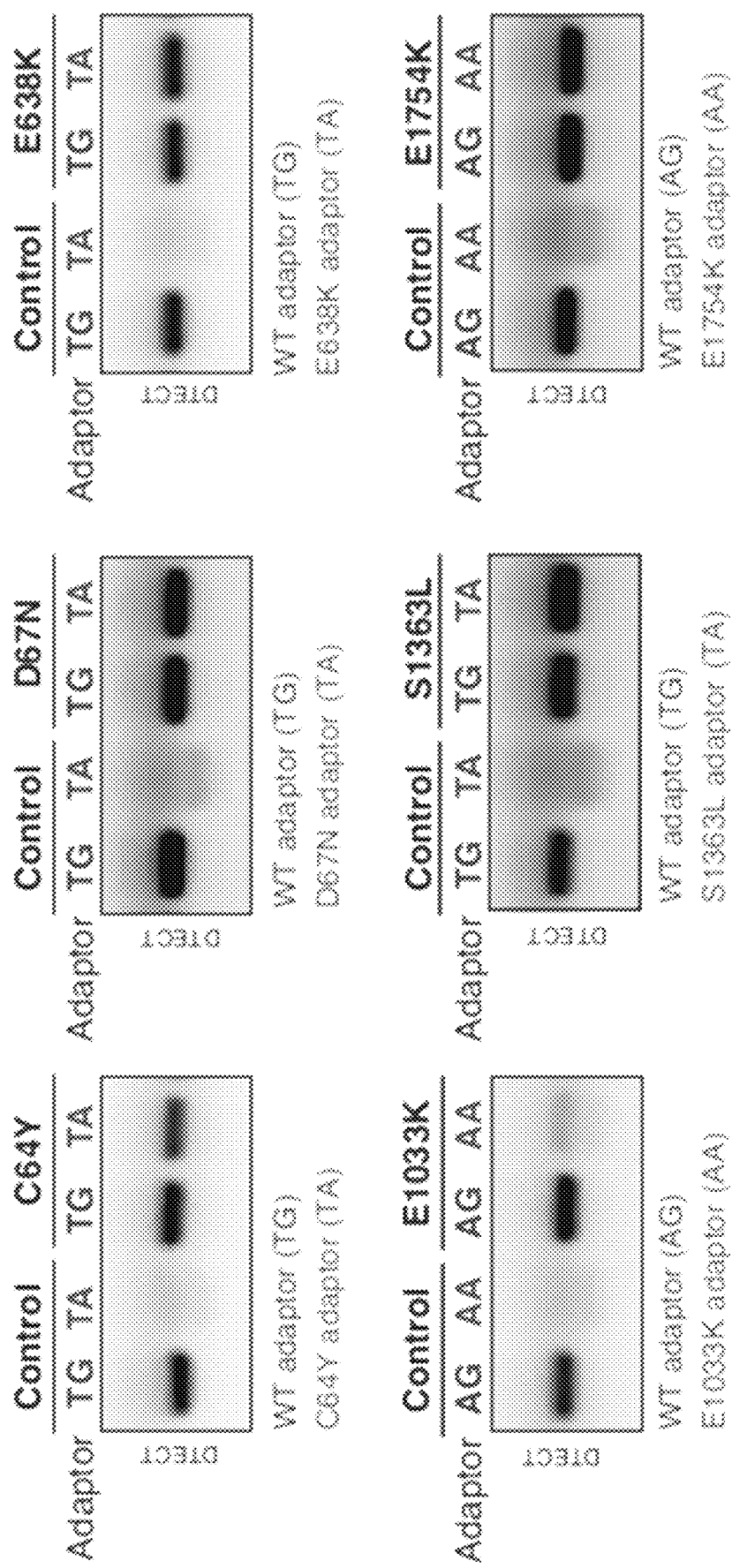

FIG. 5C shows the analytical detection of the indicated BRCA1 mutations in HEK293T cell populations by DTECT (21 PCR cycles) using adaptors specific for WT (green) or mutant (purple) alleles.

Figure 5D:
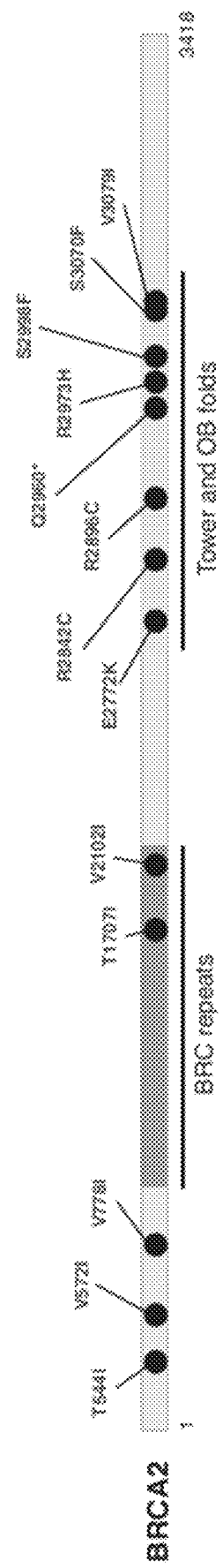

FIG. 5D shows the schematic representation of the human BRCA2 protein. BRCA2 domains and ClinVar BRCA2 mutations generated in this study are indicated.

Figure 5E:
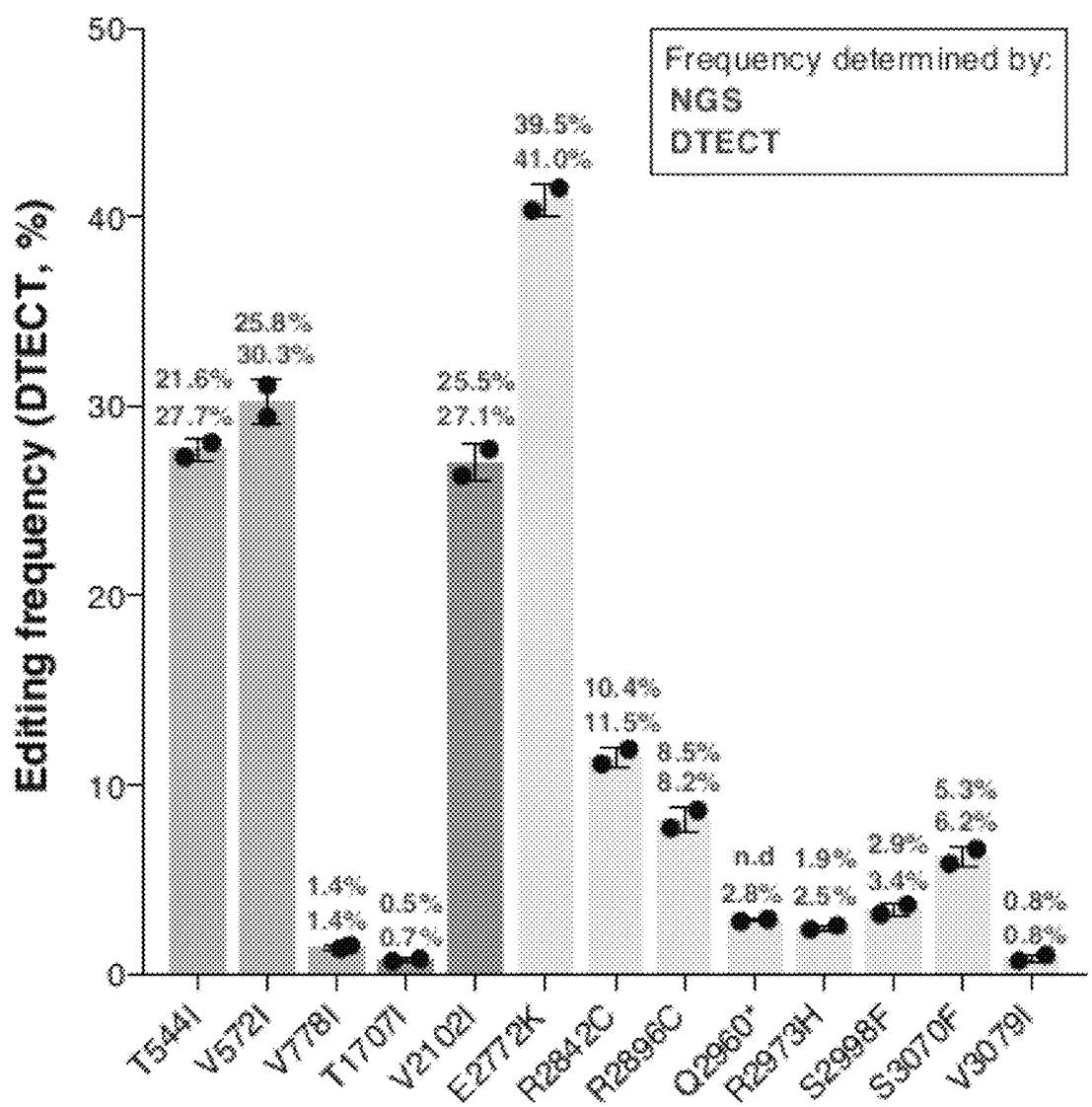

FIG. 5E shows the quantification using DTECT (red) and NGS (green) of the editing efficiency by which 13 BRCA2 mutations are introduced into HEK293T cells by CRISPR-mediated base editing, as described in FIG. 5B.

Figure 5F:
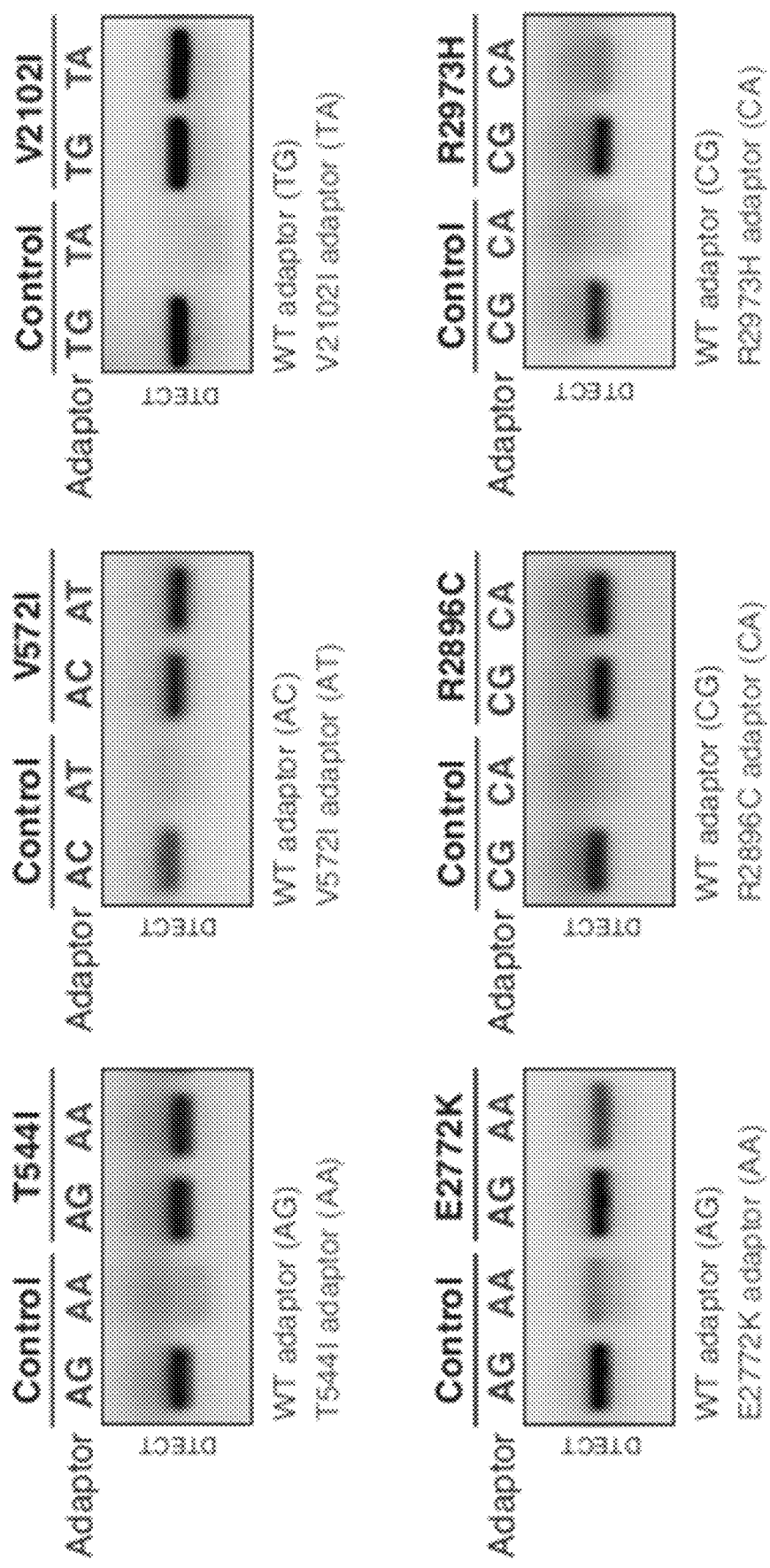

FIG. 5F shows the analytical detection of the indicated BRCA2 mutations in HEK293T cell populations by DTECT (21 PCR cycles) using adaptors specific for WT (green) or mutant (purple) alleles. Experiments were conducted as in FIG. 5C.

Figure 5G:
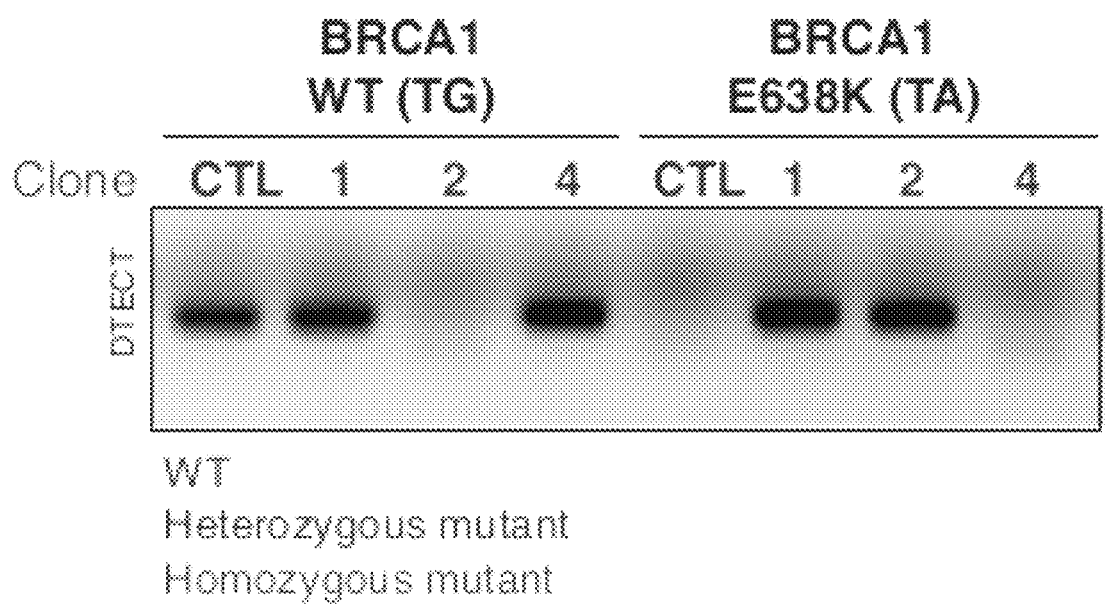

FIG. 5G shows the genotyping by DTECT-based analytical PCR (18 cycles) of single clones carrying WT and/or BRCA1 E638K mutant alleles derived from the BRCA1 E638K mutant cell population shown in FIG. 5C. WT (#4, not edited), heterozygous (#1) and homozygous (#2) BRCA1 mutant clones identified by DTECT are indicated.

Figure 5H:
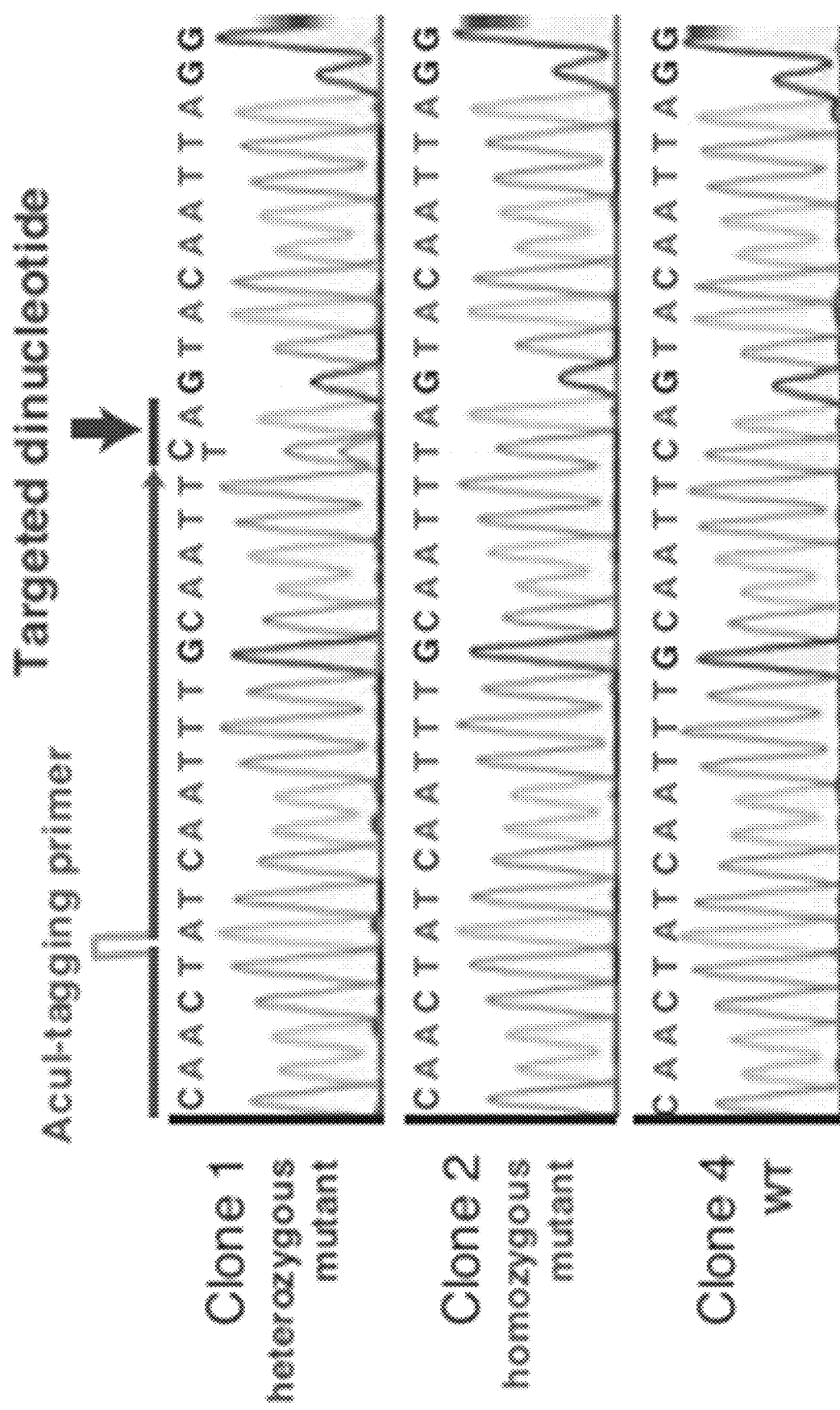

FIG. 5H shows the Sanger sequencing of WT, heterozygous and homozygous mutant amplicons shown in FIG. 5G. The targeted dinucleotide is indicated in green and part of the sequence of the AcuI-tagging primer is indicated in purple.

Figure 5I:
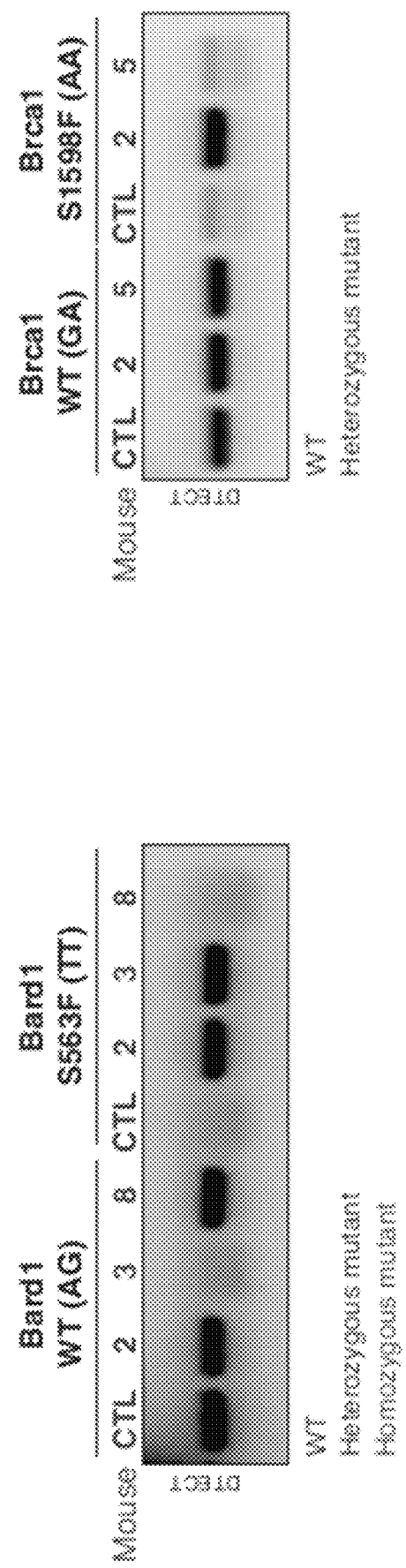

FIG. 5I shows the genotyping by DTECT-based analytical PCR of Bard1 S563F (left) and Brca1 S1598F (right) knock-in mutant mice (Bard1, 18 PCR cycles; Brca1, 20 PCR cycles). gDNA for DTECT analysis was obtained from mouse tail samples. WT (Bard1 #8 and Brca1 #5), heterozygous (Bard1 #2 and Brca1 #2) and homozygous (Bard1 #3) mutant mice identified by DTECT are indicated. No homozygous Brca1 S1598F mutant mice were identified in the analyzed mouse litters due to sub-Mendelian birth ratios (Billing et al., 2018).

Figure 5J:
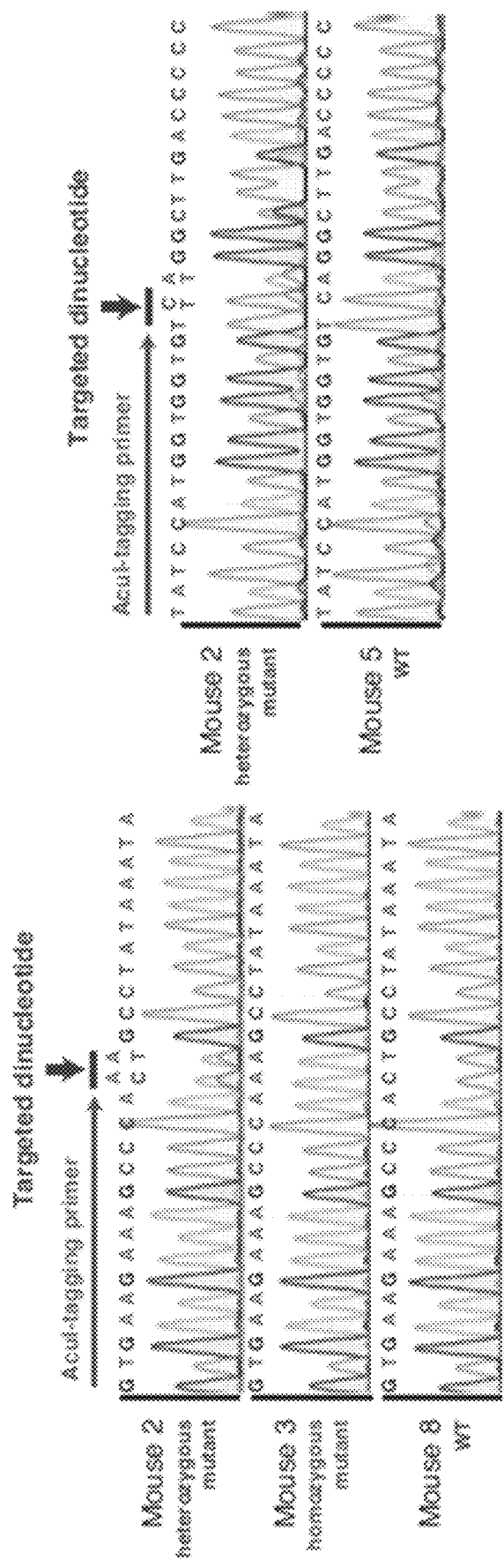

FIG. 5J shows the Sanger sequencing of WT, heterozygous and homozygous mutant amplicons shown in FIG. 5I.

FIGS. 6A-6D show the detection of oncogenic signatures in human clinical samples using DTECT.

Figure 6A:
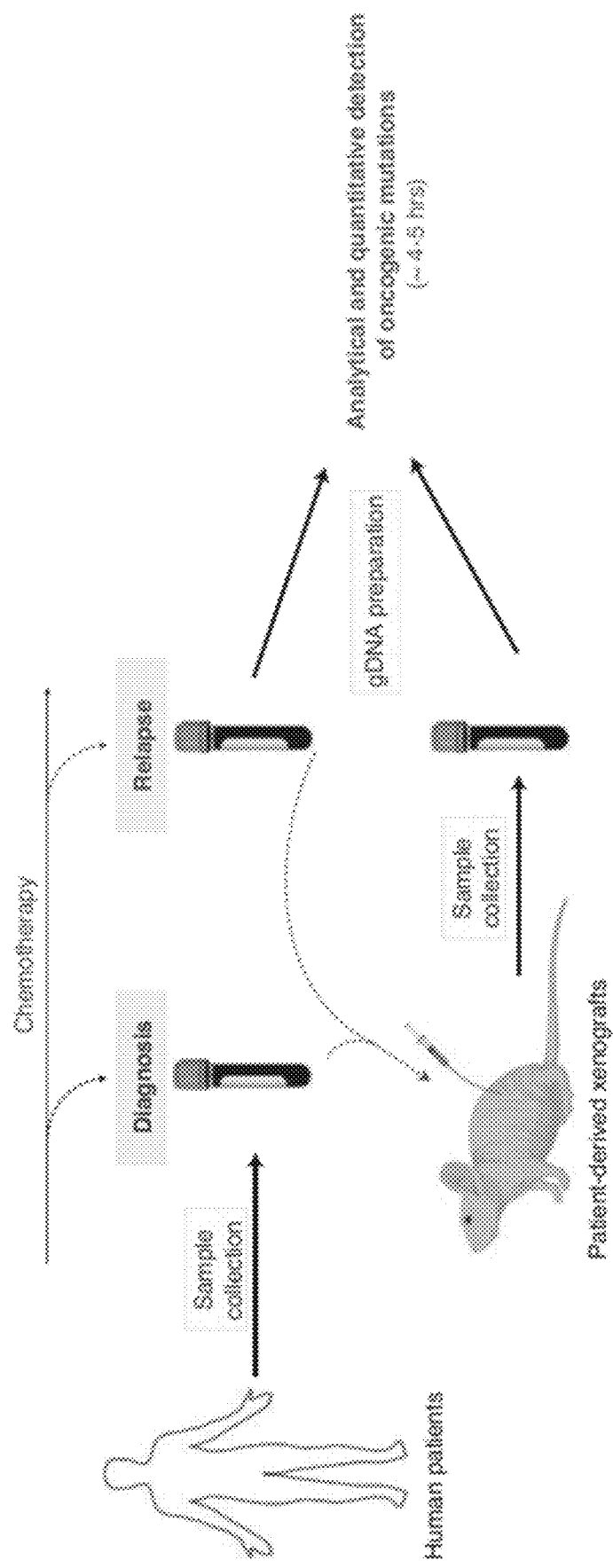

FIG. 6A shows the schematic representation of the experiments conducted on ALL patient-derived samples. Bone marrow samples from ALL patients were collected at diagnosis and after chemotherapy. PDXs were generated from the patient samples. The genomic DNA was recovered from the patient samples and PDX mouse models and subjected to analytical and quantitative detection of NT5C2 oncogenic mutations using DTECT.

Figure 6B:
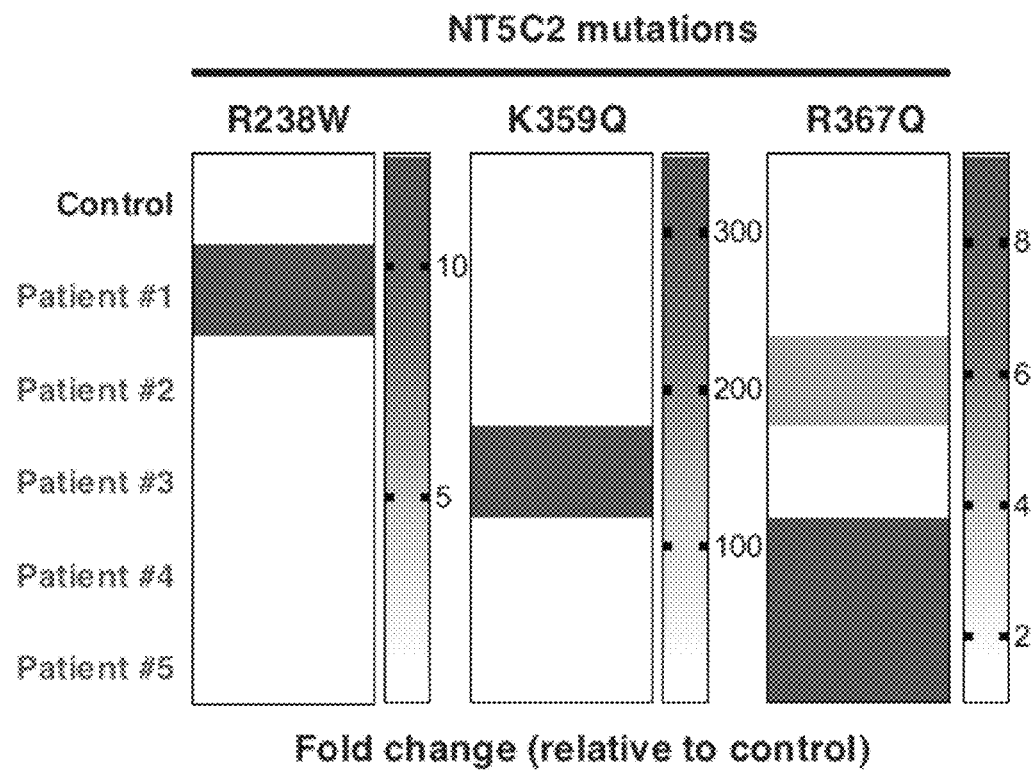

FIG. 6B provides the heat map showing the detection of NT5C2 oncogenic mutations in patient samples and a control sample using DTECT. Bone marrow samples from 5 patients were collected; genomic DNA was prepared and tested for the presence of 3 frequent NT5C2 mutations responsible for relapse to chemotherapy. A non-patient-derived gDNA sample was utilized as a control to estimate the levels of non-specific background in the DTECT assay.

Data are shown as fold change in the frequency of mutant signatures in the patient samples relative to the control sample.

Figure 6C:
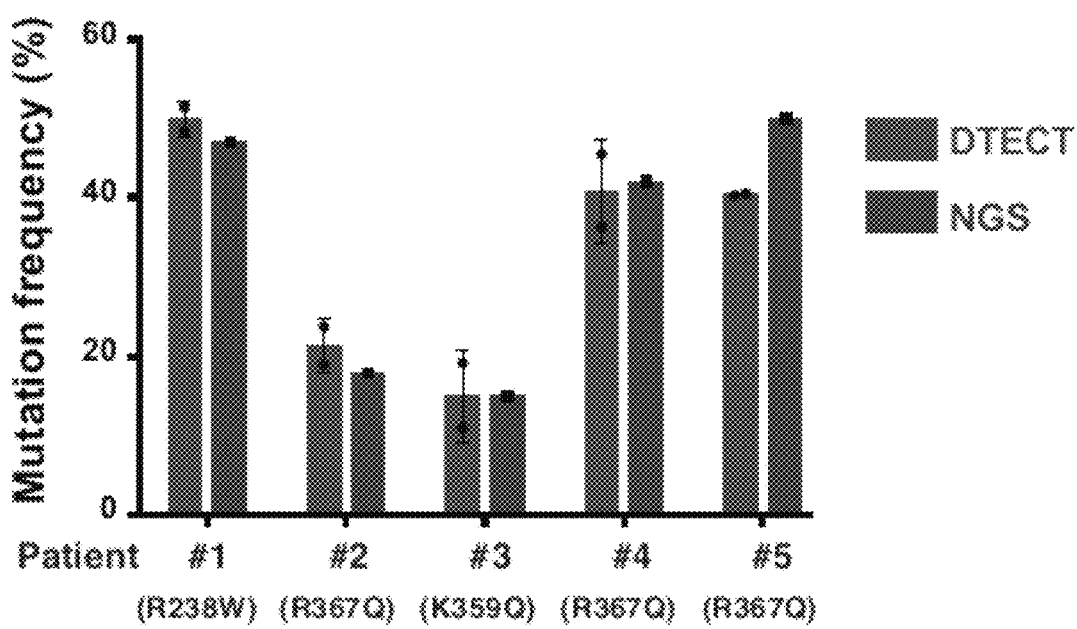

FIG. 6C shows the graphical representation of the frequency of NT5C2 mutations determined by DTECT (red) and NGS (green) in the 5 human patient samples analyzed in FIG. 6B. Error bars indicate the s.d. of 2 independent DTECT replicates.

Figure 6D:
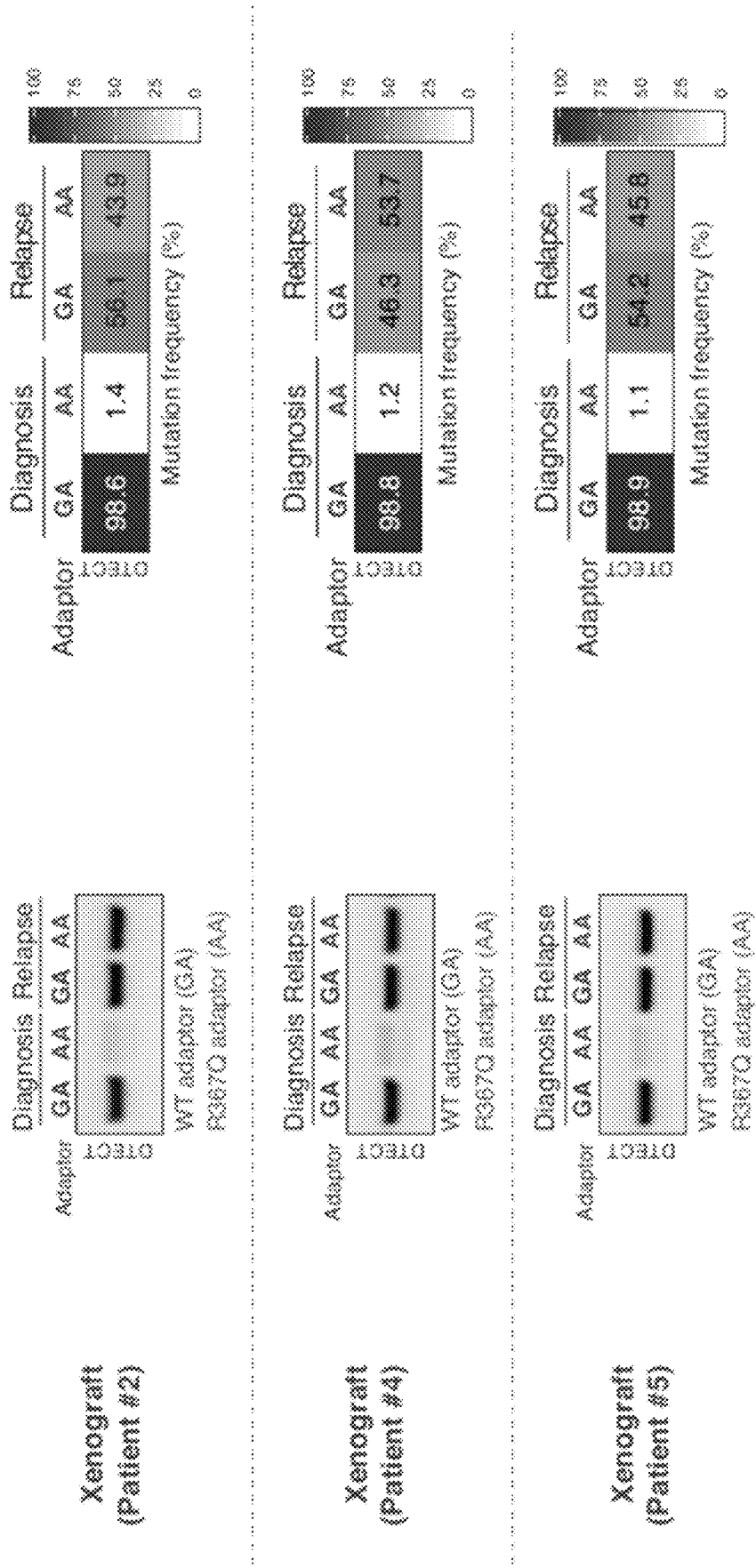

FIG. 6D shows the analytical and quantitative detection of the NT5C2R367Q mutation in PDX models generated from ALL tumors of patients #2, #4 and #5 at diagnosis and after chemotherapy relapse. WT and mutant variants were captured using adaptors specific for the WT (GA, green) or mutant (AA, purple) allele and subjected to analytical (left; 18 PCR cycles) and quantitative PCR (right).

Figure 7:
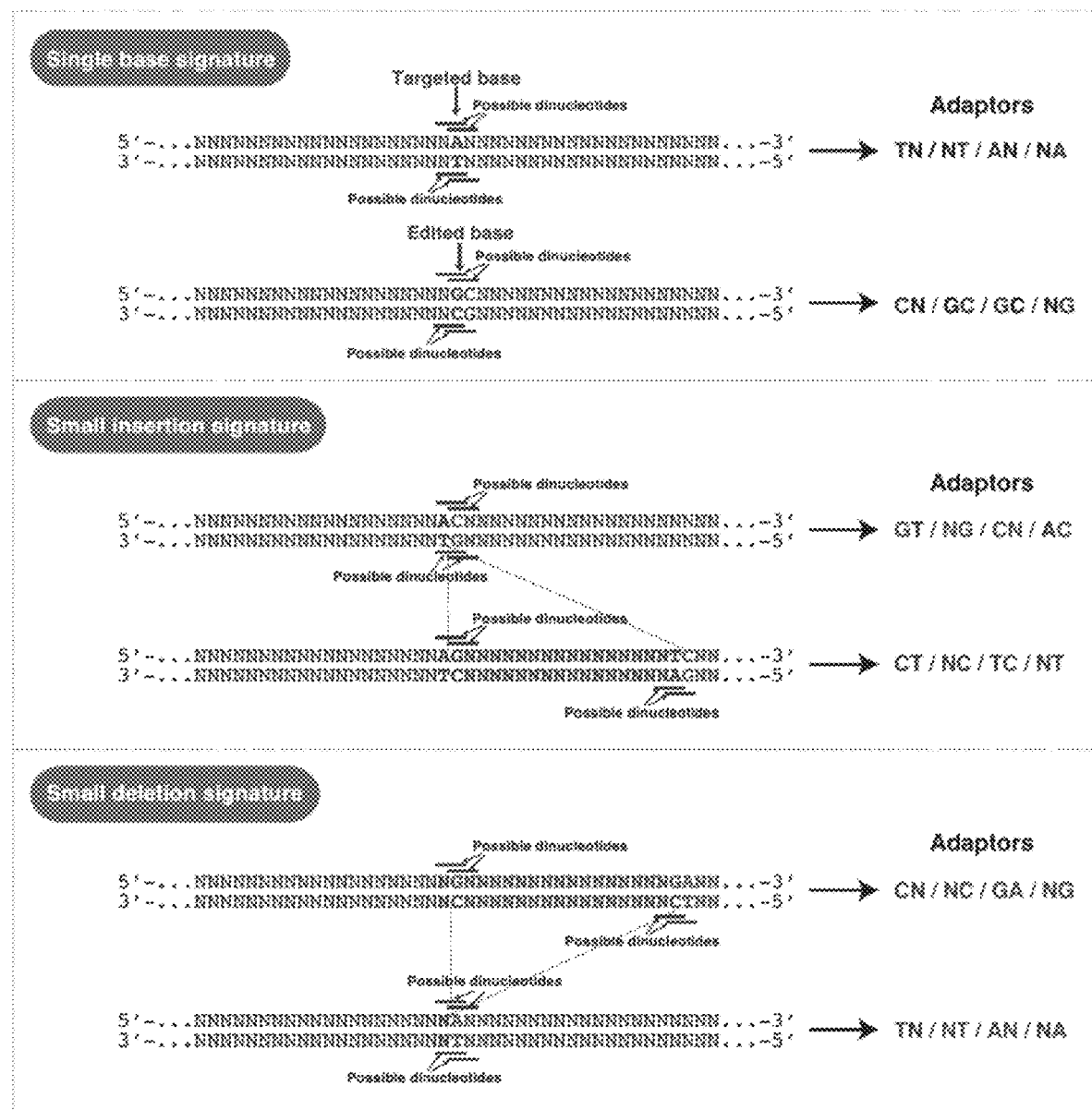

FIG. 7 shows the DTECT applications for the detection of precision genome editing and genetic variation. It shows the schematic representation of examples of targeted dinucleotide signatures generated by single base edits, small insertions and deletions that can be detected using DTECT. Examples of adaptors that can be used to detect the indicated genome editing events are shown on the right.

FIGS. 8A-8D show the features of type IIS restriction enzymes compatible with DTECT and schematic representation of the AcuI digestion pattern.

Figure 8A:
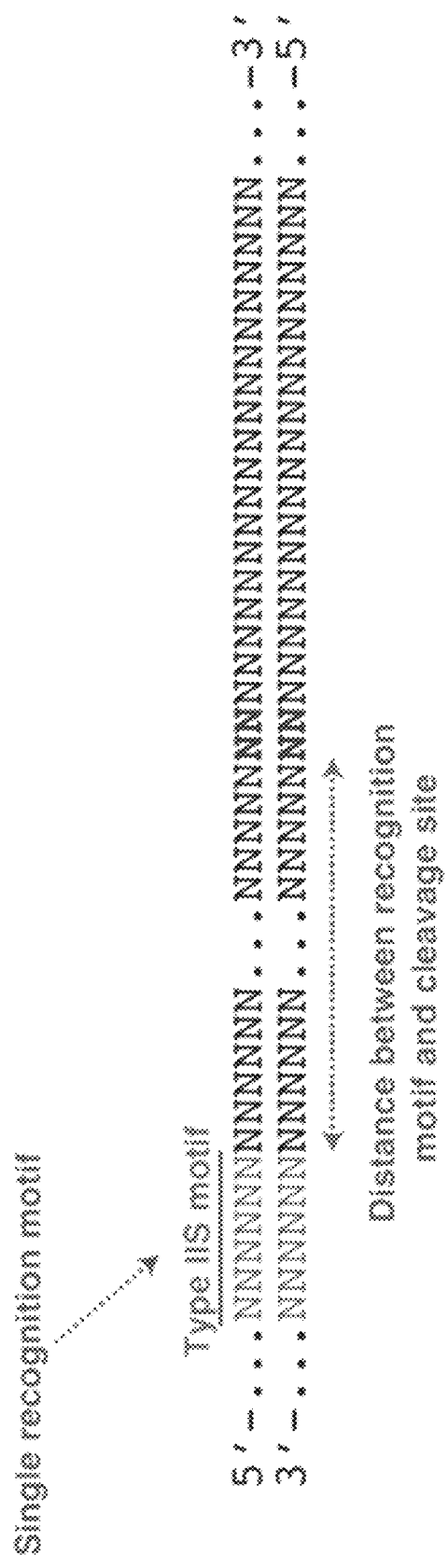

FIG. 8A shows the representation of two key features of type IIS restriction enzymes compatible with DTECT: 1) Binding of a single recognition motif (green); 2) Cleavage of a targeted DNA sequence (blue) far from the recognition motif.

Figure 8B:
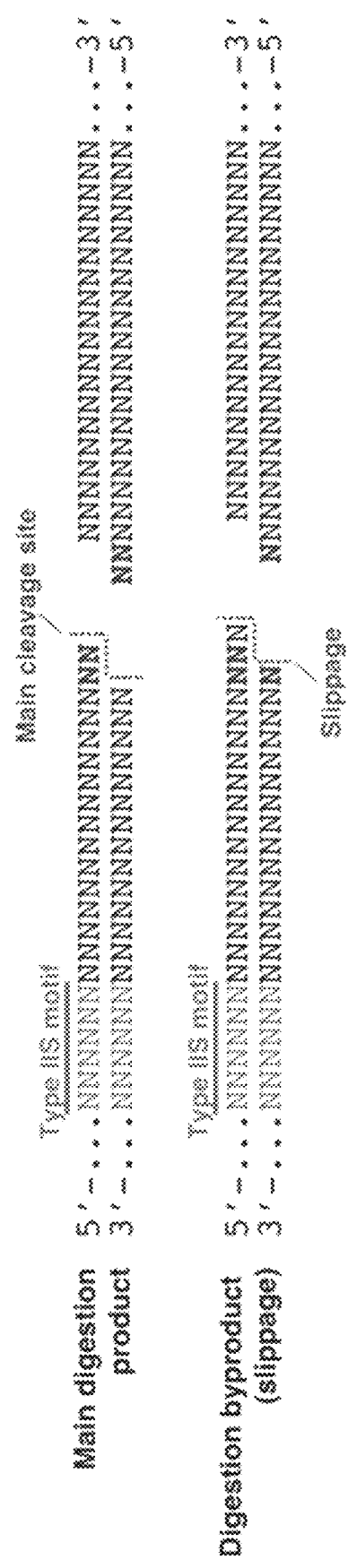

FIG. 8B shows the representation of the pattern of digestion of a type IIS enzyme, including the main digestion product and a cleavage byproduct due to slippage activity.

Figure 8C:
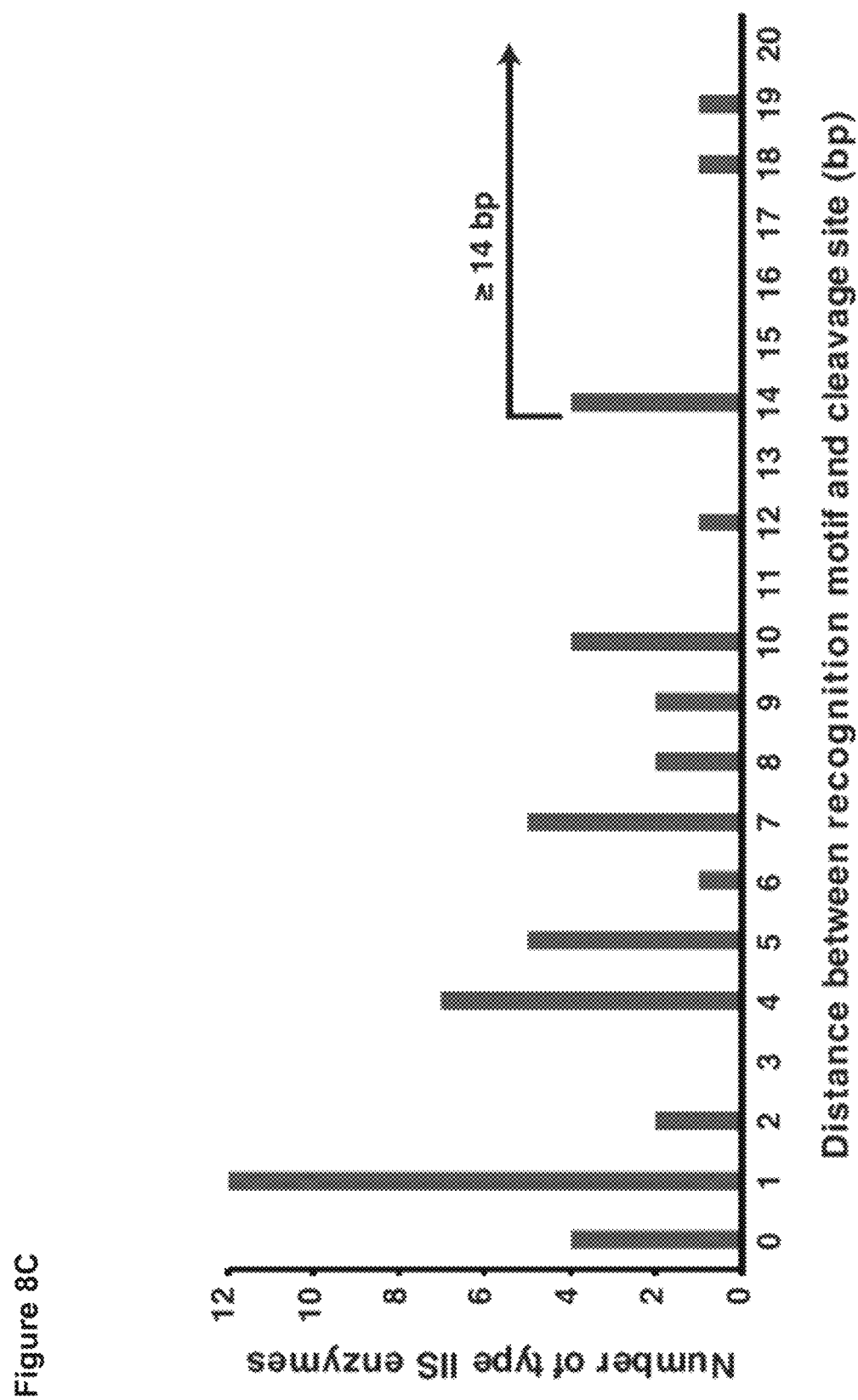

FIG. 8C shows the graphical representation of the number of type IIS enzymes in function of the distance between their recognition motif and cleavage site.

Figure 8D:
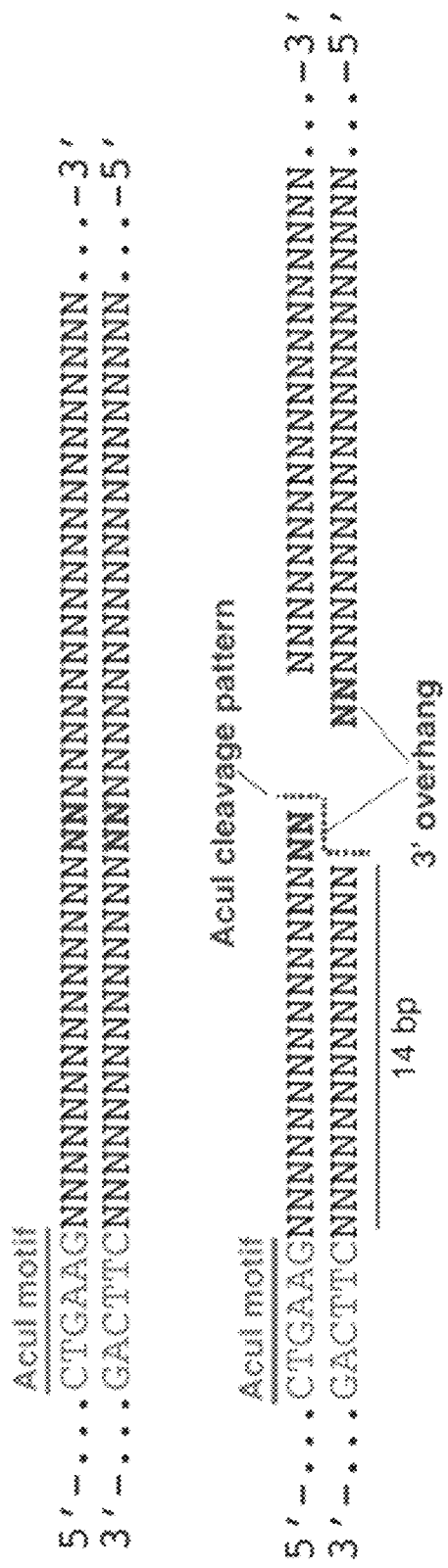

FIG. 8D shows the pattern of cleavage of the type IIS enzyme AcuI. AcuI cleaves DNA products 14/16 bp away from its recognition site (green), leaving a 3'-overhang of 2 DNA bases (blue).

Figure 9A:
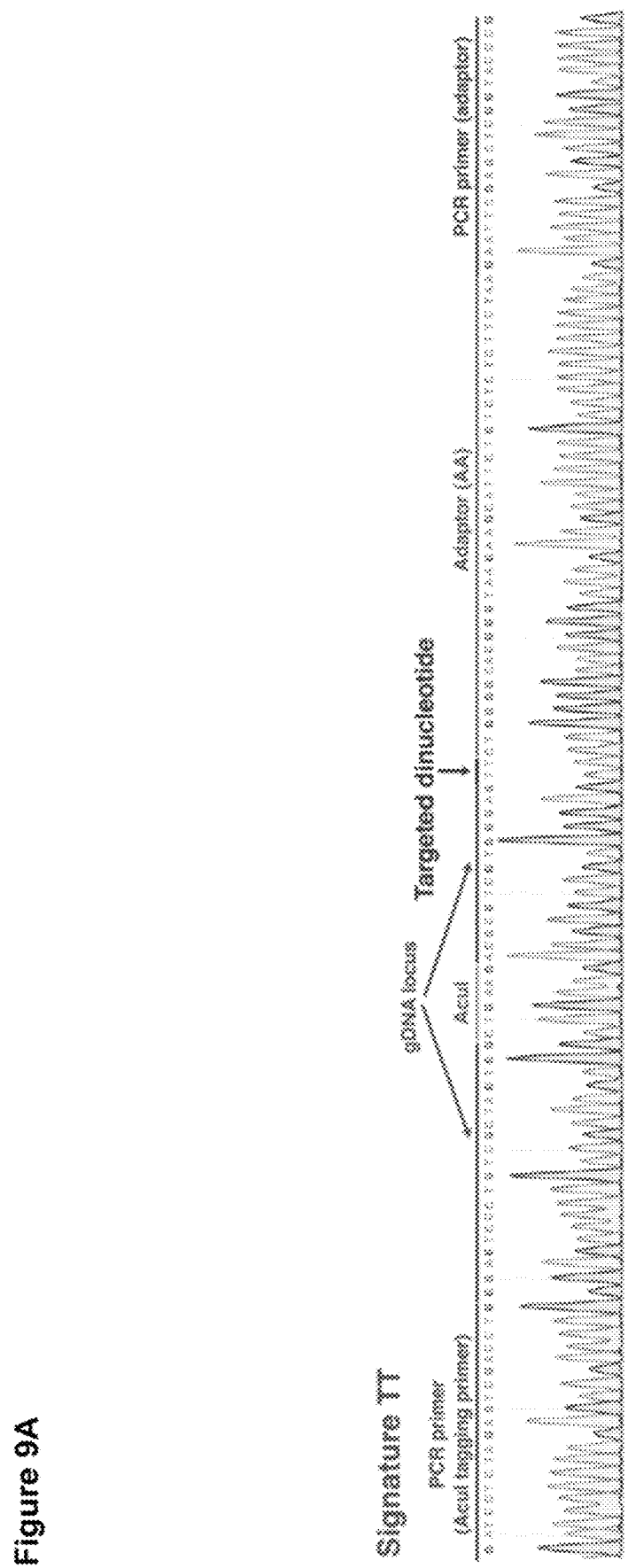
Figure 9B:
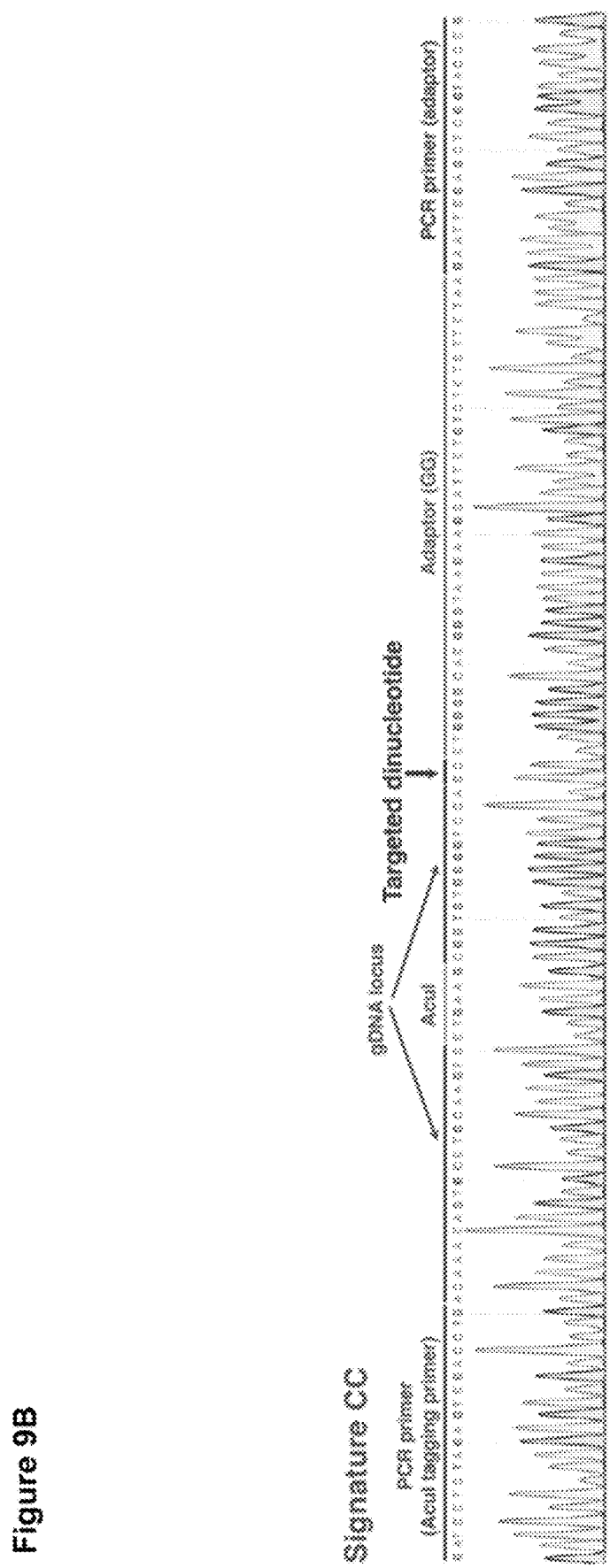
Figure 9C:
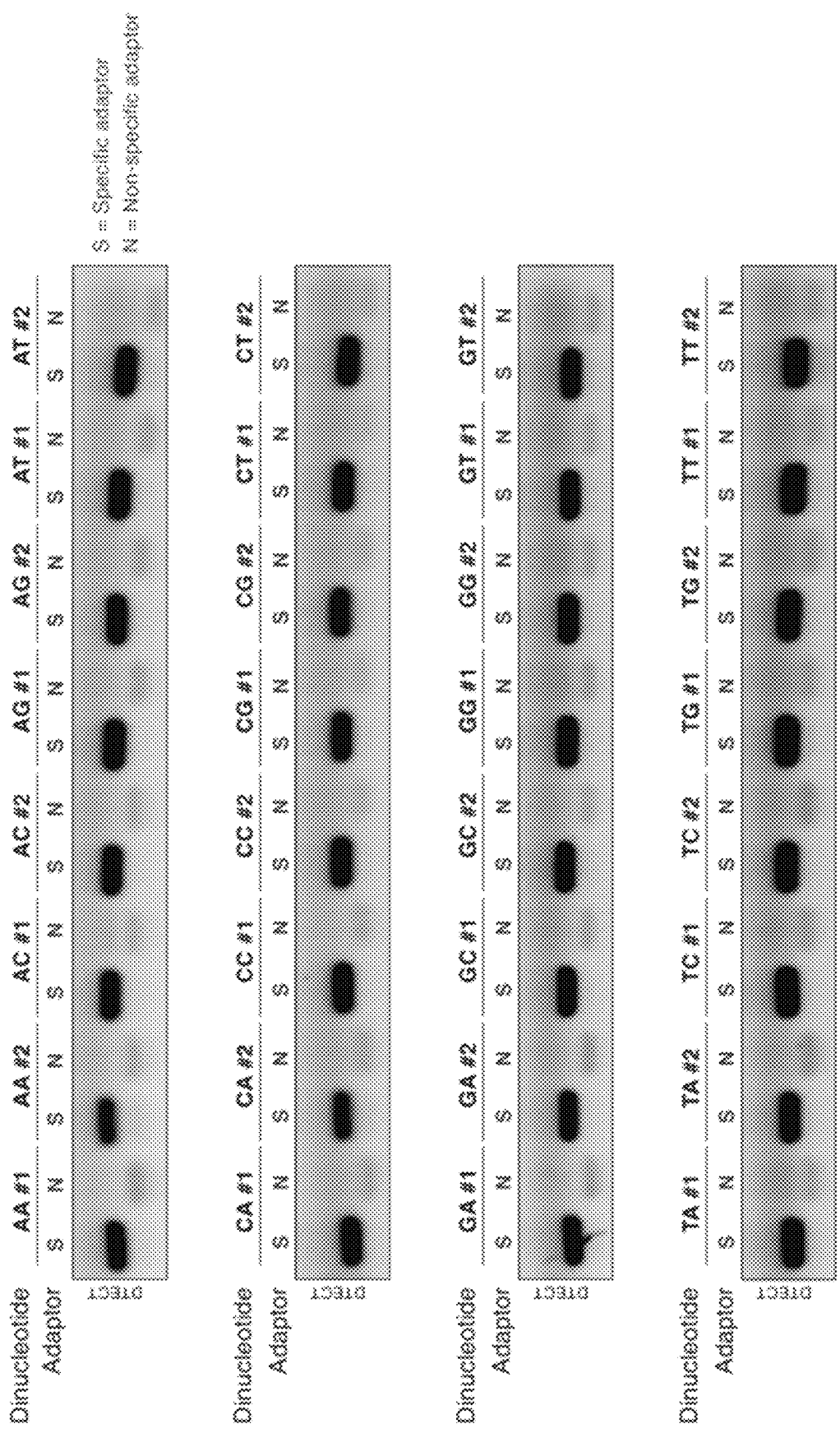

FIGS. 9A-9C show the Sanger sequencing reads of captured AcuI-digested DNA fragments and validation of the adaptor library.

Figure 2A:
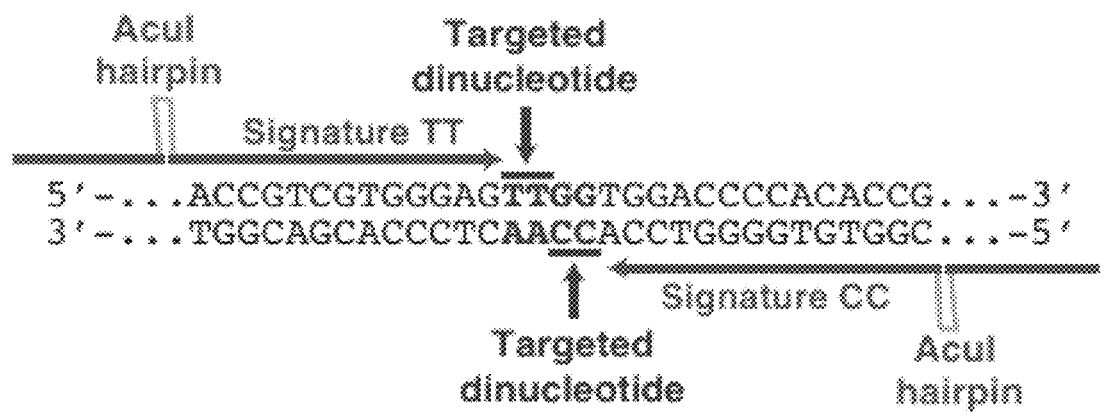
FIGS. 2A-2K show the detection and quantification of dinucleotide signatures using DTECT.
Figure 2B:
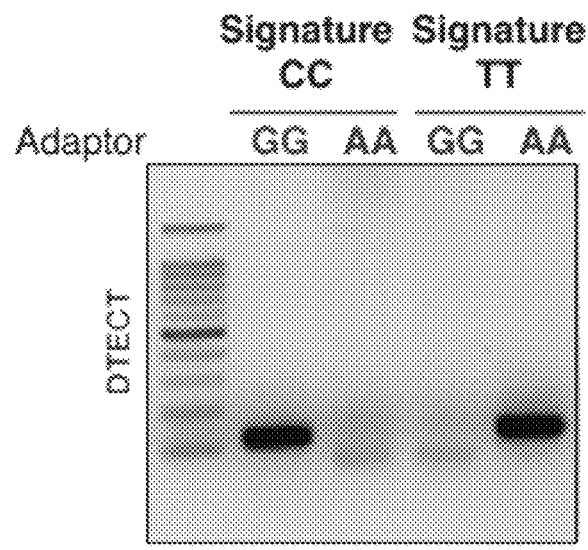

FIGS. 9A and 9B show the Sanger sequencing reads of PCR amplicons of AcuI-digested DNA products containing the TT (FIG. 9A) and CC (FIG. 9B) signatures shown in FIG. 2B, which have been captured using AA or GG adaptors. The DNA sequences of PCR primers (red), genomic locus (purple), targeted dinucleotides (blue), AcuI motif (green) and adaptors (brown) are shown.

FIG. 9C shows the PCR amplification (18 cycles) of captured AcuI-digested DNA products by DTECT using specific (green) and non-specific (blue) DNA adaptors. Each of the 16 adaptors was tested for its ability to capture two independent dinucleotide signatures (#1 and #2).

FIGS. 10A-10F show the identification of WT and STOP alleles in mixed solutions and quantification of non-specific dinucleotide capture and ligation efficiency in DTECT assays.

Figure 2C:
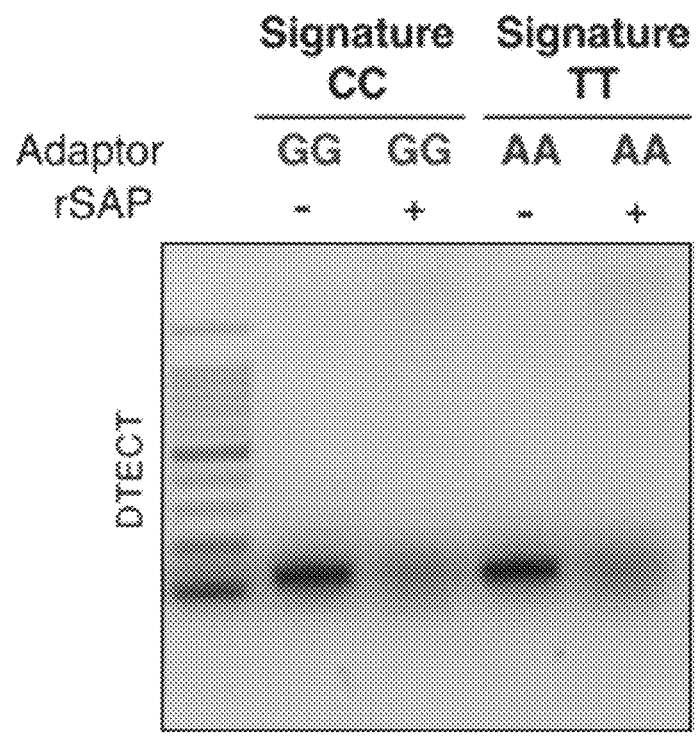
Figure 2D:
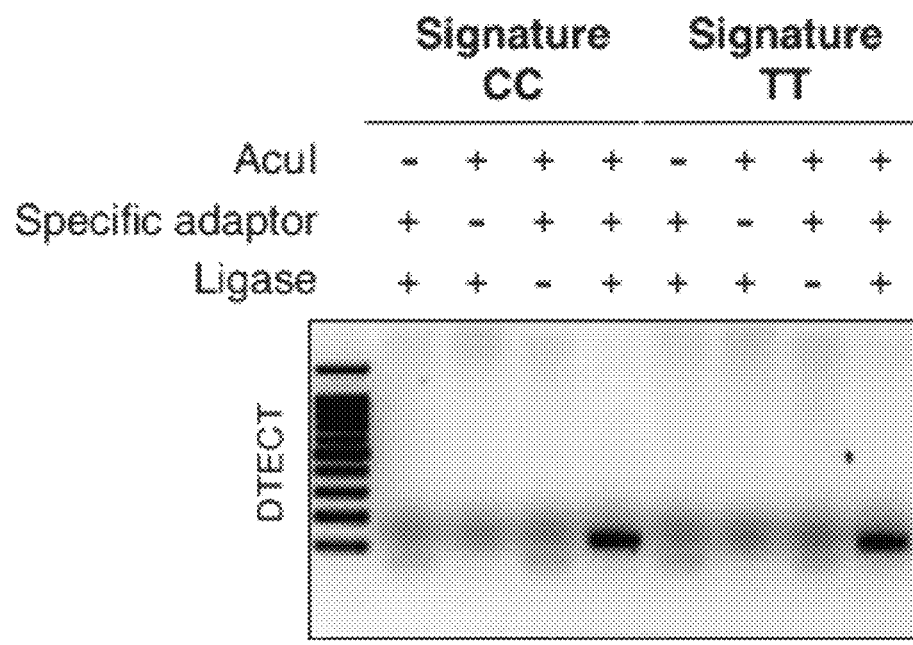
Figure 2E:
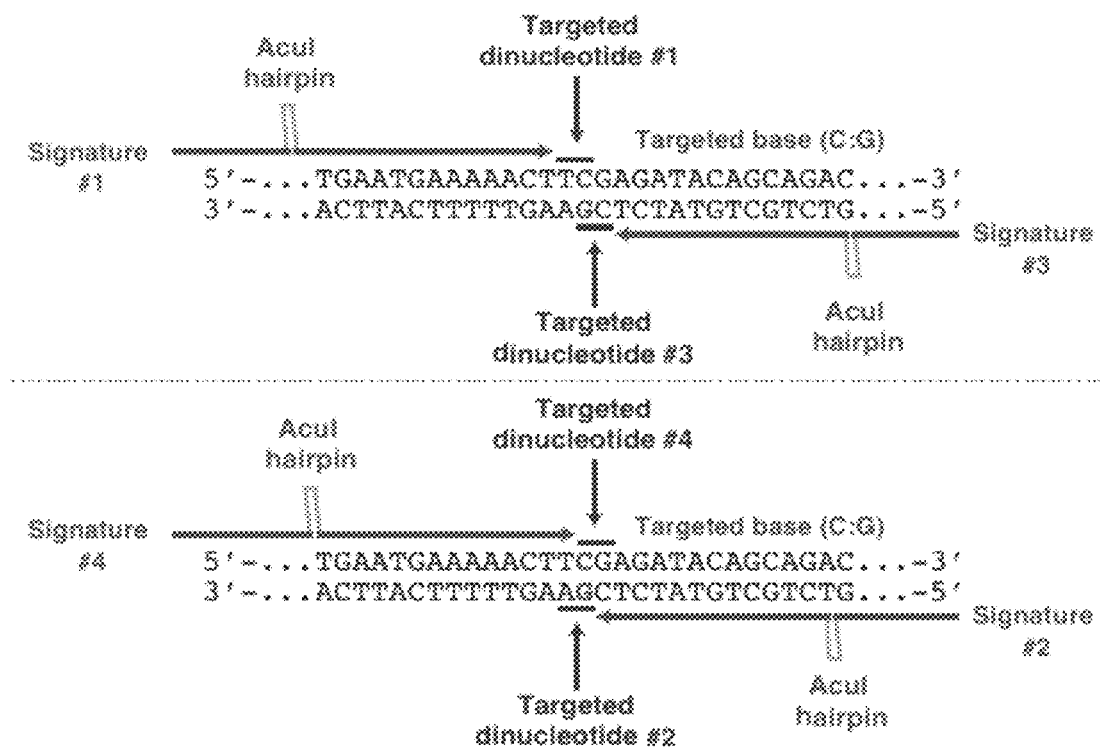
Figure 2F:
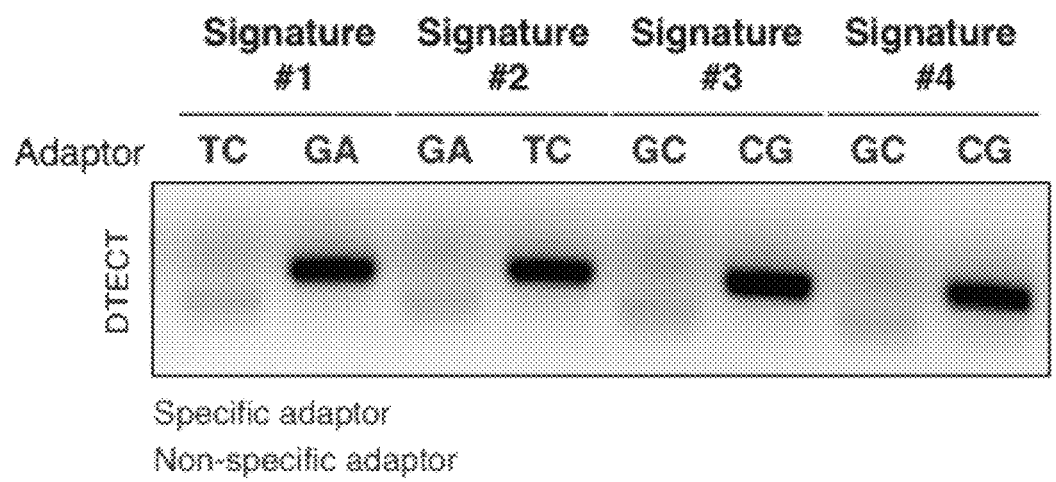
Figure 2G:
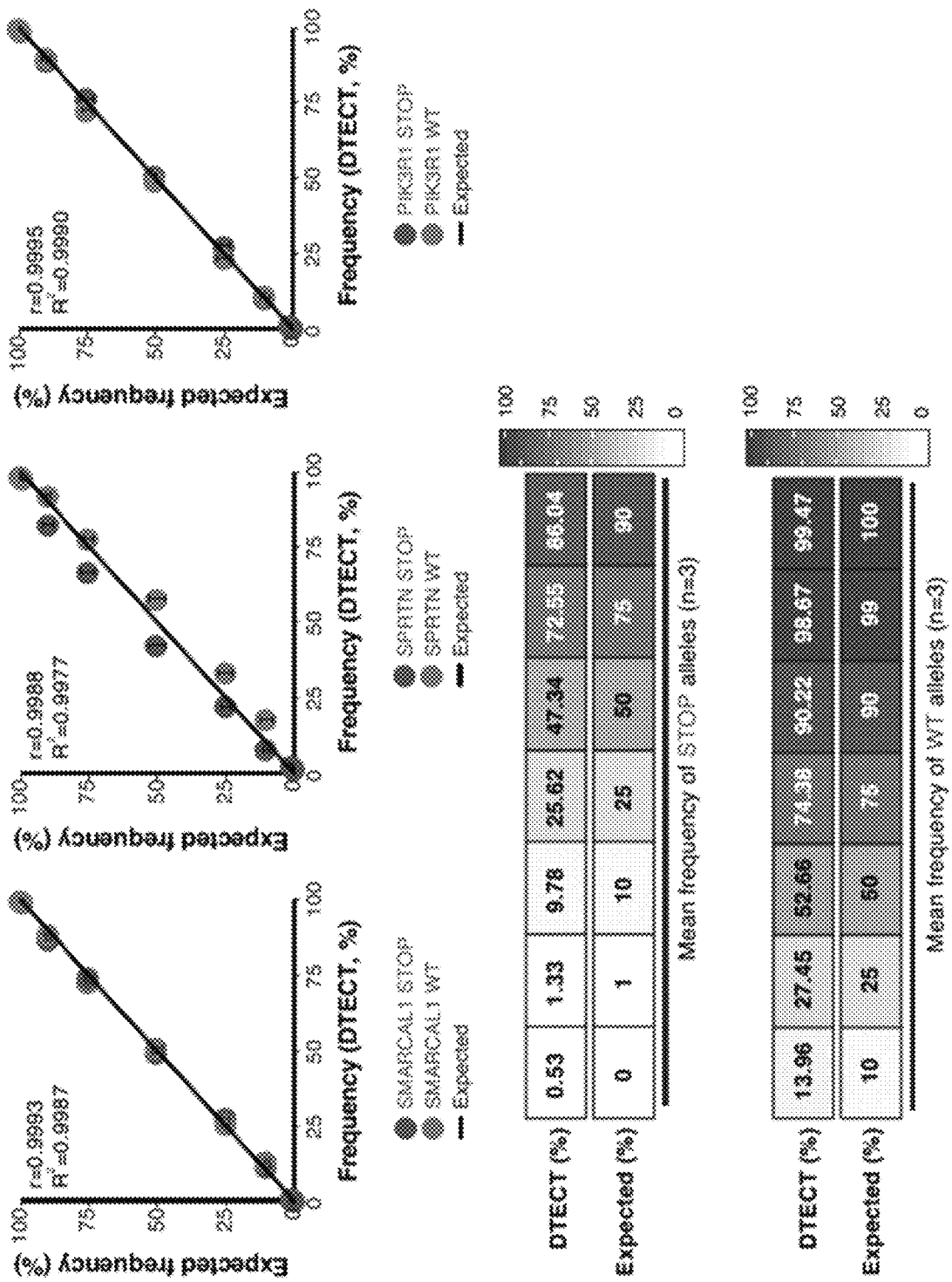
Figure 2H:
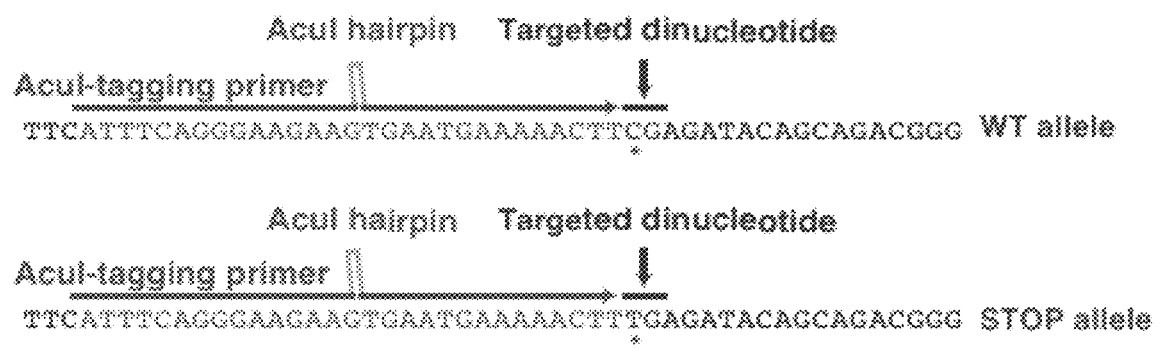
Figure 2I:
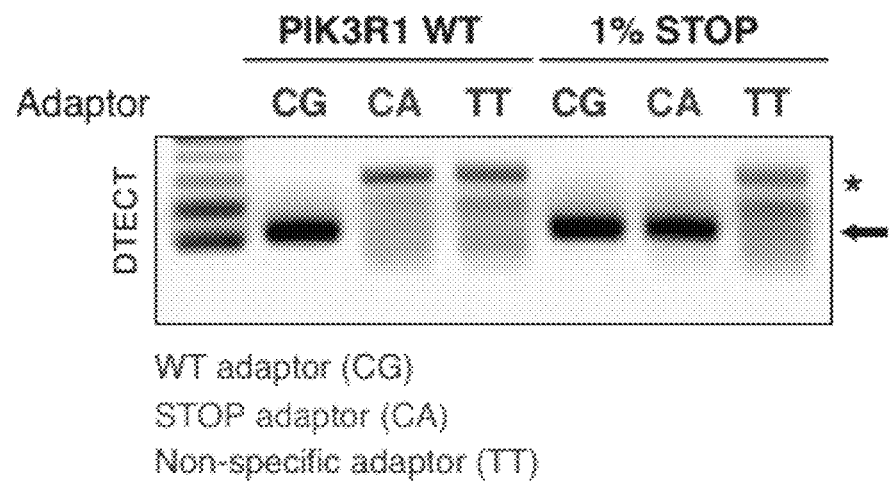
Figure 10A:
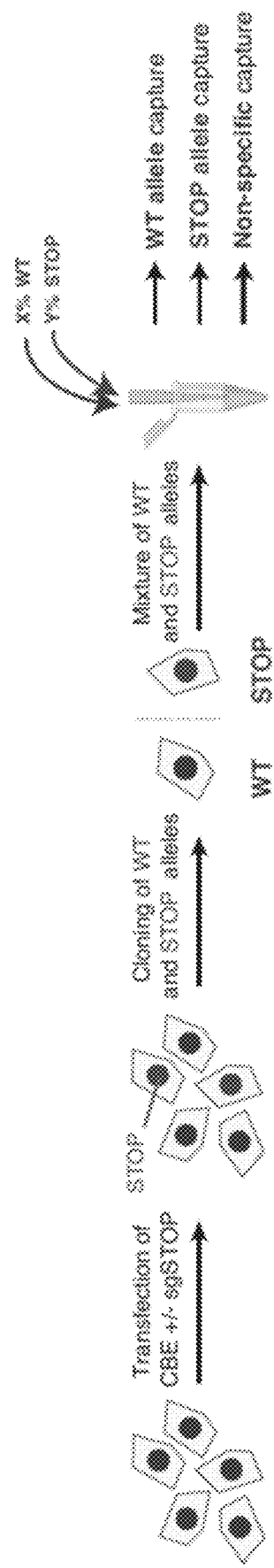

FIG. 10A shows the schematics of the protocol used to identify and quantify WT and STOP alleles in mixed solutions, as shown in FIGS. 2G-2I. Cells were transfected with the cytidine base editor (CBE) BE3 and an sgRNA to induce a STOP codon (sgSTOP) using iSTOP. WT and STOP alleles were then cloned and mixed at different WT:STOP ratios, as indicated in FIG. 2G. DTECT was then used to capture WT and STOP signatures using adaptors specific for the WT (green) or STOP (purple) allele, as well as non-specific adaptors (blue). Captured material was then subjected to analytical or quantitative PCR.

Figure 10B:
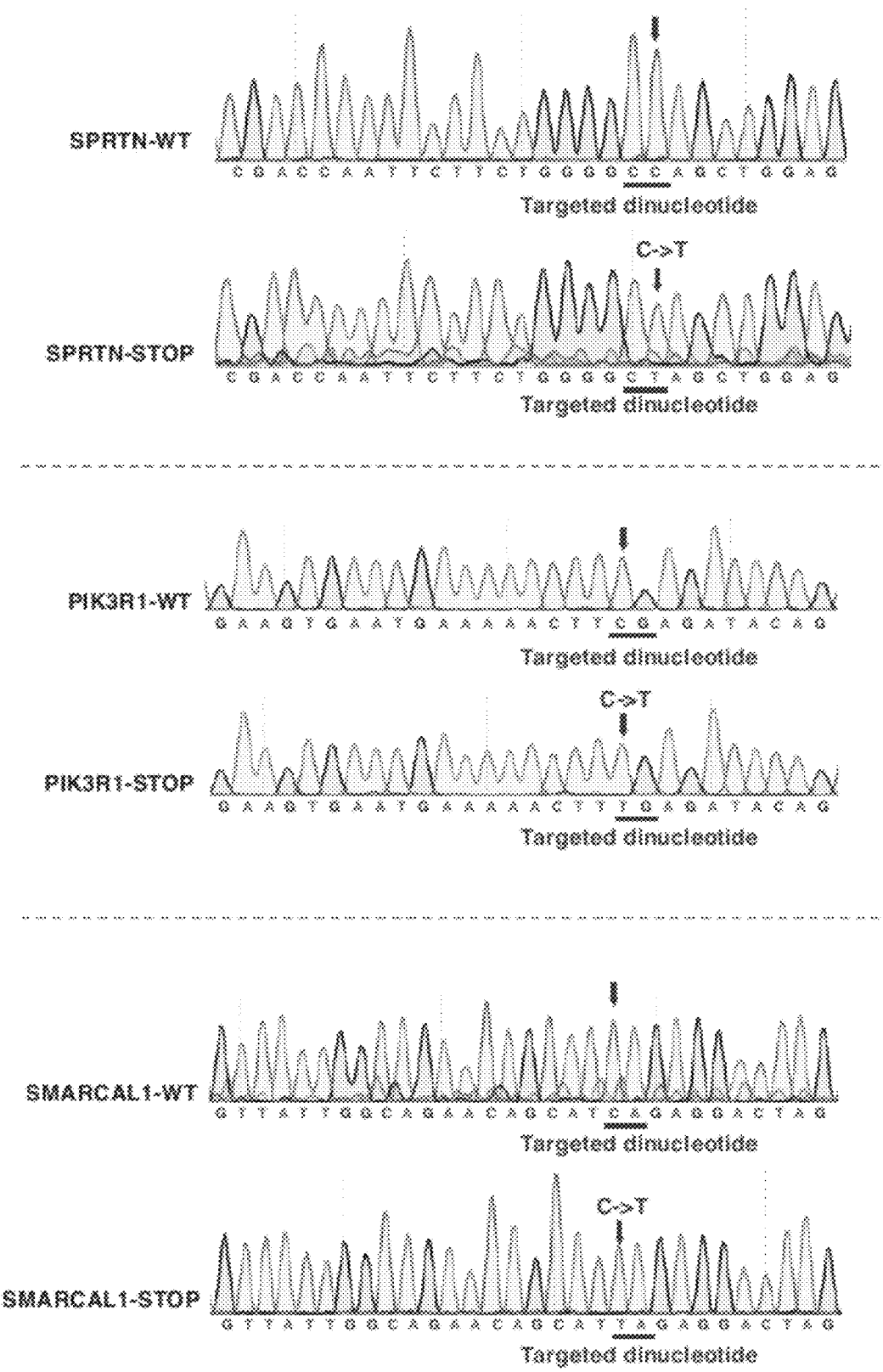

FIG. 10B shows the Sanger sequencing reads of WT and STOP alleles of SPRTN, SMARCAL1 and PIK3R1. The targeted dinucleotide signature is shown in green and the edited cytidine base (C→T) is indicated by the blue arrow.

Figure 10C:
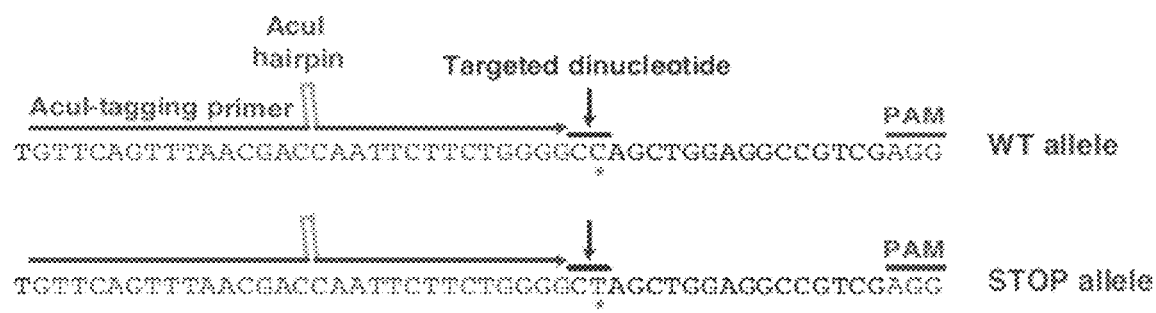

FIG. 10C shows the representation of the AcuI-tagging primers used to detect the WT and STOP alleles of the SPRTN gene. The targeted dinucleotides are shown in blue, the edited base is indicated with an asterisk, the PAM sequence is show in red and part of the AcuI-tagging primer sequence is shown in purple.

Figure 10D:
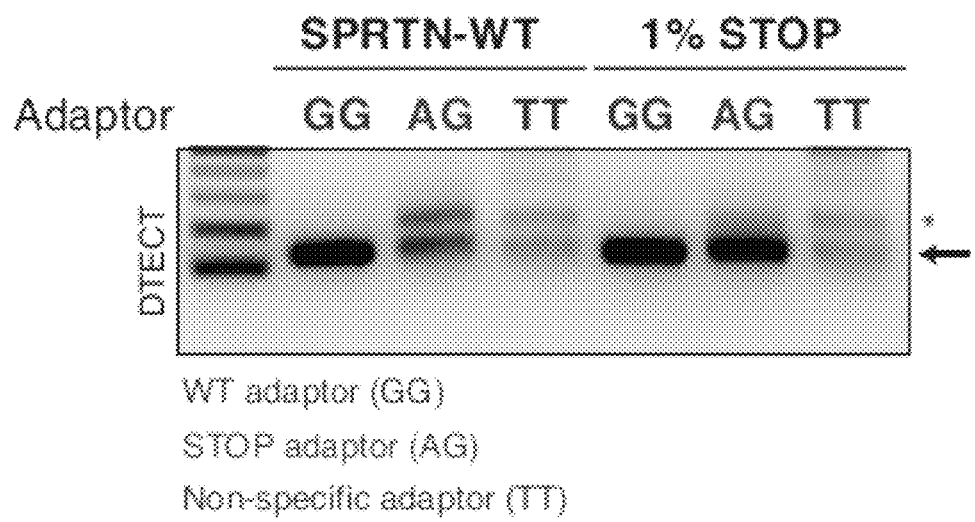

FIG. 10D shows the PCR amplification (25 cycles) of WT and STOP SPRTN alleles (arrow) captured using DTECT from WT:STOP allele mixtures (i.e., 100:0 and 99:1). An adaptor (AG) specific for the STOP SPRTN allele is utilized in the capture reaction, along with an adaptor specific for the WT allele (GG; positive control) and a non-specific adaptor (TT; negative control). Background non-specific PCR products are indicated with an asterisk.

Figure 10E:
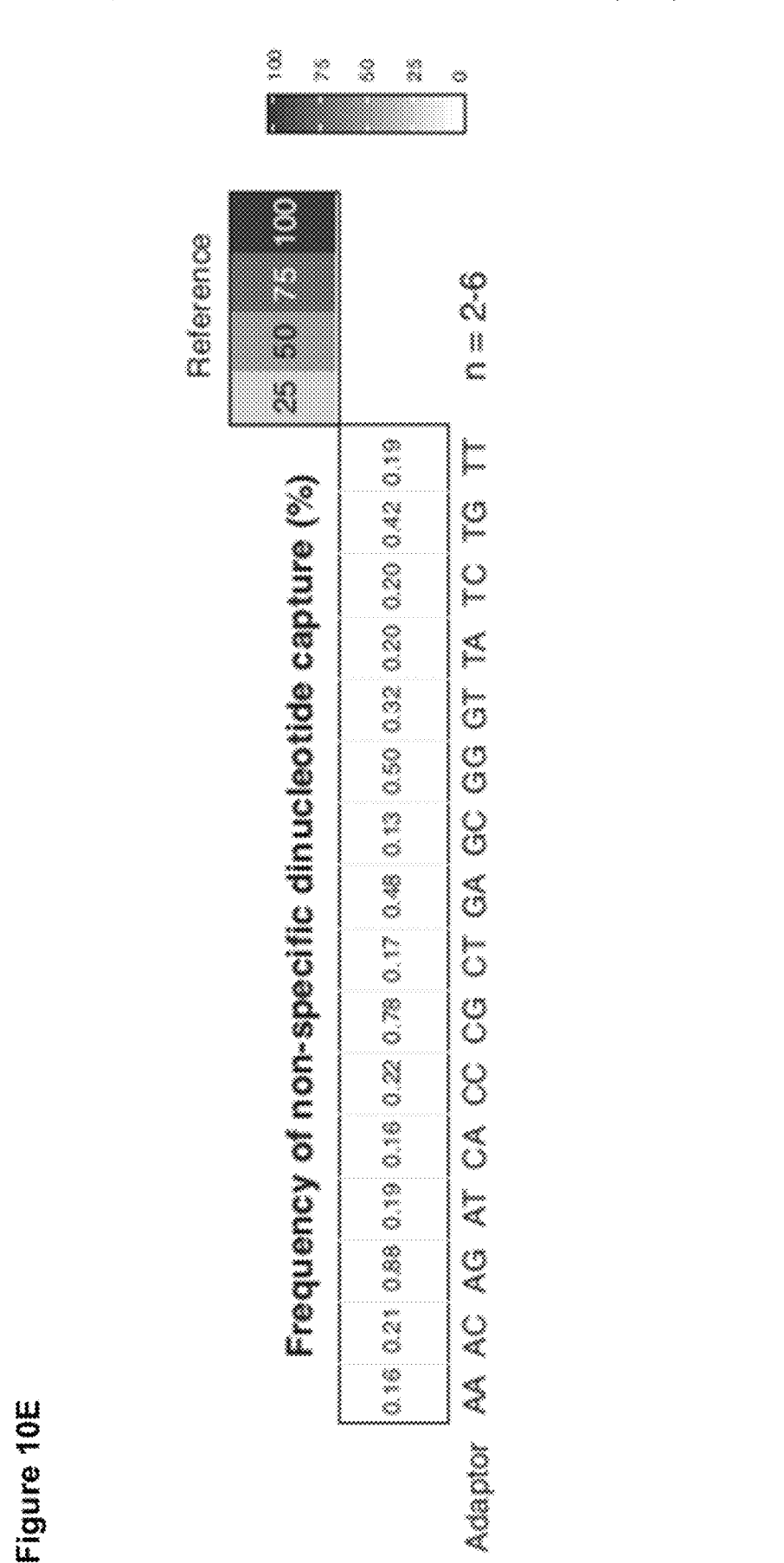

FIG. 10E shows the frequency of non-specific dinucleotide capture for each of the 16 adaptors used for DTECT. Adaptors containing the indicated dinucleotide sequences were utilized to capture AcuI-digested DNA fragments with non-complementary dinucleotides and the frequency of non-specific dinucleotide capture was quantified by qPCR. Mean frequency of non-specific dinucleotide capture is shown for 2-6 independent DNA ligation reactions using DNA fragments with distinct non-complementary dinucleotides. Adaptors complementary to +1 and −1 AcuI-dependent slippage events were excluded from the analysis.

Figure 10F:
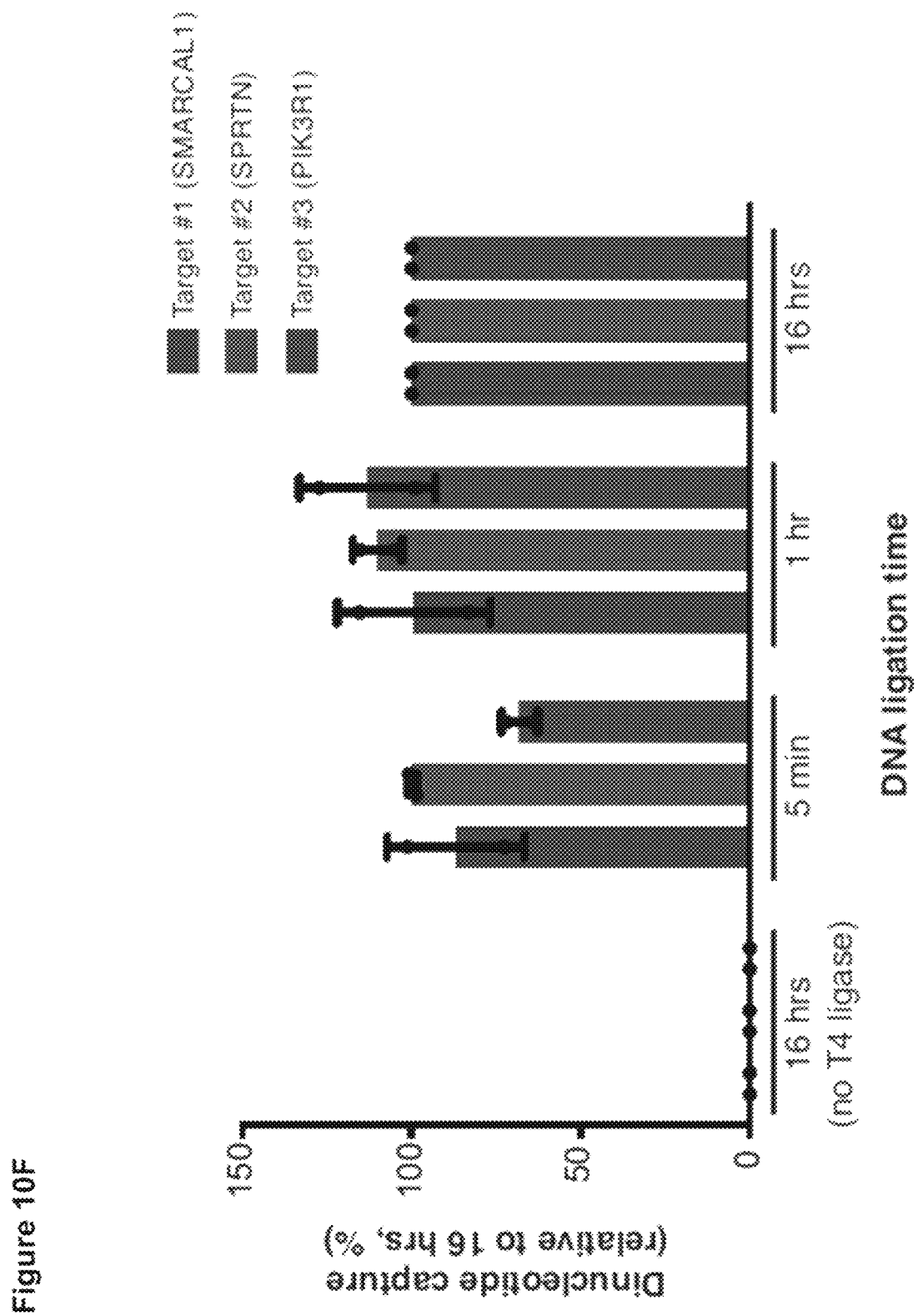

FIG. 10F shows the time course experiment to measure the efficiency of the ligation of AcuI-digested products to DNA adaptors. AcuI-digested products from 3 independent targets (SMARCAL1, SPRTN and PIK3R1), DNA adaptors and T4 ligase were incubated for 5 min, 1 hour or 16 hours, and the captured material was quantified by qPCR. A sample without T4 ligase was used as a negative control. The percentage of captured material at the different time points was obtained by normalization to the amount of captured material upon a 16-hour ligation reaction. Error-bars represent the s.d. of 2 independent experiments.

FIGS. 11A-11J show the detection of CRISPR-mediated HDR and base editing events by DTECT, NGS and RFLP assays.

FIGS. 11A-11D show the detection by analytical PCR (20 or 21 cycles) of WT and HDR-edited EMX1 (FIG. 11A), JAK2 (FIG. 11B), HBB (FIG. 11C) and BRCA2 (FIG. 11D) alleles captured using adaptors specific for the WT (green) or edited (purple) alleles. In these experiments HEK293T cells were transfected with Cas9, sgRNA and an HDR donor (ssODN) with or without the HDR stimulatory factor i53. The ssODN was omitted in control reactions. ssODNs introduce a PmeI site in EMX1 and JAK2, a sickle cell anemia mutation in HBB (i.e., G6V), and a breast cancer-associated small tandem duplication in BRCA2 (dupAGAAGAT).

Figure 11A:
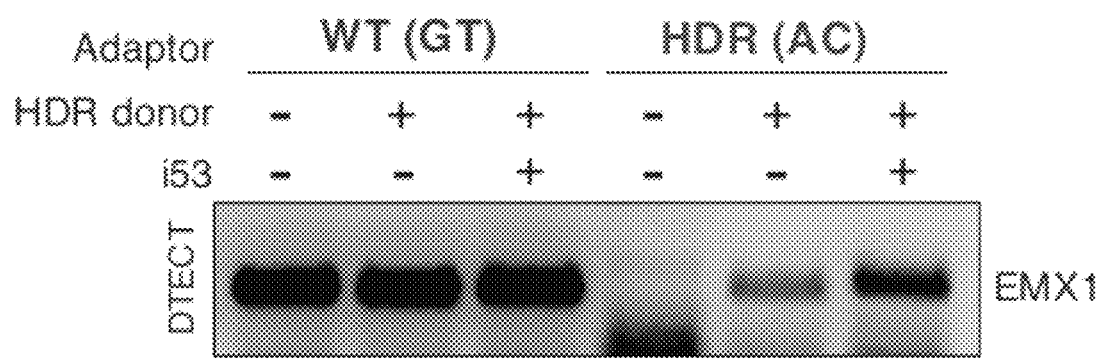
Figure 11B:
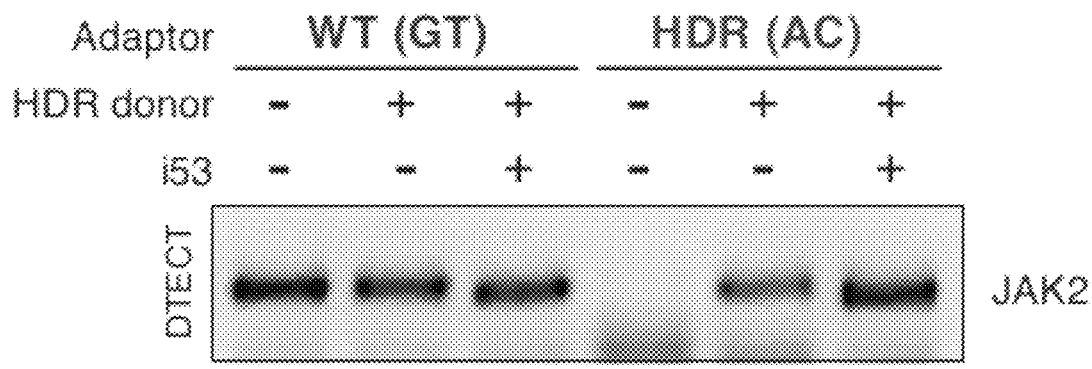
Figure 11C:
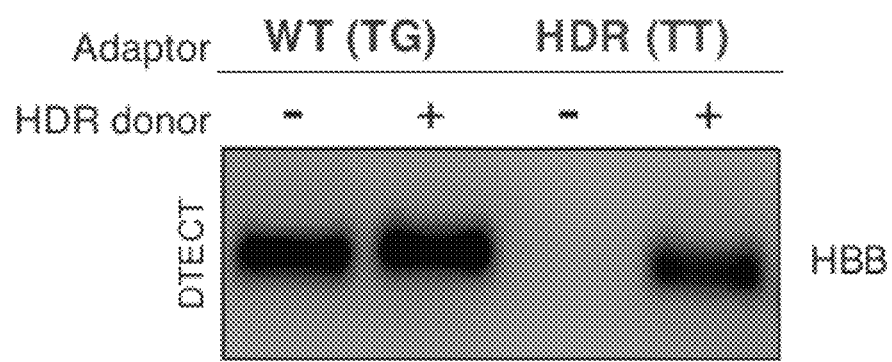
Figure 11D:
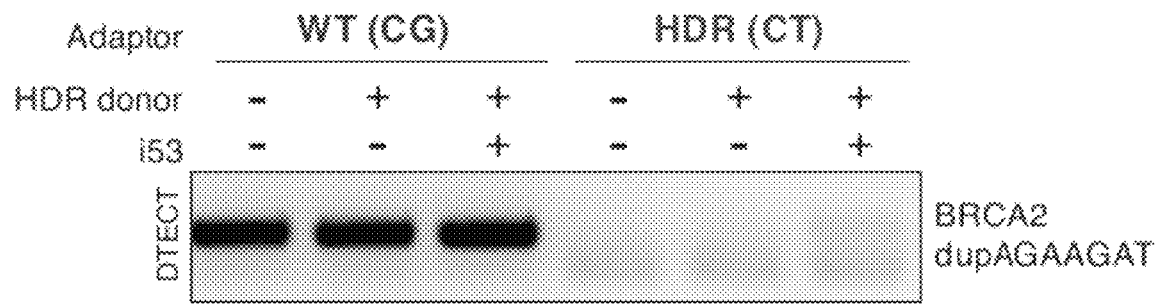
Figure 11E:
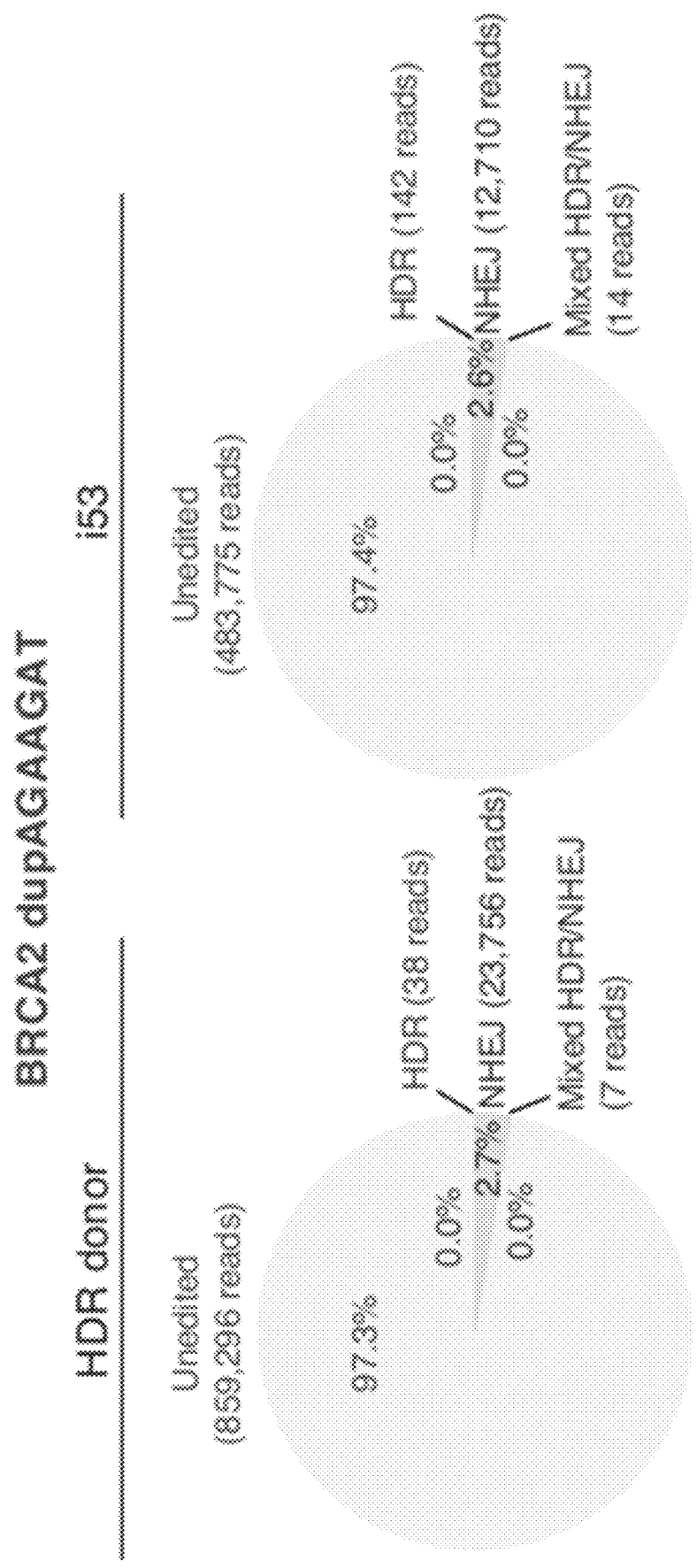

FIG. 11E shows the quantification of the efficiency of the insertion of the short tandem duplication dupAGAAGAT in the BRCA2 locus, as determined by NGS. The pie chart shows the distribution of NGS reads corresponding to HDR- and/or NHEJ-mediated repair events (HDR, red; NHEJ, blue; mixed HDR/NHEJ, green; unedited, brown) occurring at the BRCA2 locus in HEK293T cells transfected with Cas9/sgRNA and ssODN donor, with or without i53. In these experiments, the BRCA2 locus was amplified by PCR and subjected to NGS. The NGS reads were analyzed by CRISPResso.

Figure 11F:
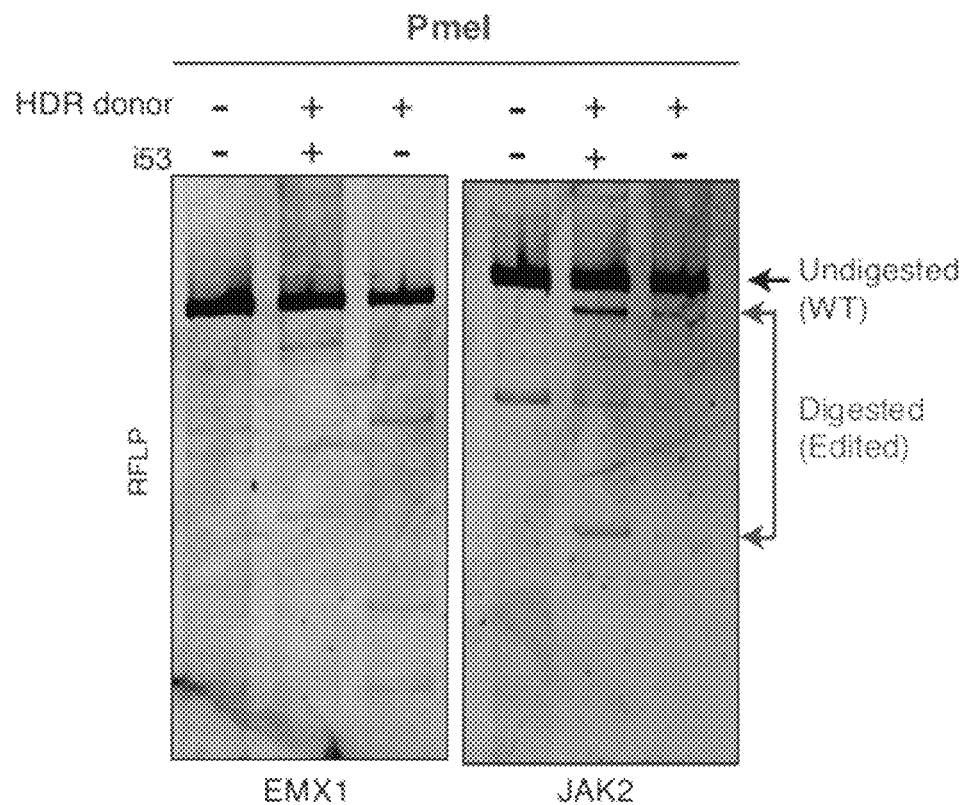

FIG. 11F shows the RFLP assay to monitor the gain of a PmeI restriction site introduced by ssODN-meditated HDR in the EMX1 and JAK2 loci under the same experimental conditions shown in FIG. 11A and FIG. 11B. Digested (edited) and undigested (WT) DNA products are indicated by arrows.

Figure 11G:
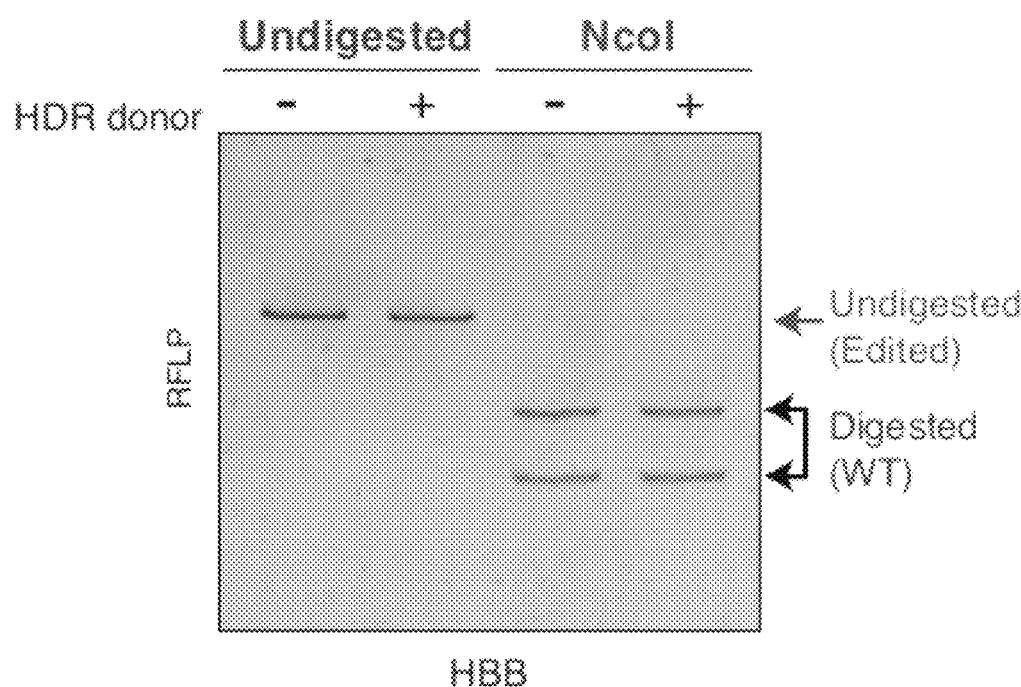
Figure 11H:
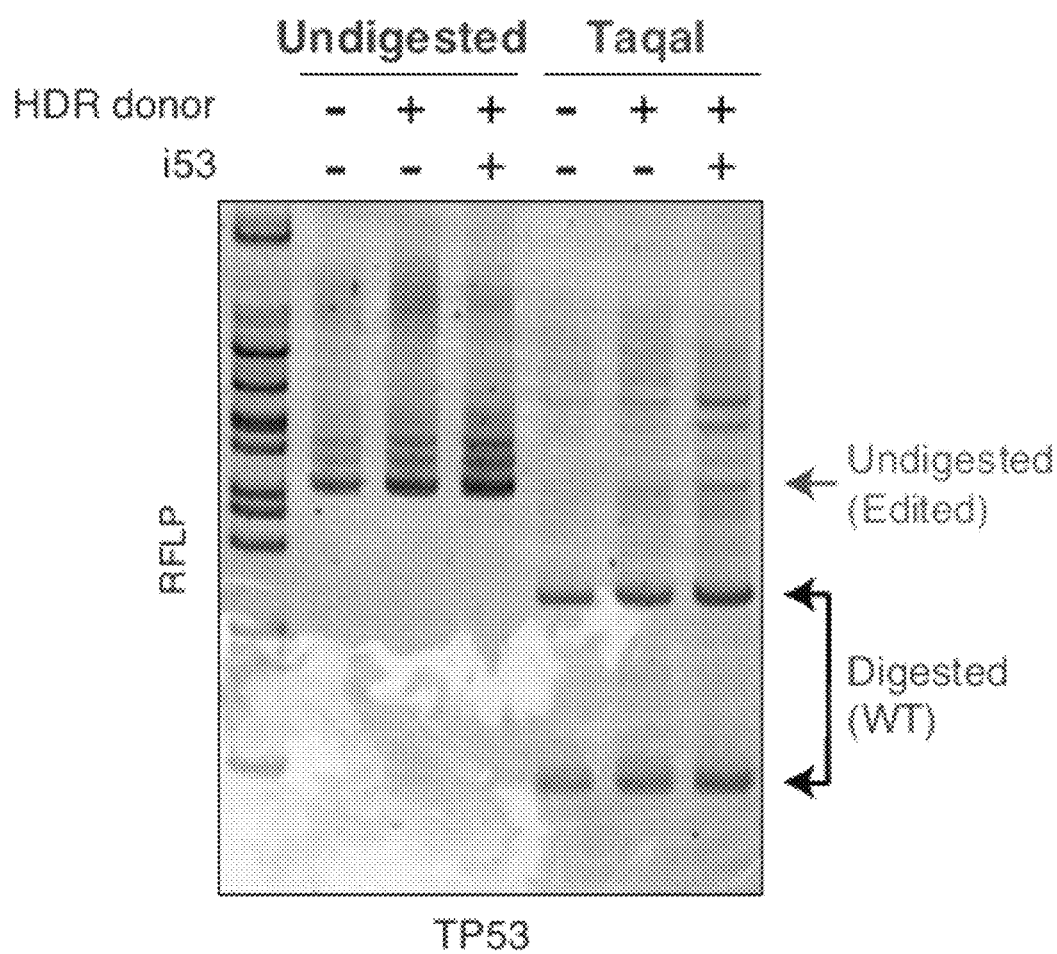

FIGS. 11G-11H show the RFLP assays to monitor the loss of NcoI (FIG. 11G) or TaqaI (FIG. 11H) restriction sites in the HBB and TP53 loci, respectively, resulting from the insertion of the G6V and R209fs*6 mutations under the same experimental conditions shown in FIG. 11C and FIG. 3B. Digested (WT) and undigested (edited) DNA products are indicated by arrows.

Figure 11I:
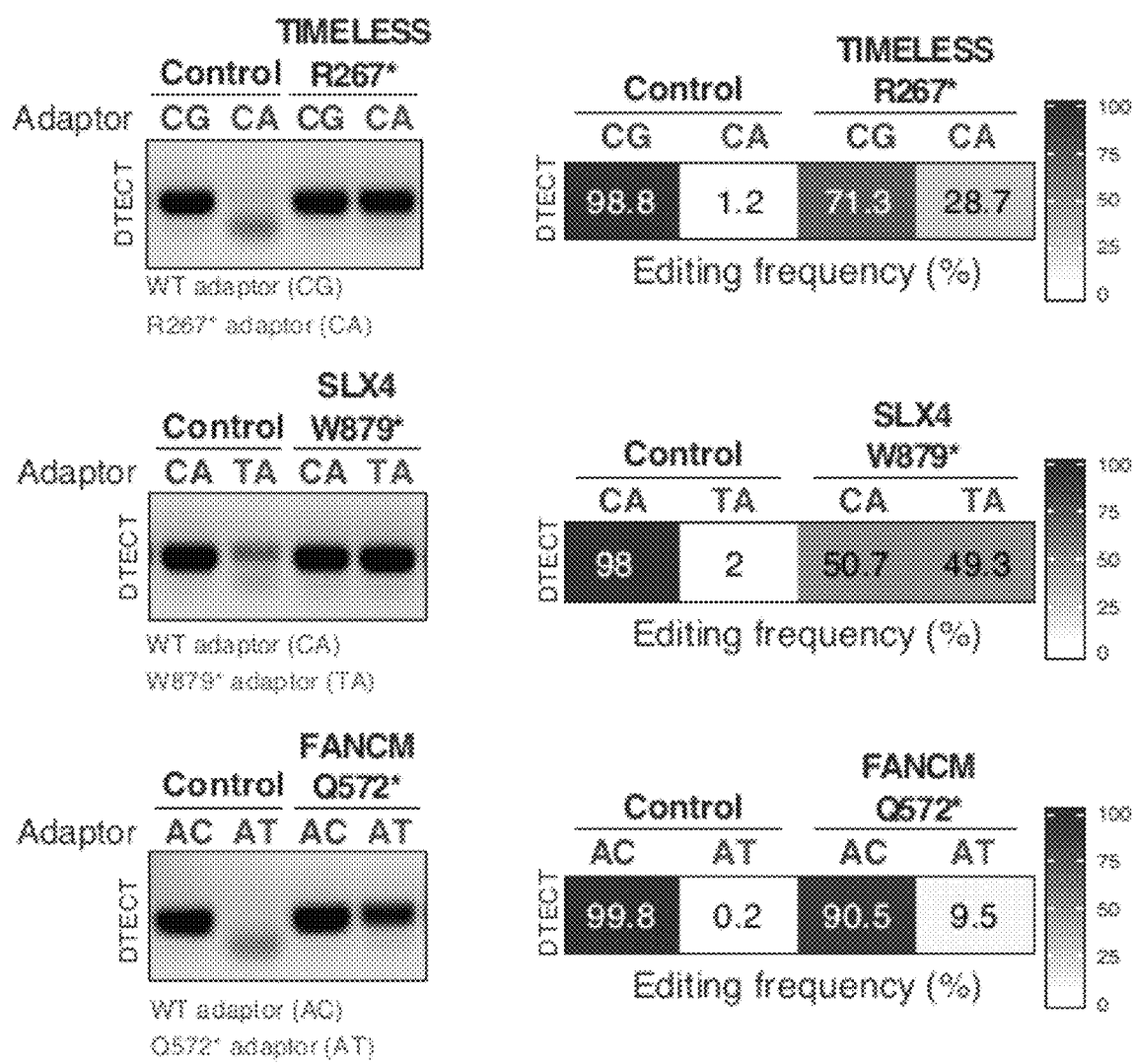

FIG. 11I shows the detection of WT and nonsense mutant TIMELESS, SLX4 and FANCM alleles by DTECT using adaptors specific for the WT (green) or edited (purple) signatures. Experiments were performed in cells transfected with the cytidine base editor BE3 and sgRNA to induce the indicated nonsense mutations, which were detected by analytical (left; 21 cycles) or quantitative PCR (right).

Figure 11J:
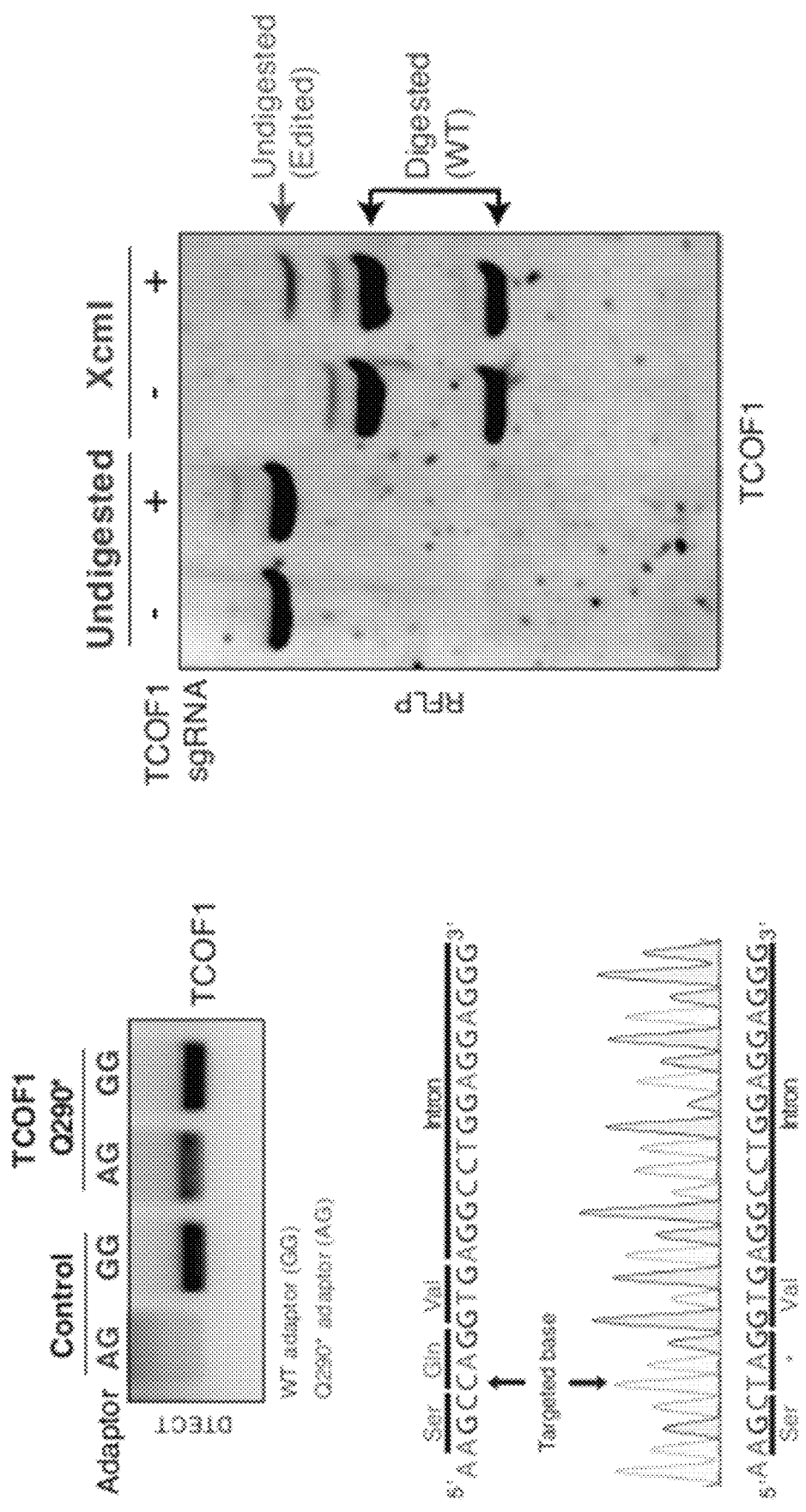

FIG. 11J shows the detection of WT and nonsense mutant TCOF1 alleles by DTECT (21 PCR cycles) using adaptors specific for the WT (GG, green) or edited (AG, purple) allele. Experiments were performed in cells transfected with BE3 and sgRNA to induce the indicated nonsense mutation in the TCOF1 gene. The introduction of the nonsense mutation was confirmed by Sanger sequencing (bottom) and by an RFLP assay that monitors the loss of an XcmI restriction site at the edited locus (right).

Figure 12A:
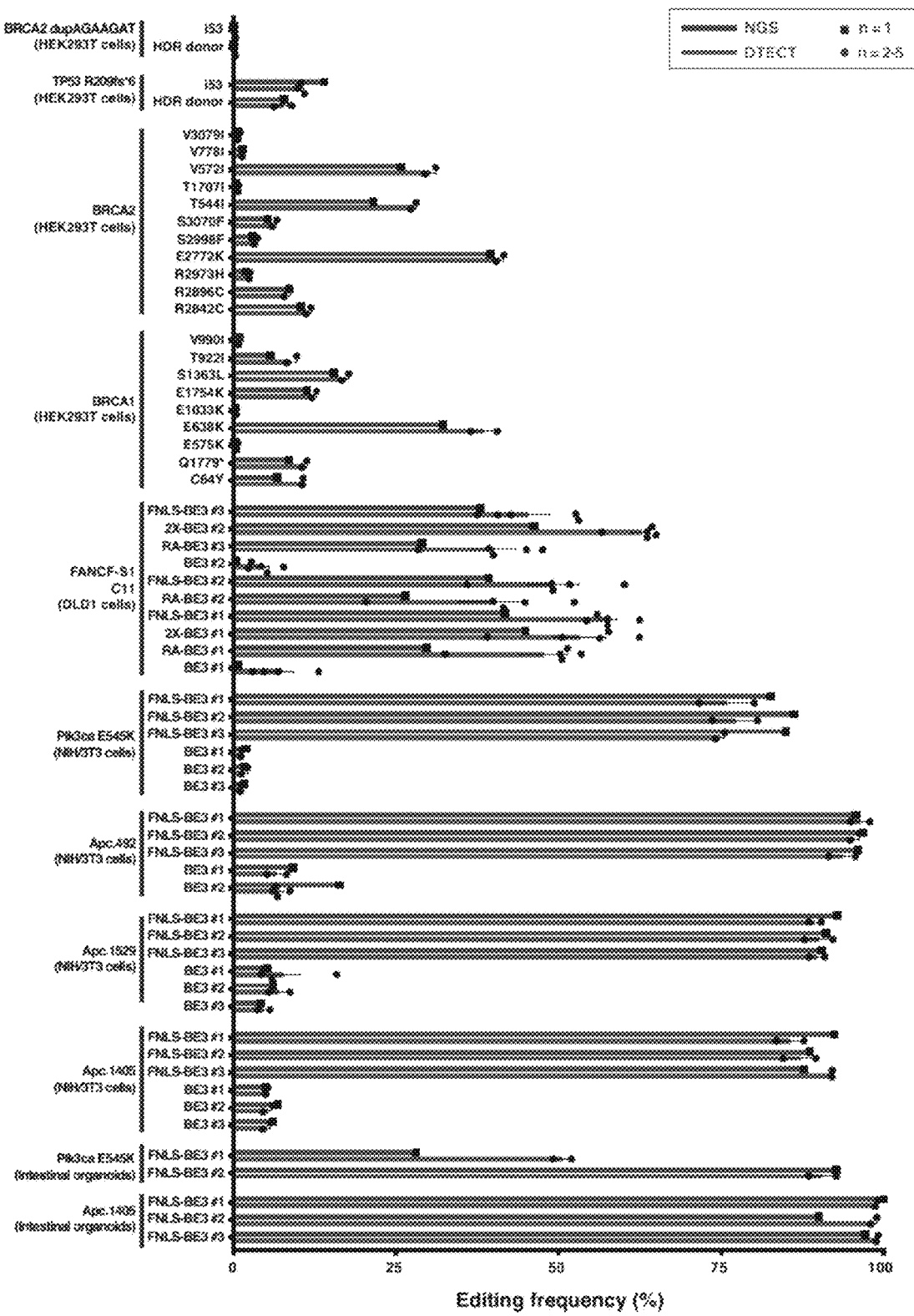
Figure 12B:
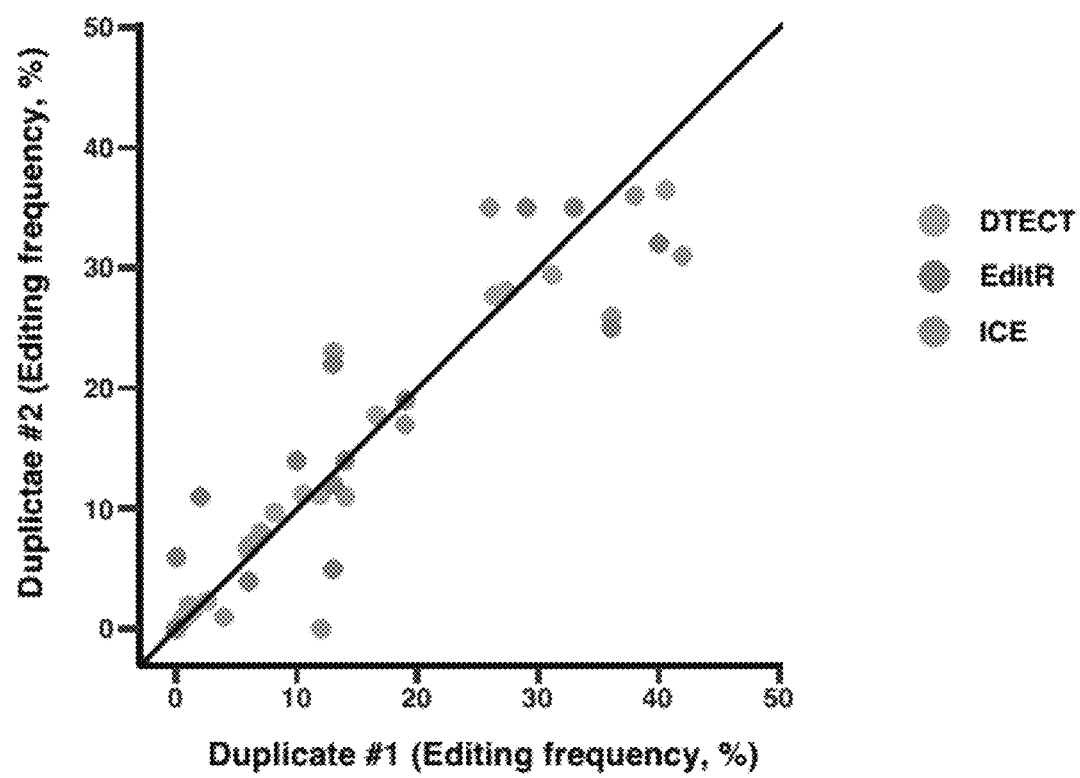

FIGS. 12A-12B show the comparative analysis of DTECT-, Sanger- and NGS-based estimations of the frequency of genetic variants generated by precision genome editing.

FIG. 12A shows the graphical representation of the frequency of mutations introduced by CRISPR-dependent HDR and base editing in human and mouse cells, and intestinal organoids. The FANCF, Pik3ca and Apc loci were edited in biological duplicate or triplicate using multiple base editors, and the resulting edited samples were previously described (Zafra et al., 2018). The BRCA1/2 loci were edited using BE3. The frequency values were determined by both DTECT (red) and NGS (green). NGS was conducted on standard PCR amplicons (FANCF, Pik3ca and Apc) or AcuI-tagged amplicons (BRCA1/2) of the edited loci. Error bars represent the s.e.m. of 2-5 independent DTECT assays per edited sample. The same frequency values are plotted in the graphs shown in FIG. 3C.

FIG. 12B shows the graphical representation of the correlation between technical duplicates obtained by DTECT (red), EditR (green) or ICE (blue). Each dot represents a distinct BRCA1/2 variant introduced in cells by precision genome editing. Technical duplicates of DTECT assays correspond to two independent ligation reactions for the same AcuI-digested amplicon and Sanger-based technical duplicates correspond to two independent sequencing reactions for the same PCR amplicon.

Figure 13A:
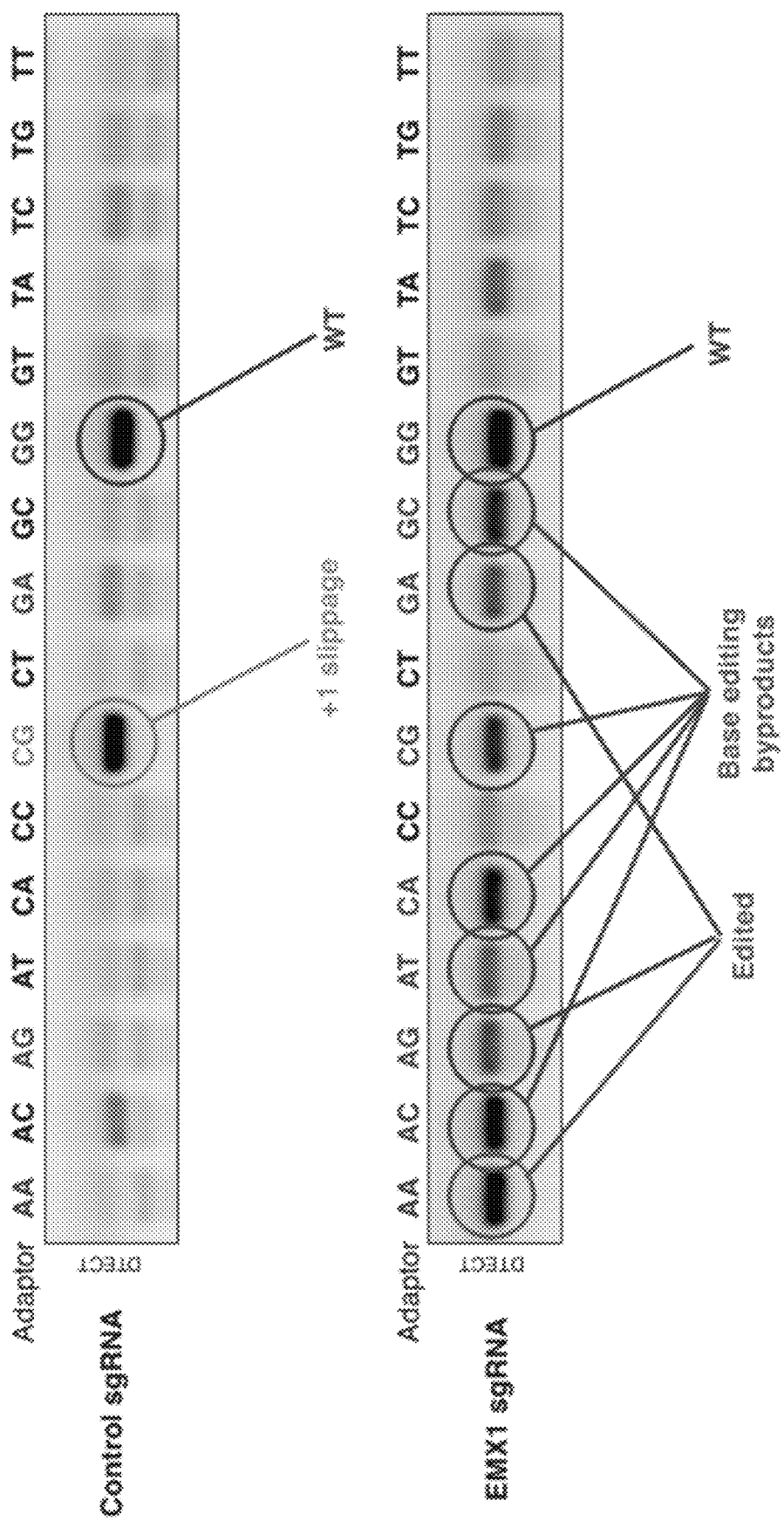
Figure 13B:
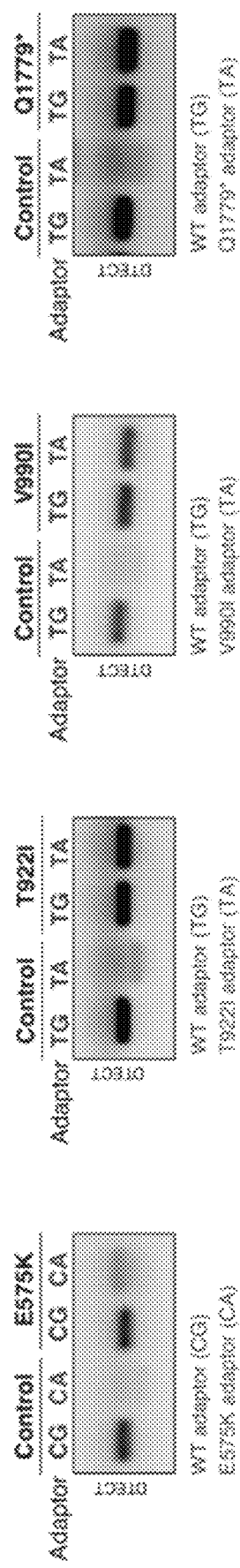
Figure 13C:
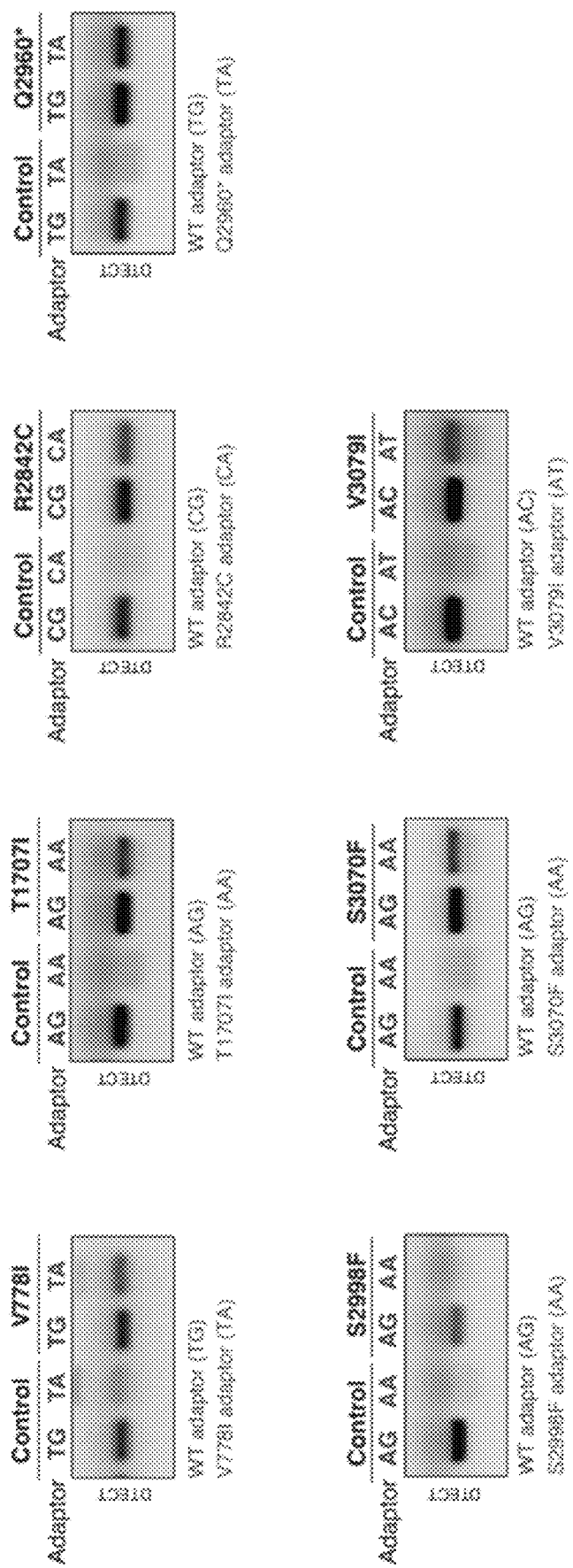

FIGS. 13A-13C show the detection of base editing byproducts and clinically relevant BRCA1/2 mutations introduced by precision genome editing.

FIG. 13A shows the detection by analytical PCR (21 cycles) of allelic mixtures induced by CRISPR-mediated base editing events occurring at a CC sequence in the EMX1 gene, as shown in FIG. 4A. In these experiments HEK293T cells constitutively expressing the base editor FNLS-BE3 were transfected with a control sgRNA (top) or an sgRNA targeting the EMX1 locus (bottom). All possible 16 adaptors were used to capture EMX1 variants. Adaptors that capture the WT allele (GG) and +1 AcuI slippage event (CG) are shown in green and orange. Adaptors that capture C→T base editing events (AA, AG, GA) and C→A and C→G base editing byproducts (AC, AT, CA, CG, GC) are also shown.

FIGS. 13B-13C show the analytical detection of the indicated BRCA1 (FIG. 13A) and BRCA2 (FIG. 13B) mutations in HEK293T cell populations by DTECT (21 PCR cycles) using adaptors specific for WT (green) or mutant (purple) alleles. Experiments were conducted as in FIGS. 5C and 5F.

Figure 14A:
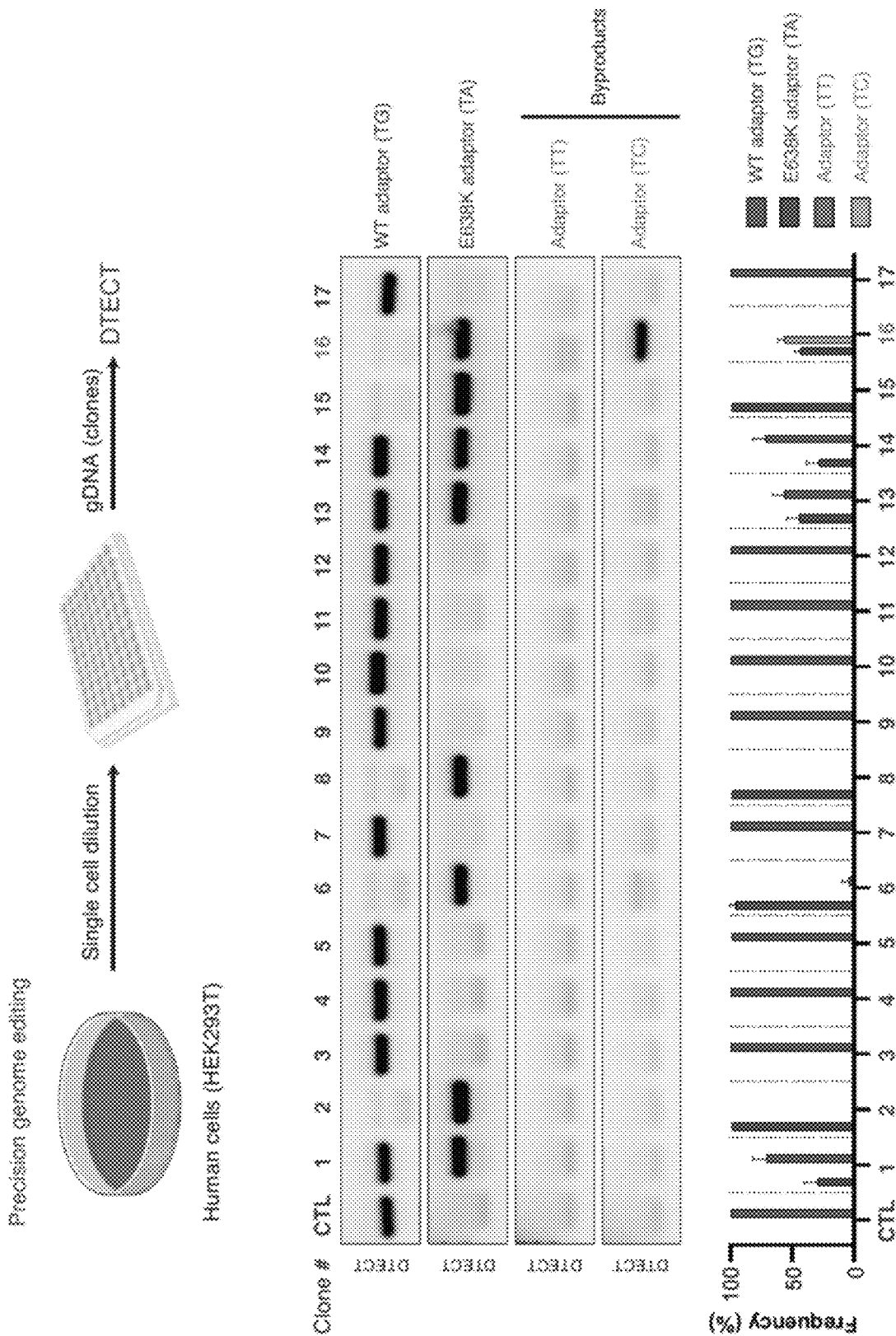
Figure 14B:
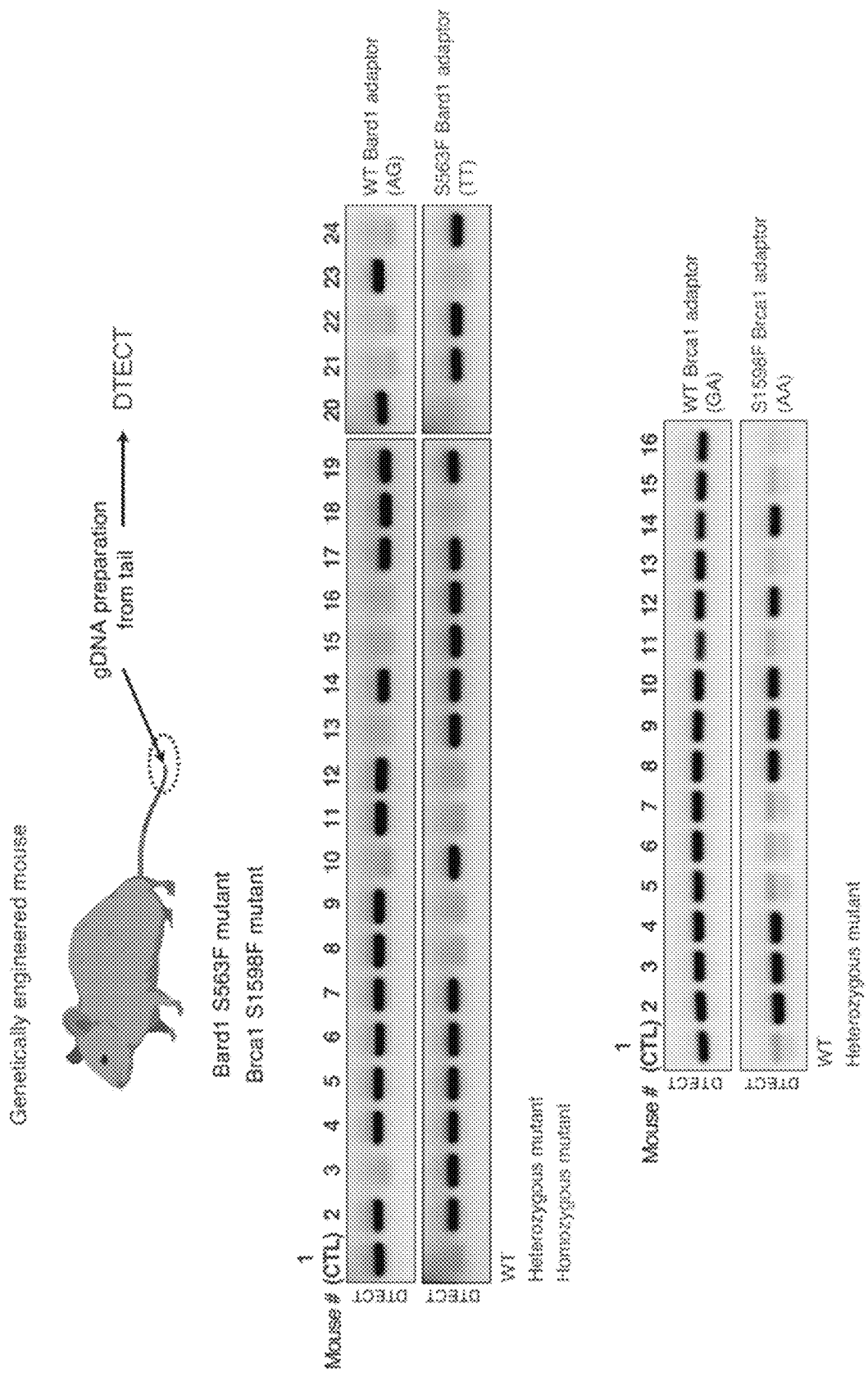

FIGS. 14A-14B show the genotyping of mutant cellular clones and knock-in mice using DTECT.

FIG. 14A shows the genotyping by DTECT-based analytical PCR (20 cycles) of HEK293T clones (17) carrying WT and/or BRCA1 E638K mutant alleles or base editing byproducts derived by single cell dilution from the BRCA1 E638K cell population shown in FIG. 5C. Heterozygous and homozygous mutant clones are indicated in blue and purple, respectively. WT clones are indicated in green and a clone with a base editing byproduct is indicated in orange. Clones #1, #2, #4 and control (CTL) are also shown in FIG. 5G. Quantification of each BRCA1 variant by qPCR is also shown (bottom). HEK293T cells have 4 BRCA1 alleles. Error bars correspond to two independent experiments.

FIG. 14B shows the genotyping by DTECT-based analytical PCR of Bard1 S563F (top) and Brca1 S1598F (bottom) knock-in mutant mice (Bard1, 18 PCR cycles; Brca1, 20 PCR cycles). DTECT assays were conducted on gDNA isolated from mouse tail samples. Heterozygous and homozygous mutant mice are indicated in blue and purple, respectively, and WT mice are indicated in green. No homozygous Brca1 S1598F mutant mice were identified in the analyzed mouse litters due to sub-Mendelian birth ratios (Billing et al., 2018). Mice #1, #2, #3 and #8 (Bard1), and #1, #2, #5 (Brca1) are also shown in FIG. 5I.

FIGS. 15A-15D show the detection of oncogenic mutations in a mouse model of myeloproliferative neoplasm and in ALL patients using DTECT.

Figure 15A:
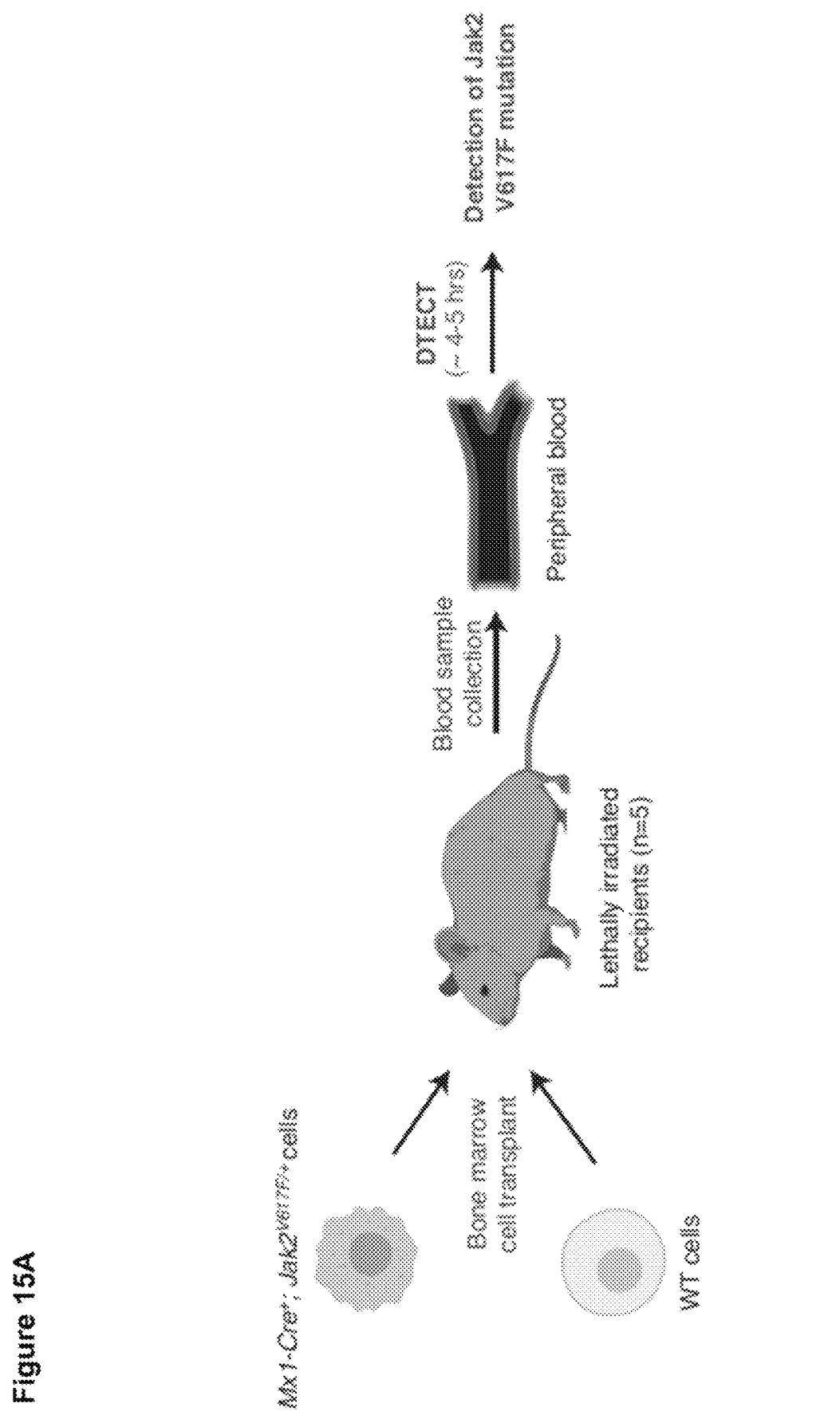

FIG. 15A shows the schematics of the experiments conducted to detect the Jak2V617F mutation in a mouse model of myeloproliferative neoplasm. Peripheral blood was collected from mice transplanted with a mixture of bone marrow cells either wild-type (WT) or carrying an inducible Jak2 V617F mutant allele (Mx1-Cre+; $Jak2^{V617F/+}$). DTECT was then utilized to determine the presence of the Jak2 V617F mutation in gDNA extracted from the collected blood samples.

Figure 15B:
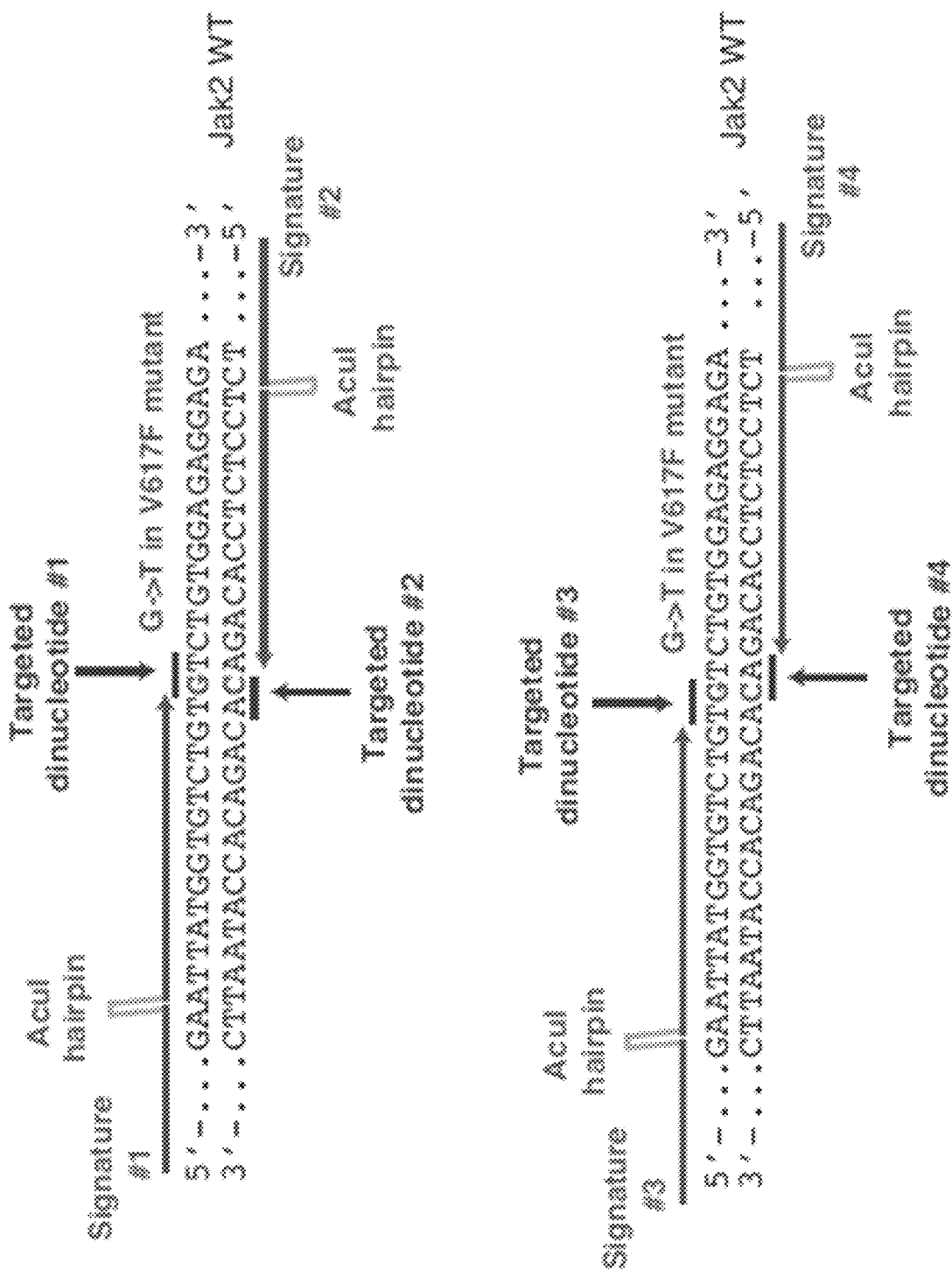

FIG. 15B shows the schematic representation of 4 AcuI-induced dinucleotide signatures that enable the identification of Jak2 WT and V617F alleles. The G in red is replaced by a T in the Jak2 V617F mutant allele.

Figure 15C:
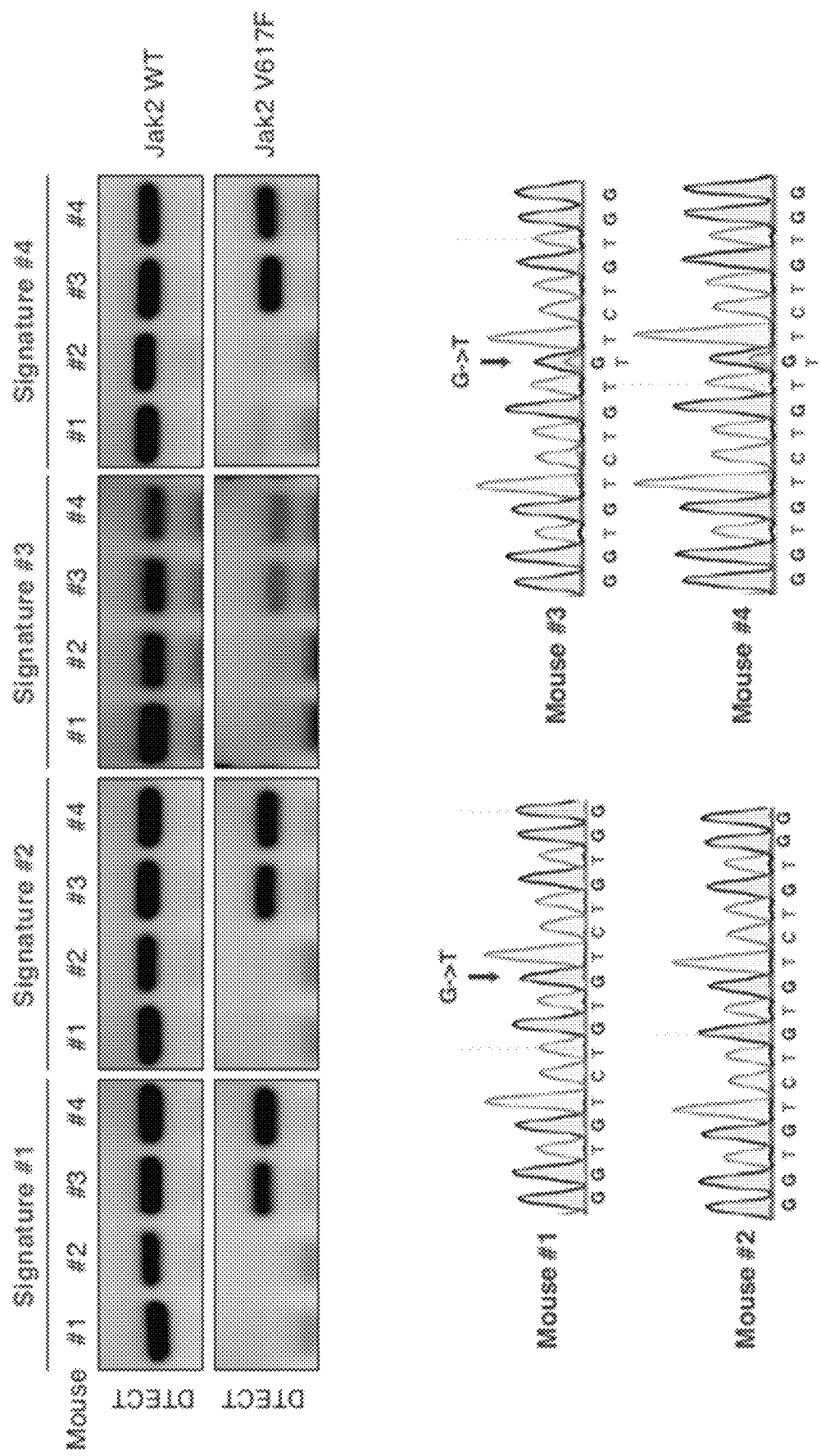

FIG. 15C shows the identification by DTECT-based analytical PCR (20 cycles) of the Jak2 V617F mutation in the blood of a mouse model of myeloproliferative neoplasm generated as described in FIG. 15A. The Jak2 V617F mutation was identified using the 4 independent dinucleotide signatures shown in FIG. 15B. gDNA samples from peripheral blood of WT mice were used as controls (#1 and #2) in this experiment. Sanger sequencing (bottom) was conducted to confirm the results obtained using DTECT.

Figure 15D:
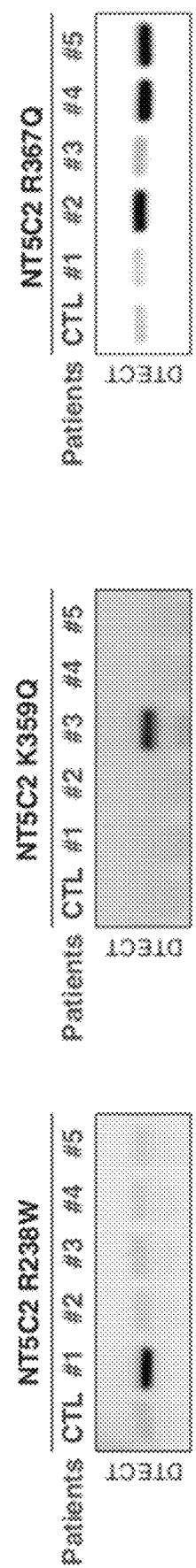

FIG. 15D shows the analytical detection of the indicated NT5C2 mutations in ALL patient samples by PCR (20 cycles). The frequency of the indicated mutations in the same patient samples is shown in FIG. 6B.

Figure 16A:
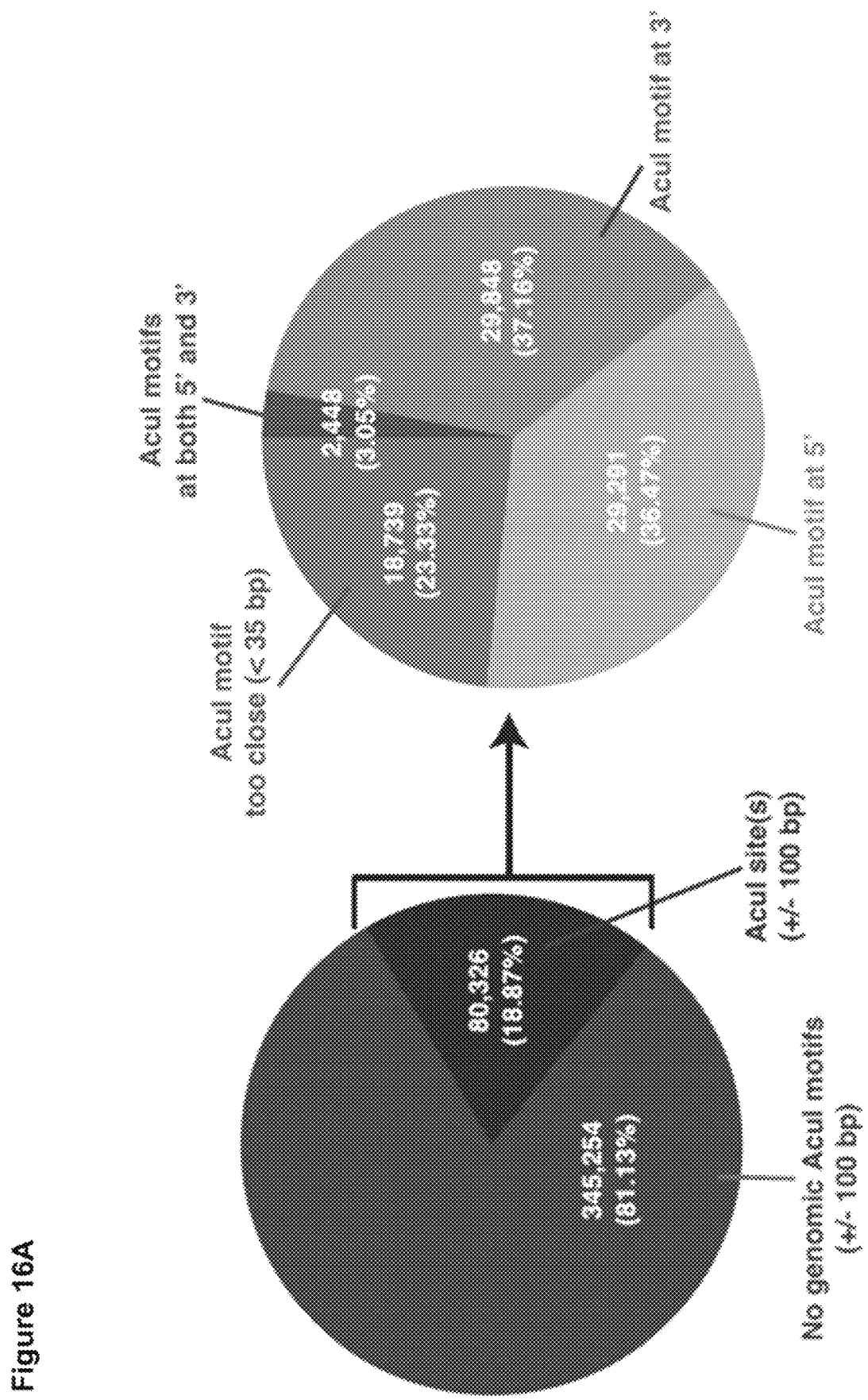
Figure 16B:
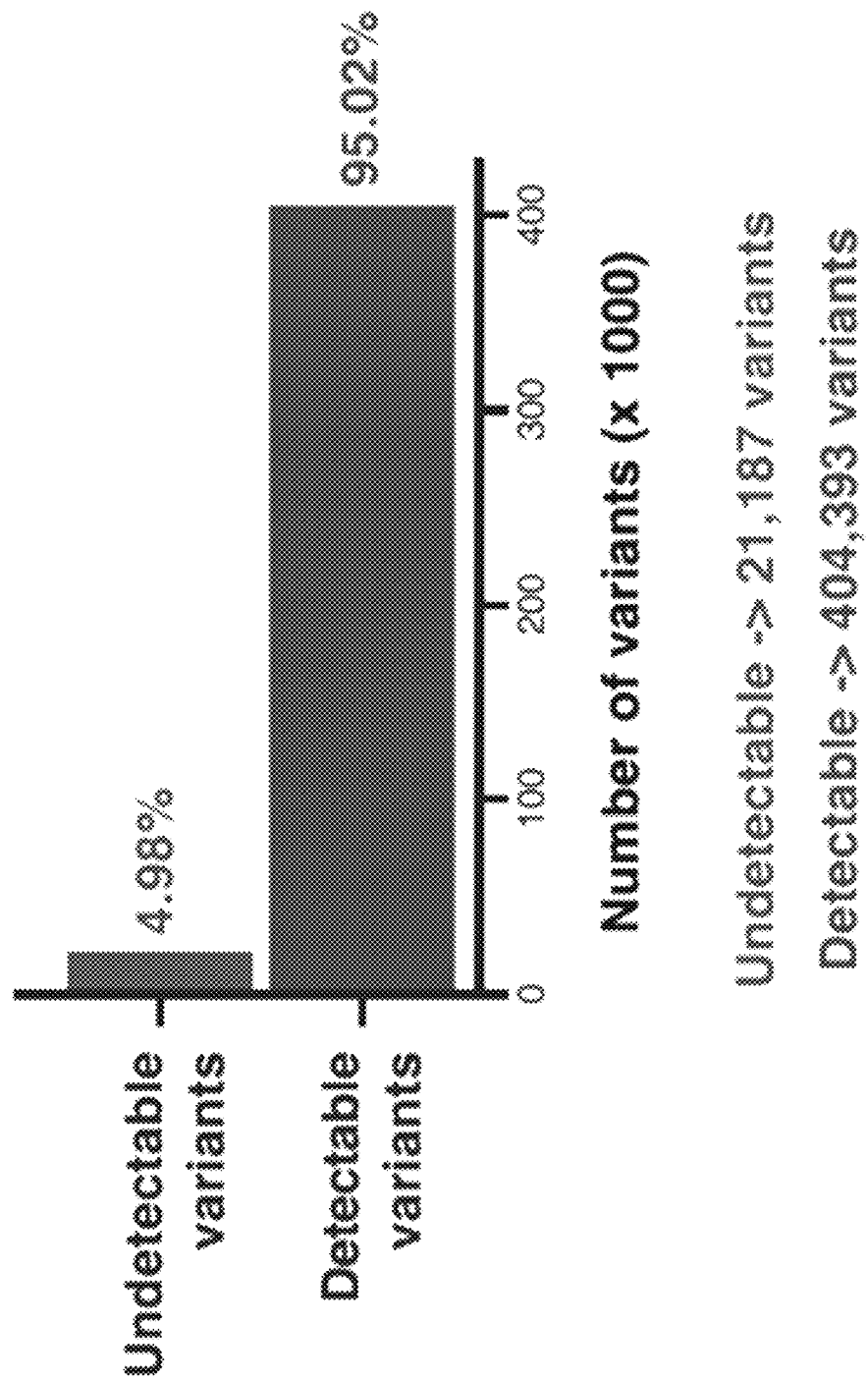
Figure 16C:
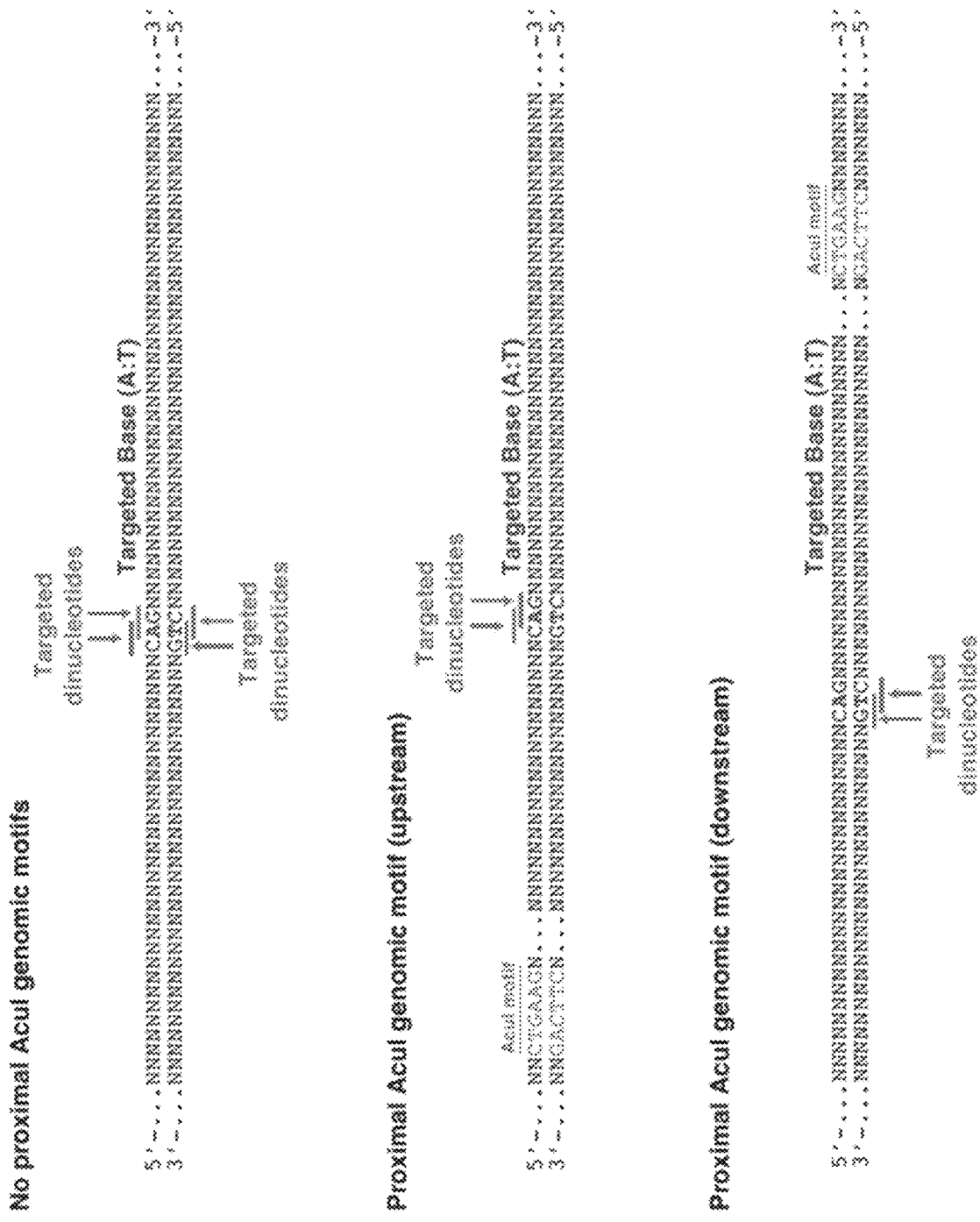

FIGS. 16A-16C show the analysis of ClinVar variants with proximal genomic AcuI motifs compatible with DTECT.

FIG. 16A shows the Bioinformatic analysis of ClinVar database variants (425,580) with (80,326; blue) or without (345,254; green) genomic AcuI sites in close proximity (+/−100 bp). Variants (green, right pie chart) with a single AcuI motif located 35 bp to 100 bp away on the 3'-(29,848) or 5'-(29,291) side can be detected using DTECT, as illustrated in FIG. 16C. Variants (red, right pie chart) with an AcuI motif located <35 bp away (18,739) or with proximal AcuI motifs on both sides (2,448) cannot be detected using DTECT.

FIG. 16B shows the percentage and number of ClinVar variants that can (95.02%, 404,393) or cannot (4.98%, 21,187) be detected using DTECT.

FIG. 16C shows the schematic representation of genomic loci with or without an AcuI site in close proximity to the edited site. When a genomic AcuI site is located 35 bp to 100 bp away from the edited site, detection of the edited site can be obtained by designing 2 AcuI-tagging primers that anneal to the targeted locus between the genomic AcuI site and the edited base(s). This approach allows the capture of two independent dinucleotide signatures for each targeted site with one proximal AcuI site. Four independent dinucleotide signatures can be captured for targeted sites with no proximal AcuI sites.

Figure 17A:
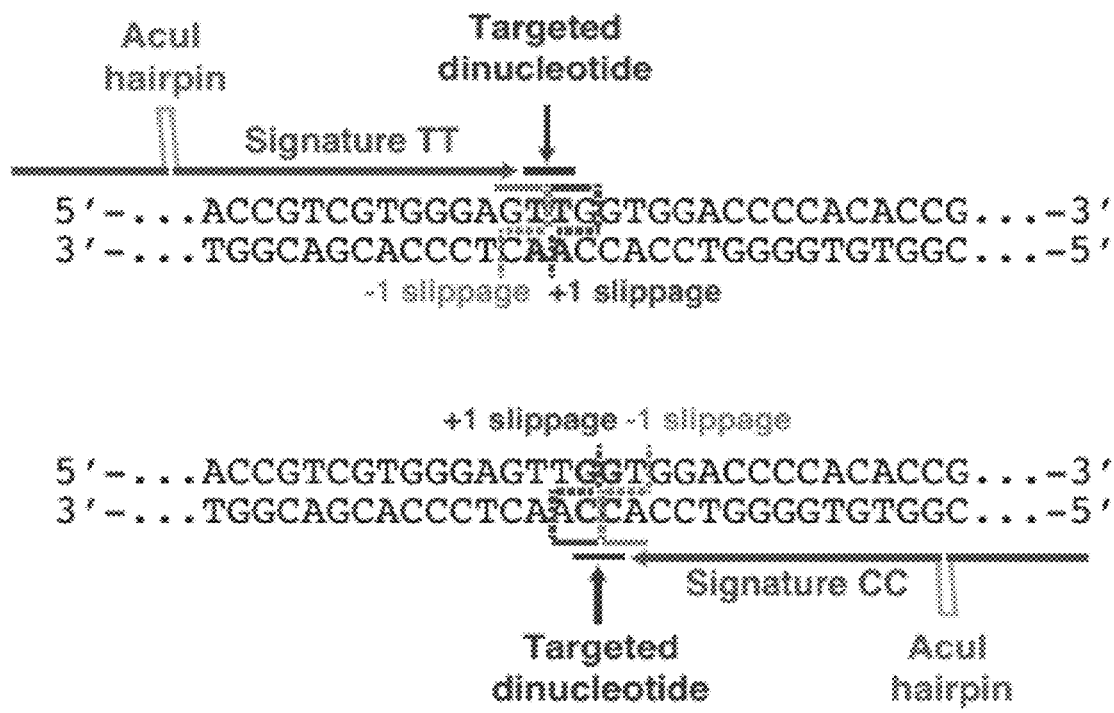
Figure 17A:
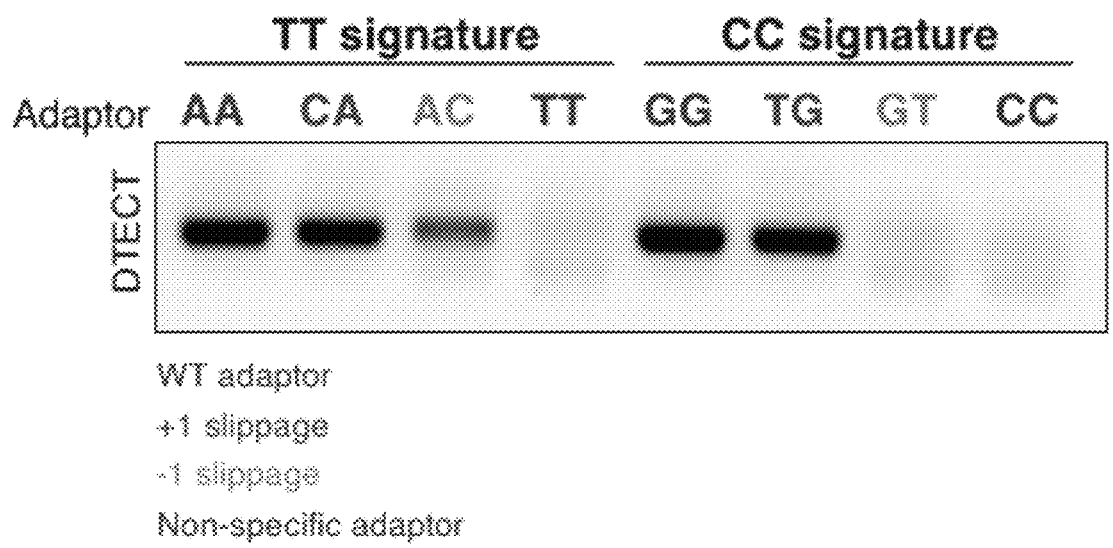
Figure 17B:
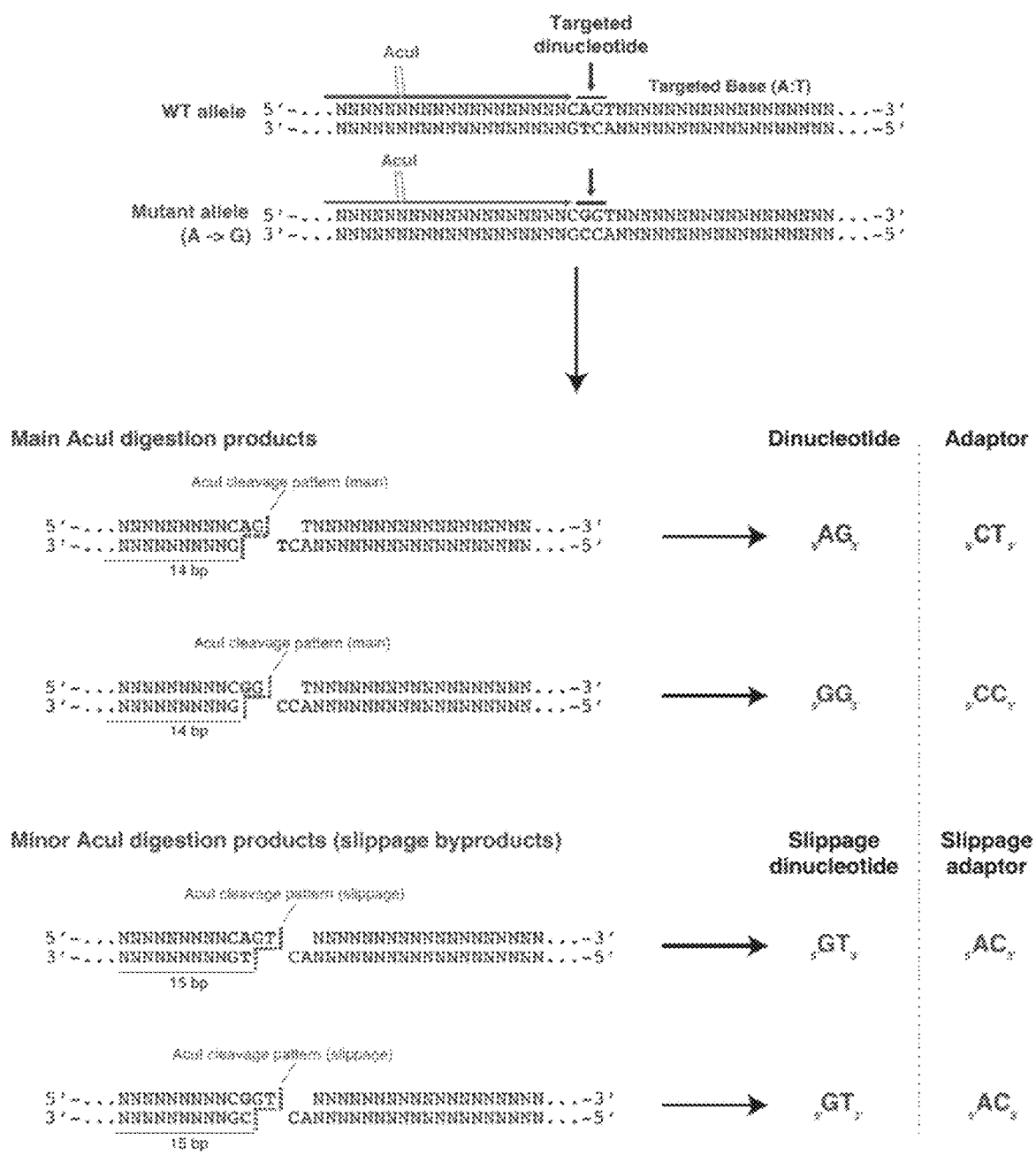

FIGS. 17A-17B show the detection of AcuI slippage events by DTECT.

FIG. 17A shows the schematics of targeted dinucleotides (blue) and +1 (red) and −1 (orange) AcuI slippage events (left). Detection of AcuI slippage byproducts by DTECT (22 PCR cycles) using adaptors complementary to the targeted dinucleotide signatures (green) and to signatures generated by AcuI+1 (red) or −1 (orange) slippage (right). A non-specific adaptor (blue) is used as a control.

FIG. 17B shows the schematic representation of DNA digestion products generated by precise AcuI cleavage (green) or +1 slippage (red) occurring at wild-type and mutant alleles. The dinucleotide signatures generated as a result of AcuI slippage byproducts and the complementary adaptors to capture them are indicated.

FIGS. 18A-18D show the design of DTECT assays to avoid indel interference in CRISPR-mediated HDR experiments.

Figure 18A:
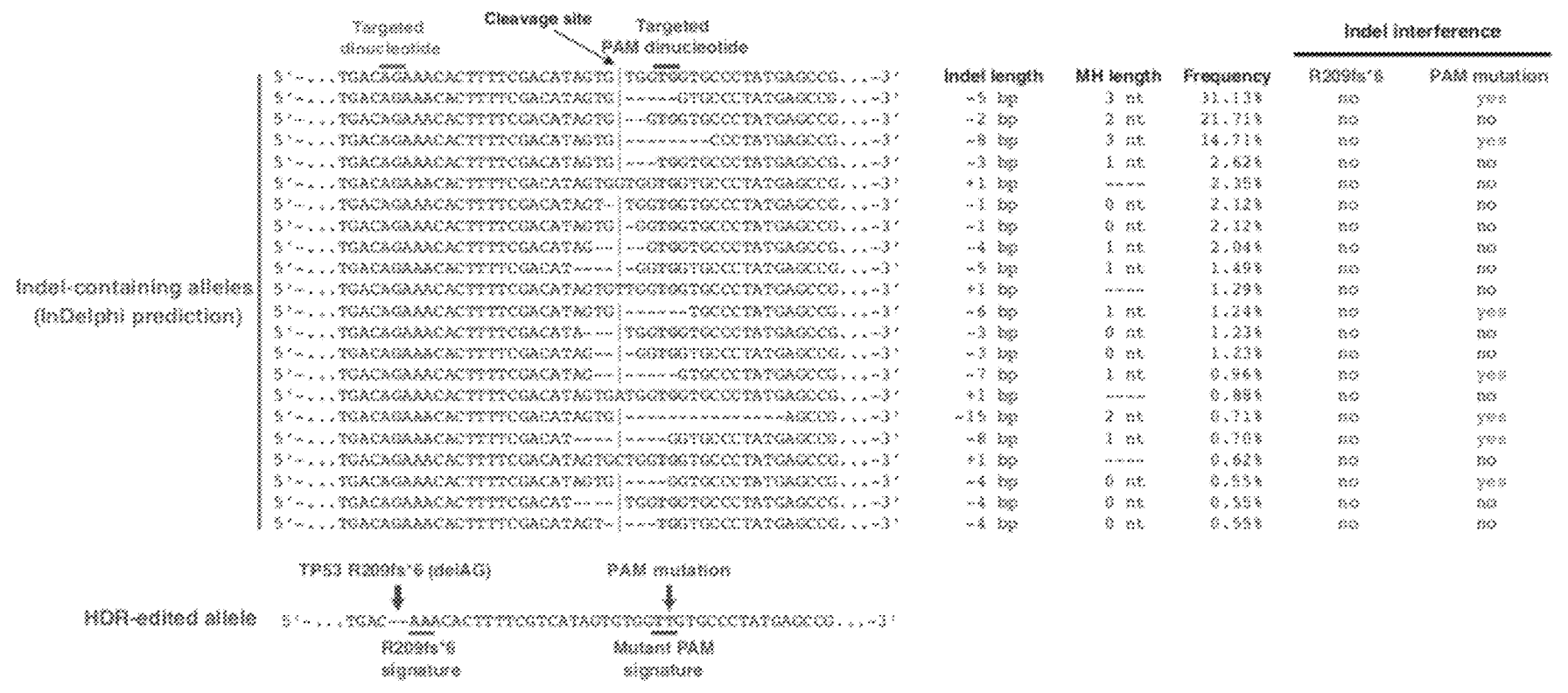

FIG. 18A shows the InDelphi prediction (https://indelphi-.giffordlab.mit.edu) of indel-containing alleles in the TP53 locus. The dinucleotides targeted to simultaneously introduce the TP53 R209fs*6 mutation and a G→T mutation in the PAM by CRISPR-dependent HDR are indicated in green and red, respectively. The Cas9 cleavage site is indicated in black. The dinucleotide signatures captured to detect the TP53 R209fs*6 and PAM mutations are shown in purple. The presence of indel interference in the distinct predicted alleles is indicated. MH, microhomology.

Figure 18B:
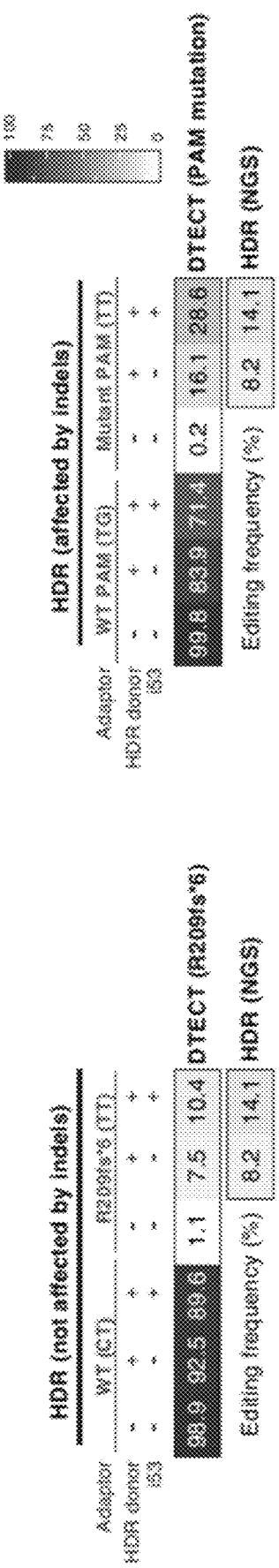

FIG. 18B shows the DTECT-based quantification of the TP53 R209fs*6 and PAM mutations introduced by HDR using a single ssODN donor template, as shown in FIG. 18A. Adaptors specific for the WT (CT and TG; green and red) or edited (TT; purple) signatures were used for quantification. HDR efficiency determined by NGS is also shown.

Figure 18C:
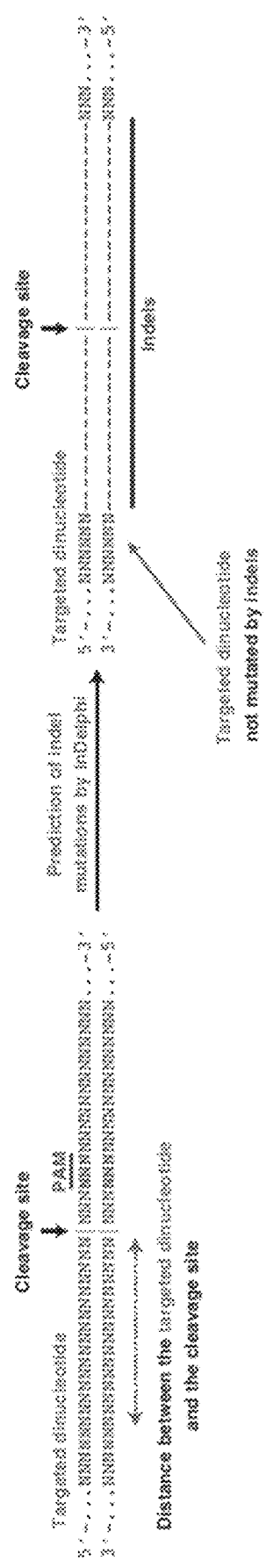

FIG. 18C shows the schematic representation of the design of DTECT experiments to avoid interference of indels formed at DSBs during CRISPR-mediated HDR. Cas9-mediated DSBs are induced at a distance from a targeted dinucleotide (green) sufficient to avoid mutation of the targeted dinucleotide by indels (blue). The pattern of indel mutations is predicted using the InDelphi website.

Figure 18D:
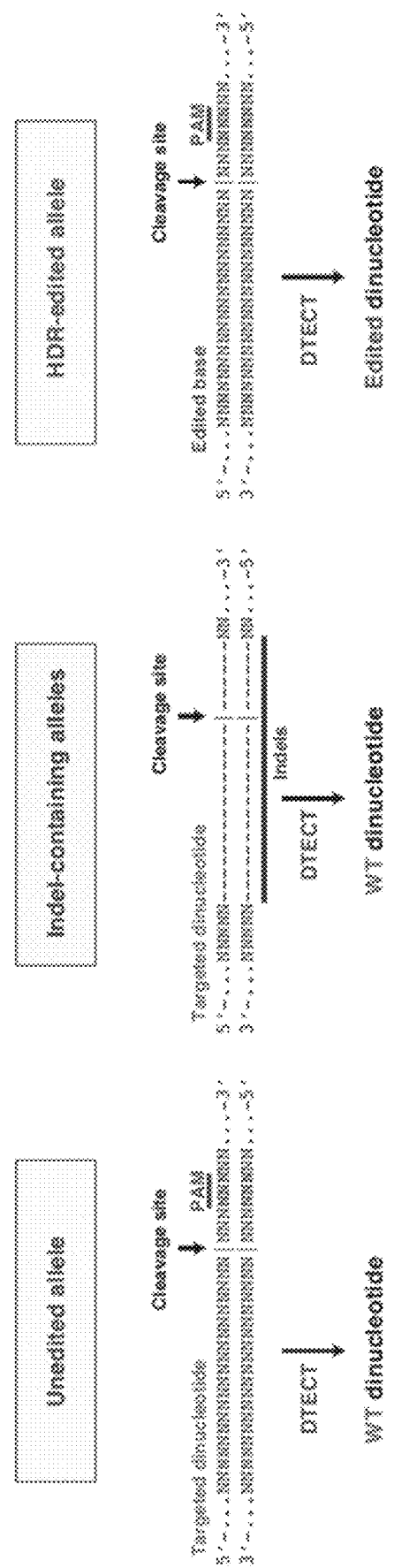

FIG. 18D shows the schematics of alleles generated by CRISPR-mediated HDR, including the unedited allele (green), indel-containing alleles (blue) and the HDR-edited allele (purple). Using the experimental design shown in FIG. 18C, DTECT captures both the unedited and the indel-containing alleles using an adaptor specific for the WT dinucleotide signature, while the HDR-edited allele is captured using an adaptor specific for the edited dinucleotide signature. The capture of indel-containing alleles with a WT adaptor ensures the accurate quantification of the frequency of the HDR-edited allele in the allele population.

DETAILED DESCRIPTION OF THE DISCLOSURE

The present disclosure provides a versatile method that uses standard molecular biology techniques to detect variants introduced by precision genome editing or resulting from genetic variation. This detection method, designated Dinucleotide signaTurE CapTure (DTECT), enables accurate and sensitive quantification of marker-free precision genome editing events induced by CRISPR-dependent HDR, base editing and prime editing. In addition, we show that DTECT can readily identify oncogenic mutations in cancer mouse models, patient-derived xenograft models and cancer patient samples. These studies establish a cost-effective method for the rapid detection of genetic variants, which will aid the generation of marker-free cellular and animal models of human disease and expedite the detection of pathogenic variants for clinical applications.

Accordingly, one embodiment of the present disclosure is a DNA adaptor comprising: (a) one strand with sequence of 5'-CTGGGGCACGGGTAAGAAGCATTCTGTCTCTC-TTCTAAGAATTCGAGCTCGGTACC CG-3' (SEQ ID NO: 230); and (b) one complementary strand with sequence of 5'-CGGGTACCGAGCTCGAATTCTTAGAAGAGA-GACAGAATGCTTCTTACCCGTGCCC CAGNN-3' with "N" corresponding to A, T, G or C (SEQ ID NOs: 231-246).

In some embodiments, the DNA adaptor is labeled with a detection molecule. Non-limiting examples of the detection molecule include a radiolabel, a fluorescent label, a biotinylated label, a non-fluorescent label, an enzyme, a hapten, a phosphorescent molecule, a chemiluminescent molecule, a chromophore, a luminescent molecule, a photoaffinity molecule, a color particle or a ligand.

Another embodiment of the present disclosure is a method of preparing a DNA adaptor disclosed herein, comprising: (a) synthesizing one constant oligonucleotide with sequence of 5'-CTGGGGCACGGGTAAGAAGCATTCTGTCTC-TCTTCTAAGAATTCGAGCTCGGTACC CG-3' (SEQ ID NO: 230); (b) synthesizing one complementary oligonucleotide with sequence of 5'-CGGGTACCGAGCTCGAAT-TCTTAGAAGAGAGACAGAATGCTTCTTACCCGTG-CCC CAGNN-3' with "N" corresponding to A, T, G or C (SEQ ID NOs: 231-246); (c) mixing the constant and complementary oligonucleotides; and (d) annealing the mixture to obtain the DNA adaptor.

Another embodiment of the present disclosure is a library of DNA adaptors prepared by methods disclosed herein, the library comprises 16 DNA adaptors, wherein each DNA adaptor has a different "NN".

Another embodiment of the present disclosure is a method for detecting a genetic modification, comprising the steps of:

(a) amplifying a genomic locus of interest using a specially designed Type IIS restriction enzyme-tagging primer, comprising: (i) extracting genomic DNA from a biological sample of interest; (ii) synthesizing the Type IIS restriction enzyme-tagging primer based on the genomic locus of interest; (iii) amplifying the genomic locus of interest using the Type IIS restriction enzyme-tagging primer and a reverse primer; and (iv) purifying a Type IIS restriction enzyme-tagged genomic amplicon; (b) digesting the Type IIS restriction enzyme-tagged genomic amplicon with the Type IIS restriction enzyme; (c) isolating the smaller DNA fragment containing a genomic signature of interest exposed in a 3' single-stranded overhang; (d) capturing the genomic signature of interest, comprising: (i) preparing the library of DNA adaptors disclosed herein; (ii) incubating the isolated smaller DNA fragment containing the 3' overhang signature with the library of DNA adaptors and performing a ligation; and (iii) obtaining a ligated product; and (e) amplifying the ligated product to detect the presence of the genetic modification.

In some embodiments, the genetic modification is selected from a base change, a deletion, or an insertion. In some embodiments, the genetic modification is selected from a single genomic change or multiple genomic changes. In some embodiments, the multiple genomic changes can occur within a single locus or distinct loci.

In some embodiments, the Type IIS restriction enzyme is selected from AcuI, BpmI, BpuEI, BsgI, MmeI and NmeAIII. In some embodiments, the Type IIS restriction enzyme is selected from AcuI and BpuEI. In some embodiments, the Type IIS restriction enzyme is AcuI.

In some embodiments, the Type IIS restriction enzyme-tagging primer is an oligonucleotide comprising: (a) a non-complementary handle sequence positioned on the 5' side; (b) a complementary sequence of the genomic locus of interest on the 5' side; (c) a recognition motif of the Type IIS restriction enzyme that is positioned at a predicted distance from its cleavage site to generate the genomic signature of interest; and (d) a complementary sequence of the genomic locus of interest on the 3' side.

In some embodiments, the reverse primer is positioned at more than 100 bp downstream of the genomic locus of interest.

In some embodiments, the non-complementary handle sequence can have any suitable length. In some embodiments, the non-complementary handle sequence is 25 bp. In some embodiments, the non-complementary handle sequence can have any suitable sequence. In some embodiments, the non-complementary handle sequence is 5'-GCAATTCCTCACGAGACCCGTCCTG-3' (SEQ ID NO: 3).

In some embodiments, the ligation in step (d)(ii) of the methods disclosed above is carried out by T4 DNA ligase.

A further embodiment of the present disclosure is a kit for detecting a genetic modification of interest, comprising a specially designed Type IIS restriction enzyme-tagging primer disclosed herein, and a library of DNA adaptors disclosed herein, packaged together with instructions for its use. In some embodiments, the Type IIS restriction enzyme is AcuI.

Another embodiment of the present disclosure is a method for detecting a genetic modification, comprising the steps of: (a) amplifying a genomic locus of interest using a specially designed AcuI-tagging primer, comprising: (i) extracting DNA of interest; (ii) synthesizing the AcuI-tagging primer based on the genomic locus of interest; (iii) amplifying the genomic locus of interest using the AcuI-tagging primer and a reverse primer; and (iv) purifying an AcuI-tagged genomic amplicon; (b) digesting the AcuI-tagged genomic amplicon with restriction enzyme AcuI; (c) isolating the smaller DNA fragment containing a genomic signature of interest produced by AcuI-digestion; (d) capturing the genomic signature of interest, comprising: (i) preparing the library of DNA adaptors disclosed herein; (ii) incubating the isolated smaller DNA fragment with the library of DNA adaptors and performing a ligation; and (iii) obtaining a ligated product; and (e) amplifying the ligated product to detect the presence of the genetic modification.

In some embodiments, the AcuI-tagging primer is an oligonucleotide comprising: (a) a non-complementary handle sequence positioned on the 5' side; and (b) a complementary sequence of the genomic locus of interest containing an AcuI motif (5'-CTGAAG-3') positioned 14 bp upstream from the genomic locus of interest.

In some embodiments, the AcuI-tagging primer can have any suitable length. In some embodiments, the AcuI-tagging primer is 60 bp.

In some embodiments, the reverse primer is positioned at more than 100 bp downstream of the genomic locus of interest.

In some embodiments, the non-complementary handle sequence can have any suitable length. In some embodiments, the non-complementary handle sequence is 25 bp.

In some embodiments, the complementary sequence has the structure of: 5'-N(20)CTGAAGN(14)-3' or 5'-N(15)CTGAAGN(14)-3', with "N" corresponding to A, T, G or C, depending on the DNA sequence of the genomic locus of interest.

In some embodiments, the non-complementary handle sequence is 5'-GCAATTCCTCACGAGACCCGTCCTG-3' (SEQ ID NO: 3) and the complementary sequence is 5'-N(15)CTGAAGN(14)-3', with "N" corresponding to A, T, G or C.

In some embodiments, the ligation in step (d)(ii) of the methods disclosed above is carried out by T4 DNA ligase.

An additional embodiment of the present disclosure is a kit for detecting a genetic modification, comprising a specially designed AcuI-tagging primer and a library of DNA adaptors disclosed herein, packaged together with instructions for its use.

Another embodiment of the present disclosure is a method for quantifying a genomic variant in a biological system, comprising the steps of: (a) obtaining a sample from the biological system; (b) amplifying a genomic locus of interest using a specially designed AcuI-tagging primer, comprising: (i) extracting DNA of interest; (ii) synthesizing the AcuI-tagging primer based on the genomic locus of interest; (iii) amplifying the genomic locus of interest using the AcuI-tagging primer and a reverse primer; and (iv) purifying an AcuI-tagged genomic amplicon; (c) digesting the AcuI-tagged genomic amplicon with restriction enzyme AcuI; (d) isolating the smaller DNA fragment containing a genomic signature of interest produced by the AcuI-digestion; (e) capturing the genomic signature of interest, comprising: (i) preparing the library of DNA adaptors disclosed herein; (ii) incubating the isolated smaller DNA fragment with the library of DNA adaptors and performing a ligation; and (iii) obtaining a ligated product; and (f) quantifying the genomic variant and determining its relative abundance.

In some embodiments, the genomic variant is generated by precision genome editing. In some embodiments, the precision genome editing is CRISPER-dependent homology-directed repair, base editing or prime editing.

In some embodiments, the biological system is a mammalian cell line, an organoid, or a tissue.

In some embodiments, the quantification in step (f) of the methods disclosed above is carried out by quantitative PCR (qPCR).

Still another embodiment of the present disclosure is a method for identifying and quantifying an oncogenic mutation of interest in a biological sample, comprising the steps of: (a) obtaining a biological sample; (b) amplifying a genomic locus of interest using a specially designed AcuI-tagging primer, comprising: (i) extracting DNA of interest; (ii) synthesizing the AcuI-tagging primer based on the genomic locus of interest; (iii) amplifying the genomic locus of interest using the AcuI-tagging primer and a reverse primer; and (iv) purifying an AcuI-tagged genomic amplicon; (c) digesting the AcuI-tagged genomic amplicon with restriction enzyme AcuI; (d) isolating the smaller DNA fragment containing a genomic signature of interest produced by the AcuI-digestion; (e) capturing the genomic signature of interest, comprising: (i) preparing the library of DNA adaptors disclosed herein; (ii) incubating the isolated smaller DNA fragment with the library of DNA adaptors and performing a ligation; and (iii) obtaining a ligated product; (f) amplifying the ligated product to identify the presence of the oncogenic mutation of interest; and (g) quantifying the oncogenic mutation of interest, if present, and determining its frequency.

In some embodiments, the biological sample is obtained from a cancer animal model, a patient-derived xenograft (PDX), or a human cancer patient sample.

In some embodiments, the quantification in step (g) of the methods disclosed above is carried out by quantitative PCR (qPCR).

A further embodiment of the present disclosure is a process for marker-free detection of a precision genome editing event comprising carrying out Dinucleotide signaTurE CapTure (DTECT) on a nucleic acid sequence of interest.

DTECT can also be used to detect genetic signatures in any organism, for example, a virus. Thus, still another embodiment of the present disclosure is a method for detecting a virus variant of interest, comprising the steps of: (a) obtaining a nucleic acid of the virus variant of interest from a biological sample; and (b) if the nucleic acid is DNA, carrying out Dinucleotide signaTurE CapTure (DTECT) to detect the variant of interest; or (c) if the nucleic acid is RNA, coverting it to DNA by reverse transcription PCR (RT-PCR) and then carrying out DTECT to detect the variant of interest. This detection method is applicable to any type of virus including but not limited to a DNA virus, an RNA virus, a retrovirus, etc. In some embodiments, the virus is an RNA virus. In some embodiments, the virus is SARS-CoV-2.

The following examples are provided to further illustrate the methods of the present disclosure. These examples are illustrative only and are not intended to limit the scope of the disclosure in any way.

EXAMPLES

Example 1

Methods and Materials

Material Availability

Plasmids for DTECT quantification and expression of base editing sgRNAs targeting BRCA1, BRCA2 and FANCD2 have been deposited to Addgene (#139321-139333, and 139511).

Cell Line Generation and Single Clone Isolation

HEK293T and DLD1 cell lines were obtained from ATCC. Cells were cultured in DMEM (ThermoFisher Scientific) supplemented with 10% Fetalgro bovine growth serum (BGS, RMBIO) and 1% penicillin-streptomycin (ThermoFisher Scientific). Cells were grown at 37° C. with 5% $CO_2$ and tested regularly for mycoplasma. NIH/3T3 were maintained in DMEM supplemented with 10% bovine calf serum. Organoids were isolated and cultured as previously described (Zafra et al., 2018). To generate cells constitutively expressing FNLS-BE3-P2A-BlastR, HEK293T cells were infected with a lentivirus expressing the above construct. Viruses were produced in HEK293T in 6-well plates by transfecting 2 µg of FNLS-BE3-P2A-BlastR, 0.2 µg of Tat, 0.2 µg of Gag/Pol, 0.2 µg of Rev, 0.4 µg of VSV-G expressing plasm ids in 250 µl of DMEM without serum. 9 µl of TransIT-293 (Mirus) were added to the DNA, mixed and incubated for 15 min at room temperature. The DNA transfection reagent mix was added dropwise to the cells and incubated at 37° C. with 5% $CO_2$. The next day the cell medium was replaced and cells were incubated for 48 hours. The medium containing lentiviruses was then collected and utilized to infect new HEK293T cells. 48 hours after infection, blasticidin was added to the medium until the uninfected control cells were killed. FNLS-BE3 expression was determined by western blot and the base editing activity of the construct was tested using previously validated sgRNAs. Single HEK293T clones were selected for high base editing efficiency. Clones were isolated by trypsinization of the initial cell population into individual cells. Cell density was evaluated by counting the cells with a hemocytometer and cells were diluted to approximately 0.13 cells/µl, equivalent to 20 cells per 150 µl. Serial dilutions were prepared and 150 µl of the diluted cell mixture were seeded into 96-well plates. Single clones were expanded and further examined for FNLS-BE3 expression and activity.

Editing of Cell Lines, Organoids and Mice

To induce CRISPR-mediated HDR editing, HEK293T cells were seeded at 50%-70% confluency into 24-well plates and reverse transfected with 0.25 µg of sgRNA and 0.25 µg of Cas9 expressing plasmid (Addgene #42230) with or without 0.5 µl of ssODN (40 µM) into 100 µl of DMEM without Fetalgro BGS and antibiotics. 3 µl of TransIT-293 (Mirus) were added to the DNA, mixed and incubated for 15 min at room temperature. Experiments involving i53 were done by adding 0.25 µg of i53 (Addgene #77939) to the transfection mixture. The gDNAs of cell populations and individual clones were recovered by resuspending the cell pellets in the Quick Extract DNA Extraction Solution (Epicentre), followed by incubation at 65° C. for 10 min and 95° C. for 5 min. The isolated gDNAs were diluted in $H_2O$, quantified using Nanodrop and stored at −20° C. or directly used in PCR reactions. In base editing experiments, we used cells constitutively expressing FNLS-BE3 or transfected with pCMV-BE3 (Addgene #73021) and sgRNAs, as described above. Empty plasmids (Addgene #100708) with no sgRNAs were used as controls. To determine the accuracy of the quantification of variant frequency by DTECT (FIG. 2G), STOP codons were introduced into SPRTN, SMARCAL1 and PIK3R1 genes using iSTOP, as previously described (Billon et al., 2017). To isolate the WT alleles, the locus was amplified by PCR and cloned into the pCR-Blunt II-TOPO vector (ThermoFisher Scientific). The STOP alleles were isolated by PCR amplification using gDNA that was partially edited as template. The PCR product was subsequently digested using restriction enzymes that specifically cleave the WT PCR alleles (i.e., PvuII for SPRTN, SfaNI for SMARCAL1 and TaqaI for PIK3R1). The digestion reaction was loaded on a 2% agarose gel and the undigested PCR products were column purified (Zymoclean #D4008). The purified products were subsequently cloned into the pCR-Blunt II-TOPO vector (ThermoFisher Scientific). Cloned WT and STOP PCR fragments were confirmed by Sanger sequencing and are shown in FIG. 10B. RFLP assays were conducted by digesting PCR amplicons of the edited genomic loci with enzymes that recognize restriction sites created or disrupted by editing of the targeted loci. Restriction digest products were run on 6% TBE polyacrylamide gels. Gels were run at 160 V in 1×TBE and stained for 5 min using SybrGold diluted in 1×TBE buffer. In prime editing experiments, 1 μg of pCMV-PE2 (Addgene #132775) was transfected into HEK293T cells along with 500 ng of control pegRNA (Addgene #132777) or pegRNA HEK3 insCTT (Addgene #132778). Three days after transfection, genomic DNA was recovered as above and the edited signature was identified with DTECT. Edited DLD1 (FANCF locus) and NIH/3T3 (Pik3ca and Apc loci) cell populations and mouse intestinal organoids (Pik3ca and Apc loci) were previously described (Zafra et al., 2018). Genomic DNA from the edited cell populations was used to quantify the editing efficiency by DTECT (FIG. 12A).

In order to introduce multiple variants into the BRCA1 and BRCA2 genes, HEK293T cells expressing FNLS-BE3 were seeded at 50%-70% confluency into 24-well plates and reverse transfected with 1 μg of sgRNA into 100 μl of DMEM without Fetalgro BGS and antibiotics. 3 μl of TransIT-293 (Mirus) were added to the DNA, mixed and incubated for 15 min at room temperature. The DNA transfection mix was added dropwise to the cells and incubated at 37° C. with 5% $CO_2$ for 4 days. Single clones were generated and the gDNAs of cell populations and individual clones were recovered as describe above. Genomic loci were Sanger sequenced by Eton Bioscience or Genewiz. Sanger sequencing data were analyzed using Serial cloner and viewed by Snapgene Viewer. The sequencing profiles shown in this manuscript were generated by SnapGene Viewer. Quantitative detection of the editing level using the AcuI-tagged amplicon was done blindly.

In vivo mouse editing was performed as previously described (Zafra et al., 2018). Briefly, eight week-old C57BL/6N mice (Charles River) were injected with 0.9% sterile sodium chloride solution containing 20 μg of pLenti-FNLS-P2A-Puro and 10 μg of sgRNA vector. The total injection volume corresponded to 20% of the individual mouse body weight and was injected into the lateral tail vein in 5-7 seconds. All animal experiments were authorized by the regional board of Karlsruhe, Germany.

Mouse Genotyping and Bone Marrow Transplantation

The generation of genetically engineered mice harboring the Brca1 S1598F and Bard1 S563F alleles was previously described (Billing et al., 2018; Shakya et al., 2011). Mouse genotyping was performed using DTECT on genomic DNA extracted from mouse tails. AcuI-tagging of the targeted loci was performed using 50 ng of gDNA (see DTECT protocol above). All primer sequences are listed in Table S1. Genotyping experiments were conducted blindly.

Competitive transplantation experiments were performed to assess chimerism of Jak2 V617F mutant cells in relation to wild-type support. Specifically, Mx1-Cre$^+$; CD45.2 Jak2$^{V617F/+}$ and Mx1Cre$^+$; CD45.1 wild-type mice were dosed with polyinosine-polycytosine (PIPC) 8 weeks prior to sacrifice to induce MPN in mutant mice. On day of sacrifice, dissected femurs and tibias were isolated and bone marrow flushed with a syringe into PBS. Red blood cells (RBCs) were lysed in ammonium chloride-potassium bicarbonate lysis buffer for 10 min on ice. $1.5 \times 10^6$ filtered whole donor Mx1-Cre$^+$; Jak2$^{V617F/+}$ bone marrow cells (CD45.2) were then mixed with wild-type $1.5 \times 10^6$ competitor bone marrow cells (CD45.1) and transplanted via tail vein injection into lethally irradiated (2×550 Rad) CD45.1 host mice. Mice were then monitored serially for the development of MPN based on blood counts and donor chimerism by retroorbital bleed draws using heparinized microhematocrit capillary tubes (ThermoFisher Scientific). After 3 consecutive hematocrits of >65%, mice were then sacrificed for peripheral blood fluorescence-activated cell sorting (FACS) analysis and DNA extraction. All animal procedures were conducted in accordance with the Guidelines for the Care and Use of Laboratory Animals and were approved by the Institutional Animal Care and Use Committees at Memorial Sloan Kettering Cancer Center. The conditional Mx1-Cre$^+$; Jak2$^{V617F/+}$ mice are all C57BL/6 background and have been previously described (Mullally et al., 2010). Automated peripheral blood counts were obtained using a ProCyte Dx (IDEXX Laboratories) according to the manufacturer's protocol. For surface flow cytometry of mouse peripheral blood, bone marrow, and spleen, RBCs were lysed and stained with monoclonal antibodies in PBS plus 1% BSA for 1 hour on ice. For flow cytometry of erythroid lineage, bone marrow or splenic cells were stained without RBC lysis. DAPI was used for live/dead cell analysis. Cell populations were analyzed using an LSR Fortessa (Becton Dickinson), and data were analyzed with FlowJo software (Tree Star). DNA extraction was performed using the QIAamp DNA Micro Kit (Qiagen) per manufacturer's protocol.

Analysis of ALL Patient Samples and PDXs

DNA samples from leukemic ALL blasts obtained at diagnosis and after relapse were provided by multiple institutions, as previously described (Oshima et al., 2016). Informed consent was obtained at study entry and samples were collected under the supervision of local Institutional Review Boards for participating institutions and analyzed under the supervision of the Columbia University Irving Medical Center Institutional Review Board. Research was conducted in compliance with ethical regulations. ALL patients received standard combination chemotherapy at diagnosis. Diagnosis and relapse samples were harvested from bone marrow. High molecular weight genomic DNA from matched diagnosis and relapse samples of ALL patients was extracted from patient leukemic blasts or from xenografts using the DNeasy Blood & Tissue Kit (Qiagen) or the AllPrep DNA/RNA Mini Kit (Qiagen). Primary human xenograft ALL cells were passaged and harvested from the spleens of NRG (NOD.Cg-ag1tm1MomIl2rgtm1WjI/SzJ, The Jackson Laboratory) mice. Whole exome sequencing was performed and analyzed as previously described (Oshima et al., 2016).

Vector Construction and Cloning sgRNAs were synthesized as complementary oligonucleotides (IDT) compatible with BbsI restriction sites located into the B52 plasmid (Addgene #100708). Oligonucleotides were designed as previously described (Billon et al., 2017). Cloned sgRNAs were verified by Sanger sequencing. Sequences of the sgRNAs are available in Table S1. ssODNs used in HDR experiments were synthesized as ultramer oligos (IDT) and their sequences are available in Table S1. To generate the FNLS-BE3-P2A-BlastR plasmid, the pLenti-FNLS-P2A-Puro plasmid (Addgene #110841) (Zafra et al., 2018) was modified by replacing the puromycin resistance gene with the blasticidin resistance gene. Briefly, the blasticidin resistance gene coding sequence was amplified by PCR and recombined using Gibson assembly into FNLS-BE3-P2A. The FNLS-BE3-P2A-BlastR sequence was verified by Sanger sequencing.

AcuI-Tagging Primer Design

The AcuI-tagging oligonucleotide enables the insertion of an AcuI motif (5'-CTGAAG-3') 14 bp away from a targeted dinucleotide. This motif is inserted as a hairpin in the middle of a sequence complementary to the targeted genomic locus. The AcuI-tagging oligonucleotide is 60 bp-long and contains a non-complementary handle sequence of 20-25 bp. Common handle sequences used are PB547 (5'-GATCCTC-TAGAGTCGACCTG-3') (SEQ ID NO: 1) or PB1072 (5'-GCAATTCCTCACGAGACCCGTCCTG-3') (SEQ ID NO: 3) (Table S1). The oligonucleotide sequence complementary to the targeted genomic locus plus the AcuI motif has the following sequence: 5'-N(20)CTGAAGN(14)-3' or 5'-N(15) CTGAAGN(14)-3', with "N" corresponding to A, T, G or C bases complementary to the targeted locus. Reverse primers used in AcuI-tagging reactions were designed by Primer 3 (http://bioinfo.ut.ee/primer3-0.4.0/) using the default parameters with the following changes: Mispriming library="HUMAN" for amplifying from human genomic DNA or Mispriming library="RODENT" for amplifying from mouse genomic DNA, Primer size "min=25, Opt=27, Max=30", Primer Tm "Min=57.0° C., Opt=60.0° C., Max=63.0° C.". Reverse primers are located >100 bp away from the targeted dinucleotides. All sequences of the primers used in this study are available in Table S1.

Adaptor Library Generation and Characterization

A set of 17 individual oligonucleotides constitutes the full adaptor library. This library contains: a) One constant oligonucleotide with the following sequence: 5'-CTGGGGC-ACGGGTAAGAAGCATTCTGTCTCTcttctaagaattcgagc-tcggtacccg-3' (SEQ ID NO: 230). The lowercase nucleotide sequence located at the 3'-end of the constant oligonucleotide (5'-cttctaagaattcgagctcggtacccg-3') (SEQ ID NO: 319) corresponds to the handle sequence used to detect the ligated products with either PB548 (5'-cgggtaccgagctcgaattc-3') (SEQ ID NO: 2) or PB1073 (5'-cgggtaccgagctcgaattct-tagaag-3') (SEQ ID NO: 4); b) 16 variable oligonucleotides that contain a sequence complementary to the constant oligonucleotide plus one of 16 different dinucleotides at their 3'-end. The variable oligonucleotides have the following sequence: 5'-cgggtaccgagctcgaattcttagaagAGAGACA-GAATGCTTCTTACCCGTGCCCCAGNN-3'. NN, with N=A, C, G or T (SEQ ID NOs: 231-246), corresponds to the dinucleotide that is different for each of the 16 oligos. The adaptor sequences are available in Table S1. The constant oligonucleotide and each variable oligonucleotide were resuspended at a concentration of 100 µM in H$_2$O. 2.5 µl of constant oligonucleotide and 2.5 µl of each variable oligonucleotide were mixed with 1× ligase buffer (ThermoFisher Scientific) and water in a 20 µl reaction. The reactions were placed in a thermocycler and oligonucleotides were annealed by incubating them for 5 min at 95° C., followed by a gradual temperature decrease from 95° C. to 15° C. After annealing was completed, 100 µl of water were added to dilute the adaptors in a 120 µl final volume. Adaptors were frozen and stored at −20° C.

The adaptor library was tested at two independent loci, as shown in FIG. 9C. In this assay, AcuI-tagging oligonucleotides targeting the ampicillin resistance gene were designed following the rules detailed above (Table S1). First, we linearized the pUC19 plasmid as follows: 1.5 µg of pUC19, 1× CutSmart Buffer (NEB) and 0.75 µl of BamHI-HF were mixed in a 30 µl reaction and incubated for 2 hours at 37° C. The digested plasmid was subsequently purified on column (Zymoclean #D4008) and used as a template in PCR reactions with each AcuI-tagging primer and a constant reverse primer (5'-CCAATGCTTAATCAGTGAGG-3') (SEQ ID NO: 320) located at the 3'-side of the ampicillin resistance gene. The PCRs were performed in a 25 µl reaction containing: 1 µM forward and reverse primers, 0.1 mM dNTP (NEB #N0447L), 1× Q5 buffer (NEB), 20 ng of digested pUC19, 1 unit of Q5 polymerase (NEB) and water. The PCR program used was the following: 95° C. for 1 min, 40 cycles of 95° C. for 10 s, 58° C. for 10 s, 72° C. for 45 s and a final amplification step of 1 min at 72° C. PCR reactions were loaded on a 2% agarose gel, extracted from gel and purified on column (Zymoclean #D4008). Finally, the DTECT protocol was applied as described below. Briefly, 0.5 pmol of AcuI-tagging PCR products were digested by AcuI for 30 min at 37° C. 10 µl of the digested products were purified with 18 µl of solid phase reversible immobilization magnetic beads (Beckman Coulter #A63881). 20 µl of supernatant (unbound fraction) were recovered and 0.5 µl of this supernatant were ligated using complementary and negative control adaptors for 1 hour at 25° C., followed by T4 ligase inactivation for 10 min at 65° C. The complementary and negative control adaptors used in FIG. 9C are the following: AA #1 (Specific adaptor: TT, Non-specific adaptor: CC), AA #2 (TT, CC), AC #1 (GT, AC), AC #2 (GT, AA), AG #1 (CT, GA), AG #2 (CT, GA), AT #1 (AT, GG), AT #2 (AT, GG), CA #1 (TG, CA), CA #2 (TG, CA), CC #1 (GG, CC), CC #2 (GG, CC), CG #1 (CG, AA), CG #2 (CG, AA), CT #1 (AG, TT), CT #2 (AG, TT), GA #1 (TC, GA), GA #2 (TC, GA), GC #1 (GC, TT), GC #2 (GC, TT), GG #1 (CC, TT), GG #2 (CC, TT), GT #1 (AC, TG), GT #2 (AC, TG), TA #1 (TA, GG), TA #2 (TA, GG), TC #1 (GA, CT), TC #2 (GA, CT), TG #1 (CA, TG), TG #2 (CA, TG), TT #1 (AA, GG) and TT #2 (AA, GG). The ligated products were subsequently detected by PCR amplification using the primers PB547 (5'-gatcctctagagtcgacctg-3') (SEQ ID NO: 1) and PB1073 (5'-cgggtaccgagctcgaattct-tagaag-3') (SEQ ID NO: 4). All primer sequences are listed in Table S1.

The measurement of the dinucleotide capture efficiency of each adaptor (FIGS. 2J-2K) was determined by ligating the 16 different adaptors to annealed oligonucleotides containing complementary dinucleotides. To mimic the 5' phosphorylation induced by AcuI in DTECT experiments, the reverse oligonucleotide (PB1449: 5'-gtagttcgccagttCT-TCAGaatagtttgcgca CAGGACGGGTCTCGTGAGGAAT-TGC-3') (SEQ ID NO: 91) was phosphorylated with PNK (NEB). The phosphorylation reaction was conducted as follows: 5 µl of PB1449 (100 µM), 4 µl of 5× ligase buffer, 0.5 µl of PNK in a 20 µl reaction. Phosphorylation was obtained upon incubation for 1 hour at 37° C., followed by heat inactivation of PNK for 20 min at 65° C. After incubation, the phosphorylated oligonucleotide PB1449 was annealed to 16 complementary oligonucleotides with the following sequence: 5'-GCAATTCCTCACGAGACCCG-TCCTGTGCGCAAACTAT TCTGAAGAACTGGC-GAACTACNN-3' (SEQ ID NOs: 231-246). The two Ns indicate the dinucleotide that is different for each of the 16 oligos, with N=A, C, G or T. In the annealing reaction, 40 µl of 5× ligase buffer and 130 µl of H$_2$O were added to the phosphorylation reaction. 9.5 µl of this mix were used for annealing with 0.5 µl of each of the above 16 oligos (50 µM). Annealing, which was performed as described above for the library of adaptors, resulted in a 5'-phosphorylated double-stranded DNA with an overhang of 2 nucleotides, mimicking the product of AcuI digestion. The ligation between the adaptors and the phosphorylated products was performed as follows: 1 µl of annealed oligonucleotides, 2 µl of T4 ligase buffer, 0.5 µl of T4 ligase and 0.5 µl of adaptors in a 10 µl reaction. The ligation reaction was incubated for 1 hour at 25° C. and 10 min at 65° C. Detection was performed using qPCR as described below in the DTECT protocol.

The assay performed to measure the efficiency of DNA ligation (FIG. 10F) was conducted in a master mix reaction equivalent to 5 µl per time point as follows: 0.5 µl of AcuI digested products, 1 µl of T4 ligase buffer and 0.5 µl of adaptors with or without 0.5 µl of T4 ligase. The reactions were incubated at 25° C. After 5 min, 5 µl were taken from the reaction and the T4 ligase was added for 10 min at 65° C. 1 hour after the start of the ligation reaction, 5 µl were additionally taken from the reaction and heat inactivated. The rest of the reaction was incubated overnight for 16 hours and heat inactivated. The amount of products captured was determined by qPCR as described below.

To calculate the frequency of non-specific dinucleotide capture shown in FIG. 10E, AcuI-generated fragments of WT SMARCAL1, SPRTN and PIK3R1 amplicons (obtained as described below) were ligated to each of the 16 library adaptors under the adaptor ligation conditions described above. The frequency of non-specific dinucleotide capture for all the adaptors non-complementary to the SMARCAL1, SPRTN and PIK3R1 dinucleotide signatures was calculated by qPCR analysis, as described below. Adaptors complementary to +1 and −1 AcuI-dependent slippage events were excluded from the analysis.

DTECT Protocol

Figure 1A:
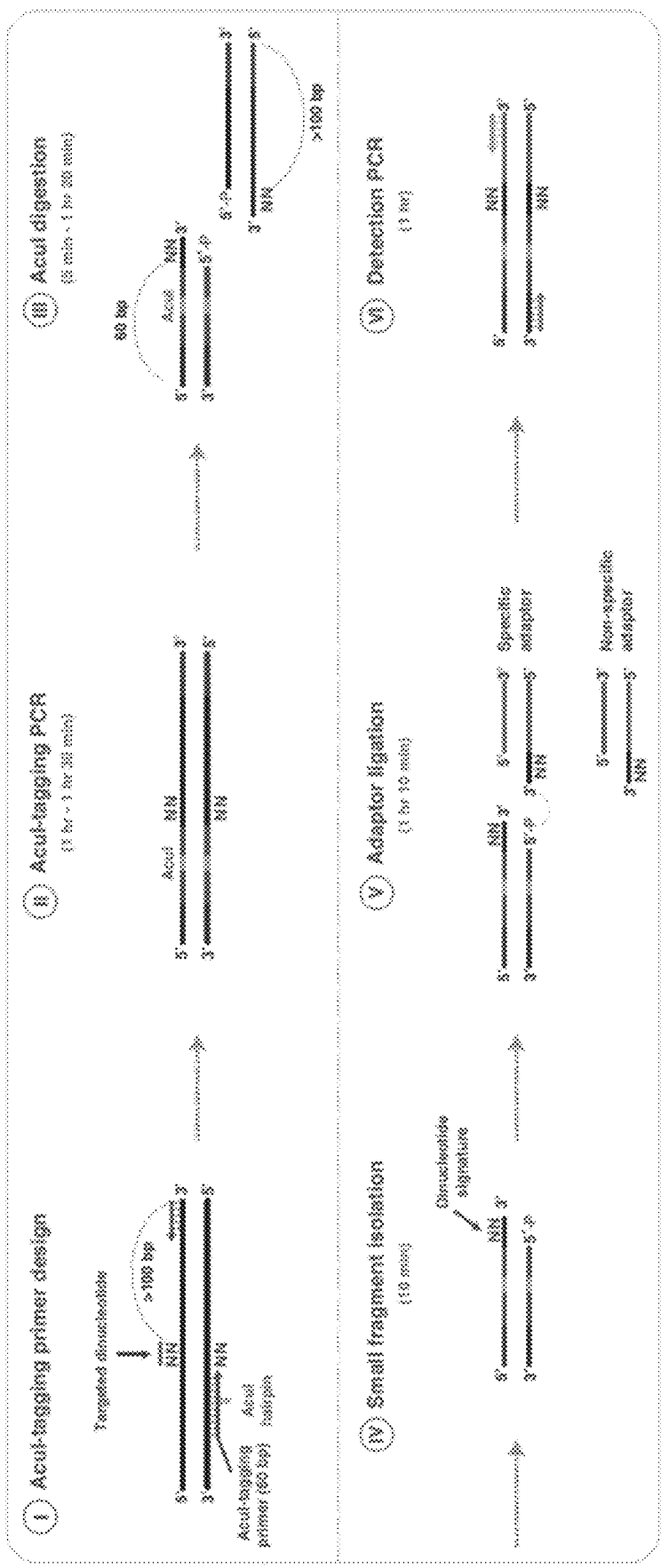

The DTECT protocol consists of 6 steps (I-VI, FIG. 1A). I) Design of the AcuI-tagging primer, as described above. II) Amplification of the genomic locus of interest using the AcuI-tagging primer. The genomic DNA (gDNA) is prepared using the Quick Extract Solution (Epicentre) by incubating the cells at 65° C. for 10 min and 95° C. for 5 min. The genomic DNA is quantified by Nanodrop, diluted to 200 ng/µl in $H_2O$ and stored at −20° C. or immediately used in PCR reactions. PCRs were performed in a 25 µl or 50 µl solution containing: 1 µM forward and reverse primers, 0.1 mM dNTP (NEB #N0447L), 1× Q5 buffer (NEB), 10-200 ng of gDNA, 1 unit of Q5 polymerase (NEB) and water. PCR reactions were conducted as follows: 95° C. for 30 s; 40 cycles of 95° C. for 10 s, 58° C. for 10 s, 72° C. for 45 s; and final amplification at 72° C. for 1 min. When the AcuI-tagging PCR did not work on gDNA (<5% of the cases), a PCR using standard locus-specific primers was performed to amplify the targeted locus and the AcuI-tagging PCR was conducted using this amplicon as template DNA. PCR products were loaded on a 2% agarose gel and run in TAE buffer. PCR products were extracted from gel and column purified (Zymo Research #D4008) and the purified products were subsequently quantified using Nanodrop. III) Digestion of the AcuI-tagged genomic amplicon with AcuI. The purified PCR products were digested by 0.25 µl AcuI (NEB #0641L) in a 20 µl reaction containing 1× CutSmart Buffer (NEB) supplemented with 40 µM S-adenosylmethionine (SAM) and 100 ng of purified PCR product. The reaction was incubated for 1 hour at 37° C. with heat inactivation at 65° C. for 20 min. IV) Isolation of the AcuI-digested genomic amplicon by solid phase reversible immobilization (SPRI). 10 µl of the digestion reaction were subsequently mixed with 18 µl of Agencourt AMPure XP magnetic beads (Beckman Coulter #A63881) by pipetting up and down the beads 10 times (volume ratio of DNA: beads=1:1.8) and then incubated at room temperature for 5 min. This procedure resulted in the binding of the larger digestion fragment (>100 bp) to the beads, while the smaller digested fragment (60 bp) remained in the supernatant. After incubation, the supernatant was isolated using a magnetic rack. 20 µl of the supernatant were recovered, diluted in 40 µl of $H_2O$ and stored at −20° C. or immediately used for capture with DNA adaptors. V) Capture of the digested 60 bp-long products using DNA adaptors. The purified 60 bp-long DNA fragments were ligated to DNA adaptors generated as described above. The adaptors and the purified products were ligated in the following reaction: 6.5 µl of water, 2 µl of 5× ligase buffer (ThermoFisher Scientific), 0.5 µl of T4 ligase (ThermoFisher Scientific), 0.5 µl of adaptors and 0.5 µl of purified DNA product. The ligation reaction was performed for 1 hour at 25° C. in a thermocycler, followed by inactivation of the T4 ligase for 10 min at 65° C. The ligated products were stored at −20° C. or used directly for detection of the captured material. VI) Analytical or quantitative detection of the captured DNA products by PCR amplification. For analytical detection, the amplification of the captured material was performed by PCR in a 12.5 or 25 µl reaction volume containing 0.5 µM forward and reverse primers, 0.05 mM dNTP (NEB #N0447L), 1× Q5 buffer (NEB), 0.5-1 µl of ligated product, 0.1-0.2 µl of Q5 polymerase (NEB), 0.5-1 µl ligation reaction and water. PCR primers (PB1072 and PB1073) contained sequences complementary to the adaptor and handle (see above). The PCR program used was the following: 95° C. for 1 min, and different number of cycles (indicated in each figure legend) of 95° C. for 10 s, 65° C. for 5 s, 72° C. for 7 s. Detection of low abundant genomic variants (≤1% frequency) was generally obtained with 23-25 PCR cycles, while detection of greater amounts of edited products was achieved with 17-22 PCR cycles. 5 µl of the PCR reactions were incubated with SYBR Gold (Thermofisher Scientific #S-11494), loaded on a 2% agarose gel and run in 1×TAE buffer until the DNA was separated. Gels were developed using LI-COR Odyssey. qPCR was performed using QuantStudio 3 (Applied Biosystems). qPCR reactions were performed as follows: 5 µl of 2×SYBR Gold master mix (ThermoFisher Scientific #4367659), 0.1 µl of forward and reverse primers (PB1072 and PB1073, 100 µM) and 1 µl of ligated products (diluted 1:100 in $H_2O$) in a 10 µl reaction. The PCR program used in the qPCR reaction was the following: 95° C. for 10 s and 40 cycles of 60° C. 30 s, 95° C. 15 s. Quantification of the frequency of genomic variants was conducted as described below (Quantification and Statistical Analysis section).

Next-Generation Sequencing

Samples for NGS were prepared by amplifying the edited regions of interest by PCR. Samples were sequenced by the Genome Sciences Facility at The Pennsylvania State College of Medicine or by Genewiz and the results were analyzed by Genewiz, or by using an R-based script of the Ciccia laboratory or CRISPResso2 (Clement et al., 2019). To ensure that no biases were introduced during DTECT assays, the AcuI-tagging amplicons for the BRCA1 and BRCA2 mutant samples were sequenced by NGS and analyzed using an R-based script. In this analysis, 7 sequences with >6000 reads were filtered out from the analysis due to incorrect sequence. The editing frequency from the NGS results were determined using the formula: ((Number of reads for the edited dinucleotide)/(total number of reads))× 100. Oligonucleotides used for PCR amplifications, Illumina sequencing adaptors and indexes are listed in Table S1.

Quantification and Statistical Analysis

Technical duplicates of each sample were performed in each qPCR reaction. A standard curve to determine the concentration of the captured material was generated using predefined concentrations of a DTECT ligation product (FIG. 1A, step V) cloned into the pCR-Blunt II-TOPO vector (ThermoFisher Scientific; B650 plasmid, Addgene #139333) and oligos PB1072 and PB1073 (Table S1). The calculated standard curve corresponds to a linear curve with the following parameters: y=−3.3245x+7.5504 and $R^2$=0.99819. Quantification of the frequency of genomic variants was determined by calculating the mean Ct score (Mean Ct) of the two technical duplicates for each sample. The concentration of the captured material for each sample was determined using the following formula: Concentration=10^((Mean Ct−7.5504)/−3.3245). The relative abundance between WT and mutant signatures was determined as follows: $Frequency^{Mutant}=(Concentration^{Mutant}/(Concentration^{Mutant}+Concentration^{WT}))\times 100$ and $Frequency^{WT}=(Concentration^{WT}/(Concentration^{Mutant}+Concentration^{WT}))\times 100$.

Data and Code Availability

R-based scripts of the Ciccia laboratory for analysis of NGS reads and ClinVar datasets are available upon request. Raw NGS reads of edited DLD1 and NIH/3T3 cells, organoids and liver samples are available under accession SRP151111 in the Sequence Read Archive. NGS reads have been deposited into the NCBI database and are and are accessible as BioProject #PRJNA603357. All uncropped gels, raw qPCR data and Sanger sequencing reads are available in Mendeley (https://data.mendeley.com/datasets/gtkk6sthtw/draft?a=ca72630e-56eb-4e29-bcdb-158b2c-7d4123).

| KEY RESOURCES TABLE | | |
|---|---|---|
| REAGENT or RESOURCE | SOURCE | IDENTIFIER |
| Bacterial and Virus Strains | | |
| Subcloning Efficiency DH5α | ThermoFisher Scientific | 1 8265-017 |
| Chemicals, Peptides, and Recombinant Proteins | | |
| Q5 High-Fidelity DNA polymerase | NEB | M0491L |
| T4 DNA ligase | ThermoFisher Scientific | 15224017 |
| AcuI | NEB | R0641L |
| rSAP | NEB | M0371L |
| SybrGold (for gel staining) | ThermoFisher Scientific | S-11494 |
| SybrGold (for qPCR) | ThermoFisher Scientific | 4367659 |
| BamHI-HF | NEB | R3136S |
| dNTPs | NEB | N0447L |
| T4 Polynucleotide Kinase | NEB | M0201S |
| Critical Commercial Assays | | |
| Agencourt AMPure XP magnetic beads | Beckman Coulter | A63881 |
| Zymoclean gel DNA recovery kit | Zymo Research | D4008 |
| Quick Extract DNA Extraction Solution | Epicentre | QE09050 |
| Zero BLUNT II TOPO PCR Cloning kit | ThermoFisher Scientific | 450245 |
| Deposited Data | | |
| Unprocessed images of gels | This disclosure, Mendeley Data | Raw gel images |
| Raw Sanger sequencing files | This disclosure, Mendeley Data | Sequences of BRCA1-2 edited cells; Repeated sequences |
| Raw NGS sequencing files | This disclosure, NCBI | BioProject # PRJNA603357 |
| Raw and processed qPCR data | This disclosure, Mendeley Data | Raw and processed qPCR data |
| Raw and processed DTECT, ICE, EditR and NGS data | This disclosure, Mendeley Data | Quantification of BRCA1-2 variants by DTECT, ICE, EditR and NGS |
| Experimental Models: Cell Lines | | |
| Human: HEK293T | ATCC | CRL-11268 |
| Human: DLD1 | ATCC | CCL-221 |
| Mouse: NIH/3T3 | ATCC | CRL-1658 |
| Experimental Models: Organisms/Strains | | |
| Mouse: C57BL/6N | Charles River | C57BL/6NCrl |
| Mouse: Brca1$^{S1598F/+}$ | Shakya et al, 2011 | N/A |
| Mouse: Bard1$^{S563F/+}$ | Billing et al, 2018 | N/A |
| Mouse: Mx1Cre$^+$; CD45.1 | Mullally et al, 2010 | N/A |

KEY RESOURCES TABLE

| REAGENT or RESOURCE | SOURCE | IDENTIFIER |
|---|---|---|
| Mouse: Mx1-Cre+; CD45.2 Jak2$^{V617F/+}$ | Mullally et al, 2010 | N/A |
| Mouse: NRG | The Jackson Laboratory | 007799 |
| *Oligonucleotides* | | |
| Primers for PCR | This disclosure | Table S1 |
| Oligonucleotides for sgRNA cloning | This disclosure | Table S1 |
| ssODNs (for HDR) | This disclosure | Table S1 |
| Oligonucleotides for adaptors | This disclosure | Table S1 |
| *Recombinant DNA* | | |
| Plasmid: B52 (containing 2 empty sgRNAs-expressing cassettes) | Addgene | 100708 |
| pCMV-PE2 | Addgene | 132775 |
| pCMV-BE3 | Addgene | 73021 |
| DTECT - Plasmid for standard curve | This disclosure, Addgene | 139333 |
| pTOPO-SPRTN WT | This disclosure | N/A |
| pTOPO-SPRTN STOP | This disclosure | N/A |
| pTOPO-SMARCAL1 WT | This disclosure | N/A |
| pTOPO-SMARCAL1 STOP | This disclosure | N/A |
| pTOPO-PIK3R1 WT | This disclosure | N/A |
| pTOPO-PIK3R1 STOP | This disclosure | N/A |
| pX330-U6-Chimeric_BB-CBh-hSpCas9 | Addgene | 42230 |
| pCDNA3-Flag::UbvG08 I44A, deltaGG | Addgene | 74939 |
| pU6-Sp-pegRNA-HEK3-CTT_ins | Addgene | 132778 |
| Plasmids expressing sgRNAs for base editing of FANCD2, BRCA1 and BRCA2 | This disclosure, Addgene | 139321-139332, and 139511 |
| *Software and Algorithms* | | |
| R Studio Desktop IDE 1.0.143 | RStudio | https://www.rstudio.com |
| Bioconductor R packages | Bioconductor | https://www.bioconductor.org |
| R 3.4.1 | The R project for statistical computing | https://www.r-project.org |
| *Other* | | |
| ClinVar database | NCBI | https://www.ncbi.nlm.nih.gov/clinvar/ |
| Li-COR Odyssey | N/A | https://www.licor.com/bio/products/imaging_systems/odyssey |
| q-PCR QuantStudio 3 | Applied Biosystems | N/A |

Example 2

Design of DTECT, a Detection Method Based on the Capture of Dinucleotide Signatures In our detection method, we take advantage of the property of type IIS restriction enzymes to generate single-stranded DNA overhangs at a specific distance from their recognition motif. Based on the above property, we hypothesized that single-stranded DNA overhangs generated by digestion of genomic DNA sequences with type IIS restriction enzymes could be captured and identified using DNA adaptors containing overhangs complementary to the exposed DNA signatures (FIG. 1A). To identify type IIS enzymes with efficient and accurate endonuclease activity, we analyzed the properties of known type IIS enzymes. Restriction enzymes optimal for our method exhibit the following characteristics: a) they cleave far from their recognition motif, thus enabling the incorporation of non-complementary type IIS recognition motifs into PCR primers without disrupting genomic DNA amplification (FIGS. 1A and 8A); b) they bind a single recognition motif (Bath et al., 2002) (FIG. 8A); and c) they possess highly specific endonuclease activity, therefore generating a limited number of cleavage byproducts due to slippage activity (Lundin et al., 2015) (FIG. 8B). Among the >40 known type IIS endonucleases, only 6 enzymes cleave at a distance ≥14 bp from their recognition motif (AcuI, BpmI, BpuEI, BsgI, MmeI and NmeAIII) (FIG. 8C). Of those enzymes, only AcuI and BpuEI have a single recognition motif, and AcuI exhibits the lowest slippage activity of the two enzymes (slippage byproducts: AcuI, 1.1%; BpuEI, 41.4%) (Lundin et al., 2015). In particular, upon DNA cleavage AcuI exposes a dinucleotide signature located 15/16 nucleotides away from its recognition site (FIG. 8D). Based on the above considerations, AcuI is the most suitable restriction enzyme for our detection method.

Figure 1B:
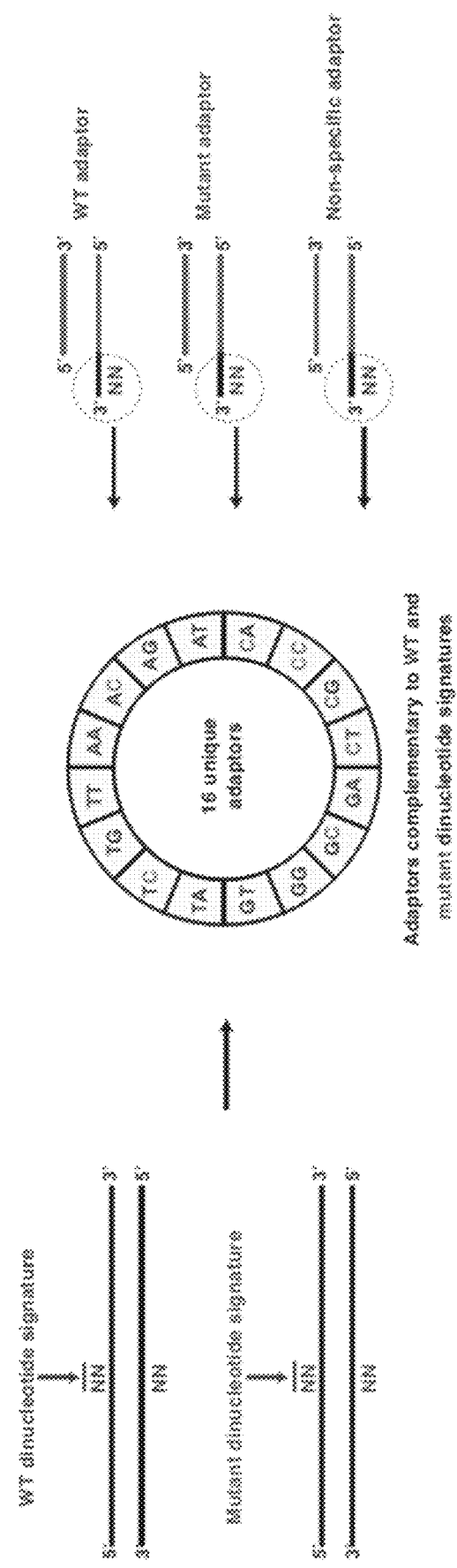
Figure 1C:
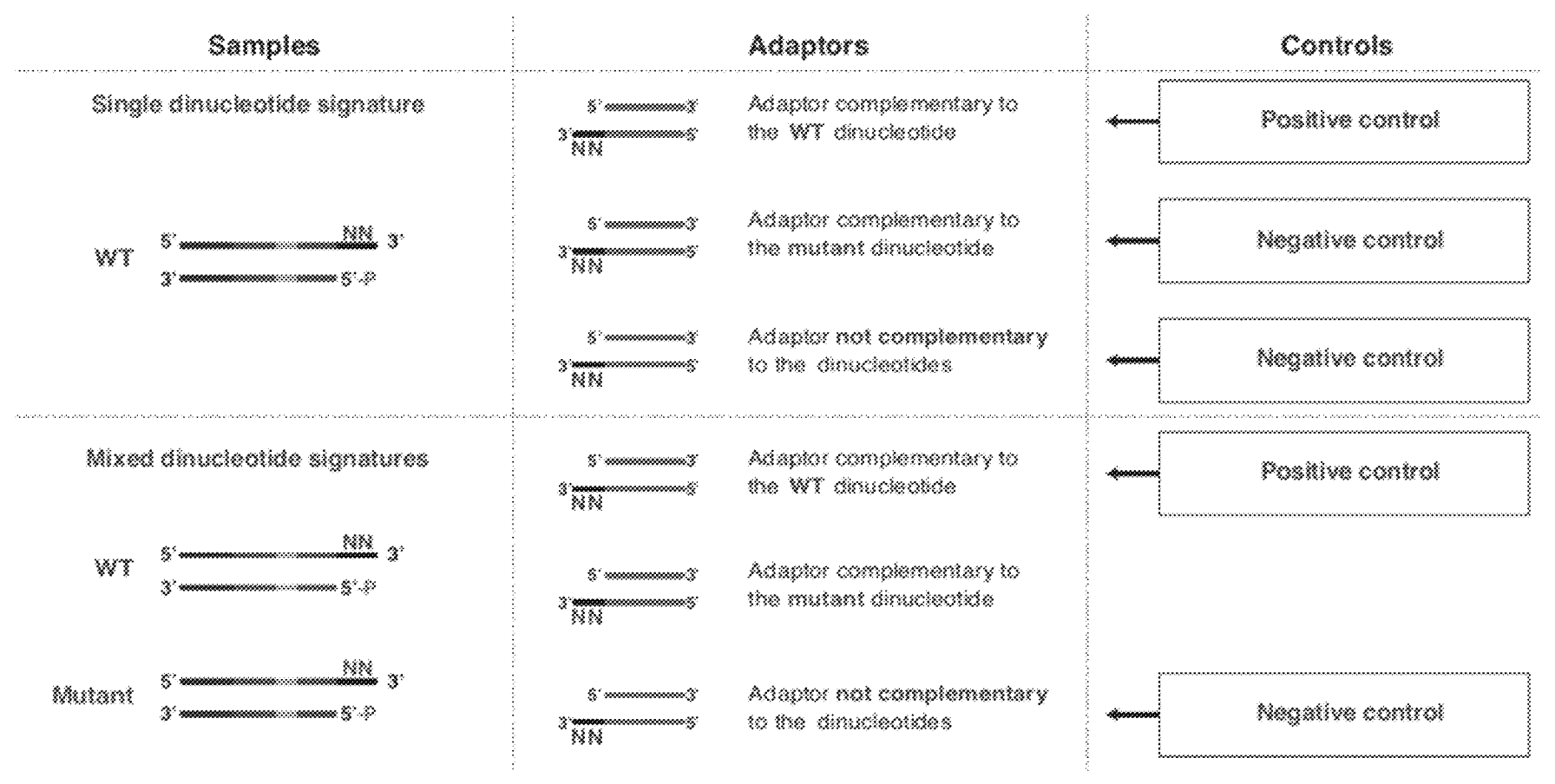

In our approach, the genomic locus of interest is PCR-amplified using a locus-specific DNA primer (red) and a DNA oligonucleotide (AcuI-tagging primer) containing two regions of complementarity to the genomic locus (purple) interrupted by an AcuI recognition site (AcuI hairpin, green) positioned 14 bp upstream of a dinucleotide of interest (FIG. 1A, steps I and II). Tagging of the genomic amplicon with an AcuI motif allows AcuI-mediated digestion of the sequence of interest on the 3'-side of the targeted dinucleotide. Upon AcuI-mediated digestion, the signature of the targeted dinucleotide becomes exposed (FIG. 1A, step III). To proceed with a single DNA fragment containing the targeted dinucleotide, the larger DNA fragment (>100 bp) resulting from AcuI-mediated digestion is removed using solid phase reversible immobilization (SPRI) beads (FIG. 1A, step IV) and the smaller DNA fragment (60 bp) containing the targeted dinucleotide is ligated to an adaptor with a 3'-overhang complementary to the exposed signature (FIG. 1A, step V). The ligated DNA products are subsequently detected by analytical or quantitative PCR (qPCR) (FIG. 1A, step VI). This method, which we named DTECT (Dinucleotide signaTurE CapTure), can be completed within 4-5 hours (FIG. 1A). A common set of DNA primers that anneal to constant regions in the AcuI-digested fragments (blue) and the ligated adaptors (brown) is utilized in all DTECT experiments (FIG. 1A, step VI), avoiding locus-specific amplification bias and variability in qPCR efficiency among distinct sets of samples. Considering the total number of 16 unique dinucleotides ($2^4$), a library of 16 distinct adaptors is sufficient to capture all dinucleotide signatures that can be generated by AcuI (FIG. 1B). Given the possible use of positive and negative controls to determine the efficiency and specificity of dinucleotide capture (FIG. 1C), DTECT provides a highly controlled assessment of successful and specific capture of dinucleotide signatures Example 3

DTECT Efficiently Captures Dinucleotide Signatures Generated by AcuI-Mediated Digestion To demonstrate the feasibility of DTECT, we designed two AcuI-tagging DNA primers flanking four adjacent bases (5'-TTGG-3') on opposite DNA strands (TT and CC signatures, blue) (FIG. 2A). Upon PCR amplification using AcuI-tagging primers and locus-specific DNA primers, the PCR amplicons were digested and ligated to adaptors with either complementary or non-specific 3'-overhangs (GG or AA). Detection of the ligated products by PCR, as described above, revealed that the GG and AA adaptors specifically captured the DNA fragments containing the CC and TT dinucleotides, respectively (FIG. 2B). Sanger sequencing confirmed that the amplicons of the ligated DNA products had the expected genomic sequence (purple) adjacent to the AcuI motif (green) and the GG or AA adaptors (brown) (FIGS. 9A-9B). Importantly, robust amplification of captured DNA products was observed only upon 1) capture of the AcuI-digested products with complementary adaptors (FIG. 2B), 2) AcuI-mediated cutting and generation of 5'-phosphorylated DNA fragments (FIGS. 2C-2D), and 3) DNA ligation by the T4 DNA ligase (FIG. 2D). We additionally showed that each individual DNA base can be identified by designing 4 independent AcuI-tagging primers (2 on each DNA strand), thus enabling the capture of 4 distinct signatures per genomic DNA base (FIGS. 2E-2F). This DTECT feature allows flexible AcuI-mediated cleavage of genomic DNA amplicons containing targeted DNA sequences. In additional studies, we confirmed that each of the 16 possible dinucleotide signatures generated by AcuI at two independent target sites can be efficiently captured using DNA adaptors containing complementary DNA overhangs (FIG. 9C). Together, these studies establish DTECT as a rapid and efficient method to identify DNA bases through the capture of AcuI-induced dinucleotide signatures using a common and unique set of adaptors.

Example 4

DTECT Enables Specific and Sensitive Quantification of DNA Variants

Figure 2J:
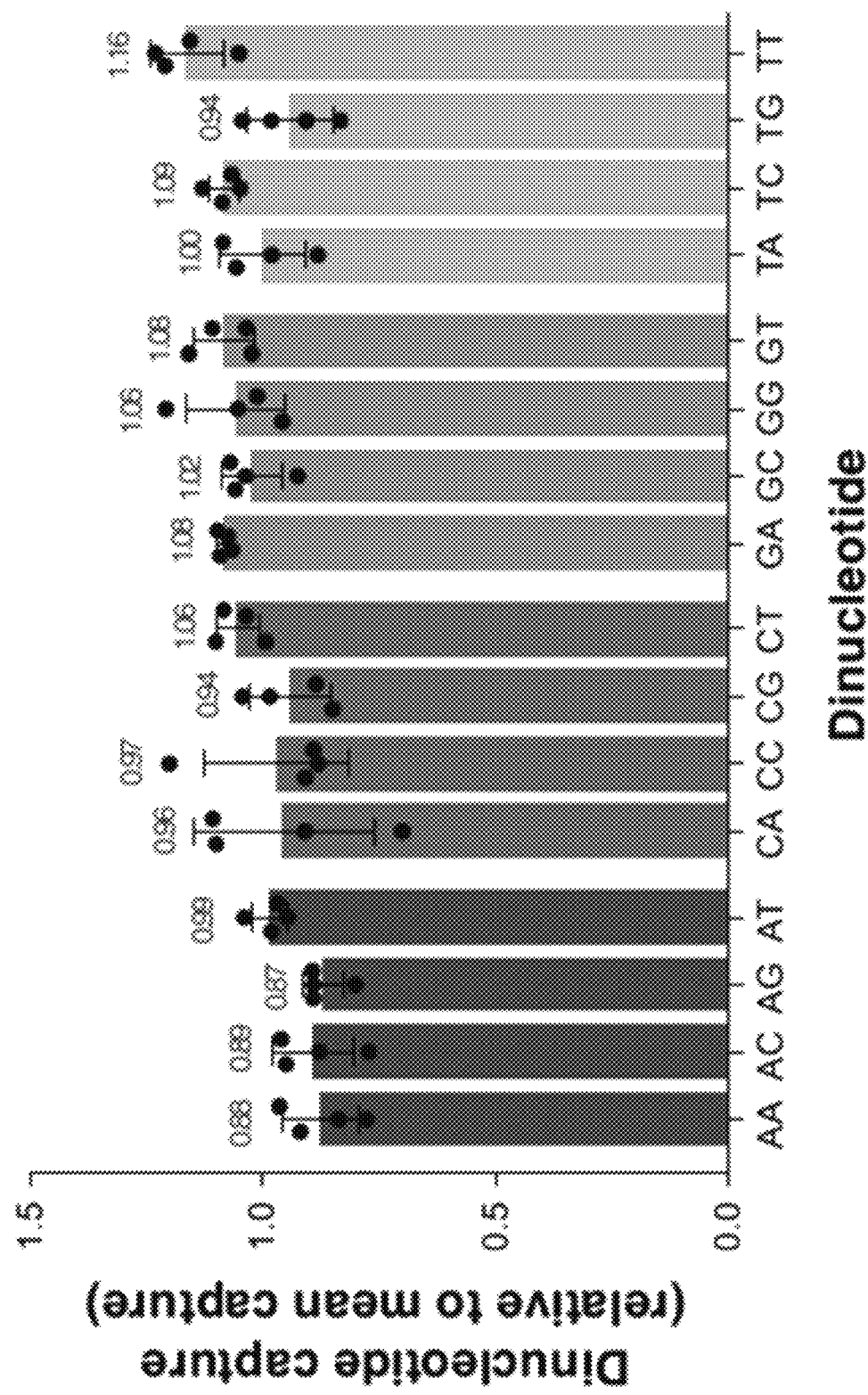
Figure 2K:
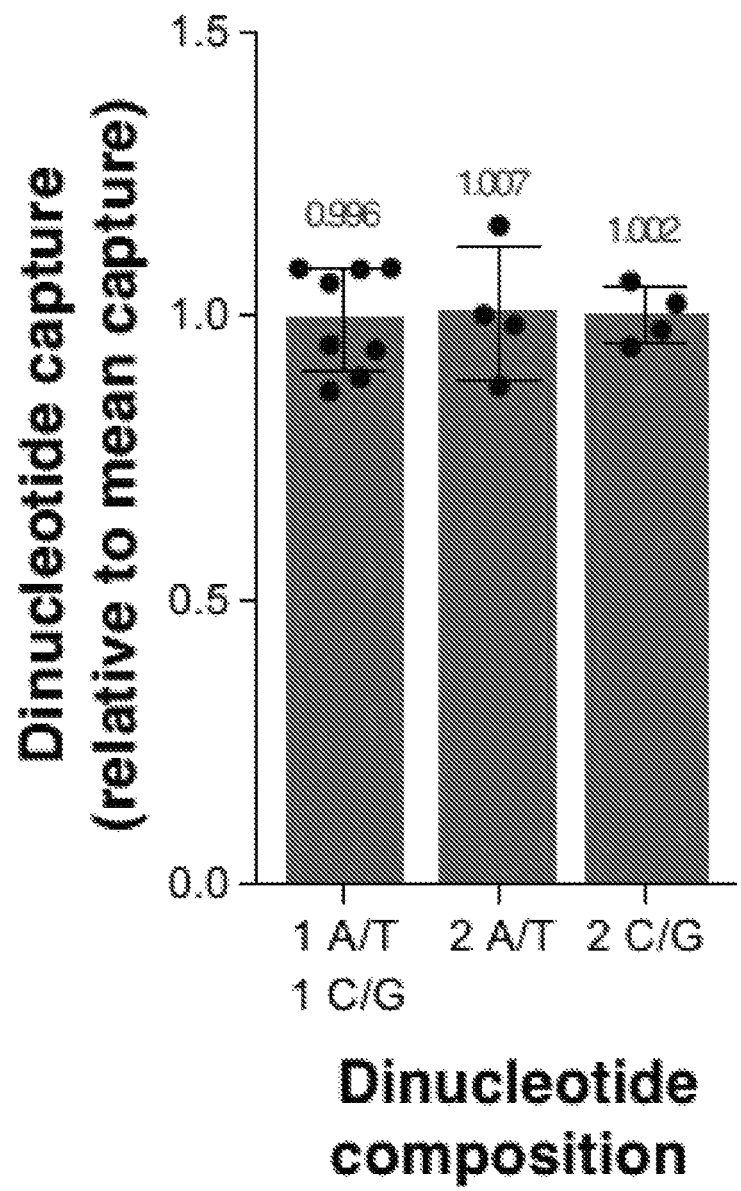

Next, we examined whether DTECT can determine the relative abundance of DNA variants with distinct DNA signatures, including low abundance DNA variants. To this end, we transfected HEK293T cells with sgRNAs that introduce nonsense mutations into the SPRTN, PIK3R1 and SMARCAL1 genes using iSTOP, a CRISPR-mediated base editing approach that creates STOP codons within genes of interest (Billon et al., 2017) (FIG. 10A). We then cloned both WT and mutant alleles, which differ by a single base change (C→T) (FIG. 10B), and subjected them to PCR amplification using a locus-specific DNA primer and an AcuI-tagging primer flanking the iSTOP-targeted DNA base (FIG. 10C). The WT and edited PCR products were then mixed at different ratios (WT- STOP allele=100-0, 99-1, 90-10, 75-25, 50-50, 25-75 or 10-90) and digested with AcuI. The resulting DNA fragments were then captured using adaptors complementary to WT (green) and STOP (purple) dinucleotide signatures (FIG. 10A). Remarkably, qPCR analysis of the captured DNA fragments accurately determined the relative abundance of the WT and STOP alleles at the three loci indicated above (FIG. 2G), demonstrating that DTECT can estimate the frequency of dinucleotide signatures in a mixed population with high precision, including variants with low abundance (1%) (FIG. 2G). Low abundance STOP variants in SPRTN and PIK3R1 were also detectable by analytical PCR (FIGS. 2H-2I and 10C-10D), confirming the high sensitivity and accuracy of DTECT. Importantly, direct comparison of the 16 DTECT adaptors revealed comparable efficiency in the capture of oligonucleotides containing complementary dinucleotide signatures (FIGS. 2J-2K). In addition, all adaptors exhibited low levels of non-specific capture background (mean=0.325%, ranging from 0.16% to 0.876%) (FIG. 10E). The above observations indicate that the adaptor ligation is conducted under optimal conditions, as confirmed by kinetic analysis of the adaptor ligation reaction (FIG. 10F). Together, these findings demonstrate that DTECT captures dinucleotide variants and quantifies their relative abundance with high specificity and sensitivity.

Example 5

DTECT Accurately Identifies Genomic Changes Introduced by CRISPR-Dependent HDR, Base Editing and Prime Editing in Mammalian Cells To examine the ability of DTECT to identify precise genomic changes introduced into mammalian cell populations, we utilized CRISPR-mediated HDR for generating various types of disease-related mutations using single-stranded oligodeoxynucleotides (ssODNs), including a cancer-associated frameshift mutation in TP53 (i.e., R209fs*6), a missense mutation in HBB (i.e., G6V) that causes sickle cell anemia, a small tandem duplication in BRCA2 (dupA-GAAGAT) identified in breast cancer, and small insertions into JAK2 and EMX1 (Paulsen et al., 2017), two genes associated with myeloproliferative disorders and Kallmann syndrome, respectively. Three days after co-transfection of Cas9 with site-specific sgRNAs and ssODNs into HEK293T cells, we harvested the cellular genomic DNA and utilized DTECT to determine by analytical and quantitative PCR whether the desired changes were incorporated into the targeted chromosomal loci (FIG. 3A). For comparison, a restriction fragment length polymorphism (RFLP) assay that monitors restriction sites disrupted or created by the above mutations in the targeted genomic loci was conducted in parallel. In these experiments, DTECT readily captured the specific signature of the mutant variants (FIGS. 3B and 11A-11C), while the RFLP assay either failed to detect or weakly detected the same mutant variants (FIGS. 11F-11H). In addition, DTECT was able to discern the HDR stimulatory effect induced by i53 (FIGS. 3B and 11A-11B), a genetically-encoded 53BP1 inhibitor that was previously shown to increase the frequency of HDR events (Canny et al., 2018), indicating that DTECT can be employed to compare the editing levels between distinct experimental conditions. Importantly, DTECT also clearly determined which mutations failed to be incorporated by the HDR machinery (e.g., BRCA2 dupAGAAGAT), as confirmed by NGS analysis (FIGS. 11D-11E). Next, to determine whether DTECT can identify precise genomic changes introduced by CRISPR-mediated base editing in mammalian cell populations, we used a cytidine base editor to install nonsense mutations into the Fanconi anemia-associated genes FANCD2, FANCM and SLX4, the DNA replication and circadian clock gene TIMELESS and the Treacher Collins syndrome gene TCOF1. These experiments showed that DTECT was able to capture the signatures of the newly introduced variants in all of the above genes (FIGS. 3B and 11I-11J). Finally, to test whether DTECT is also able to identify genomic signatures generated by prime editing, we transiently transfected into HEK293T cells a prime editor and a pegRNA to introduce a 3-bp insertion (CTT_ins) in the HEK3 locus (Anzalone et al., 2019). As shown in FIG. 3B, DTECT specifically identified the newly created signature and quantified its frequency in the transfected cell population, indicating that DTECT is also suitable to identify prime editing events. The specificity and accuracy of the above DTECT studies was confirmed by both positive and negative controls (e.g., CG and TT adaptors in the control unedited sample of FIG. 3B).

To further confirm the accuracy of DTECT in quantifying precision genome editing, we compared the frequency of editing events determined by either DTECT or NGS across 62 samples derived from human cells, mouse cells and intestinal organoids, which were modified using CRISPR-mediated HDR or base editing (Zafra et al., 2018). As shown in FIGS. 3C (left panel) and 12A, the frequencies of editing events obtained by DTECT and NGS were comparable (mean frequency: DTECT, 35.43%; NGS, 33.47%; r=0.9857, n=62), indicating that the quantification of precision genome editing by DTECT is accurate. Similar to NGS, DTECT is also accurate in the detection of less abundant (<20% frequency) variants (mean frequency: DTECT, 5.41%; NGS, 5.06%, r=0.843, n=33) (FIG. 3C, right panel). Together, these experiments demonstrate that DTECT precisely identifies and quantifies genetic variants introduced by precision genome editing in various biological systems.

Recent studies led to the development of Sanger sequencing-based methods, such as ICE (Synthego; https://ice.synthego.com/#/) or EditR (Kluesner et al., 2018), that enable the detection of genomic variants based on the deconvolution of chromatogram peaks. To compare DTECT with the above methods, we subjected to Sanger sequencing the genomic amplicons of 23 samples edited by precision genome editing. In these experiments, we used two primers annealing to opposite DNA strands to obtain independent sequencing duplicates of the same amplicons, and analyzed the Sanger sequencing reads using either ICE or EditR. Notably, ~10% of the sequencing reactions failed to generate high quality reads required for ICE or EditR, despite using high quality amplicons for sequencing (Mendeley dataset, Data availability section). Independent repeats using new genomic amplicons did not improve the sequencing outcome (Mendeley dataset, Data availability section). In addition, we noted that technical duplicates of Sanger sequencing reactions analyzed by ICE or EditR displayed lower levels of consistency relative to technical replicates of DTECT assays (FIG. 12B). These studies indicate that DTECT displays greater robustness and reliability compared to Sanger-based detection methods, which heavily rely on the quality of Sanger sequencing reactions.

Example 6

DTECT Enables the Identification of Precision Genome Editing Events In Vivo

The modeling and correction of pathogenic mutations in adult mice is critical for the development of novel approaches to therapeutic intervention against cancer and other diseases (Chadwick et al., 2017; Gao et al., 2018; Levy et al., 2020; Ryu et al., 2018; Song et al., 2020; Villiger et al., 2018; Yin et al., 2016; Yin et al., 2014). To determine whether DTECT can determine editing levels in adult mouse tissue, we hydrodynamically delivered into the mouse liver (Tschaharganeh et al., 2014) a cytidine base editor and an sgRNA introducing the oncogenic Pik3ca E545K mutation (Zafra et al., 2018) (FIG. 3D). We then used both DTECT and NGS to quantify the oncogenic Pik3ca signature in DNA samples derived from the edited livers of two mice. DTECT analysis identified base editing events in the mouse liver at a ~1-2% frequency, comparable to the editing rates obtained by NGS (FIG. 3E). This study revealed that DTECT can accurately quantify low abundance genetic variants introduced by precision genome editing in vivo.

Example 7

DTECT is Capable of Identifying Multiple Genome Editing Events Occurring within a Single Locus or Distinct Loci The above studies indicate that DTECT can determine the identity of individual genomic changes. To examine whether DTECT can also identify complex sets of mutations, we employed CRISPR-dependent base editing to target two adjacent cytosines in the EMX1 locus that had previously been converted into four distinct dinucleotide combinations (i.e., CC, CT, TC or TT) by base editing (Komor et al., 2016) (FIG. 4A). As shown in FIG. 4A, DTECT readily distinguished each of the four combinations in an sgRNA-dependent manner, demonstrating that DTECT can identify a complex mixture of allelic variants. Furthermore, we also detected base editing byproducts (FIG. 13A), suggesting that DTECT could be used to optimize conditions that reduce the formation of these byproducts (Komor et al., 2017; Wang et al., 2017). Additionally, to determine whether DTECT can be employed to monitor genomic changes at multiple loci, we simultaneously introduced two clinically relevant point mutations into two distinct genes (i.e., BRCA1 and BRCA2) (FIG. 4B). As shown in FIG. 4C, DTECT correctly identified these genomic changes, indicating that it can readily detect complex genome editing events occurring within single or multiple genomic loci.

Example 8

DTECT Expedites the Derivation of Marker-Free Cell Lines Carrying Clinically Relevant Mutations and Facilitates the Genotyping of Cellular and Animal Disease Models Precision genome editing allows the modeling of clinically relevant gene variants. Given that DTECT enables the identification of newly created DNA signatures without requiring the insertion of markers or elaborate experimental design specific for each edited site, we tested whether DTECT could facilitate the generation of multiple cell lines harboring clinically relevant mutations. In particular, we focused our attention on mutations in the BRCA1 and BRCA2 genes, which in heterozygosity can predispose women to the development of breast and/or ovarian cancer (Apostolou and Fostira, 2013), whereas in homozygosity can cause Fanconi anemia (Ceccaldi et al., 2016). More than 7,000 clinically associated SNVs have been identified in BRCA1/2, according to the ClinVar database, but efforts to characterize their functional impact and pathogenic potential have been limited in part due to the challenge of generating cell lines that carry such a large number of individual homozygous and heterozygous variants. To determine whether DTECT can facilitate the production of cell lines harboring clinically relevant BRCA1/2 SNVs, we expressed a cytidine base editor in HEK293T cells along with individual sgRNAs to generate 23 different BRCA1/2 mutations identified in patients with ovarian and breast cancers, as reported in ClinVar (FIGS. 5A and 5D). We then used DTECT to determine by analytical PCR which variants were introduced in the transfected cell populations and quantify the editing efficiency for each variant by qPCR (FIGS. 5B-5C, 5E-5F and 13B-13C). The accuracy of DTECT in the quantification of the editing events was confirmed by NGS (FIGS. 5B and 5E). The above approach proved effective for rapidly identifying cell populations with high levels of editing. Upon isolation of single clones from edited cell populations (e.g., BRCA1 E638K mutant cells), we tested whether DTECT could be used for clone genotyping. Importantly, DTECT allowed rapid genotyping of multiple clones (FIG. 14A) and accurately determined the genotype of each clone, including WT, homozygous and heterozygous mutant clones (FIGS. 5G-5H), thus expediting the production of marker-free isogenic heterozygous and homozygous mutant cells.

Given the ability of DTECT to correctly determine the genotype of cellular clones, we then tested whether DTECT could also be applied to mouse genotyping. To this end, we obtained tail DNA samples from genetically engineered mice carrying knock-in mutations in Brca1 (S1598F) and its partner protein Bard1 (S563F) (Billing et al., 2018). As shown in FIGS. 5I-5J and 14B, DTECT accurately determined the genotype of 24 Bard1 S563F mutant mice and 16 Brca1 S1598F mutant mice. These findings indicate that DTECT can be employed to rapidly determine the genotype of genetically engineered mice, thus facilitating the derivation, maintenance and analysis of marker-free animal models.

Example 9

DTECT Identifies the Presence of Oncogenic Mutations in Cancer Mouse Models and Human Cancer Patient Samples Precise and rapid detection of pathogenic variants in patients is critical for accurate diagnosis and personalized therapy. Given the ability of DTECT to identify genetic variants rapidly and accurately, we tested whether DTECT could be utilized to expedite the identification of pathogenic variants in pre-clinical and clinical settings. In particular, we examined whether DTECT could identify the presence of oncogenic variants in various biological systems. In our studies we focused our attention on the JAK2 V617F variant, which is present in the majority of patients with myeloproliferative neoplasm (MPN) (Levine et al., 2005). Mice transplanted with Jak2 V617F mutant bone marrow cells develop MPN and recapitulate the human disease (Mullally et al., 2010). Therefore, we analyzed the Jak2 V617F variant in the peripheral blood of mice transplanted with a mixture of bone marrow cells that do or do not carry an inducible Jak2 V617F variant (Bhagwat et al., 2014) (FIG. 15A). As shown in FIGS. 15B-15C, DTECT readily distinguished wild-type from V617F mutant Jak2 in the examined mouse blood samples, as detected using any of the four distinct AcuI-tagging primers specific for the targeted bases. These experiments show that DTECT can identify oncogenic signatures of interest in mouse tissues in a marker-free manner, thus enabling the tracking of genetic variants in mouse models without requiring complex selection markers.

We next examined whether DTECT can identify the presence of specific oncogenic mutations in human samples from patients diagnosed with acute lymphoblastic leukemia (ALL), the most common form of childhood cancer (Inaba et al., 2013). Although most ALL patients respond to chemotherapy, ~20% suffer a relapse as a result of resistance to chemotherapy (Bhojwani and Pui, 2013). Moreover, secondary genetic alterations that promote chemoresistance, including mutations in the NT5C2 gene (Tzoneva et al., 2018; Tzoneva et al., 2013), are found in a large fraction of ALL relapse cases (Dieck and Ferrando, 2019; Oshima et al., 2016). To test whether DTECT can identify these relapse-specific oncogenic signatures, we obtained matched DNA samples from the bone marrow of ALL patients at diagnosis and relapse and analyzed them for the presence of three common NT5C2 mutations (R238W, K359Q and R367Q) (FIGS. 6A-6B). Remarkably, DTECT unambiguously detected the presence of oncogenic NT5C2 variants in all five patient samples (patient #1, R238W; patients #2, #4 and #5, R367Q; patient #3, K359Q) and accurately quantified their frequency in a manner comparable to NGS (FIGS. 6B-6C and 15D). Moreover, DTECT also identified the presence of the above NT5C2 variants in the patient-derived xenograft (PDX) models generated from these relapsed ALL patients (FIGS. 6A and 6D). These studies demonstrate that DTECT can identify oncogenic mutations of interest in PDX models and cancer patient samples.

Example 10

Discussion

In this study, we established DTECT as a sensitive method for the identification of genomic DNA signatures. In particular, we show that DTECT readily identifies precision genome editing events induced by CRISPR-dependent HDR, base editing and prime editing, including low abundance and complex genomic changes. In addition, we show that DTECT can be employed to identify pathogenic lesions of interest, such as oncogenic mutations, in cancer mouse models, PDXs, and cancer patient specimens. DTECT is a rapid (~4-5 hours) and easy-to-perform detection method that relies on standard molecular biology techniques (PCR, DNA digestion and ligation) and common laboratory reagents. This methodology is also not labor-intensive, given that it entails short periods (5-10 min) of sample processing followed by hands-free incubations. Importantly, DTECT assays utilize a unique and common set of adaptors that includes positive and negative controls to ensure specificity and accuracy. The ease, speed and cost efficiency by which DTECT identifies genetic variants in a wide variety of cellular and animal systems (e.g., cell lines, organoids, animal models, patient samples) should facilitate the generation and study of biological models of human diseases and expedite the detection of pathogenic variants for both pre-clinical and clinical applications.

Although highly robust, DTECT has three potential limitations. First, AcuI-induced dinucleotide byproducts can be generated if a genomic AcuI restriction site located in close proximity to the targeted dinucleotide is incorporated into the amplicon of the targeted locus. However, an analysis of the ClinVar database revealed that genomic AcuI sites occur relatively infrequently and 95% of clinically relevant variants (404,393 variants) are compatible with DTECT (FIGS. 16A-16B). Second, dinucleotide byproducts may also occur due to AcuI slippage activity, resulting in the cleavage of DNA molecules 13 (−1) or 15 (+1), instead of 14, bases away from the AcuI recognition site. Nonetheless, we found that DTECT is able to identify AcuI slippage events, which occur mostly at position +1 relative to the standard AcuI cleavage site (Lundin et al., 2015) (FIG. 17A). It is reasonable to anticipate that future optimization of AcuI architecture and improvements in the AcuI digestion protocol will limit its slippage activity. It is also important to note that AcuI byproducts resulting from either genomic AcuI motifs or AcuI slippage activity are easily predictable based on the sequence of the nucleotides flanking the targeted dinucleotide and they can be completely avoided by optimal design of the AcuI-tagging primer and appropriate adaptor selection, as shown in FIGS. 16C and 17B. Third, indel mutations formed at DSB sites generated by Cas nucleases in CRISPR-mediated HDR experiments can result in defective PCR amplification of indel-containing loci that have not undergone HDR and therefore cause an overestimation of the frequency of HDR events by DTECT (FIGS. 18A and 18B). However, given that the mutagenic spectrum of indel mutations induced by any sgRNA is predictable (Allen et al., 2018; Leenay et al., 2019; Shen et al., 2018; van Overbeek et al., 2016) (inDelphi web portal; https://indelphi.gifford-lab.mit.edu/), the negative impact of indel mutations on DTECT-based quantification of CRISPR-mediated HDR events can be avoided by introducing the desired genomic changes in indel-free regions adjacent to CRISPR-induced cut sites (FIGS. 18C and 18D). This limitation does not affect the detection of CRISPR-mediated base editing and prime editing events, and naturally occurring genetic variants, which are accompanied by either very low frequency (Anzalone et al., 2019; Gaudelli et al., 2017; Komor et al., 2017; Yeh et al., 2018) or complete absence of DSB-induced indel formation, respectively.

In addition to its ease of use, speed and cost efficiency, DTECT has several advantages compared to other detection methods. A major benefit of DTECT is its versatility, which allows the detection and quantification of nucleotide substitutions, precise base insertions and deletions using the same small set of 16 predefined adaptors (FIGS. 1B and 7). Each editing event can be identified using 4 distinct signatures resulting from AcuI-mediated digestion of genomic DNA amplicons, indicating that the design of DTECT studies is flexible (FIGS. 2E-2F and 15B-15C). These features distinguish DTECT from strategies that employ allele-specific DNA oligonucleotides or probes to identify SNVs, which work with variable efficiency due to the competition between WT and mutant alleles and the number of variant DNA bases, thus requiring unique experimental design for the detection of each individual genetic variant. Given that both wild-type and mutant DNA signatures are captured from the same AcuI-digested PCR amplicon and that a common set of PCR primers is utilized for both analytical and quantitative detection of all variants (FIG. 1A, step VI), DTECT exhibits limited technical variability across distinct experimental conditions. This aspect differentiates DTECT from Sanger sequencing-based detection methods, such as ICE and EditR, in which efficiency depends on the quality of the sequencing reads, which can vary greatly between sequencing platforms, samples and reactions (FIG. 12B). In addition, DTECT displays greater sensitivity and flexibility compared to RFLP-based assays (FIGS. 11A-11J) and exhibits similar precision to NGS (FIG. 3C) at a lower cost and with a faster turnaround time (hours vs. days/weeks). Finally, DTECT directly identifies genetic variants independently of genomic markers, therefore enabling the analysis of scarless and marker-free cellular and animal models generated by precision genome editing. Given its ability to identify multiple independent genetic variants simultaneously (FIGS. 4A-4C), DTECT could expedite the generation of complex genomic changes, especially for genetic interaction studies, synthetic biology applications and molecular recording (Fahim Farzadfard, 2018).

The ability to model clinically relevant mutations in a marker-free manner is critical for assessing their potential pathogenicity, especially in the case of genes, such as BRCA1 and BRCA2, which have thousands of clinically-associated SNVs. Recent studies have led to the development of high-throughput saturation genome editing (SGE) to examine en masse the pathogenicity of BRCA1 variants (Findlay et al., 2018). Although highly useful for classifying BRCA1 SNVs, SGE requires the use of haploid cells and is therefore not compatible with the study of the functional impact of BRCA1 mutations in heterozygosity, as observed in BRCA1 mutation carriers (Apostolou and Fostira, 2013). BRCA1/2 heterozygous mutations have been recently shown to cause genome instability induced by DNA replication stress (Billing et al., 2018; Pathania et al., 2014; Tan et al., 2017). By facilitating the derivation of both heterozygous and homozygous BRCA1/2 mutant cells and animal models (FIGS. 5A-5J), DTECT could help elucidate the underlying mechanisms by which genome instability causes breast and ovarian cancer development in BRCA1/2 mutation carriers. Our work demonstrated that DTECT can expedite the generation of a large variety of human genetic variants in various complex biological systems.

In addition to facilitating precision genome editing, we showed that DTECT can also be used to detect pathogenic variants in pre-clinical and clinical settings. In particular, DTECT can rapidly identify the presence of oncogenic variants in cancer mouse models (FIGS. 15A-15D), thus facilitating the study of cancer pathogenesis and the development of novel cancer therapies. Furthermore, DTECT can also identify oncogenic mutations in samples from cancer patients and PDX mouse models (FIGS. 6A-6D). The speed by which DTECT accurately and unambiguously identifies pathogenic variants could accelerate cancer diagnosis and expedite the testing of cancer therapies in PDX models, thus leading to more effective cancer treatments. We envision that future developments and implementations of the DTECT protocol may further simplify the detection of desired genomic signatures and increase the sensitivity of DTECT, thus expanding the number of possible DTECT applications and enabling early diagnosis of cancer and hereditary disorders through the detection of pathogenic variants in circulating cell-free tumor and fetal DNA (Zhang et al., 2019).

Collectively, our work established DTECT as a facile, rapid and cost-effective method for identifying genomic variants in various biological systems, such as mammalian cell lines, organoids, mouse tissues, PDX models and human patient samples. Given the growing number of genetic variants identified in the human population (Lek et al., 2016) and in human genetic disorders (McClellan and King, 2010), this versatile method for the detection of genomic signatures should facilitate the study of human genetic variation and expedite the diagnosis and treatment of human disease.

TABLE S1

Primers, ssODNs, adaptors and other oligos used in this disclosure.

| Detection primers | Sequence (5'- -> 3') | Notes |
|---|---|---|
| PB547 | gatcctctagagtcgacctg (SEQ ID NO: 1) | Oligos for detection (step VI) |
| PB548 | cgggtaccgagctcgaattc (SEQ ID NO: 2) | Oligos for detection (step VI) |
| PB1072 | gcaattcctcacgagacccgtcctg (SEQ ID NO: 3) | Oligos for detection (step VI) - Only these oligos were used for qPCR |
| PB1073 | cgggtaccgagctcgaattcttagaag (SEQ ID NO: 4) | Oligos for detection (step VI) - Only these oligos were used for qPCR |

| AcuI-tagging primers | Sequence (5'- -> 3'): Handle for detection-gDNA-AcuI hairpin-gDNA | Notes |
|---|---|---|
| PB1021 | gatcctctagagtcgacctgGGAGTCCCTGTCGCTAGTGG CTGAAGACGCGTCGTGGGAG (SEQ ID NO: 5) | AcuI for signature TT |
| PB1022 | gatcctctagagtcgacctgACAAACAGTGCCTGCAAGTCC TGAAGCGGTGTGGGGTCCA (SEQ ID NO: 6) | AcuI for signature CC |
| PB1071 | GCAATTCCTCACGAGACCCGTCCTGATTTCAGGG AAGAAGCTGAAGTGAATGAAAAACTT (SEQ ID NO: 7) | AcuI for PIK3R1-STOP |
| PB1153 | GCAATTCCTCACGAGACCCGTCCTGTGTAGTTTTA CTTACCTGAAGTCTCGTCTCCACAG (SEQ ID NO: 8) | AcuI for JAK2 (HDR) |
| PB1151 | GCAATTCCTCACGAGACCCGTCCTGAGGACATCG ATGTCACTGAAGCCTCCAATGACTAG (SEQ ID NO: 9) | AcuI for EMX1 (HDR) |
| PB1019 | gatcctctagagtcgacctgAAACGGCAGAAGCTGGAGGA CTGAAGGGAAGGGCCTGAGT (SEQ ID NO: 10) | AcuI for EMX1 (Base editing) |
| PB1080 | GCAATTCCTCACGAGACCCGTCCTGGTTCAGTTTA ACGACCTGAAGCAATTCTTCTGGGG (SEQ ID NO: 11) | AcuI for SPRTN-STOP |
| PB1149 | GCAATTCCTCACGAGACCCGTCCTGTGTGTTCACT AGCAACTGAAGCCTCAAACAGACAC (SEQ ID NO: 12) | AcuI for HBB (HDR) |
| PB1211 | GCAATTCCTCACGAGACCCGTCCTGGAGGAGGAG GCCCCTCTGAAGGCAGGGACACGAAG (SEQ ID NO: 13) | AcuI for TCOF1 (Base editing) |
| oligo plate | GAT CCT CTA GAG TCG ACC TGC AAA ATT ATA TAC CTT TTG GCT GAA GTT ATA TCA TTC TTA (SEQ ID NO: 14) | BRCA1 C64Y AcuI |
| oligo plate | GAT CCT CTA GAG TCG ACC TGT CTT CAC TGC TAG AAC AAC TCT GAA GAT CAA TTT GCA ATT (SEQ ID NO: 15) | BRCA1 E638K AcuI |

TABLE S1-continued

Primers, ssODNs, adaptors and other oligos used in this disclosure.

| | | |
|---|---|---|
| oligo plate | GAT CCT CTA GAG TCG ACC TGA TAT TGC TTG AGC TGG CTT CCT GAA GTT TAA AAA CAT TTT (SEQ ID NO: 16) | BRCA1 E1033K AcuI |
| oligo plate | GAT CCT CTA GAG TCG ACC TGG GTT CAG CTT TCG TTT TGA ACT GAA GAG CAG ATT CTT TTT (SEQ ID NO: 17) | BRCA1 E575K AcuI |
| oligo plate | GAT CCT CTA GAG TCG ACC TGT CCT CTA GCA GAT TTT TCT TCT GAA GAC ATT TAG TTT TAA (SEQ ID NO: 18) | BRCA1 V990I AcuI |
| oligo plate | GAT CCT CTA GAG TCG ACC TGG GAA AGA ATG AGT CTA ATA TCT GAA GCA AGC CTG TAC AGA (SEQ ID NO: 19) | BRCA1 T922I AcuI |
| oligo plate | GAT CCT CTA GAG TCG ACC TGC ATC ATT ACC AAA TTA TAT ACT GAA GCC TTT TGG TTA TAT (SEQ ID NO: 20) | BRCA1 D67N AcuI |
| oligo plate | GAT CCT CTA GAG TCG ACC TGG AGG GAG GGA GCT TTA CCT TCT GAA GTC TGT CCT GGG ATT (SEQ ID NO: 21) | BRCA1 E1754K AcuI |
| oligo plate | GAT CCT CTA GAG TCG ACC TGG AAG AAA ATA ATC AAG AAG ACT GAA GGC AAA GCA TGG ATT (SEQ ID NO: 22) | BRCA1 S1363L AcuI |
| oligo plate | GAT CCT CTA GAG TCG ACC TGG CAG TGA TTT TAC ATC TAA ACT GAA GTG TCC ATT TTA GAT (SEQ ID NO: 23) | BRCA1 Q1779* AcuI |
| oligo plate | GAT CCT CTA GAG TCG ACC TGG ATG GAG AAG ACA TCA TCT GCT GAA GGA TTA TAC ATA TTT (SEQ ID NO: 24) | BRCA2 R2842C AcuI |
| oligo plate | GAT CCT CTA GAG TCG ACC TGT GAA TCT TTT TCT TTT TTT GCT GAA GAA TAG CTT ACA ATA (SEQ ID NO: 25) | BRCA2 R2973H AcuI |
| oligo plate | GAT CCT CTA GAG TCG ACC TGC TGA GTA TTT GGC GTC CAT CCT GAA GAT CAG ATT TAT ATT (SEQ ID NO: 26) | BRCA2 S2998F AcuI |
| oligo plate | GAT CCT CTA GAG TCG ACC TGC AAA TTT TTA GAT CCA GAC TCT GAA GTC AGC ATC TTG TT (SEQ ID NO: 27) | BRCA2 S3070F AcuI |
| oligo plate | GAT CCT CTA GAG TCG ACC TGA GTG CAA ATT AAT TTA CCT TCT GAA GTA ACA TAA GAG ATT (SEQ ID NO: 28) | BRCA2 E2772K AcuI |
| oligo plate | GAT CCT CTA GAG TCG ACC TGG AAT ATT TG ATG GTC AAC CCT GAA GAG AAA GAA TAA ATA (SEQ ID NO: 29) | BRCA2 T1707I AcuI |
| oligo plate | GAT CCT CTA GAG TCG ACC TGA TCT TGT TCT GAG GTG GAC CCT GAA GTA ATA GGA TTT GTC (SEQ ID NO: 30) | BRCA2 V3079I AcuI |
| oligo plate | GAT CCT CTA GAG TCG ACC TGT AGG AAG GCC ATG GAA TCT GCT GAA GCT GAA CAA AAG GAA (SEQ ID NO: 31) | BRCA2 Q2960* AcuI |
| oligo plate | GAT CCT CTA GAG TCG ACC TGA ACT GAA GCC TCT GAA AGT GCT GAA GAC TGG AAA TAC ATA (SEQ ID NO: 32) | BRCA2 T544I AcuI |
| oligo plate | GAT CCT CTA GAG TCG ACC TGT TTA CCA TCA CGT GCA CTA ACT GAA GCA AGA CAG CAA GTT (SEQ ID NO: 33) | BRCA2 R2896C AcuI |
| oligo plate | GAT CCT CTA GAG TCG ACC TGT GGA AGC TGG CCA GCC ACC ACT GAA GCC ACA CAG AAT TCT (SEQ ID NO: 34) | BRCA2 V572I AcuI |

TABLE S1-continued

Primers, ssODNs, adaptors and other oligos used in this disclosure.

| | | |
|---|---|---|
| oligo plate | GAT CCT CTA GAG TCG ACC TGT TGC CTC TAG AAA TCA TGA CCT GAA GTA GGT TTG ACA GAA (SEQ ID NO: 35) | BRCA2 V778I AcuI |
| oligo plate | GAT CCT CTA GAG TCG ACC TGT TTC TCT TAT CAA CAC GAG GCT GAA GAA GTA TTT TTG ATA (SEQ ID NO: 36) | BRCA2 V2102I AcuI |
| AA1 | GAT CCT CTA GAG TCG ACC TGC AAA CGA CGA GCG TGA CAC CCT GAA GAC GAT GCC TGT AGC (SEQ ID NO: 37) | For adaptor library testing |
| AA2 | GAT CCT CTA GAG TCG ACC TGT CGT TGG GAA CCG GAG CTG ACT GAA GAT GAA GCC ATA CCA (SEQ ID NO: 38) | For adaptor library testing |
| AC1 | GAT CCT CTA GAG TCG ACC TGG AGC TGA ATG AAG CCA TAC CCT GAA GAA ACG ACG AGC GTG (SEQ ID NO: 39) | For adaptor library testing |
| AC2 | GAT CCT CTA GAG TCG ACC TGG CTG AAT GAA GCC ATA CCA ACT GAA GAC GAC GAG CGT GAC (SEQ ID NO: 40) | For adaptor library testing |
| AG1 | GAT CCT CTA GAG TCG ACC TGG AAC CGG AGC TGA ATG AAG CCT GAA GCA TAC CAA ACG ACG (SEQ ID NO: 41) | For adaptor library testing |
| AG2 | GAT CCT CTA GAG TCG ACC TGT ACC AAA CGA CGA GCG TGA CCT GAA GAC CAC GAT GCC TGT (SEQ ID NO: 42) | For adaptor library testing |
| AT1 | GAT CCT CTA GAG TCG ACC TGT GAA GCC ATA CCA AAC GAC GCT GAA GAG CGT GAC ACC ACG (SEQ ID NO: 43) | For adaptor library testing |
| AT2 | GAT CCT CTA GAG TCG ACC TGA AAC GAC GAG CGT GAC ACC ACT GAA GCG ATG CCT GTA GCA (SEQ ID NO: 44) | For adaptor library testing |
| CA1 | GAT CCT CTA GAG TCG ACC TGG ATC GTT GGG AAC CGG AGC TCT GAA GGA ATG AAG CCA TAC (SEQ ID NO: 45) | For adaptor library testing |
| CA2 | GAT CCT CTA GAG TCG ACC TGA GCT GAA TGA AGC CAT ACC ACT GAA GAA CGA CGA GCG TGA (SEQ ID NO: 46) | For adaptor library testing |
| CC1 | GAT CCT CTA GAG TCG ACC TGC TGA ATG AAG CCA TAC CAA ACT GAA GCG ACG AGC GTG ACA (SEQ ID NO: 47) | For adaptor library testing |
| CC2 | GAT CCT CTA GAG TCG ACC TGA GCC ATA CCA AAC GAC GAG CCT GAA GGT GAC ACC ACG ATG (SEQ ID NO: 48) | For adaptor library testing |
| CG1 | GAT CCT CTA GAG TCG ACC TGA CCG GAG CTG AAT GAA GCC ACT GAA GTA CCA AAC GAC GAG (SEQ ID NO: 49) | For adaptor library testing |
| CG2 | GAT CCT CTA GAG TCG ACC TGA ATG AAG CCA TAC CAA ACG ACT GAA GCG AGC GTG ACA CCA (SEQ ID NO: 50) | For adaptor library testing |
| CT1 | GAT CCT CTA GAG TCG ACC TGG CCA TAC CAA ACG ACG AGC GCT GAA GTG ACA CCA CGA TGC (SEQ ID NO: 51) | For adaptor library testing |
| CT2 | GAT CCT CTA GAG TCG ACC TGT CAT GTA ACT CGC CTT GAT CCT GAA GGT TGG AAA CCG GAG (SEQ ID NO: 52) | For adaptor library testing |
| GA1 | GAT CCT CTA GAG TCG ACC TGG GAG CTG AAT GAA GCC ATA CCT GAA GCA AAC GAC GAG CGT (SEQ ID NO: 53) | For adaptor library testing |

TABLE S1-continued

Primers, ssODNs, adaptors and other oligos used in this disclosure.

| | | |
|---|---|---|
| GA2 | GAT CCT CTA GAG TCG ACC TGG GAA CCG GAG CTG AAT GAA GCT GAA GCC ATA CCA AAC GAC (SEQ ID NO: 54) | For adaptor library testing |
| GC1 | GAT CCT CTA GAG TCG ACC TGA ACC GGA GCT GAA TGA AGC CTG AAG ATA CCA AAC GAC GA (SEQ ID NO: 55) | For adaptor library testing |
| GC2 | GAT CCT CTA GAG TCG ACC TGA AGC CAT ACC AAA CGA CGA GCT GAA GCG TGA CAC CAC GAT (SEQ ID NO: 56) | For adaptor library testing |
| GG1 | GAT CCT CTA GAG TCG ACC TGA CGA CGA GCG TGA CAC CAC GCT GAA GAT GCC TGT AGC AAT (SEQ ID NO: 57) | For adaptor library testing |
| GG2 | GAT CCT CTA GAG TCG ACC TGA GCA ATG GCA ACA ACG TTG CCT GAA GGC AAA CTA TTA ACT (SEQ ID NO: 58) | For adaptor library testing |
| GT1 | GAT CCT CTA GAG TCG ACC TGC CGG AGC TGA ATG AAG CCA TCT GAA GAC CAA ACG ACG AGC (SEQ ID NO: 59) | For adaptor library testing |
| GT2 | GAT CCT CTA GAG TCG ACC TGC ATA CCA AAC GAC GAG CGT GCT GAA GAC ACC ACG ATG CCT (SEQ ID NO: 60) | For adaptor library testing |
| TA1 | GAT CCT CTA GAG TCG ACC TGC TTG ATC GTT GGG AAC CGG ACT GAA GGC TGA ATG AAG CCA (SEQ ID NO: 61) | For adaptor library testing |
| TA2 | GAT CCT CTA GAG TCG ACC TGA TAC CAA ACG ACG AGC GTG ACT GAA GCA CCA CGA TGC CTG (SEQ ID NO: 62) | For adaptor library testing |
| TC1 (PB1040) | GAT CCT CTA GAG TCG ACC TGc cgc ttt ttt gca caa cat gCT GAA Ggg gga tca tgt aac (SEQ ID NO: 63) | For adaptor library testing |
| TC2 | GAT CCT CTA GAG TCG ACC TGC GTT GCG CAA ACT ATT AAC TCT GAA GGG CGA ACT ACT TAC (SEQ ID NO: 64) | For adaptor library testing |
| TG1 | GAT CCT CTA GAG TCG ACC TGC GGA GCT GAA TGA AGC ATA CT GAA GCC AAA CGA CGA GCG (SEQ ID NO: 65) | For adaptor library testing |
| TG2 (PB1070) | gat cct cta gag tcg acc tgc cat acc aaa cga cga gcg tCT GAA Gga cac cac gat gcc (SEQ ID NO: 66) | For adaptor library testing |
| TT1 | GAT CCT CTA GAG TCG ACC TGT GAC ACC ACG ATG CCT GTA GCT GAA GCA ATG GCA ACA ACG (SEQ ID NO: 67) | For adaptor library testing |
| TT2 | GAT CCT CTA GAG TCG ACC TGG CCT GTA GCA ATG GCA ACA ACT GAA GCG TTG CGC AAA CTA (SEQ ID NO: 68) | For adaptor library testing |
| PB1477 | GCAATTCCTCACGAGACCCGTCCTGACCTGAGTT CTTTCCCTGAAGCCACATCAGCGTGC (SEQ ID NO: 69) | FANCD2 AcuI |
| PB1257 | GATCCTCTAGAGTCGACCTGCCGCAGAGCTGAGA AGTTATCTGAAGTGGCAGAACAGCAT (SEQ ID NO: 70) | SMARCAL1 AcuI |
| PB1264 | gatcctctagagtcgacctgGTTTTCATTTCAGGGAAGAAC TGAAGGTGAATGAAAAACT (SEQ ID NO: 71) | PIK3R1 signatures |
| PB1265 | gatcctctagagtcgacctgTCTCGTACCAAAAAGGTCCCC TGAAGGTCTGCTGTATCTC (SEQ ID NO: 72) | PIK3R1 signatures |
| PB1266 | gatcctctagagtcgacctgATCTCGTACCAAAAAGGTCCC TGAAGCGTCTGCTGTATCT (SEQ ID NO: 73) | PIK3R1 signatures |

TABLE S1-continued

Primers, ssODNs, adaptors and other oligos used in this disclosure.

| | | |
|---|---|---|
| PB1010 | gatcctctagagtcgacctgTTTTCATTTCAGGGAAGAAGC TGAAGTGAATGAAAAACTT (SEQ ID NO: 74) | PIK3R1 signatures |
| PB1433 | GCAATTCCTCACGAGACCCGTCCTGtgcgcaaactattC TGAAGaactggcgaactacAA (SEQ ID NO: 75) | AA-Oligo to test dinucleotide capture efficiency (DTECT) |
| PB1434 | GCAATTCCTCACGAGACCCGTCCTGtgcgcaaactattC TGAAGaactggcgaactacAC (SEQ ID NO: 76) | AC-Oligo to test dinucleotide capture efficiency (DTECT) |
| PB1435 | GCAATTCCTCACGAGACCCGTCCTGtgcgcaaactattC TGAAGaactggcgaactacAG (SEQ ID NO: 77) | AG-Oligo to test dinucleotide capture efficiency (DTECT) |
| PB1436 | GCAATTCCTCACGAGACCCGTCCTGtgcgcaaactattC TGAAGaactggcgaactacAT (SEQ ID NO: 78) | AT-Oligo to test dinucleotide capture efficiency (DTECT) |
| PB1437 | GCAATTCCTCACGAGACCCGTCCTGtgcgcaaactattC TGAAGaactggcgaactacCA (SEQ ID NO: 79) | CA-Oligo to test dinucleotide capture efficiency (DTECT) |
| PB1438 | GCAATTCCTCACGAGACCCGTCCTGtgcgcaaactattC TGAAGaactggcgaactacCC (SEQ ID NO: 80) | CC-Oligo to test dinucleotide capture efficiency (DTECT) |
| PB1439 | GCAATTCCTCACGAGACCCGTCCTGtgcgcaaactattC TGAAGaactggcgaactacCG (SEQ ID NO: 81) | CG-Oligo to test dinucleotide capture efficiency (DTECT) |
| PB1440 | GCAATTCCTCACGAGACCCGTCCTGtgcgcaaactattC TGAAGaactggcgaactacCT (SEQ ID NO: 82) | CT-Oligo to test dinucleotide capture efficiency (DTECT) |
| PB1441 | GCAATTCCTCACGAGACCCGTCCTGtgcgcaaactattC TGAAGaactggcgaactacGA (SEQ ID NO: 83) | GA-Oligo to test dinucleotide capture efficiency (DTECT) |
| PB1442 | GCAATTCCTCACGAGACCCGTCCTGtgcgcaaactattC TGAAGaactggcgaactacGC (SEQ ID NO: 84) | GC-Oligo to test dinucleotide capture efficiency (DTECT) |
| PB1443 | GCAATTCCTCACGAGACCCGTCCTGtgcgcaaactattC TGAAGaactggcgaactacGG (SEQ ID NO: 85) | GG-Oligo to test dinucleotide capture efficiency (DTECT) |
| PB1444 | GCAATTCCTCACGAGACCCGTCCTGtgcgcaaactattC TGAAGaactggcgaactacGT (SEQ ID NO: 86) | GT-Oligo to test dinucleotide capture efficiency (DTECT) |
| PB1445 | GCAATTCCTCACGAGACCCGTCCTGtgcgcaaactattC TGAAGaactggcgaactacTA (SEQ ID NO: 87) | TA-Oligo to test dinucleotide capture efficiency (DTECT) |
| PB1446 | GCAATTCCTCACGAGACCCGTCCTGtgcgcaaactattC TGAAGaactggcgaactacTC (SEQ ID NO: 88) | TC-Oligo to test dinucleotide capture efficiency (DTECT) |
| PB1447 | GCAATTCCTCACGAGACCCGTCCTGtgcgcaaactattC TGAAGaactggcgaactacTG (SEQ ID NO: 89) | TG-Oligo to test dinucleotide capture efficiency (DTECT) |

TABLE S1-continued

Primers, ssODNs, adaptors and other oligos used in this disclosure.

| | | |
|---|---|---|
| PB1448 | GCAATTCCTCACGAGACCCGTCCTGtgcgcaaactattCTGAAGaactggcgaactacTT (SEQ ID NO: 90) | TT-Oligo to test dinucleotide capture efficiency (DTECT) |
| PB1449 | gtagttcgccagttCTTCAGaatagtttgcgcaCAGGACGGGTCTCGTGAGGAATTGC (SEQ ID NO: 91) | Complementary 5'-phosphorylated oligo |
| PB1321 | GCAATTCCTCACGAGACCCGTCCTGGTGGCTCCATAGGAACTGAAGGTCTTTCTCTTGTT (SEQ ID NO: 92) | mouse Pik3ca (545) AcuI |
| PB1380 | GCAATTCCTCACGAGACCCGTCCTGTTATATACCTTTTGGCTGAAGTTATATCATTCTTA (SEQ ID NO: 93) | BRCA1 Cys64Tyr AcuI |
| PB1381 | GCAATTCCTCACGAGACCCGTCCTGACTGCTAGAACAACTCTGAAGATCAATTTGCAATT (SEQ ID NO: 94) | BRCA1 Glu638Lys AcuI |
| PB1382 | GCAATTCCTCACGAGACCCGTCCTGGCTTGAGCTGGCTTCCTGAAGTTAAAAACATTTT (SEQ ID NO: 95) | BRCA1 Glu1033Lys AcuI |
| PB1383 | GCAATTCCTCACGAGACCCGTCCTGAGCTTTCGTTTTGAACTGAAGAGCAGATTCTTTTT (SEQ ID NO: 96) | BRCA1 Glu575Lys AcuI |
| PB1386 | GCAATTCCTCACGAGACCCGTCCTGTAGCAGATTTTCTTCTGAAGACATTTAGTTTTAA (SEQ ID NO: 97) | BRCA1 Val990Ile AcuI |
| PB1388 | GCAATTCCTCACGAGACCCGTCCTGGAATGAGTCTAATATCTGAAGCAAGCCTGTACAGA (SEQ ID NO: 98) | BRCA1 Thr922Ile AcuI |
| PB1389 | GCAATTCCTCACGAGACCCGTCCTGTTACCAAATTATATACTGAAGCCTTTTGGTTATAT (SEQ ID NO: 99) | BRCA1 Asp67Asn AcuI |
| PB1390 | GCAATTCCTCACGAGACCCGTCCTGAGGGAGCTTTACCTTCTGAAGTCTGTCCTGGGATT (SEQ ID NO: 100) | BRCA1 Glu1754Lys AcuI |
| PB1393 | GCAATTCCTCACGAGACCCGTCCTGAAATAATCAAGAAGACTGAAGGCAAAGCATGGATT (SEQ ID NO: 101) | BRCA1 Ser1363Leu AcuI |
| PB1394 | GCAATTCCTCACGAGACCCGTCCTGGATTTTACATCTAAACTGAAGTGTCCATTTTAGAT (SEQ ID NO: 102) | BRCA1 Gln1779Ter AcuI |
| PB1396 | GCAATTCCTCACGAGACCCGTCCTGAGAAGACATCATCTGCTGAAGGATTATACATATTT (SEQ ID NO: 103) | BRCA2 Arg2842Cys AcuI |
| PB1397 | GCAATTCCTCACGAGACCCGTCCTGCTTTTTCTTTTTTTGCTGAAGAATAGCTTACAATA (SEQ ID NO: 104) | BRCA2 Arg2973His AcuI |
| PB1398 | GCAATTCCTCACGAGACCCGTCCTGTATTTGGCGTCCATCCTGAAGATCAGATTTATATT (SEQ ID NO: 105) | BRCA2 Ser2998Phe AcuI |
| PB1399 | GCAATTCCTCACGAGACCCGTCCTGTTTTAGATCCAGACTCTGAAGTCAGCCATCTTGTT (SEQ ID NO: 106) | BRCA2 Ser3070Phe AcuI |
| PB1400 | GCAATTCCTCACGAGACCCGTCCTGAAATTAATTTACCTTCTGAAGTAACATAAGAGATT (SEQ ID NO: 107) | BRCA2 Glu2772Lys AcuI |
| PB1401 | GCAATTCCTCACGAGACCCGTCCTGATTTGATGGTCAACCCTGAAGAGAAAGAATAAATA (SEQ ID NO: 108) | BRCA2 Thr1707Ile AcuI |

TABLE S1-continued

Primers, ssODNs, adaptors and other oligos used in this disclosure.

| | | |
|---|---|---|
| PB1402 | GCAATTCCTCACGAGACCCGTCCTGGTTCTGAGG TGGACCCTGAAGTAATAGGATTTGTC (SEQ ID NO: 109) | BRCA2 Val3079Ile AcuI |
| PB1403 | GCAATTCCTCACGAGACCCGTCCTGAGGCCATGG AATCTGCTGAAGCTGAACAAAAGGAA (SEQ ID NO: 110) | BRCA2 Gln2960Ter AcuI |
| PB1405 | GCAATTCCTCACGAGACCCGTCCTGAAGCCTCTG AAAGTGCTGAAGACTGGAAATACATA (SEQ ID NO: 111) | BRCA2 Thr544Ile AcuI |
| PB1406 | GCAATTCCTCACGAGACCCGTCCTGCTTATCAACA CGAGGCTGAAGAAGTATTTTTGATA (SEQ ID NO: 112) | BRCA2 Val2102Ile AcuI |
| PB1407 | GCAATTCCTCACGAGACCCGTCCTGCATCACGTG CACTAACTGAAGCAAGACAGCAAGTT (SEQ ID NO: 113) | BRCA2 Arg2896Cys AcuI |
| PB1408 | GCAATTCCTCACGAGACCCGTCCTGGCTGGCCAG CCACCACTGAAGCCACACAGAATTCT (SEQ ID NO: 114) | BRCA2 Val572Ile AcuI |
| PB1409 | GCAATTCCTCACGAGACCCGTCCTGTCTAGAAATC ATGACCTGAAGTAGGTTTGACAGAA (SEQ ID NO: 115) | BRCA2 Val778Ile AcuI |
| PB1509 | GCAATTCCTCACGAGACCCGTCCTGGCATTTTCTG CTGCTCTGAAGGTGAAGAAAGCCCA (SEQ ID NO: 116) | Bard1 S563F AcuI |
| PB1513 | GCAATTCCTCACGAGACCCGTCCTGgagcggatagag acaCTGAAGtatccatggtggtg (SEQ ID NO: 117) | Brca1 S1598F AcuI |
| PB1483 | GCAATTCCTCACGAGACCCGTCCTGTGTGCGAGT TCAGGACTGAAGATCACCAAAAAAGT (SEQ ID NO: 118) | NT5C2 R367Q AcuI |
| PB1486 | GCAATTCCTCACGAGACCCGTCCTGTTGGAGATC ACATTTCTGAAGTTGGGGACATTTTA (SEQ ID NO: 119) | NT5C2 K359Q AcuI |
| PB1493 | GCAATTCCTCACGAGACCCGTCCTGTTTCAGGGA AAACTGCTGAAGCCTTTGCTTCTGAG (SEQ ID NO: 120) | NT5C2 R238W AcuI |
| PB1296 | GCAATTCCTCACGAGACCCGTCCTGTGATACTGA AATTGACTGAAGTAGAAGCAGAAGAT (SEQ ID NO: 121) | BRCA2 dupAGAAGAT AcuI |
| PB1473 | GCAATTCCTCACGAGACCCGTCCTGGCCAGCGAG AGATGGCTGAAGCAGAAAAGAAGACT (SEQ ID NO: 122) | TIMELESS AcuI |
| PB1476 | GCAATTCCTCACGAGACCCGTCCTGGGGCAGCG GGTGCCGCTGAAGGCGAGGACGCTGAC (SEQ ID NO: 123) | SLX4 AcuI |
| PB1472 | GCAATTCCTCACGAGACCCGTCCTGACGTTTACG GCCAGTCTGAAGTCTACCCATTCGTT (SEQ ID NO: 124) | FANCM AcuI |
| PB1427 | GCAATTCCTCACGAGACCCGTCCTGGAAGCTCGG AAAAGCCTGAAGGATCCAGGTGCTGC (SEQ ID NO: 125) | FANCF AcuI |
| PB1430 | GCAATTCCTCACGAGACCCGTCCTGATGTAGAATT AAGAACTGAAGTCATGCCTCCAGTT (SEQ ID NO: 126) | AcuI Apc. 1529 |
| PB1431 | GCAATTCCTCACGAGACCCGTCCTGCCCGGGGCA TTTCATCTGAAGCCCAGGAGCTAGGT (SEQ ID NO: 127) | AcuI Apc. 492 |
| PB1318 | GCAATTCCTCACGAGACCCGTCCTGTTGAGAGTC GCTCCACTGAAGTTGCCAGCTCTGTT (SEQ ID NO: 128) | AcuI Apc. 1405 |

TABLE S1-continued

Primers, ssODNs, adaptors and other oligos used in this disclosure.

| | | |
|---|---|---|
| PB1332 | GCAATTCCTCACGAGACCCGTCCTGAGCATTTGG TTTTGACTGAAGATTATGGTGTCTGT (SEQ ID NO: 129) | AcuI Jak2 #1 |
| PB1333 | GCAATTCCTCACGAGACCCGTCCTGCTGGCTTTA CTTACTCTGAAGCTCCTCTCCACAGA (SEQ ID NO: 130) | AcuI Jak2 #2 |
| PB1460 | GCAATTCCTCACGAGACCCGTCCTGAAGCATTTG GTTTTGCTGAAGAATTATGGTGTCTG (SEQ ID NO: 131) | AcuI Jak2 #3 |
| PB1461 | GCAATTCCTCACGAGACCCGTCCTGGCTGGCTTT ACTTACCTGAAGTCTCCTCTCCACAG (SEQ ID NO: 132) | AcuI Jak2 #4 |
| PB1545 | GCAATTCCTCACGAGACCCGTCCTGGAAGCAGGG CTTCCTCTGAAGTTCCTCTGCCATCA (SEQ ID NO: 133) | AcuI HEK3 |
| PB1301 | GCAATTCCTCACGAGACCCGTCCTGGAAATTTGC GTGTGGCTGAAGAGTATTTGGATGAC (SEQ ID NO: 134) | AcuI TP53 R209fs delGA |
| PB1535 | GCAATTCCTCACGAGACCCGTCCTGAACCAGACC TCAGGCCTGAAGGGCTCATAGGGCAC (SEQ ID NO: 135) | AcuI TP53 delAG (PAM) |

| Standard PCR primers | Sequence (5'- ->3') | Notes |
|---|---|---|
| Ampicillin reverse | CCA ATG CTT AAT CAG TGA GG (SEQ ID NO: 136) | For adaptor library testing |
| AcuI-tagging oligo reverse | AAT CGC TTG ATC ACA GAT GTA TGT A (SEQ ID NO: 137) | PCR BRCA1 C64Y and BRCA1 D67N |
| AcuI-tagging oligo reverse | GAA GAC AAA ATA TTT GGG AAA ACC T (SEQ ID NO: 138) | PCR BRCA1 E638K and BRCA1 E575K |
| AcuI-tagging oligo reverse | TCT CGT TAC TGG AAG TTA GCA CTC T (SEQ ID NO: 139) | PCR BRCA1 E1033K and BRCA1 V990I |
| AcuI-tagging oligo reverse | ATT TCA CCA TCA TCT AAC AGG TCA T (SEQ ID NO: 140) | PCR BRCA1 T922I |
| AcuI-tagging oligo reverse | CAC CTC CTG CAT TCA AAA GAT TC (SEQ ID NO: 141) | PCR BRCA1 E1754K |
| AcuI-tagging oligo reverse | GCT GCT TCA CCT TAA ATA ACA AAA A (SEQ ID NO: 142) | PCR BRCA1 S1363L |
| AcuI-tagging oligo reverse | AGG GAC ATA TGG GAA AAA GAG TTA G (SEQ ID NO: 143) | PCR BRCA1 Q1779* |
| AcuI-tagging oligo reverse | TTA GAC CTG ATA TTT CTG TCC CTT G (SEQ ID NO: 144) | PCR BRCA2 R2842C |
| AcuI-tagging oligo reverse | ACC TCT ACT ACC TAT GTG GCT TGT G (SEQ ID NO: 145) | PCR BRCA2 R2973H |
| AcuI-tagging oligo reverse | GGT TTG TAC CGG TAG TTG TTG ATA C (SEQ ID NO: 146) | PCR BRCA2 S2998F and BRCA2 Q2960* |
| AcuI-tagging oligo reverse | AAA TAG CCC TGT ACA ATG AAA AGT AGA (SEQ ID NO: 147) | PCR BRCA2 S3070F and BRCA2 V3079I |
| AcuI-tagging oligo reverse | TCA TAT ACG GCA GTA TGG TTA AGG T (SEQ ID NO: 148) | PCR BRCA2 E2772K |
| AcuI-tagging oligo reverse | GTG GCC CTA CCT CAA AAT TAT TAC T (SEQ ID NO: 149) | PCR BRCA2 T1707I |
| AcuI-tagging oligo reverse | TAT CTA CCA TGT TTG AGT GAC CTG A (SEQ ID NO: 150) | PCR BRCA T544I and BRCA2 V572I |

TABLE S1-continued

Primers, ssODNs, adaptors and other oligos used in this disclosure.

| | | |
|---|---|---|
| AcuI-tagging oligo reverse | CTT CAT AAG TCA GTC TCA TCT GCA A (SEQ ID NO: 151) | PCR BRCA2 V2102I |
| AcuI-tagging oligo reverse | GTA CAG GAG GGA CAA AAA TAA AAC A (SEQ ID NO: 152) | PCR BRCA2 R2896C |
| AcuI-tagging oligo reverse | CCT TAA CTA GCT CTT TTG GGA CAA T (SEQ ID NO: 153) | PCR BRCA2 V778I |
| PB1150 | GAAAATAGACCAATAGGCAGAGAGAGTC (SEQ ID NO: 154) | HBB PCR rev |
| PB1152 | TGTCATTAAGAGAGAGACTTTTATTATTCC (SEQ ID NO: 155) | EMX1 PCR rev |
| PB1154 | ATCCATCTACCTCAGTTTCCTATATCTATC (SEQ ID NO: 156) | JAK2 PCR rev |
| PB783 | CCCTTTCCTGTAAAAACAATATAAAAA (SEQ ID NO: 157) | PIK3R1 PCR rev |
| PB764 | TTCTGGAAAATGGATCTAAAGCTAATA (SEQ ID NO: 158) | TCOF1 PCR RFLP for |
| PB765 | TCACAATTCGTAGTCCTACTTCTACCT (SEQ ID NO: 159) | TCOF1 PCR RFLP rev |
| TP226 | ACGTTGATGGCAGTTGCAGGTC (SEQ ID NO: 160) | JAK2 (HDR) for |
| TP227 | CTGACAGAGTTGCTAGACACTGGGTTG (SEQ ID NO: 161) | JAK2 (HDR) rev |
| PB969 | AACGATCTTCAATATGCTTACCAAG (SEQ ID NO: 162) | HBB PCR RFLP for |
| PB970 | CTTAACCATAGAAAAGAAGGGGAAA (SEQ ID NO: 163) | HBB PCR RFLP rev |
| PB327 | GCCATCCCCTTCTGTGAATGTTAGAC (SEQ ID NO: 164) | EMX1 PCR for |
| PB328 | GGAGATTGGAGACACGGAGAGCAG (SEQ ID NO: 165) | EMX1 PCR rev |
| PB1302 | AACTGTGCAATAGTTAAACCCATTTAC (SEQ ID NO: 166) | PCR TP53 (HDR) |
| PB862 | GTAGGTGTTCGGTAAATGTTAATGG (SEQ ID NO: 167) | PCR FANCD2 |
| PB863 | AAGTCAAATCCCATACCCTACTCAT (SEQ ID NO: 168) | PCR FANCD2 |
| PB1334 | TACTTGCTTTCAGTGTTGTGTTATAGG (SEQ ID NO: 169) | PCR Jak2 (mouse) |
| PB1335 | ATTTGTTTACTGTAATCCTCATCCATC (SEQ ID NO: 170) | PCR Jak2 (mouse) |
| PB1319 | GGAAAAGTTTATAGGTGTCCCTTCTAC (SEQ ID NO: 171) | PCR Apc. 1405 |
| PB1320 | AGCAGGTGTACTTCTGTCAGCTC (SEQ ID NO: 172) | PCR Apc. 1405 |
| PB1432 | AATATTCTGCAGACTGATATTCTGGTT (SEQ ID NO: 173) | PCR Apc. 492 |
| PB1428 | CGTTACTTAATTTTGAAAAACCTCAAC (SEQ ID NO: 174) | PCR FANCF |
| PB1429 | AGATTTGGGTTCTCTCTATAGCCATT (SEQ ID NO: 175) | PCR FANCF |
| PB745 | GACTCCAGTCAAAAATTCTCCTAGTTA (SEQ ID NO: 176) | PCR FANCM |

TABLE S1-continued

Primers, ssODNs, adaptors and other oligos used in this disclosure.

| | | |
|---|---|---|
| PB858 | ATGTCTGCAGCTATAGTTAGGAAGC (SEQ ID NO: 177) | PCR SLX4 |
| PB859 | ATCTCTCCCTGAGTTGATGAGAAG (SEQ ID NO: 178) | PCR SLX4 |
| PB764 | TTCTGGAAAATGGATCTAAAGCTAATA (SEQ ID NO: 179) | PCR TCOF1 |
| PB765 | TCACAATTCGTAGTCCTACTTCTACCT (SEQ ID NO: 180) | PCR TCOF1 |
| PB746 | CTGTTTGTCCTAAACAAGATGTGAAT (SEQ ID NO: 181) | PCR TIMELESS |
| PB747 | CATTGGAGCAAGTTAAAACTACAAAAT (SEQ ID NO: 182) | PCR TIMELESS |
| PB1297 | CCTTAACCTCTTGATGTATGAGAAGAA (SEQ ID NO: 183) | PCR BRCA2 dupAGAAGAT |
| PB1298 | AGTACATCTAAGAAATTGAGCATCCTT (SEQ ID NO: 184) | PCR BRCA2 dupAGAAGAT |
| PB590 | GTGTGTGTGCAATTATAAAAGAAACTT (SEQ ID NO: 185) | PCR SMARCAL1 |
| PB591 | GTCAGCATTAGATGAGCTACTGAGATT (SEQ ID NO: 186) | PCR SMARCAL1 |
| PB1322 | CTGTTCTACTTGTTGGTGGTGATAATA (SEQ ID NO: 187) | PCR mouse Pik3ca (545) |
| PB1323 | ATGGTAAGAAATATGGTTAACACCAAG (SEQ ID NO: 188) | PCR mouse Pik3ca (545) |
| PB1510 | CTATTTTAGGTTACTGGGAACAGAATG (SEQ ID NO: 189) | Oligos for Bard1 S563F genotyping |
| PB1511 | AAACTACATAACTACAACCCAATGCTT (SEQ ID NO: 190) | Oligos for Bard1 S563F genotyping |
| PB1514 | GAACCCCATACCTGGGATCT (SEQ ID NO: 191) | Oligos for Brca1 S1598F genotyping |
| PB1515 | tcatacctcacaaggtgccta (SEQ ID NO: 192) | Oligos for Brca1 S1598F genotyping |
| PB1548 | TTATCAGTTTTGGAGGATGTACATAAA (SEQ ID NO: 193) | PCR HEK3 rev |
| PB780 | CTCCTTCCTCTTCCTACAGTACTCC (SEQ ID NO: 194) | TP53 gDNA for (PAM) |
| Illumina primers (NGS) | Sequence (5'- ->3') | Notes |

Primers for amplifying AcuI-tagged amplicons

| | | |
|---|---|---|
| SAM175 | ACACTCTTTCCCTACACGACGCTCTTCCGATC TTTCCTCACGAGACCCGTCCTG (SEQ ID NO: 195) | Adaptor constant forward - Forward primer used with all amplicons - binds AcuI-tagging primer sequence |
| SAM176 | AGACGTGTGCTCTTCCGATCTCTTGATCACAG ATGTATGTA (SEQ ID NO: 196) | NGS BRCA1 C64Y AcuI |
| SAM177 | AGACGTGTGCTCTTCCGATCTCAAAATATTTG GGAAAACCT (SEQ ID NO: 197) | NGS BRCA1 E638K AcuI |
| SAM178 | AGACGTGTGCTCTTCCGATCTTTACTGGAAGT TAGCACTCT (SEQ ID NO: 198) | NGS BRCA1 E1033K AcuI |

TABLE S1-continued

Primers, ssODNs, adaptors and other oligos used in this disclosure.

| | | |
|---|---|---|
| SAM179 | AGACGTGTGCTCTTCCGATCTCAAAATATTTG GGAAAACCT (SEQ ID NO: 199) | NGS BRCA1 E575K AcuI |
| SAM182 | AGACGTGTGCTCTTCCGATCTTTACTGGAAGT TAGCACTCT (SEQ ID NO: 200) | NGS BRCA1 V990I AcuI |
| SAM184 | AGACGTGTGCTCTTCCGATCTACCATCATCTA ACAGGTCAT (SEQ ID NO: 201) | NGS BRCA1 T922I AcuI |
| SAM185 | AGACGTGTGCTCTTCCGATCTCTTGATCACAG ATGTATGTA (SEQ ID NO: 202) | NGS BRCA1 D67N AcuI |
| SAM186 | AGACGTGTGCTCTTCCGATCTCTCCTGCATTC AAAAGATTC (SEQ ID NO: 203) | NGS BRCA1 E1754K AcuI |
| SAM189 | AGACGTGTGCTCTTCCGATCTTTCACCTTAAA TAACAAAAA (SEQ ID NO: 204) | NGS BRCA1 S1363L AcuI |
| SAM190 | AGACGTGTGCTCTTCCGATCTCATATGGGAAA AAGAGTTAG (SEQ ID NO: 205) | NGS BRCA1 Q1779* AcuI |
| SAM192 | AGACGTGTGCTCTTCCGATCTCCTGATATTTC TGTCCCTTG (SEQ ID NO: 206) | NGS BRCA2 R2842C AcuI |
| SAM193 | AGACGTGTGCTCTTCCGATCTTACTACCTATG TGGCTTGTG (SEQ ID NO: 207) | NGS BRCA2 R2973H AcuI |
| SAM194 | AGACGTGTGCTCTTCCGATCTGTACCGGTAGT TGTTGATAC (SEQ ID NO: 208) | NGS BRCA2 S2998F AcuI |
| SAM195 | AGACGTGTGCTCTTCCGATCTCCTGTACAATG AAAAGTAGA (SEQ ID NO: 209) | NGS BRCA2 S3070F AcuI |
| SAM196 | AGACGTGTGCTCTTCCGATCTTACGGCAGTAT GGTTAAGGT (SEQ ID NO: 210) | NGS BRCA2 E2772K AcuI |
| SAM197 | AGACGTGTGCTCTTCCGATCTCCTACCTCAAA ATTATTACT (SEQ ID NO: 211) | NGS BRCA2 T1707I AcuI |
| SAM198 | AGACGTGTGCTCTTCCGATCTCCTGTACAATG AAAAGTAGA (SEQ ID NO: 212) | NGS BRCA2 V3079I AcuI |
| SAM199 | AGACGTGTGCTCTTCCGATCTGTACCGGTAGT TGTTGATAC (SEQ ID NO: 213) | NGS BRCA2 Q2960* AcuI |
| SAM201 | AGACGTGTGCTCTTCCGATCTACCATGTTTGA GTGACCTGA (SEQ ID NO: 214) | NGS BRCA2 T544I AcuI |
| SAM202 | AGACGTGTGCTCTTCCGATCTTAAGTCAGTCT CATCTGCAA (SEQ ID NO: 215) | NGS BRCA2 V2102I AcuI |
| SAM203 | AGACGTGTGCTCTTCCGATCTGGAGGGACAA AAATAAAACA (SEQ ID NO: 216) | NGS BRCA2 R2896C AcuI |
| SAM204 | AGACGTGTGCTCTTCCGATCTACCATGTTTGA GTGACCTGA (SEQ ID NO: 217) | NGS BRCA2 V572I AcuI |
| SAM205 | AGACGTGTGCTCTTCCGATCTACTAGCTCTTT TGGGACAAT (SEQ ID NO: 218) | NGS BRCA2 V778I AcuI |

Primers for indexing the above amplicons

| | | |
|---|---|---|
| SAM113 | caagcagaagacggcatacgagatTGCCTCTTgtgactgga gttcagacgtgtgctcttccgatct (SEQ ID NO: 219) | N711 |
| SAM64 | aatgatacggcgaccaccgagatctacacACTGCATAacact ctttccctacacgacg (SEQ ID NO: 220) | S506 |
| TP370 | acactctttccctacacgacgctcttccgatctGTTTAAACAGT GGAATTCTAGAGTCA (SEQ ID NO: 221) | BRCA2_NGS_F |
| TP371 | agacgtgtgctcttccgatctTTTTTGCAGCTGTGTCATC C (SEQ ID NO: 222) | BRCA2_NGS_R |
| TP372 | acactctttccctacacgacgctcttccgatctGCCCCTCCTC AGCATCTTAT (SEQ ID NO: 223) | TP53_NGS_F |

TABLE S1-continued

Primers, ssODNs, adaptors and other oligos used in this disclosure.

| | | |
|---|---|---|
| TP373 | agacgtgtgctcttccgatctCTTAACCCCTCCTCCCAG AG (SEQ ID NO: 224) | TP53_NGS_R | ssODNs:

| Sequence (5'- ->3') | Targeted gene |
|---|---|
| TTCCTTAGTCTTTCTTTGAAGCAGCAAGTATGATGAGCAAGCTTTCTCA CAAGCATTTGGTTTTAAATTATGGAGTATGTGTgtttaaacCTGTGGAGACG AGAGTAAGTAAAACTACAGGCTTTCTAATGCCTTTCTCAGAGCATCTGT TTTTGTTTATATAGAAAATTCAGTTTCAGGATCA (SEQ ID NO: 225) | JAK2 |
| AAGAAGGGCTCCCATCACATCAACCGGTGGCGCATTGCCACGAAGCA GGCCAATGGGGAGGACATCGATGTCACCTCCAATGACTAGtttaaacGGG TGGGCAACCACAAACCCACGAGGGCAGAGTGCTGCTTGCTGCTGGCC AGGCCCCTGCGTGGGCCCAAGCTGGACTCTGGCCACTCCC (SEQ ID NO: 226) | EMX1 |
| TACATTTGCTTCTGACACAACTGTGTTCACTAGCAACCTCAAACAGACA CAATGGTGCATCTGACTCCTGTCGAGAAGTCTGCCGTTACTGCCCTGT GGGGCAAGGTGAACGTGGATGAAGTTGGTGGTGAGGCCCTGGG (SEQ ID NO: 227) | HBB |
| TCTTAGGTCTGGCCCCTCCTCAGCATCTTATCCGAGTGGAAGGAAATT TGCGTGTGGAGTATTTGGATGACAAACACTTTTCGTCATAGTGTGGTTG TGCCCTATGAGCCGCCTGAGGTCTGGTTTGCAACTGGGGTCTCTGGG AGGAGGGGTTAAGGGTGGTTGT (SEQ ID NO: 228) | TP53 R209fs*6 |
| TTGTTTAAACAGTGGAATTCTAGAGTCACACTTCCTAAAATATGCATTTT TGTTTTCACTTTTAGATATGATACTGAAATTGATAGAAGCAGAAGATAG AAGATCGGCTATAAAAAAGATAATGGAAAGGGATGACACAGCTGCAAA AACACTTGTTCTCTGTGTTTCTGACATAAT (SEQ ID NO: 229) | BRCA2 dupAGA AGAT |

Libray of adaptors:

| Oligo | Sequence (5'- ->3') | Notes |
|---|---|---|
| PB984 | CTGGGGCACGGGTAAGAAGCATTCTGTCTCTCT TCTAAgaattcgagctcggtacccg (SEQ ID NO: 230) | Oligo corresponds to the constant strand of the adaptor |
| PB985 | cgggtaccgagctcgaattcTTAGAAGAGAGACAGAATG CTTCTTACCCGTGCCCCAGGG (SEQ ID NO: 231) | Oligo corresponds to the variable strand of the adaptor. It contains a 3' GG, expected to ligate to CC |
| PB986 | cgggtaccgagctcgaattcTTAGAAGAGAGACAGAATG CTTCTTACCCGTGCCCCAGAG (SEQ ID NO: 232) | Oligo corresponds to the variable strand of the adaptor. It contains a 3' AG, expected to ligate to CT |
| PB987 | cgggtaccgagctcgaattcTTAGAAGAGAGACAGAATG CTTCTTACCCGTGCCCCAGAA (SEQ ID NO: 233) | Oligo corresponds to the variable strand of the adaptor. It contains a 3' AA, expected to ligate to TT |
| PB988 | cgggtaccgagctcgaattcTTAGAAGAGAGACAGAATG CTTCTTACCCGTGCCCCAGTG (SEQ ID NO: 234) | Oligo corresponds to the variable strand of the adaptor. It contains a 3' TG, expected to ligate to CA |
| PB989 | cgggtaccgagctcgaattcTTAGAAGAGAGACAGAATG CTTCTTACCCGTGCCCCAGTA (SEQ ID NO: 235) | Oligo corresponds to the variable strand of the adaptor. It contains a 3' TA, expected to ligate to TA |
| PB990 | cgggtaccgagctcgaattcTTAGAAGAGAGACAGAATG CTTCTTACCCGTGCCCCAGCG (SEQ ID NO: 236) | Oligo corresponds to the variable strand of the adaptor. It contains a 3' CG, expected to ligate to CG |

TABLE S1-continued

Primers, ssODNs, adaptors and other oligos used in this disclosure.

| | | |
|---|---|---|
| PB991 | cgggtaccgagctcgaattcTTAGAAGAGAGACAGAATGCTTCTTACCCGTGCCCCAGCA (SEQ ID NO: 237) | Oligo corresponds to the variable strand of the adaptor. It contains a 3' CA, expected to ligate to TG |
| PB992 | cgggtaccgagctcgaattcTTAGAAGAGAGACAGAATGCTTCTTACCCGTGCCCCAGCT (SEQ ID NO: 238) | Oligo corresponds to the variable strand of the adaptor. It contains a 3' CT, expected to ligate to AG |
| PB993 | cgggtaccgagctcgaattcTTAGAAGAGAGACAGAATGCTTCTTACCCGTGCCCCAGGA (SEQ ID NO: 239) | Oligo corresponds to the variable strand of the adaptor. It contains a 3' GA, expected to ligate to TC |
| PB1000 | cgggtaccgagctcgaattcTTAGAAGAGAGACAGAATGCTTCTTACCCGTGCCCCAGAC (SEQ ID NO: 240) | Oligo corresponds to the variable strand of the adaptor. It contains a 3' AC, expected to ligate to GT |
| PB1001 | cgggtaccgagctcgaattcTTAGAAGAGAGACAGAATGCTTCTTACCCGTGCCCCAGAT (SEQ ID NO: 241) | Oligo corresponds to the variable strand of the adaptor. It contains a 3' AT, expected to ligate to AT |
| PB1002 | cgggtaccgagctcgaattcTTAGAAGAGAGACAGAATGCTTCTTACCCGTGCCCCAGCC (SEQ ID NO: 242) | Oligo corresponds to the variable strand of the adaptor. It contains a 3' CC, expected to ligate to GG |
| PB1003 | cgggtaccgagctcgaattcTTAGAAGAGAGACAGAATGCTTCTTACCCGTGCCCCAGGC (SEQ ID NO: 243) | Oligo corresponds to the variable strand of the adaptor. It contains a 3' GC, expected to ligate to GC |
| PB1004 | cgggtaccgagctcgaattcTTAGAAGAGAGACAGAATGCTTCTTACCCGTGCCCCAGGT (SEQ ID NO: 244) | Oligo corresponds to the variable strand of the adaptor. It contains a 3' GT, expected to ligate to AC |
| PB1005 | cgggtaccgagctcgaattcTTAGAAGAGAGACAGAATGCTTCTTACCCGTGCCCCAGTC (SEQ ID NO: 245) | Oligo corresponds to the variable strand of the adaptor. It contains a 3' TC, expected to ligate to GA |
| PB1006 | cgggtaccgagctcgaattcTTAGAAGAGAGACAGAATGCTTCTTACCCGTGCCCCAGTT (SEQ ID NO: 246) | Oligo corresponds to the variable strand of the adaptor. It contains a 3' TT, expected to ligate to AA |

Oligos (sgRNAs cloning):

| Oligo | Sequence (5'- ->3') | Target/Notes |
|---|---|---|
| oligo plate | CAC CGT ACA TAA AGG ACA CTG TGA (SEQ ID NO: 247) | BRCA1 C64Y for |
| oligo plate | CAC CGC AAT TCA GTA CAA TTA GGT (SEQ ID NO: 248) | BRCA1 E638K for |
| oligo plate | CAC CGA TTT TCT CTA ATG TTA TTA (SEQ ID NO: 249) | BRCA1 E1033K for |
| oligo plate | CAC CGT TTT TCG AGT GAT TCT ATT (SEQ ID NO: 250) | BRCA1 E575K for |
| oligo plate | CAC CGT TTT AAC AAA TGA CTT GAT (SEQ ID NO: 251) | BRCA1 V990I for |

TABLE S1-continued

Primers, ssODNs, adaptors and other oligos used in this disclosure.

| | | |
|---|---|---|
| oligo plate | CAC CGA GAC AGT TAA TAT CAC TGC (SEQ ID NO: 252) | BRCA1 T922I for |
| oligo plate | CAC CGT TAT ATC ATT CTT ACA TAA (SEQ ID NO: 253) | BRCA1 D67N for |
| oligo plate | CAC CGG GGA TTC TCT TGC TCG CTT (SEQ ID NO: 254) | BRCA1 E1754K for |
| oligo plate | CAC CGT GGA TTC AAA CTT AGG TAT (SEQ ID NO: 255) | BRCA1 S1363L for |
| oligo plate | CAC CGT TAG ATC AAC TGG AAT GGA (SEQ ID NO: 256) | BRCA1 Q1779* for |
| oligo plate | CAC CGA TAT TTC GCA ATG AAA GAG (SEQ ID NO: 257) | BRCA2 R2842C for |
| oligo plate | CAC CGA CAA TAC GCA ACT TCC ACA (SEQ ID NO: 258) | BRCA2 R2973H for |
| oligo plate | CAC CGT ATA TTC TCT GTT AAC AGA (SEQ ID NO: 259) | BRCA2 S2998F for |
| oligo plate | CAC CGG TTC TGA GGT GGA CCT AAT (SEQ ID NO: 260) | BRCA2 S3070F for |
| oligo plate | CAC CGG AGA TTC TGG GGC TTC AAG (SEQ ID NO: 261) | BRCA2 E2772K for |
| oligo plate | CAC CGT AAA TAC TGC AGA TTA TGT (SEQ ID NO: 262) | BRCA2 T1707I for |
| oligo plate | CAC CGA GAA ACG ACA AAT CCT ATT (SEQ ID NO: 263) | BRCA2 V3079I for |
| oligo plate | CAC CGA AGG AAC AAG GTT TAT CAA (SEQ ID NO: 264) | BRCA2 Q2960* for |
| oligo plate | CAC CGC ATA CTG TTT GCT CAC AGA (SEQ ID NO: 265) | BRCA2 T544I for |
| oligo plate | CAC CGG CTA CAG AAT TCT GTG TGG (SEQ ID NO: 266) | BRCA2 V572I for |
| oligo plate | CAC CGA CAG AAC ATC CTT GGA AGT (SEQ ID NO: 267) | BRCA2 V778I for |
| oligo plate | AAA CTC ACA GTG TCC TTT ATG TAC (SEQ ID NO: 268) | BRCA1 C64Y rev |
| oligo plate | AAA CAC CTA ATT GTA CTG AAT TGC (SEQ ID NO: 269) | BRCA1 E638K rev |
| oligo plate | AAA CTA ATA ACA TTA GAG AAA ATC (SEQ ID NO: 270) | BRCA1 E1033K rev |
| oligo plate | AAA CAA TAG AAT CAC TCG AAA AAC (SEQ ID NO: 271) | BRCA1 E575K rev |
| oligo plate | AAA CAT CAA GTC ATT TGT TAA AAC (SEQ ID NO: 272) | BRCA1 V990I rev |
| oligo plate | AAA CGC AGT GAT ATT AAC TGT CTC (SEQ ID NO: 273) | BRCA1 T922I rev |
| oligo plate | AAA CTT ATG TAA GAA TGA TAT AAC (SEQ ID NO: 274) | BRCA1 D67N rev |
| oligo plate | AAA CAA GCG AGC AAG AGA ATC CCC (SEQ ID NO: 275) | BRCA1 E1754K rev |
| oligo plate | AAA CAT ACC TAA GTT TGA ATC CAC (SEQ ID NO: 276) | BRCA1 S1363L rev |
| oligo plate | AAA CTC CAT TCC AGT TGA TCT AAC (SEQ ID NO: 277) | BRCA1 Q1779* rev |

TABLE S1-continued

Primers, ssODNs, adaptors and other oligos used in this disclosure.

| | | |
|---|---|---|
| oligo plate | AAA CCT CTT TCA TTG CGA AAT ATC (SEQ ID NO: 278) | BRCA2 R2842C rev |
| oligo plate | AAA CTG TGG AAG TTG CGT ATT GTC (SEQ ID NO: 279) | BRCA2 R2973H rev |
| oligo plate | AAA CTC TGT TAA CAG AGA ATA TAC (SEQ ID NO: 280) | BRCA2 S2998F rev |
| oligo plate | AAA CAT TAG GTC CAC CTC AGA ACC (SEQ ID NO: 281) | BRCA2 S3070F rev |
| oligo plate | AAA CCT TGA AGC CCC AGA ATC TCC (SEQ ID NO: 282) | BRCA2 E2772K rev |
| oligo plate | AAA CAC ATA ATC TGC AGT ATT TAC (SEQ ID NO: 283) | BRCA2 T1707I rev |
| oligo plate | AAA CAA TAG GAT TTG TCG TTT CTC (SEQ ID NO: 284) | BRCA2 V3079I rev |
| oligo plate | AAA CTT GAT AAA CCT TGT TCC TTC (SEQ ID NO: 285) | BRCA2 Q2960* rev |
| oligo plate | AAA CTC TGT GAG CAA ACA GTA TGC (SEQ ID NO: 286) | BRCA2 T544I rev |
| oligo plate | AAA CCC ACA CAG AAT TCT GTA GCC (SEQ ID NO: 287) | BRCA2 V572I rev |
| oligo plate | AAA CAC TTC CAA GGA TGT TCT GTC (SEQ ID NO: 288) | BRCA2 V778I rev |
| PB776 | CACCGAACTTcGAGATACAGCAGAC (SEQ ID NO: 289) | PIK3R1 R348* for |
| PB777 | AAACGTCTGCTGTATCTCgAAGTTC (SEQ ID NO: 290) | PIK3R1 R348* rev |
| PB551 | CACCGGGCCAGCTGGAGGCCGTCG (SEQ ID NO: 291) | SPRTN Q60* for |
| PB552 | AAACCGACGGCCTCCAGCTGGCCC (SEQ ID NO: 292) | SPRTN Q60* rev |
| PB756 | CACCGAGCcAGGTGAGGCCTGGAGG (SEQ ID NO: 293) | TCOF1 Q290* for |
| PB757 | AAACCCTCCAGGCCTCACCTgGCTC (SEQ ID NO: 294) | TCOF1 Q290* rev |
| TP212 | CACCGAATTATGGAGTATGTGTCTG (SEQ ID NO: 295) | JAK2 HDR for |
| TP213 | AAACCAGACACATACTCCATAATTC (SEQ ID NO: 296) | JAK2 HDR rev |
| PB963 | CACCGATGGTGCATCTGACTCCTG (SEQ ID NO: 297) | HBB E6V HDR for |
| PB964 | AAACCAGGAGTCAGATGCACCATC (SEQ ID NO: 298) | HBB E6V HDR rev |
| PB1017 | CACCGAGTCCGAGCAGAAGAAGAA (SEQ ID NO: 299) | EMX1 Base editing for |
| PB1018 | AAACTTCTTCTTCTGCTCGGACTC (SEQ ID NO: 300) | EMX1 Base editing rev |
| PB325 | CACCGGTCACCTCCAATGACTAGGG (SEQ ID NO: 301) | EMX1 HDR for |
| PB326 | AAACCCCTAGTCATTGGAGGTGACC (SEQ ID NO: 302) | EMX1 HDR rev |
| PB1299 | CACCGCACTTTTCGACATAGTGTGG (SEQ ID NO: 303) | TP53 R209fs*6 |

TABLE S1-continued

Primers, ssODNs, adaptors and other oligos used in this disclosure.

| | | |
|---|---|---|
| PB1300 | AAACCCACACTATGTCGAAAAGTGC (SEQ ID NO: 304) | TP53 R209fs*6 |
| PB580 | CACCGCAGCATCAGAGGACTAGCTC (SEQ ID NO: 305) | SMARCAL1 Q34* |
| PB581 | AAACGAGCTAGTCCTCTGATGCTGC (SEQ ID NO: 306) | SMARCAL1 Q34* |
| PB838 | CACCGATTCCcAGCACGCTGATGTG (SEQ ID NO: 307) | FANCD2 Q223* for |
| PB839 | AAACCACATCAGCGTGCTgGGAATC (SEQ ID NO: 308) | FANCD2 Q223* rev |
| E12 | CAC CGA TAC ATT TTG TCT AGA CGT (SEQ ID NO: 309) | BRCA2 V2102I for |
| H06 | AAA CAC GTC TAG ACA AAA TGT ATC (SEQ ID NO: 310) | BRCA2 V2102I rev |
| PB1294 | CACCGTTTCACTTTTAGATATGATA (SEQ ID NO: 311) | BRCA2 dupAGAAGAT for |
| PB1295 | AAACTATCATATCTAAAAGTGAAAC (SEQ ID NO: 312) | BRCA2 dupAGAAGAT rev |
| PB738 | CACCGAAGACTCGAGCCCTCCAGCG (SEQ ID NO: 313) | TIMELESS R267* for |
| PB739 | AAACCGCTGGAGGGCTCGAGTCTTC (SEQ ID NO: 314) | TIMELESS R267* rev |
| PB834 | CACCGCAGCcAGTCAGCGTCCTCGC (SEQ ID NO: 315) | SLX4 W879* for |
| PB835 | AAACGCGAGGACGCTGACTgGCTGC (SEQ ID NO: 316) | SLX4 W879* rev |
| PB736 | CACCGGTACAACGAATGGGTAGAAC (SEQ ID NO: 317) | FANCM Q572* for |
| PB737 | AAACGTTCTACCCATTCGTTGTACC (SEQ ID NO: 318) | FANCM Q572* rev |

DOCUMENTS CITED

Allen, F., Crepaldi, L., Alsinet, C., Strong, A. J., Kleshchevnikov, V., De Angeli, P., Palenikova, P., Khodak, A., Kiselev, V., Kosicki, M., et al. (2018). Predicting the mutations generated by repair of Cas9-induced double-strand breaks. Nature biotechnology.

Anzalone, A. V., Randolph, P. B., Davis, J. R., Sousa, A. A., Koblan, L. W., Levy, J. M., Chen, P. J., Wilson, C., Newby, G. A., Raguram, A., et al. (2019). Search-and-replace genome editing without double-strand breaks or donor DNA. Nature.

Apostolou, P., and Fostira, F. (2013). Hereditary breast cancer: the era of new susceptibility genes. Biomed Res Int 2013, 747318.

Barbieri, E. M., Muir, P., Akhuetie-Oni, B. O., Yellman, C. M., and Isaacs, F. J. (2017). Precise Editing at DNA Replication Forks Enables Multiplex Genome Engineering in Eukaryotes. Cell 171, 1453-1467 e1413.

Bath, A. J., Milsom, S. E., Gormley, N. A., and Halford, S. E. (2002). Many type IIs restriction endonucleases interact with two recognition sites before cleaving DNA. J Biol Chem 277, 4024-4033.

Bhagwat, N., Koppikar, P., Keller, M., Marubayashi, S., Shank, K., Rampal, R., Qi, J., Kleppe, M., Patel, H. J., Shah, S. K., et al. (2014). Improved targeting of JAK2 leads to increased therapeutic efficacy in myeloproliferative neoplasms. Blood 123, 2075-2083.

Bhojwani, D., and Pui, C. H. (2013). Relapsed childhood acute lymphoblastic leukaemia. Lancet Oncol 14, e205-217.

Billing, D., Horiguchi, M., Wu-Baer, F., Taglialatela, A., Leuzzi, G., Nanez, S. A., Jiang, W., Zha, S., Szabolcs, M., Lin, C. S., et al. (2018). The BRCT Domains of the BRCA1 and BARD1 Tumor Suppressors Differentially Regulate Homology-Directed Repair and Stalled Fork Protection. Mol Cell 72, 127-139 e128.

Billon, P., Bryant, E. E., Joseph, S. A., Nambiar, T. S., Hayward, S. B., Rothstein, R., and Ciccia, A. (2017). CRISPR-Mediated Base Editing Enables Efficient Disruption of Eukaryotic Genes through Induction of STOP Codons. Mol Cell 67, 1068-1079 e1064.

Brinkman, E. K., Chen, T., Amendola, M., and van Steensel, B. (2014). Easy quantitative assessment of genome editing by sequence trace decomposition. Nucleic Acids Res 42, e168.

Brinkman, E. K., Kousholt, A. N., Harmsen, T., Leemans, C., Chen, T., Jonkers, J., and van Steensel, B. (2018). Easy quantification of template-directed CRISPR/Cas9 editing. Nucleic Acids Res 46, e58.

Canny, M. D., Moatti, N., Wan, L. C. K., Fradet-Turcotte, A., Krasner, D., Mateos-Gomez, P. A., Zimmermann, M., Orthwein, A., Juang, Y. C., Zhang, W., et al. (2018). Inhibition of 53BP1 favors homology-dependent DNA repair and increases CRISPR-Cas9 genome-editing efficiency. Nat Biotechnol 36, 95-102.

Ceccaldi, R., Sarangi, P., and D'Andrea, A. D. (2016). The Fanconi anaemia pathway: new players and new functions. Nat Rev Mol Cell Biol 17, 337-349.

Chadwick, A. C., Wang, X., and Musunuru, K. (2017). In Vivo Base Editing of PCSK9 (Proprotein Convertase Subtilisin/Kexin Type 9) as a Therapeutic Alternative to Genome Editing. Arterioscler Thromb Vasc Biol 37, 1741-1747.

Clement, K., Rees, H., Canver, M. C., Gehrke, J. M., Farouni, R., Hsu, J. Y., Cole, M. A., Liu, D. R., Joung, J. K., Bauer, D. E., et al. (2019). CRISPResso2 provides accurate and rapid genome editing sequence analysis. Nature biotechnology 37, 224-226.

Cong, L., Ran, F. A., Cox, D., Lin, S., Barretto, R., Habib, N., Hsu, P. D., Wu, X., Jiang, W., Marraffini, L. A., et al. (2013). Multiplex genome engineering using CRISPR/Cas systems. Science 339, 819-823.

Dieck, C. L., and Ferrando, A. A. (2019). Genetics and mechanisms of NT5C2-driven chemotherapy resistance in relapsed ALL. Blood.

Dow, L. E. (2015). Modeling Disease In Vivo With CRISPR/Cas9. Trends Mol Med 21, 609-621.

Fahim Farzadfard, T. K. L. (2018). Emerging applications for DNA writers and molecular recorders. Science 361, 870-875.

Findlay, G. M., Daza, R. M., Martin, B., Zhang, M. D., Leith, A. P., Gasperini, M., Janizek, J. D., Huang, X., Starita, L. M., and Shendure, J. (2018). Accurate classification of BRCA1 variants with saturation genome editing. Nature.

Gao, X., Tao, Y., Lamas, V., Huang, M., Yeh, W. H., Pan, B., Hu, Y. J., Hu, J. H., Thompson, D. B., Shu, Y., et al. (2018). Treatment of autosomal dominant hearing loss by in vivo delivery of genome editing agents. Nature 553, 217-221.

Gaudelli, N. M., Komor, A. C., Rees, H. A., Packer, M. S., Badran, A. H., Bryson, D. I., and Liu, D. R. (2017). Programmable base editing of A*T to G*C in genomic DNA without DNA cleavage. Nature.

Germini, D., Tsfasman, T., Zakharova, V. V., Sjakste, N., Lipinski, M., and Vassetzky, Y. (2018). A Comparison of Techniques to Evaluate the Effectiveness of Genome Editing. Trends Biotechnol 36, 147-159.

Guo, X., Chavez, A., Tung, A., Chan, Y., Kaas, C., Yin, Y., Cecchi, R., Garnier, S. L., Kelsic, E. D., Schubert, M., et al. (2018). High-throughput creation and functional profiling of DNA sequence variant libraries using CRISPR-Cas9 in yeast. Nat Biotechnol 36, 540-546.

Inaba, H., Greaves, M., and Mullighan, C. G. (2013). Acute lymphoblastic leukaemia. Lancet 381, 1943-1955.

Jasin, M., and Haber, J. E. (2016). The democratization of gene editing: Insights from site-specific cleavage and double-strand break repair. DNA Repair (Amst) 44, 6-16.

Kluesner, M. G., Nedveck, D. A., Lahr, W. S., Garbe, J. R., Abrahante, J. E., Webber, B. R., and Moriarity, B. S. (2018). EditR: A Method to Quantify Base Editing from Sanger Sequencing. CRISPR J 1, 239-250.

Komor, A. C., Kim, Y. B., Packer, M. S., Zuris, J. A., and Liu, D. R. (2016). Programmable editing of a target base in genomic DNA without double-stranded DNA cleavage. Nature 533, 420-424.

Komor, A. C., Zhao, K. T., Packer, M. S., Gaudelli, N. M., Waterbury, A. L., Koblan, L. W., Kim, Y. B., Badran, A. H., and Liu, D. R. (2017). Improved base excision repair inhibition and bacteriophage Mu Gam protein yields C:G-to-T:A base editors with higher efficiency and product purity. Sci Adv 3, eaao4774.

Leenay, R. T., Aghazadeh, A., Hiatt, J., Tse, D., Roth, T. L., Apathy, R., Shifrut, E., Hultquist, J. F., Krogan, N., Wu, Z., et al. (2019). Large dataset enables prediction of repair after CRISPR-Cas9 editing in primary T cells. Nature biotechnology 37, 1034-1037.

Lek, M., Karczewski, K. J., Minikel, E. V., Samocha, K. E., Banks, E., Fennell, T., O'Donnell-Luria, A. H., Ware, J. S., Hill, A. J., Cummings, B. B., et al. (2016). Analysis of protein-coding genetic variation in 60,706 humans. Nature 536, 285-291.

Levine, R. L., Wadleigh, M., Cools, J., Ebert, B. L., Wernig, G., Huntly, B. J., Boggon, T. J., Wlodarska, I., Clark, J. J., Moore, S., et al. (2005). Activating mutation in the tyrosine kinase JAK2 in polycythemia vera, essential thrombocythemia, and myeloid metaplasia with myelofibrosis. Cancer Cell 7, 387-397.

Levy, J. M., Yeh, W. H., Pendse, N., Davis, J. R., Hennessey, E., Butcher, R., Koblan, L. W., Comander, J., Liu, Q., and Liu, D. R. (2020). Cytosine and adenine base editing of the brain, liver, retina, heart and skeletal muscle of mice via adeno-associated viruses. Nat Biomed Eng 4, 97-110.

Lindsay, H., Burger, A., Biyong, B., Felker, A., Hess, C., Zaugg, J., Chiavacci, E., Anders, C., Jinek, M., Mosimann, C., et al. (2016). CrispRVariants charts the mutation spectrum of genome engineering experiments. Nat Biotechnol 34, 701-702.

Liu, Z., Lu, Z., Yang, G., Huang, S., Li, G., Feng, S., Liu, Y., Li, J., Yu, W., Zhang, Y., et al. (2018). Efficient generation of mouse models of human diseases via ABE- and BE-mediated base editing. Nat Commun 9, 2338.

Lundin, S., Jemt, A., Terje-Hegge, F., Foam, N., Pettersson, E., Kaller, M., Wirta, V., Lexow, P., and Lundeberg, J. (2015). Endonuclease specificity and sequence dependence of type IIS restriction enzymes. PLoS One 10, e0117059.

Mali, P., Yang, L., Esvelt, K. M., Aach, J., Guell, M., DiCarlo, J. E., Norville, J. E., and Church, G. M. (2013). RNA-guided human genome engineering via Cas9. Science 339, 823-826.

Mashal, R. D., Koontz, J., and Sklar, J. (1995). Detection of mutations by cleavage of DNA heteroduplexes with bacteriophage resolvases. Nat Genet 9, 177-183.

McClellan, J., and King, M. C. (2010). Genetic heterogeneity in human disease. Cell 141, 210-217.

Mullally, A., Lane, S. W., Ball, B., Megerdichian, C., Okabe, R., Al-Shahrour, F., Paktinat, M., Haydu, J. E., Housman, E., Lord, A. M., et al. (2010). Physiological Jak2V617F expression causes a lethal myeloproliferative neoplasm with differential effects on hematopoietic stem and progenitor cells. Cancer Cell 17, 584-596.

Oshima, K., Khiabanian, H., da Silva-Almeida, A. C., Tzoneva, G., Abate, F., Ambesi-Impiombato, A., Sanchez-Martin, M., Carpenter, Z., Penson, A., Perez-Garcia, A., et al. (2016). Mutational landscape, clonal evolution patterns, and role of RAS mutations in relapsed acute lymphoblastic leukemia. Proc Natl Acad Sci USA 113, 11306-11311.

Pathania, S., Bade, S., Le Guillou, M., Burke, K., Reed, R., Bowman-Colin, C., Su, Y., Ting, D. T., Polyak, K., Richardson, A. L., et al. (2014). BRCA1 haploinsufficiency for replication stress suppression in primary cells. Nature communications 5, 5496.

Paulsen, B. S., Mandal, P. K., Frock, R. L., Boyraz, B., Yadav, R., Upadhyayula, S., Gutierrez-Martinez, P., Ebina, W., Fasth, A., Kirchhausen, T., et al. (2017). Ectopic expression of RAD52 and dn53BP1 improves homology-directed repair during CRISPR-Cas9 genome editing. Nat Biomed Eng 1, 878-888.

Pinello, L., Canver, M. C., Hoban, M. D., Orkin, S. H., Kohn, D. B., Bauer, D. E., and Yuan, G. C. (2016). Analyzing CRISPR genome-editing experiments with CRISPResso. Nature biotechnology 34, 695-697.

Qiu, P., Shandilya, H., D'Alessio, J. M., O'Connor, K., Durocher, J., and Gerard, G. F. (2004). Mutation detection using Surveyor nuclease. Biotechniques 36, 702-707.

Ran, F. A., Hsu, P. D., Wright, J., Agarwala, V., Scott, D. A., and Zhang, F. (2013). Genome engineering using the CRISPR-Cas9 system. Nature protocols 8, 2281-2308.

Rees, H. A., and Liu, D. R. (2018). Base editing: precision chemistry on the genome and transcriptome of living cells. Nat Rev Genet 19, 770-788.

Roy, K. R., Smith, J. D., Vonesch, S. C., Lin, G., Tu, C. S., Lederer, A. R., Chu, A., Suresh, S., Nguyen, M., Horecka, J., et al. (2018). Multiplexed precision genome editing with trackable genomic barcodes in yeast. Nat Biotechnol 36, 512-520.

Ryu, S. M., Koo, T., Kim, K., Lim, K., Baek, G., Kim, S. T., Kim, H. S., Kim, D. E., Lee, H., Chung, E., et al. (2018). Adenine base editing in mouse embryos and an adult mouse model of Duchenne muscular dystrophy. Nature biotechnology 36, 536-539.

Shakya, R., Reid, L. J., Reczek, C. R., Cole, F., Egli, D., Lin, C. S., deRooij, D. G., Hirsch, S., Ravi, K., Hicks, J. B., et al. (2011). BRCA1 tumor suppression depends on BRCT phosphoprotein binding, but not its E3 ligase activity. Science 334, 525-528.

Shen, M. W., Arbab, M., Hsu, J. Y., Worstell, D., Culbertson, S. J., Krabbe, O., Cassa, C. A., Liu, D. R., Gifford, D. K., and Sherwood, R. I. (2018). Predictable and precise template-free CRISPR editing of pathogenic variants. Nature 563, 646-651.

Song, C. Q., Jiang, T., Richter, M., Rhym, L. H., Koblan, L. W., Zafra, M. P., Schatoff, E. M., Doman, J. L., Cao, Y., Dow, L. E., et al. (2020). Adenine base editing in an adult mouse model of tyrosinaemia. Nat Biomed Eng 4, 125-130.

Tan, S. L. W., Chadha, S., Liu, Y., Gabasova, E., Perera, D., Ahmed, K., Constantinou, S., Renaudin, X., Lee, M., Aebersold, R., et al. (2017). A Class of Environmental and Endogenous Toxins Induces BRCA2 Haploinsufficiency and Genome Instability. Cell 169, 1105-1118 e1115.

Tschaharganeh, D. F., Xue, W., Calvisi, D. F., Evert, M., Michurina, T. V., Dow, L. E., Banito, A., Katz, S. F., Kastenhuber, E. R., Weissmueller, S., et al. (2014). p53-dependent Nestin regulation links tumor suppression to cellular plasticity in liver cancer. Cell 158, 579-592.

Tzoneva, G., Dieck, C. L., Oshima, K., Ambesi-Impiombato, A., Sanchez-Martin, M., Madubata, C. J., Khiabanian, H., Yu, J., Waanders, E., Iacobucci, I., et al. (2018). Clonal evolution mechanisms in NT5C2 mutant-relapsed acute lymphoblastic leukaemia. Nature 553, 511-514.

Tzoneva, G., Perez-Garcia, A., Carpenter, Z., Khiabanian, H., Tosello, V., Allegretta, M., Paietta, E., Racevskis, J., Rowe, J. M., Tallman, M. S., et al. (2013). Activating mutations in the NT5C2 nucleotidase gene drive chemotherapy resistance in relapsed ALL. Nat Med 19, 368-371.

van Overbeek, M., Capurso, D., Carter, M. M., Thompson, M. S., Frias, E., Russ, C., Reece-Hoyes, J. S., Nye, C., Gradia, S., Vidal, B., et al. (2016). DNA Repair Profiling Reveals Nonrandom Outcomes at Cas9-Mediated Breaks. Mol Cell 63, 633-646.

Villiger, L., Grisch-Chan, H. M., Lindsay, H., Ringnalda, F., Pogliano, C. B., Allegri, G., Fingerhut, R., Haberle, J., Matos, J., Robinson, M. D., et al. (2018). Treatment of a metabolic liver disease by in vivo genome base editing in adult mice. Nat Med 24, 1519-1525.

Wang, L., Xue, W., Yan, L., Li, X., Wei, J., Chen, M., Wu, J., Yang, B., Yang, L., and Chen, J. (2017). Enhanced base editing by co-expression of free uracil DNA glycosylase inhibitor. Cell Res 27, 1289-1292.

Yeh, W. H., Chiang, H., Rees, H. A., Edge, A. S. B., and Liu, D. R. (2018). In vivo base editing of post-mitotic sensory cells. Nature communications 9, 2184.

Yin, H., Song, C. Q., Dorkin, J. R., Zhu, L. J., Li, Y., Wu, Q., Park, A., Yang, J., Suresh, S., Bizhanova, A., et al. (2016). Therapeutic genome editing by combined viral and non-viral delivery of CRISPR system components in vivo. Nature biotechnology 34, 328-333.

Yin, H., Xue, W., Chen, S., Bogorad, R. L., Benedetti, E., Grompe, M., Koteliansky, V., Sharp, P. A., Jacks, T., and Anderson, D. G. (2014). Genome editing with Cas9 in adult mice corrects a disease mutation and phenotype. Nature biotechnology 32, 551-553.

Zafra, M. P., Schatoff, E. M., Katti, A., Foronda, M., Breinig, M., Schweitzer, A. Y., Simon, A., Han, T., Goswami, S., Montgomery, E., et al. (2018). Optimized base editors enable efficient editing in cells, organoids and mice. Nature biotechnology 36, 888-893.

Zhang, J., Li, J., Saucier, J. B., Feng, Y., Jiang, Y., Sinson, J., McCombs, A. K., Schmitt, E. S., Peacock, S., Chen, S., et al. (2019). Non-invasive prenatal sequencing for multiple Mendelian monogenic disorders using circulating cell-free fetal DNA. Nat Med 25, 439-447.

All documents cited in this application are hereby incorporated by reference as if recited in full herein.

Although illustrative embodiments of the present disclosure have been described herein, it should be understood that the disclosure is not limited to those described, and that various other changes or modifications may be made by one skilled in the art without departing from the scope or spirit of the disclosure.

What is claimed is:

1. A method for detecting a genetic modification in a DNA sequence of interest, comprising the steps of:
   (a) amplifying the DNA sequence of interest using a specially designed Type IIS restriction enzyme-tagging primer, comprising:
      (i) obtaining the DNA sequence of interest from a biological sample;
      (ii) synthesizing the Type IIS restriction enzyme-tagging primer based on the DNA sequence of interest;
      (iii) amplifying the DNA sequence of interest using the Type IIS restriction enzyme-tagging primer and a reverse primer; and
      (iv) purifying a Type IIS restriction enzyme-tagged amplicon;
   (b) digesting the Type IIS restriction enzyme-tagged amplicon with the Type IIS restriction enzyme;

(c) isolating the smaller DNA fragment containing the genetic modification exposed in a 3' single-stranded overhang;
(d) capturing the genetic modification, comprising:
  (i) preparing a library of 16 DNA adaptors, wherein each DNA adaptor comprises one strand with sequence of 5'-CTGGGGCACGGGT- AAGAAGC-ATTCTGTCTCTCTTCTAAGAATTCGAG CTC-GGTACCCG-3' (SEQ ID NO: 230); and one complementary strand with sequence of 5'-CGGGTACCGAGCTCGAATTCTTAGAAG-AGAGACAGAATGCTTCTTACCCGTGCCCC-AGNN-3' with "N" corresponding to A, T, G or C (SEQ ID NOs: 231-246), and wherein each DNA adaptor has a different "NN";
  (ii) incubating the isolated smaller DNA fragment containing the 3' overhang with the library of DNA adaptors and performing a ligation; and
  (iii) obtaining a ligated product; and
(e) amplifying the ligated product to detect the presence of the genetic modification, wherein the DNA sequence of interest is a genomic locus or corresponds to a genomic locus of an RNA virus variant.

2. The method of claim 1, wherein the DNA sequence of interest corresponds to a genomic locus of an RNA virus variant, and wherein obtaining the DNA sequence of interest comprises obtaining the RNA sequence from the RNA virus variant and converting it to the corresponding DNA sequence by reverse transcription PCR (RT-PCR).

3. The method of claim 2, wherein the RNA virus is SARS-CoV-2.

4. The method of claim 1, wherein the Type IIS restriction enzyme is selected from AcuI, BpmI, BpuEI, BsgI, MmeI and NmeAIII.

5. The method of claim 4, wherein the Type IIS restriction enzyme is AcuI.

6. The method of claim 1, wherein the Type IIS restriction enzyme-tagging primer is an oligonucleotide comprising:
  (a) a non-complementary handle sequence positioned on the 5' side;
  (b) a complementary sequence of the genomic locus of interest on the 5' side;
  (c) a recognition motif of the Type IIS restriction enzyme that is positioned at a predicted distance from its cleavage site to generate the genomic signature of interest; and
  (d) a complementary sequence of the genomic locus of interest on the 3' side.

7. A kit for detecting a genetic modification of interest, comprising a specially designed Type IIS restriction enzyme-tagging primer according to claim 6, and a library of DNA adaptors according to claim 1, packaged together with instructions for its use.

8. The method of claim 5, wherein the AcuI-tagging primer is an oligonucleotide comprising:
  (a) a non-complementary handle sequence positioned on the 5' side; and
  (b) a complementary sequence of the genomic locus of interest containing an AcuI motif (5'-CTGAAG-3') positioned 14 bp upstream from the genomic locus of interest.

9. The method of claim 8, wherein the reverse primer is positioned at more than 100 bp downstream of the genomic locus of interest.

10. The method of claim 8, wherein the non-complementary handle sequence is 25 bp.

11. The method of claim 8, wherein the complementary sequence has the structure of: 5'-N(20)CTGAAGN(14)-3' or 5'-N(15)CTGAAGN(14)-3', with "N" corresponding to A, T, G or C, depending on the DNA sequence of the genomic locus of interest.

12. The method of claim 8, wherein the non-complementary handle sequence is 5'-GCAATTCCTCACGA-GACCCGTCCTG-3' (SEQ ID NO: 3) and the complementary sequence is 5'-N(15)CTGAAGN(14)-3', with "N" corresponding to A, T, G or C.

13. A kit for detecting a genetic modification, comprising a specially designed AcuI-tagging primer and a library of DNA adaptors according to claim 1, packaged together with instructions for its use.

14. A method for quantifying a genomic variant in a biological system, comprising the steps of:
  (a) obtaining a sample from the biological system;
  (b) amplifying a DNA sequence of interest using a specially designed AcuI-tagging primer, wherein the DNA sequence of interest is a genomic locus or corresponds to a genomic locus of an RNA virus variant, comprising:
    (i) obtaining the DNA sequence of interest by (1) genomic extraction or (2) obtaining the RNA sequence from the RNA virus variant and converting it to the corresponding DNA sequence by reverse transcription PCR (RT-PCR);
    (ii) synthesizing the AcuI-tagging primer based on the DNA sequence of interest;
    (iii) amplifying the DNA sequence of interest using the AcuI-tagging primer and a reverse primer; and
    (iv) purifying an AcuI-tagged amplicon;
  (c) digesting the AcuI-tagged amplicon with restriction enzyme AcuI;
  (d) isolating the smaller DNA fragment containing the genomic variant of interest produced by the AcuI-digestion;
  (e) capturing the genomic variant of interest, comprising:
    (i) preparing the library of DNA adaptors according to claim 1;
    (ii) incubating the isolated smaller DNA fragment with the library of DNA adaptors and performing a ligation; and
    (iii) obtaining a ligated product; and
  (f) quantifying the genomic variant and determining its relative abundance.

15. The method of claim 14, wherein the genomic variant is generated by precision genome editing.

16. The method of claim 15, wherein the precision genome editing is CRISPER-dependent homology-directed repair, base editing or prime editing.

17. The method of claim 14, wherein the quantification in step (f) is carried out by quantitative PCR (qPCR).

18. A method for identifying and quantifying an oncogenic mutation of interest in a biological sample, comprising the steps of:
  (a) obtaining a biological sample;
  (b) amplifying a genomic locus of interest using a specially designed AcuI-tagging primer, comprising:
    (i) extracting DNA of interest;
    (ii) synthesizing the AcuI-tagging primer based on the genomic locus of interest;
    (iii) amplifying the genomic locus of interest using the AcuI-tagging primer and a reverse primer; and
    (iv) purifying an AcuI-tagged genomic amplicon;
  (c) digesting the AcuI-tagged genomic amplicon with restriction enzyme AcuI;

(d) isolating the smaller DNA fragment containing the oncogenic mutation of interest produced by the AcuI-digestion;
(e) capturing the genomic signature of interest, comprising:
  (i) preparing the library of DNA adaptors according to claim 1;
  (ii) incubating the isolated smaller DNA fragment with the library of DNA adaptors and performing a ligation; and
  (iii) obtaining a ligated product;
(f) amplifying the ligated product to identify the presence of the oncogenic mutation of interest; and
(g) quantifying the oncogenic mutation of interest, if present, and determining its frequency.

19. The method of claim 18, wherein the biological sample is obtained from a cancer animal model, a patient-derived xenograft (PDX), or a human cancer patient sample.

20. The method of claim 18, wherein the quantification in step (g) is carried out by quantitative PCR (qPCR).

* * * * *

SEQUENCE LISTING

<160> NUMBER OF SEQ ID NOS: 320

<210> SEQ ID NO 1
<211> LENGTH: 20
<212> TYPE: DNA
<213> ORGANISM: Artificial Sequence
<220> FEATURE:

<223> OTHER INFORMATION: Laboratory Synthesized

<400> SEQUENCE: 1
gatcctctag agtcgacctg					20

<210> SEQ ID NO 2
<211> LENGTH: 20
<212> TYPE: DNA
<213> ORGANISM: Artificial Sequence
<220> FEATURE:
<223> OTHER INFORMATION: Laboratory Synthesized

<400> SEQUENCE: 2
cgggtaccga gctcgaattc					20

<210> SEQ ID NO 3
<211> LENGTH: 25
<212> TYPE: DNA
<213> ORGANISM: Artificial Sequence
<220> FEATURE:
<223> OTHER INFORMATION: Laboratory Synthesized

<400> SEQUENCE: 3
gcaattcctc acgagacccg tcctg					25

<210> SEQ ID NO 4
<211> LENGTH: 27
<212> TYPE: DNA
<213> ORGANISM: Artificial Sequence
<220> FEATURE:
<223> OTHER INFORMATION: Laboratory Synthesized

<400> SEQUENCE: 4
cgggtaccga gctcgaattc ttagaag					27

<210> SEQ ID NO 5
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 5
gatcctctag agtcgacctg ggagtccctg tcgctagtgg ctgaagacgc gtcgtgggag					60

<210> SEQ ID NO 6
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 6
gatcctctag agtcgacctg acaaacagtg cctgcaagtc ctgaagcggt gtgggtcca					60

<210> SEQ ID NO 7
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 7
gcaattcctc acgagacccg tcctgatttc agggaagaag ctgaagtgaa tgaaaaactt					60

```
<210> SEQ ID NO 8
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 8
gcaattcctc acgagacccg tcctgtgtag ttttacttac ctgaagtctc gtctccacag    60

<210> SEQ ID NO 9
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 9
gcaattcctc acgagacccg tcctgaggac atcgatgtca ctgaagcctc caatgactag    60

<210> SEQ ID NO 10
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 10
gatcctctag agtcgacctg aaacggcaga agctggagga ctgaagggaa gggcctgagt    60

<210> SEQ ID NO 11
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 11
gcaattcctc acgagacccg tcctggttca gtttaacgac ctgaagcaat tcttctgggg    60

<210> SEQ ID NO 12
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 12
gcaattcctc acgagacccg tcctgtgtgt tcactagcaa ctgaagcctc aaacagacac    60

<210> SEQ ID NO 13
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 13
gcaattcctc acgagacccg tcctggagga ggaggcccct ctgaaggcag ggacacgaag    60

<210> SEQ ID NO 14
<211> LENGTH: 60
<212> TYPE: DNA
<213> ORGANISM: Artificial Sequence
<220> FEATURE:
<223> OTHER INFORMATION: Laboratory Synthesized
```

<400> SEQUENCE: 14
gatcctctag agtcgacctg ccaaattata tacctttttgg ctgaagttat atcattctta    60

<210> SEQ ID NO 15
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 15
gatcctctag agtcgacctg tcttcactgc tagaacaact ctgaagatca atttgcaatt    60

<210> SEQ ID NO 16
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 16
gatcctctag agtcgacctg atattgcttg agctggcttc ctgaagttta aaaacatttt    60

<210> SEQ ID NO 17
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 17
gatcctctag agtcgacctg ggttcagctt tcgttttgaa ctgaagagca gattcttttt    60

<210> SEQ ID NO 18
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 18
gatcctctag agtcgacctg tcctctagca gatttttctt ctgaagacat ttagttttaa    60

<210> SEQ ID NO 19
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 19
gatcctctag agtcgacctg ggaaagaatg agtctaatat ctgaagcaag cctgtacaga    60

<210> SEQ ID NO 20
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 20
gatcctctag agtcgacctg catcattacc aaattatata ctgaagcctt ttggttatat    60

<210> SEQ ID NO 21
<211> LENGTH: 60

```
<212> TYPE: DNA
<213> ORGANISM: Artificial Sequence
<220> FEATURE:
<223> OTHER INFORMATION: Laboratory Synthesized

<400> SEQUENCE: 21
gatcctctag agtcgacctg gagggaggga gctttacctt ctgaagtctg tcctgggatt     60

<210> SEQ ID NO 22
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 22
gatcctctag agtcgacctg gaagaaaata atcaagaaga ctgaaggcaa agcatggatt     60

<210> SEQ ID NO 23
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 23
gatcctctag agtcgacctg gcagtgattt tacatctaaa ctgaagtgtc cattttagat     60

<210> SEQ ID NO 24
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 24
gatcctctag agtcgacctg gatggagaag acatcatctg ctgaaggatt atacatattt     60

<210> SEQ ID NO 25
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 25
gatcctctag agtcgacctg tgaatctttt tcttttttg ctgaagaata gcttacaata     60

<210> SEQ ID NO 26
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 26
gatcctctag agtcgacctg ctgagtattt ggcgtccatc ctgaagatca gatttatatt     60

<210> SEQ ID NO 27
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 27
```
gatcctctag agtcgacctg caaatttta gatccagact ctgaagtcag ccatcttgtt    60

<210> SEQ ID NO 28
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 28
gatcctctag agtcgacctg agtgcaaatt aatttacctt ctgaagtaac ataagagatt    60

<210> SEQ ID NO 29
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 29
gatcctctag agtcgacctg ggaatatttg atggtcaacc ctgaagagaa agaataaata    60

<210> SEQ ID NO 30
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 30
gatcctctag agtcgacctg atcttgttct gaggtggacc ctgaagtaat aggatttgtc    60

<210> SEQ ID NO 31
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 31
gatcctctag agtcgacctg taggaaggcc atggaatctg ctgaagctga acaaaaggaa    60

<210> SEQ ID NO 32
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 32
gatcctctag agtcgacctg aactgaagcc tctgaaagtg ctgaagactg gaaatacata    60

<210> SEQ ID NO 33
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 33
gatcctctag agtcgacctg tttaccatca cgtgcactaa ctgaagcaag acagcaagtt    60

<210> SEQ ID NO 34
<211> LENGTH: 60
<212> TYPE: DNA
<213> ORGANISM: Artificial Sequence

```
<220> FEATURE:
<223> OTHER INFORMATION: Laboratory Synthesized

<400> SEQUENCE: 34
gatcctctag agtcgacctg tggaagctgg ccagccacca ctgaagccac acagaattct    60

<210> SEQ ID NO 35
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 35
gatcctctag agtcgacctg ttgcctctag aaatcatgac ctgaagtagg tttgacagaa    60

<210> SEQ ID NO 36
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 36
gatcctctag agtcgacctg tttctcttat caacacgagg ctgaagaagt atttttgata    60

<210> SEQ ID NO 37
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 37
gatcctctag agtcgacctg caaacgacga gcgtgacacc ctgaagacga tgcctgtagc    60

<210> SEQ ID NO 38
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 38
gatcctctag agtcgacctg tcgttgggaa ccggagctga ctgaagatga agccatacca    60

<210> SEQ ID NO 39
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 39
gatcctctag agtcgacctg gagctgaatg aagccatacc ctgaagaaac gacgagcgtg    60

<210> SEQ ID NO 40
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 40
gatcctctag agtcgacctg gctgaatgaa gccataccaa ctgaagacga cgagcgtgac    60
```

```
<210> SEQ ID NO 41
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 41
gatcctctag agtcgacctg aaccggagc tgaatgaagc ctgaagcata ccaaacgacg    60

<210> SEQ ID NO 42
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 42
gatcctctag agtcgacctg taccaaacga cgagcgtgac ctgaagacca cgatgcctgt    60

<210> SEQ ID NO 43
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 43
gatcctctag agtcgacctg tgaagccata ccaaacgacg ctgaagagcg tgacaccacg    60

<210> SEQ ID NO 44
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 44
gatcctctag agtcgacctg aaacgacgag cgtgacacca ctgaagcgat gcctgtagca    60

<210> SEQ ID NO 45
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 45
gatcctctag agtcgacctg gatcgttggg aaccggagct ctgaaggaat gaagccatac    60

<210> SEQ ID NO 46
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 46
gatcctctag agtcgacctg agctgaatga agccatacca ctgaagaacg acgagcgtga    60

<210> SEQ ID NO 47
<211> LENGTH: 60
<212> TYPE: DNA
<213> ORGANISM: Artificial Sequence
<220> FEATURE:
<223> OTHER INFORMATION: Laboratory Synthesized
```

```
<400> SEQUENCE: 47
gatcctctag agtcgacctg ctgaatgaag ccataccaaa ctgaagcgac gagcgtgaca    60

<210> SEQ ID NO 48
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 48
gatcctctag agtcgacctg agccatacca acgacgagc ctgaaggtga caccacgatg     60

<210> SEQ ID NO 49
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 49
gatcctctag agtcgacctg accggagctg aatgaagcca ctgaagtacc aaacgacgag    60

<210> SEQ ID NO 50
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 50
gatcctctag agtcgacctg aatgaagcca taccaaacga ctgaagcgag cgtgacacca    60

<210> SEQ ID NO 51
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 51
gatcctctag agtcgacctg gccataccaa acgacgagcg ctgaagtgac accacgatgc    60

<210> SEQ ID NO 52
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 52
gatcctctag agtcgacctg tcatgtaact cgccttgatc ctgaaggttg ggaaccggag    60

<210> SEQ ID NO 53
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 53
gatcctctag agtcgacctg ggagctgaat gaagccatac ctgaagcaaa cgacgagcgt    60

<210> SEQ ID NO 54
```

```
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 54
gatcctctag agtcgacctg ggaaccggag ctgaatgaag ctgaagccat accaaacgac    60

<210> SEQ ID NO 55
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 55
gatcctctag agtcgacctg aaccggagct gaatgaagcc ctgaagatac caaacgacga    60

<210> SEQ ID NO 56
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 56
gatcctctag agtcgacctg aagccatacc aaacgacgag ctgaagcgtg acaccacgat    60

<210> SEQ ID NO 57
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 57
gatcctctag agtcgacctg acgacgagcg tgacaccacg ctgaagatgc ctgtagcaat    60

<210> SEQ ID NO 58
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 58
gatcctctag agtcgacctg agcaatggca acaacgttgc ctgaaggcaa actattaact    60

<210> SEQ ID NO 59
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 59
gatcctctag agtcgacctg ccggagctga atgaagccat ctgaagacca aacgacgagc    60

<210> SEQ ID NO 60
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 60
```
gatcctctag agtcgacctg cataccaaac gacgagcgtg ctgaagacac cacgatgcct    60

<210> SEQ ID NO 61
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 61
gatcctctag agtcgacctg cttgatcgtt gggaaccgga ctgaaggctg aatgaagcca    60

<210> SEQ ID NO 62
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 62
gatcctctag agtcgacctg ataccaaacg acgagcgtga ctgaagcacc acgatgcctg    60

<210> SEQ ID NO 63
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 63
gatcctctag agtcgacctg ccgctttttt gcacaacatg ctgaaggggg atcatgtaac    60

<210> SEQ ID NO 64
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 64
gatcctctag agtcgacctg cgttgcgcaa actattaact ctgaagggcg aactacttac    60

<210> SEQ ID NO 65
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 65
gatcctctag agtcgacctg cggagctgaa tgaagccata ctgaagccaa acgacgagcg    60

<210> SEQ ID NO 66
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 66
gatcctctag agtcgacctg ccataccaaa cgacgagcgt ctgaaggaca ccacgatgcc    60

<210> SEQ ID NO 67
<211> LENGTH: 60
<212> TYPE: DNA

<213> ORGANISM: Artificial Sequence
<220> FEATURE:
<223> OTHER INFORMATION: Laboratory Synthesized

<400> SEQUENCE: 67
gatcctctag agtcgacctg tgacaccacg atgcctgtag ctgaagcaat ggcaacaacg    60

<210> SEQ ID NO 68
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 68
gatcctctag agtcgacctg gcctgtagca atggcaacaa ctgaagcgtt gcgcaaacta    60

<210> SEQ ID NO 69
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 69
gcaattcctc acgagacccg tcctgacctg agttctttcc ctgaagccac atcagcgtgc    60

<210> SEQ ID NO 70
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 70
gatcctctag agtcgacctg ccgcagagct gagaagttat ctgaagtggc agaacagcat    60

<210> SEQ ID NO 71
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 71
gatcctctag agtcgacctg gttttcattt cagggaagaa ctgaaggtga atgaaaaact    60

<210> SEQ ID NO 72
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 72
gatcctctag agtcgacctg tctcgtacca aaaaggtccc ctgaaggtct gctgtatctc    60

<210> SEQ ID NO 73
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 73
gatcctctag agtcgacctg atctcgtacc aaaaaggtcc ctgaagcgtc tgctgtatct    60

<210> SEQ ID NO 74
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 74
gatcctctag agtcgacctg ttttcatttc agggaagaag ctgaagtgaa tgaaaaactt    60

<210> SEQ ID NO 75
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 75
gcaattcctc acgagacccg tcctgtgcgc aaactattct gaagaactgg cgaactacaa    60

<210> SEQ ID NO 76
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 76
gcaattcctc acgagacccg tcctgtgcgc aaactattct gaagaactgg cgaactacac    60

<210> SEQ ID NO 77
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 77
gcaattcctc acgagacccg tcctgtgcgc aaactattct gaagaactgg cgaactacag    60

<210> SEQ ID NO 78
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 78
gcaattcctc acgagacccg tcctgtgcgc aaactattct gaagaactgg cgaactacat    60

<210> SEQ ID NO 79
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 79
gcaattcctc acgagacccg tcctgtgcgc aaactattct gaagaactgg cgaactacca    60

<210> SEQ ID NO 80
<211> LENGTH: 60
<212> TYPE: DNA
<213> ORGANISM: Artificial Sequence
<220> FEATURE:

<223> OTHER INFORMATION: Laboratory Synthesized

<400> SEQUENCE: 80
gcaattcctc acgagacccg tcctgtgcgc aaactattct gaagaactgg cgaactaccc        60

<210> SEQ ID NO 81
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 81
gcaattcctc acgagacccg tcctgtgcgc aaactattct gaagaactgg cgaactaccg        60

<210> SEQ ID NO 82
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 82
gcaattcctc acgagacccg tcctgtgcgc aaactattct gaagaactgg cgaactacct        60

<210> SEQ ID NO 83
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 83
gcaattcctc acgagacccg tcctgtgcgc aaactattct gaagaactgg cgaactacga        60

<210> SEQ ID NO 84
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 84
gcaattcctc acgagacccg tcctgtgcgc aaactattct gaagaactgg cgaactacgc        60

<210> SEQ ID NO 85
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 85
gcaattcctc acgagacccg tcctgtgcgc aaactattct gaagaactgg cgaactacgg        60

<210> SEQ ID NO 86
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 86
gcaattcctc acgagacccg tcctgtgcgc aaactattct gaagaactgg cgaactacgt        60

```
<210> SEQ ID NO 87
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 87
gcaattcctc acgagacccg tcctgtgcgc aaactattct gaagaactgg cgaactacta      60

<210> SEQ ID NO 88
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 88
gcaattcctc acgagacccg tcctgtgcgc aaactattct gaagaactgg cgaactactc      60

<210> SEQ ID NO 89
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 89
gcaattcctc acgagacccg tcctgtgcgc aaactattct gaagaactgg cgaactactg      60

<210> SEQ ID NO 90
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 90
gcaattcctc acgagacccg tcctgtgcgc aaactattct gaagaactgg cgaactactt      60

<210> SEQ ID NO 91
<211> LENGTH: 58
<212> TYPE: DNA
<213> ORGANISM: Artificial Sequence
<220> FEATURE:
<223> OTHER INFORMATION: Laboratory Synthesized

<400> SEQUENCE: 91
gtagttcgcc agttcttcag aatagtttgc gcacaggacg ggtctcgtga ggaattgc        58

<210> SEQ ID NO 92
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 92
gcaattcctc acgagacccg tcctggtggc tccataggaa ctgaaggtct ttctcttgtt      60

<210> SEQ ID NO 93
<211> LENGTH: 60
<212> TYPE: DNA
<213> ORGANISM: Artificial Sequence
<220> FEATURE:
<223> OTHER INFORMATION: Laboratory Synthesized
```

```
<400> SEQUENCE: 93
gcaattcctc acgagacccg tcctgttata tacctttgg ctgaagttat atcattctta    60

<210> SEQ ID NO 94
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 94
gcaattcctc acgagacccg tcctgactgc tagaacaact ctgaagatca atttgcaatt    60

<210> SEQ ID NO 95
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 95
gcaattcctc acgagacccg tcctggcttg agctggcttc ctgaagttta aaacatttt    60

<210> SEQ ID NO 96
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 96
gcaattcctc acgagacccg tcctgagctt tcgttttgaa ctgaagagca gattcttttt    60

<210> SEQ ID NO 97
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 97
gcaattcctc acgagacccg tcctgtagca gattttctt ctgaagacat ttagttttaa    60

<210> SEQ ID NO 98
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 98
gcaattcctc acgagacccg tcctggaatg agtctaatat ctgaagcaag cctgtacaga    60

<210> SEQ ID NO 99
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 99
gcaattcctc acgagacccg tcctgttacc aaattatata ctgaagcctt ttggttatat    60

<210> SEQ ID NO 100
<211> LENGTH: 60
```

<212> TYPE: DNA
<213> ORGANISM: Artificial Sequence
<220> FEATURE:
<223> OTHER INFORMATION: Laboratory Synthesized

<400> SEQUENCE: 100
gcaattcctc acgagacccg tcctgaggga gctttacctt ctgaagtctg tcctgggatt    60

<210> SEQ ID NO 101
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 101
gcaattcctc acgagacccg tcctgaaata atcaagaaga ctgaaggcaa agcatggatt    60

<210> SEQ ID NO 102
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 102
gcaattcctc acgagacccg tcctggattt tacatctaaa ctgaagtgtc cattttagat    60

<210> SEQ ID NO 103
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 103
gcaattcctc acgagacccg tcctgagaag acatcatctg ctgaaggatt atacatattt    60

<210> SEQ ID NO 104
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 104
gcaattcctc acgagacccg tcctgctttt tcttttttg ctgaagaata gcttacaata    60

<210> SEQ ID NO 105
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 105
gcaattcctc acgagacccg tcctgtattt ggcgtccatc ctgaagatca gatttatatt    60

<210> SEQ ID NO 106
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 106

```
gcaattcctc acgagacccg tcctgtttta gatccagact ctgaagtcag ccatcttgtt    60
```

<210> SEQ ID NO 107
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 107

```
gcaattcctc acgagacccg tcctgaaatt aatttacctt ctgaagtaac ataagagatt    60
```

<210> SEQ ID NO 108
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 108

```
gcaattcctc acgagacccg tcctgatttg atggtcaacc ctgaagagaa agaataaata    60
```

<210> SEQ ID NO 109
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 109

```
gcaattcctc acgagacccg tcctggttct gaggtggacc ctgaagtaat aggatttgtc    60
```

<210> SEQ ID NO 110
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 110

```
gcaattcctc acgagacccg tcctgaggcc atggaatctg ctgaagctga acaaaaggaa    60
```

<210> SEQ ID NO 111
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 111

```
gcaattcctc acgagacccg tcctgaagcc tctgaaagtg ctgaagactg gaaatacata    60
```

<210> SEQ ID NO 112
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 112

```
gcaattcctc acgagacccg tcctgcttat caacacgagg ctgaagaagt attttttgata    60
```

<210> SEQ ID NO 113
<211> LENGTH: 60
<212> TYPE: DNA
<213> ORGANISM: Artificial Sequence

```
<220> FEATURE:
<223> OTHER INFORMATION: Laboratory Synthesized

<400> SEQUENCE: 113
gcaattcctc acgagacccg tcctgcatca cgtgcactaa ctgaagcaag acagcaagtt    60

<210> SEQ ID NO 114
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 114
gcaattcctc acgagacccg tcctggctgg ccagccacca ctgaagccac acagaattct    60

<210> SEQ ID NO 115
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 115
gcaattcctc acgagacccg tcctgtctag aaatcatgac ctgaagtagg tttgacagaa    60

<210> SEQ ID NO 116
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 116
gcaattcctc acgagacccg tcctggcatt ttctgctgct ctgaaggtga agaaagccca    60

<210> SEQ ID NO 117
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 117
gcaattcctc acgagacccg tcctggagcg gatagagaca ctgaagtatc catggtggtg    60

<210> SEQ ID NO 118
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 118
gcaattcctc acgagacccg tcctgtgtgc gagttcagga ctgaagatca ccaaaaaagt    60

<210> SEQ ID NO 119
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 119
gcaattcctc acgagacccg tcctgttgga gatcacattt ctgaagttgg ggacattta    60
```

```
<210> SEQ ID NO 120
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 120
gcaattcctc acgagacccg tcctgtttca gggaaaactg ctgaagcctt tgcttctgag      60

<210> SEQ ID NO 121
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 121
gcaattcctc acgagacccg tcctgtgata ctgaaattga ctgaagtaga agcagaagat      60

<210> SEQ ID NO 122
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 122
gcaattcctc acgagacccg tcctggccag cgagagatgg ctgaagcaga aagaagact      60

<210> SEQ ID NO 123
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 123
gcaattcctc acgagacccg tcctggggca gcgggtgccg ctgaaggcga ggacgctgac      60

<210> SEQ ID NO 124
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 124
gcaattcctc acgagacccg tcctgacgtt tacggccagt ctgaagtcta cccattcgtt      60

<210> SEQ ID NO 125
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 125
gcaattcctc acgagacccg tcctggaagc tcggaaaagc ctgaaggatc caggtgctgc      60

<210> SEQ ID NO 126
<211> LENGTH: 60
<212> TYPE: DNA
<213> ORGANISM: Artificial Sequence
<220> FEATURE:
<223> OTHER INFORMATION: Laboratory Synthesized
```

<400> SEQUENCE: 126
gcaattcctc acgagacccg tcctgatgta gaattaagaa ctgaagtcat gcctccagtt    60

<210> SEQ ID NO 127
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 127
gcaattcctc acgagacccg tcctgcccgg ggcatttcat ctgaagccca ggagctaggt    60

<210> SEQ ID NO 128
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 128
gcaattcctc acgagacccg tcctgttgag agtcgctcca ctgaagttgc cagctctgtt    60

<210> SEQ ID NO 129
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 129
gcaattcctc acgagacccg tcctgagcat ttggttttga ctgaagatta tggtgtctgt    60

<210> SEQ ID NO 130
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 130
gcaattcctc acgagacccg tcctgctggc tttacttact ctgaagctcc tctccacaga    60

<210> SEQ ID NO 131
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 131
gcaattcctc acgagacccg tcctgaagca tttggttttg ctgaagaatt atggtgtctg    60

<210> SEQ ID NO 132
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 132
gcaattcctc acgagacccg tcctggctgg ctttacttac ctgaagtctc ctctccacag    60

<210> SEQ ID NO 133

-continued

```
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 133
gcaattcctc acgagacccg tcctggaagc agggcttcct ctgaagttcc tctgccatca    60

<210> SEQ ID NO 134
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 134
gcaattcctc acgagacccg tcctggaaat ttgcgtgtgg ctgaagagta tttggatgac    60

<210> SEQ ID NO 135
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 135
gcaattcctc acgagacccg tcctgaacca gacctcaggc ctgaagggct catagggcac    60

<210> SEQ ID NO 136
<211> LENGTH: 20
<212> TYPE: DNA
<213> ORGANISM: Artificial Sequence
<220> FEATURE:
<223> OTHER INFORMATION: Laboratory Synthesized

<400> SEQUENCE: 136
ccaatgctta atcagtgagg                                                20

<210> SEQ ID NO 137
<211> LENGTH: 25
<212> TYPE: DNA
<213> ORGANISM: Artificial Sequence
<220> FEATURE:
<223> OTHER INFORMATION: Laboratory Synthesized

<400> SEQUENCE: 137
aatcgcttga tcacagatgt atgta                                          25

<210> SEQ ID NO 138
<211> LENGTH: 25
<212> TYPE: DNA
<213> ORGANISM: Artificial Sequence
<220> FEATURE:
<223> OTHER INFORMATION: Laboratory Synthesized

<400> SEQUENCE: 138
gaagacaaaa tatttgggaa aacct                                          25

<210> SEQ ID NO 139
<211> LENGTH: 25
<212> TYPE: DNA
<213> ORGANISM: Artificial Sequence
<220> FEATURE:
<223> OTHER INFORMATION: Laboratory Synthesized

<400> SEQUENCE: 139
```
tctcgttact ggaagttagc actct                                         25

<210> SEQ ID NO 140
<211> LENGTH: 25
<212> TYPE: DNA
<213> ORGANISM: Artificial Sequence
<220> FEATURE:
<223> OTHER INFORMATION: Laboratory Synthesized

<400> SEQUENCE: 140
atttcaccat catctaacag gtcat                                         25

<210> SEQ ID NO 141
<211> LENGTH: 23
<212> TYPE: DNA
<213> ORGANISM: Artificial Sequence
<220> FEATURE:
<223> OTHER INFORMATION: Laboratory Synthesized

<400> SEQUENCE: 141
cacctcctgc attcaaaaga ttc                                           23

<210> SEQ ID NO 142
<211> LENGTH: 25
<212> TYPE: DNA
<213> ORGANISM: Artificial Sequence
<220> FEATURE:
<223> OTHER INFORMATION: Laboratory Synthesized

<400> SEQUENCE: 142
gctgcttcac cttaaataac aaaaa                                         25

<210> SEQ ID NO 143
<211> LENGTH: 25
<212> TYPE: DNA
<213> ORGANISM: Artificial Sequence
<220> FEATURE:
<223> OTHER INFORMATION: Laboratory Synthesized

<400> SEQUENCE: 143
agggacatat gggaaaaaga gttag                                         25

<210> SEQ ID NO 144
<211> LENGTH: 25
<212> TYPE: DNA
<213> ORGANISM: Artificial Sequence
<220> FEATURE:
<223> OTHER INFORMATION: Laboratory Synthesized

<400> SEQUENCE: 144
ttagacctga tatttctgtc ccttg                                         25

<210> SEQ ID NO 145
<211> LENGTH: 25
<212> TYPE: DNA
<213> ORGANISM: Artificial Sequence
<220> FEATURE:
<223> OTHER INFORMATION: Laboratory Synthesized

<400> SEQUENCE: 145
acctctacta cctatgtggc ttgtg                                         25

<210> SEQ ID NO 146
<211> LENGTH: 25
<212> TYPE: DNA

```
<213> ORGANISM: Artificial Sequence
<220> FEATURE:
<223> OTHER INFORMATION: Laboratory Synthesized

<400> SEQUENCE: 146
ggtttgtacc ggtagttgtt gatac                                             25

<210> SEQ ID NO 147
<211> LENGTH: 27
<212> TYPE: DNA
<213> ORGANISM: Artificial Sequence
<220> FEATURE:
<223> OTHER INFORMATION: Laboratory Synthesized

<400> SEQUENCE: 147
aaatagccct gtacaatgaa aagtaga                                           27

<210> SEQ ID NO 148
<211> LENGTH: 25
<212> TYPE: DNA
<213> ORGANISM: Artificial Sequence
<220> FEATURE:
<223> OTHER INFORMATION: Laboratory Synthesized

<400> SEQUENCE: 148
tcatatacgg cagtatggtt aaggt                                             25

<210> SEQ ID NO 149
<211> LENGTH: 25
<212> TYPE: DNA
<213> ORGANISM: Artificial Sequence
<220> FEATURE:
<223> OTHER INFORMATION: Laboratory Synthesized

<400> SEQUENCE: 149
gtggccctac ctcaaaatta ttact                                             25

<210> SEQ ID NO 150
<211> LENGTH: 25
<212> TYPE: DNA
<213> ORGANISM: Artificial Sequence
<220> FEATURE:
<223> OTHER INFORMATION: Laboratory Synthesized

<400> SEQUENCE: 150
tatctaccat gtttgagtga cctga                                             25

<210> SEQ ID NO 151
<211> LENGTH: 25
<212> TYPE: DNA
<213> ORGANISM: Artificial Sequence
<220> FEATURE:
<223> OTHER INFORMATION: Laboratory Synthesized

<400> SEQUENCE: 151
cttcataagt cagtctcatc tgcaa                                             25

<210> SEQ ID NO 152
<211> LENGTH: 25
<212> TYPE: DNA
<213> ORGANISM: Artificial Sequence
<220> FEATURE:
<223> OTHER INFORMATION: Laboratory Synthesized

<400> SEQUENCE: 152
gtacaggagg gacaaaaata aaaca                                             25
```

<210> SEQ ID NO 153
<211> LENGTH: 25
<212> TYPE: DNA
<213> ORGANISM: Artificial Sequence
<220> FEATURE:
<223> OTHER INFORMATION: Laboratory Synthesized

<400> SEQUENCE: 153
ccttaactag ctcttttggg acaat                                        25

<210> SEQ ID NO 154
<211> LENGTH: 28
<212> TYPE: DNA
<213> ORGANISM: Artificial Sequence
<220> FEATURE:
<223> OTHER INFORMATION: Laboratory Synthesized

<400> SEQUENCE: 154
gaaaatagac caataggcag agagagtc                                     28

<210> SEQ ID NO 155
<211> LENGTH: 30
<212> TYPE: DNA
<213> ORGANISM: Artificial Sequence
<220> FEATURE:
<223> OTHER INFORMATION: Laboratory Synthesized

<400> SEQUENCE: 155
tgtcattaag agagagactt ttattattcc                                   30

<210> SEQ ID NO 156
<211> LENGTH: 30
<212> TYPE: DNA
<213> ORGANISM: Artificial Sequence
<220> FEATURE:
<223> OTHER INFORMATION: Laboratory Synthesized

<400> SEQUENCE: 156
atccatctac ctcagtttcc tatatctatc                                   30

<210> SEQ ID NO 157
<211> LENGTH: 27
<212> TYPE: DNA
<213> ORGANISM: Artificial Sequence
<220> FEATURE:
<223> OTHER INFORMATION: Laboratory Synthesized

<400> SEQUENCE: 157
ccctttcctg taaaaacaat ataaaaa                                      27

<210> SEQ ID NO 158
<211> LENGTH: 27
<212> TYPE: DNA
<213> ORGANISM: Artificial Sequence
<220> FEATURE:
<223> OTHER INFORMATION: Laboratory Synthesized

<400> SEQUENCE: 158
ttctggaaaa tggatctaaa gctaata                                      27

<210> SEQ ID NO 159
<211> LENGTH: 27
<212> TYPE: DNA
<213> ORGANISM: Artificial Sequence
<220> FEATURE:

<223> OTHER INFORMATION: Laboratory Synthesized

<400> SEQUENCE: 159
tcacaattcg tagtcctact tctacct                               27

<210> SEQ ID NO 160
<211> LENGTH: 22
<212> TYPE: DNA
<213> ORGANISM: Artificial Sequence
<220> FEATURE:
<223> OTHER INFORMATION: Laboratory Synthesized

<400> SEQUENCE: 160
acgttgatgg cagttgcagg tc                                    22

<210> SEQ ID NO 161
<211> LENGTH: 27
<212> TYPE: DNA
<213> ORGANISM: Artificial Sequence
<220> FEATURE:
<223> OTHER INFORMATION: Laboratory Synthesized

<400> SEQUENCE: 161
ctgacagagt tgctagacac tgggttg                               27

<210> SEQ ID NO 162
<211> LENGTH: 25
<212> TYPE: DNA
<213> ORGANISM: Artificial Sequence
<220> FEATURE:
<223> OTHER INFORMATION: Laboratory Synthesized

<400> SEQUENCE: 162
aacgatcttc aatatgctta ccaag                                 25

<210> SEQ ID NO 163
<211> LENGTH: 25
<212> TYPE: DNA
<213> ORGANISM: Artificial Sequence
<220> FEATURE:
<223> OTHER INFORMATION: Laboratory Synthesized

<400> SEQUENCE: 163
cttaaccata gaaagaagg ggaaa                                  25

<210> SEQ ID NO 164
<211> LENGTH: 26
<212> TYPE: DNA
<213> ORGANISM: Artificial Sequence
<220> FEATURE:
<223> OTHER INFORMATION: Laboratory Synthesized

<400> SEQUENCE: 164
gccatcccct tctgtgaatg ttagac                                26

<210> SEQ ID NO 165
<211> LENGTH: 24
<212> TYPE: DNA
<213> ORGANISM: Artificial Sequence
<220> FEATURE:
<223> OTHER INFORMATION: Laboratory Synthesized

<400> SEQUENCE: 165
ggagattgga gacacggaga gcag                                  24

<210> SEQ ID NO 166
<211> LENGTH: 27
<212> TYPE: DNA
<213> ORGANISM: Artificial Sequence
<220> FEATURE:
<223> OTHER INFORMATION: Laboratory Synthesized

<400> SEQUENCE: 166
aactgtgcaa tagttaaacc catttac                                27

<210> SEQ ID NO 167
<211> LENGTH: 25
<212> TYPE: DNA
<213> ORGANISM: Artificial Sequence
<220> FEATURE:
<223> OTHER INFORMATION: Laboratory Synthesized

<400> SEQUENCE: 167
gtaggtgttc ggtaaatgtt aatgg                                  25

<210> SEQ ID NO 168
<211> LENGTH: 25
<212> TYPE: DNA
<213> ORGANISM: Artificial Sequence
<220> FEATURE:
<223> OTHER INFORMATION: Laboratory Synthesized

<400> SEQUENCE: 168
aagtcaaatc ccatacccta ctcat                                  25

<210> SEQ ID NO 169
<211> LENGTH: 27
<212> TYPE: DNA
<213> ORGANISM: Artificial Sequence
<220> FEATURE:
<223> OTHER INFORMATION: Laboratory Synthesized

<400> SEQUENCE: 169
tacttgcttt cagtgttgtg ttatagg                                27

<210> SEQ ID NO 170
<211> LENGTH: 27
<212> TYPE: DNA
<213> ORGANISM: Artificial Sequence
<220> FEATURE:
<223> OTHER INFORMATION: Laboratory Synthesized

<400> SEQUENCE: 170
atttgtttac tgtaatcctc atccatc                                27

<210> SEQ ID NO 171
<211> LENGTH: 27
<212> TYPE: DNA
<213> ORGANISM: Artificial Sequence
<220> FEATURE:
<223> OTHER INFORMATION: Laboratory Synthesized

<400> SEQUENCE: 171
ggaaaagttt ataggtgtcc cttctac                                27

<210> SEQ ID NO 172
<211> LENGTH: 23
<212> TYPE: DNA
<213> ORGANISM: Artificial Sequence
<220> FEATURE:
<223> OTHER INFORMATION: Laboratory Synthesized -continued

<400> SEQUENCE: 172
agcaggtgta cttctgtcag ctc                                          23

<210> SEQ ID NO 173
<211> LENGTH: 27
<212> TYPE: DNA
<213> ORGANISM: Artificial Sequence
<220> FEATURE:
<223> OTHER INFORMATION: Laboratory Synthesized

<400> SEQUENCE: 173
aatattctgc agactgatat tctggtt                                      27

<210> SEQ ID NO 174
<211> LENGTH: 27
<212> TYPE: DNA
<213> ORGANISM: Artificial Sequence
<220> FEATURE:
<223> OTHER INFORMATION: Laboratory Synthesized

<400> SEQUENCE: 174
cgttacttaa ttttgaaaaa cctcaac                                      27

<210> SEQ ID NO 175
<211> LENGTH: 26
<212> TYPE: DNA
<213> ORGANISM: Artificial Sequence
<220> FEATURE:
<223> OTHER INFORMATION: Laboratory Synthesized

<400> SEQUENCE: 175
agatttgggt tctctctata gccatt                                       26

<210> SEQ ID NO 176
<211> LENGTH: 27
<212> TYPE: DNA
<213> ORGANISM: Artificial Sequence
<220> FEATURE:
<223> OTHER INFORMATION: Laboratory Synthesized

<400> SEQUENCE: 176
gactccagtc aaaaattctc ctagtta                                      27

<210> SEQ ID NO 177
<211> LENGTH: 25
<212> TYPE: DNA
<213> ORGANISM: Artificial Sequence
<220> FEATURE:
<223> OTHER INFORMATION: Laboratory Synthesized

<400> SEQUENCE: 177
atgtctgcag ctatagttag gaagc                                        25

<210> SEQ ID NO 178
<211> LENGTH: 24
<212> TYPE: DNA
<213> ORGANISM: Artificial Sequence
<220> FEATURE:
<223> OTHER INFORMATION: Laboratory Synthesized

<400> SEQUENCE: 178
atctctccct gagttgatga gaag                                         24

<210> SEQ ID NO 179
<211> LENGTH: 27

```
<212> TYPE: DNA
<213> ORGANISM: Artificial Sequence
<220> FEATURE:
<223> OTHER INFORMATION: Laboratory Synthesized

<400> SEQUENCE: 179
ttctggaaaa tggatctaaa gctaata                                              27

<210> SEQ ID NO 180
<211> LENGTH: 27
<212> TYPE: DNA
<213> ORGANISM: Artificial Sequence
<220> FEATURE:
<223> OTHER INFORMATION: Laboratory Synthesized

<400> SEQUENCE: 180
tcacaattcg tagtcctact tctacct                                              27

<210> SEQ ID NO 181
<211> LENGTH: 26
<212> TYPE: DNA
<213> ORGANISM: Artificial Sequence
<220> FEATURE:
<223> OTHER INFORMATION: Laboratory Synthesized

<400> SEQUENCE: 181
ctgtttgtcc taaacaagat gtgaat                                               26

<210> SEQ ID NO 182
<211> LENGTH: 27
<212> TYPE: DNA
<213> ORGANISM: Artificial Sequence
<220> FEATURE:
<223> OTHER INFORMATION: Laboratory Synthesized

<400> SEQUENCE: 182
cattggagca agttaaaact acaaaat                                              27

<210> SEQ ID NO 183
<211> LENGTH: 27
<212> TYPE: DNA
<213> ORGANISM: Artificial Sequence
<220> FEATURE:
<223> OTHER INFORMATION: Laboratory Synthesized

<400> SEQUENCE: 183
ccttaacctc ttgatgtatg agaagaa                                              27

<210> SEQ ID NO 184
<211> LENGTH: 27
<212> TYPE: DNA
<213> ORGANISM: Artificial Sequence
<220> FEATURE:
<223> OTHER INFORMATION: Laboratory Synthesized

<400> SEQUENCE: 184
agtacatcta agaaattgag catcctt                                              27

<210> SEQ ID NO 185
<211> LENGTH: 27
<212> TYPE: DNA
<213> ORGANISM: Artificial Sequence
<220> FEATURE:
<223> OTHER INFORMATION: Laboratory Synthesized

<400> SEQUENCE: 185
```
gtgtgtgtgc aattataaaa gaaactt                                    27

<210> SEQ ID NO 186
<211> LENGTH: 27
<212> TYPE: DNA
<213> ORGANISM: Artificial Sequence
<220> FEATURE:
<223> OTHER INFORMATION: Laboratory Synthesized

<400> SEQUENCE: 186
gtcagcatta gatgagctac tgagatt                                    27

<210> SEQ ID NO 187
<211> LENGTH: 27
<212> TYPE: DNA
<213> ORGANISM: Artificial Sequence
<220> FEATURE:
<223> OTHER INFORMATION: Laboratory Synthesized

<400> SEQUENCE: 187
ctgttctact tgttggtggt gataata                                    27

<210> SEQ ID NO 188
<211> LENGTH: 27
<212> TYPE: DNA
<213> ORGANISM: Artificial Sequence
<220> FEATURE:
<223> OTHER INFORMATION: Laboratory Synthesized

<400> SEQUENCE: 188
atggtaagaa atatggttaa caccaag                                    27

<210> SEQ ID NO 189
<211> LENGTH: 27
<212> TYPE: DNA
<213> ORGANISM: Artificial Sequence
<220> FEATURE:
<223> OTHER INFORMATION: Laboratory Synthesized

<400> SEQUENCE: 189
ctattttagg ttactgggaa cagaatg                                    27

<210> SEQ ID NO 190
<211> LENGTH: 27
<212> TYPE: DNA
<213> ORGANISM: Artificial Sequence
<220> FEATURE:
<223> OTHER INFORMATION: Laboratory Synthesized

<400> SEQUENCE: 190
aaactacata actacaaccc aatgctt                                    27

<210> SEQ ID NO 191
<211> LENGTH: 20
<212> TYPE: DNA
<213> ORGANISM: Artificial Sequence
<220> FEATURE:
<223> OTHER INFORMATION: Laboratory Synthesized

<400> SEQUENCE: 191 gaacccata cctgggatct                                             20

<210> SEQ ID NO 192
<211> LENGTH: 21
<212> TYPE: DNA
<213> ORGANISM: Artificial Sequence

```
<220> FEATURE:
<223> OTHER INFORMATION: Laboratory Synthesized

<400> SEQUENCE: 192
tcatacctca caaggtgcct a                                              21

<210> SEQ ID NO 193
<211> LENGTH: 27
<212> TYPE: DNA
<213> ORGANISM: Artificial Sequence
<220> FEATURE:
<223> OTHER INFORMATION: Laboratory Synthesized

<400> SEQUENCE: 193
ttatcagttt tggaggatgt acataaa                                        27

<210> SEQ ID NO 194
<211> LENGTH: 25
<212> TYPE: DNA
<213> ORGANISM: Artificial Sequence
<220> FEATURE:
<223> OTHER INFORMATION: Laboratory Synthesized

<400> SEQUENCE: 194
ctccttcctc ttcctacagt actcc                                          25

<210> SEQ ID NO 195
<211> LENGTH: 54
<212> TYPE: DNA
<213> ORGANISM: Artificial Sequence
<220> FEATURE:
<223> OTHER INFORMATION: Laboratory Synthesized

<400> SEQUENCE: 195
acactctttc cctacacgac gctcttccga tctttcctca cgagacccgt cctg          54

<210> SEQ ID NO 196
<211> LENGTH: 41
<212> TYPE: DNA
<213> ORGANISM: Artificial Sequence
<220> FEATURE:
<223> OTHER INFORMATION: Laboratory Synthesized

<400> SEQUENCE: 196
agacgtgtgc tcttccgatc tcttgatcac agatgtatgt a                        41

<210> SEQ ID NO 197
<211> LENGTH: 41
<212> TYPE: DNA
<213> ORGANISM: Artificial Sequence
<220> FEATURE:
<223> OTHER INFORMATION: Laboratory Synthesized

<400> SEQUENCE: 197
agacgtgtgc tcttccgatc tcaaaatatt tgggaaaacc t                        41

<210> SEQ ID NO 198
<211> LENGTH: 41
<212> TYPE: DNA
<213> ORGANISM: Artificial Sequence
<220> FEATURE:
<223> OTHER INFORMATION: Laboratory Synthesized

<400> SEQUENCE: 198
agacgtgtgc tcttccgatc tttactggaa gttagcactc t                        41
```

<210> SEQ ID NO 199
<211> LENGTH: 41
<212> TYPE: DNA
<213> ORGANISM: Artificial Sequence
<220> FEATURE:
<223> OTHER INFORMATION: Laboratory Synthesized

<400> SEQUENCE: 199
agacgtgtgc tcttccgatc tcaaaatatt tgggaaaacc t                     41

<210> SEQ ID NO 200
<211> LENGTH: 41
<212> TYPE: DNA
<213> ORGANISM: Artificial Sequence
<220> FEATURE:
<223> OTHER INFORMATION: Laboratory Synthesized

<400> SEQUENCE: 200
agacgtgtgc tcttccgatc tttactggaa gttagcactc t                     41

<210> SEQ ID NO 201
<211> LENGTH: 41
<212> TYPE: DNA
<213> ORGANISM: Artificial Sequence
<220> FEATURE:
<223> OTHER INFORMATION: Laboratory Synthesized

<400> SEQUENCE: 201
agacgtgtgc tcttccgatc taccatcatc taacaggtca t                     41

<210> SEQ ID NO 202
<211> LENGTH: 41
<212> TYPE: DNA
<213> ORGANISM: Artificial Sequence
<220> FEATURE:
<223> OTHER INFORMATION: Laboratory Synthesized

<400> SEQUENCE: 202
agacgtgtgc tcttccgatc tcttgatcac agatgtatgt a                     41

<210> SEQ ID NO 203
<211> LENGTH: 41
<212> TYPE: DNA
<213> ORGANISM: Artificial Sequence
<220> FEATURE:
<223> OTHER INFORMATION: Laboratory Synthesized

<400> SEQUENCE: 203
agacgtgtgc tcttccgatc tctcctgcat tcaaaagatt c                     41

<210> SEQ ID NO 204
<211> LENGTH: 41
<212> TYPE: DNA
<213> ORGANISM: Artificial Sequence
<220> FEATURE:
<223> OTHER INFORMATION: Laboratory Synthesized

<400> SEQUENCE: 204
agacgtgtgc tcttccgatc tttcacctta aataacaaaa a                     41

<210> SEQ ID NO 205
<211> LENGTH: 41
<212> TYPE: DNA
<213> ORGANISM: Artificial Sequence
<220> FEATURE:
<223> OTHER INFORMATION: Laboratory Synthesized -continued

<400> SEQUENCE: 205
agacgtgtgc tcttccgatc tcatatggga aaaagagtta g     41

<210> SEQ ID NO 206
<211> LENGTH: 41
<212> TYPE: DNA
<213> ORGANISM: Artificial Sequence
<220> FEATURE:
<223> OTHER INFORMATION: Laboratory Synthesized

<400> SEQUENCE: 206
agacgtgtgc tcttccgatc tcctgatatt tctgtccctt g     41

<210> SEQ ID NO 207
<211> LENGTH: 41
<212> TYPE: DNA
<213> ORGANISM: Artificial Sequence
<220> FEATURE:
<223> OTHER INFORMATION: Laboratory Synthesized

<400> SEQUENCE: 207
agacgtgtgc tcttccgatc ttactaccta tgtggcttgt g     41

<210> SEQ ID NO 208
<211> LENGTH: 41
<212> TYPE: DNA
<213> ORGANISM: Artificial Sequence
<220> FEATURE:
<223> OTHER INFORMATION: Laboratory Synthesized

<400> SEQUENCE: 208
agacgtgtgc tcttccgatc tgtaccggta gttgttgata c     41

<210> SEQ ID NO 209
<211> LENGTH: 41
<212> TYPE: DNA
<213> ORGANISM: Artificial Sequence
<220> FEATURE:
<223> OTHER INFORMATION: Laboratory Synthesized

<400> SEQUENCE: 209
agacgtgtgc tcttccgatc tcctgtacaa tgaaaagtag a     41

<210> SEQ ID NO 210
<211> LENGTH: 41
<212> TYPE: DNA
<213> ORGANISM: Artificial Sequence
<220> FEATURE:
<223> OTHER INFORMATION: Laboratory Synthesized

<400> SEQUENCE: 210
agacgtgtgc tcttccgatc ttacggcagt atggttaagg t     41

<210> SEQ ID NO 211
<211> LENGTH: 41
<212> TYPE: DNA
<213> ORGANISM: Artificial Sequence
<220> FEATURE:
<223> OTHER INFORMATION: Laboratory Synthesized

<400> SEQUENCE: 211
agacgtgtgc tcttccgatc tcctacctca aaattattac t     41

<210> SEQ ID NO 212

<211> LENGTH: 41
<212> TYPE: DNA
<213> ORGANISM: Artificial Sequence
<220> FEATURE:
<223> OTHER INFORMATION: Laboratory Synthesized

<400> SEQUENCE: 212
agacgtgtgc tcttccgatc tcctgtacaa tgaaaagtag a          41

<210> SEQ ID NO 213
<211> LENGTH: 41
<212> TYPE: DNA
<213> ORGANISM: Artificial Sequence
<220> FEATURE:
<223> OTHER INFORMATION: Laboratory Synthesized

<400> SEQUENCE: 213
agacgtgtgc tcttccgatc tgtaccggta gttgttgata c          41

<210> SEQ ID NO 214
<211> LENGTH: 41
<212> TYPE: DNA
<213> ORGANISM: Artificial Sequence
<220> FEATURE:
<223> OTHER INFORMATION: Laboratory Synthesized

<400> SEQUENCE: 214
agacgtgtgc tcttccgatc taccatgttt gagtgacctg a          41

<210> SEQ ID NO 215
<211> LENGTH: 41
<212> TYPE: DNA
<213> ORGANISM: Artificial Sequence
<220> FEATURE:
<223> OTHER INFORMATION: Laboratory Synthesized

<400> SEQUENCE: 215
agacgtgtgc tcttccgatc ttaagtcagt ctcatctgca a          41

<210> SEQ ID NO 216
<211> LENGTH: 41
<212> TYPE: DNA
<213> ORGANISM: Artificial Sequence
<220> FEATURE:
<223> OTHER INFORMATION: Laboratory Synthesized

<400> SEQUENCE: 216
agacgtgtgc tcttccgatc tggagggaca aaaataaaac a          41

<210> SEQ ID NO 217
<211> LENGTH: 41
<212> TYPE: DNA
<213> ORGANISM: Artificial Sequence
<220> FEATURE:
<223> OTHER INFORMATION: Laboratory Synthesized

<400> SEQUENCE: 217
agacgtgtgc tcttccgatc taccatgttt gagtgacctg a          41

<210> SEQ ID NO 218
<211> LENGTH: 41
<212> TYPE: DNA
<213> ORGANISM: Artificial Sequence
<220> FEATURE:
<223> OTHER INFORMATION: Laboratory Synthesized

<400> SEQUENCE: 218

```
agacgtgtgc tcttccgatc tactagctct tttgggacaa t         41
```

<210> SEQ ID NO 219
<211> LENGTH: 66
<212> TYPE: DNA
<213> ORGANISM: Artificial Sequence
<220> FEATURE:
<223> OTHER INFORMATION: Laboratory Synthesized

<400> SEQUENCE: 219

```
caagcagaag acggcatacg agattgcctc ttgtgactgg agttcagacg tgtgctcttc    60
cgatct                                                               66
```

<210> SEQ ID NO 220
<211> LENGTH: 58
<212> TYPE: DNA
<213> ORGANISM: Artificial Sequence
<220> FEATURE:
<223> OTHER INFORMATION: Laboratory Synthesized

<400> SEQUENCE: 220

```
aatgatacgg cgaccaccga gatctacaca ctgcataaca ctctttccct acacgacg    58
```

<210> SEQ ID NO 221
<211> LENGTH: 59
<212> TYPE: DNA
<213> ORGANISM: Artificial Sequence
<220> FEATURE:
<223> OTHER INFORMATION: Laboratory Synthesized

<400> SEQUENCE: 221

```
acactctttc cctacacgac gctcttccga tctgtttaaa cagtggaatt ctagagtca    59
```

<210> SEQ ID NO 222
<211> LENGTH: 41
<212> TYPE: DNA
<213> ORGANISM: Artificial Sequence
<220> FEATURE:
<223> OTHER INFORMATION: Laboratory Synthesized

<400> SEQUENCE: 222

```
agacgtgtgc tcttccgatc tttttttgcag ctgtgtcatc c        41
```

<210> SEQ ID NO 223
<211> LENGTH: 53
<212> TYPE: DNA
<213> ORGANISM: Artificial Sequence
<220> FEATURE:
<223> OTHER INFORMATION: Laboratory Synthesized

<400> SEQUENCE: 223

```
acactctttc cctacacgac gctcttccga tctgcccctc ctcagcatct tat           53
```

<210> SEQ ID NO 224
<211> LENGTH: 41
<212> TYPE: DNA
<213> ORGANISM: Artificial Sequence
<220> FEATURE:
<223> OTHER INFORMATION: Laboratory Synthesized

<400> SEQUENCE: 224

```
agacgtgtgc tcttccgatc tcttaacccc tcctcccaga g         41
```

<210> SEQ ID NO 225

```
<211> LENGTH: 184
<212> TYPE: DNA
<213> ORGANISM: Artificial Sequence
<220> FEATURE:
<223> OTHER INFORMATION: Laboratory Synthesized

<400> SEQUENCE: 225
ttccttagtc tttctttgaa gcagcaagta tgatgagcaa gctttctcac aagcatttgg    60
ttttaaatta tggagtatgt gtgtttaaac ctgtggagac gagagtaagt aaaactacag   120
gctttctaat gcctttctca gagcatctgt ttttgtttat atagaaaatt cagtttcagg   180
atca                                                                184

<210> SEQ ID NO 226
<211> LENGTH: 184
<212> TYPE: DNA
<213> ORGANISM: Artificial Sequence
<220> FEATURE:
<223> OTHER INFORMATION: Laboratory Synthesized

<400> SEQUENCE: 226
aagaagggct cccatcacat caaccggtgg cgcattgcca cgaagcaggc caatggggag    60
gacatcgatg tcacctccaa tgactagttt aaacgggtgg gcaaccacaa acccacgagg   120
gcagagtgct gcttgctgct ggccaggccc ctgcgtgggc ccaagctgga ctctggccac   180
tccc                                                                184

<210> SEQ ID NO 227
<211> LENGTH: 140
<212> TYPE: DNA
<213> ORGANISM: Artificial Sequence
<220> FEATURE:
<223> OTHER INFORMATION: Laboratory Synthesized

<400> SEQUENCE: 227
tacatttgct tctgacacaa ctgtgttcac tagcaacctc aaacagacac aatggtgcat    60
ctgactcctg tcgagaagtc tgccgttact gccctgtggg gcaaggtgaa cgtggatgaa   120
gttggtggtg aggccctggg                                               140

<210> SEQ ID NO 228
<211> LENGTH: 166
<212> TYPE: DNA
<213> ORGANISM: Artificial Sequence
<220> FEATURE:
<223> OTHER INFORMATION: Laboratory Synthesized

<400> SEQUENCE: 228
tcttaggtct ggcccctcct cagcatctta tccgagtgga aggaaatttg cgtgtggagt    60
atttggatga caaacacttt tcgtcatagt gtggttgtgc cctatgagcc gcctgaggtc   120
tggtttgcaa ctggggtctc tgggaggagg ggttaagggt ggttgt                  166

<210> SEQ ID NO 229
<211> LENGTH: 177
<212> TYPE: DNA
<213> ORGANISM: Artificial Sequence
<220> FEATURE:
<223> OTHER INFORMATION: Laboratory Synthesized

<400> SEQUENCE: 229
ttgtttaaac agtggaattc tagagtcaca cttcctaaaa tatgcatttt tgttttcact    60
tttagatatg atactgaaat tgatagaagc agaagataga agatcggcta taaaaaagat   120
```
aatggaaagg gatgacacag ctgcaaaaac acttgttctc tgtgtttctg acataat      177

<210> SEQ ID NO 230
<211> LENGTH: 58
<212> TYPE: DNA
<213> ORGANISM: Artificial Sequence
<220> FEATURE:
<223> OTHER INFORMATION: Laboratory Synthesized

<400> SEQUENCE: 230
ctggggcacg ggtaagaagc attctgtctc tcttctaaga attcgagctc ggtacccg     58

<210> SEQ ID NO 231
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 231
cgggtaccga gctcgaattc ttagaagaga cagaatgc ttcttacccg tgccccaggg     60

<210> SEQ ID NO 232
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 232
cgggtaccga gctcgaattc ttagaagaga cagaatgc ttcttacccg tgccccagag     60

<210> SEQ ID NO 233
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 233
cgggtaccga gctcgaattc ttagaagaga cagaatgc ttcttacccg tgccccagaa     60

<210> SEQ ID NO 234
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 234
cgggtaccga gctcgaattc ttagaagaga cagaatgc ttcttacccg tgccccagtg     60

<210> SEQ ID NO 235
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 235
cgggtaccga gctcgaattc ttagaagaga cagaatgc ttcttacccg tgccccagta     60

<210> SEQ ID NO 236
<211> LENGTH: 60
<212> TYPE: DNA

```
<213> ORGANISM: Artificial Sequence
<220> FEATURE:
<223> OTHER INFORMATION: Laboratory Synthesized

<400> SEQUENCE: 236
cgggtaccga gctcgaattc ttagaagaga gacagaatgc ttcttacccg tgccccagcg    60

<210> SEQ ID NO 237
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 237
cgggtaccga gctcgaattc ttagaagaga gacagaatgc ttcttacccg tgccccagca    60

<210> SEQ ID NO 238
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 238
cgggtaccga gctcgaattc ttagaagaga gacagaatgc ttcttacccg tgccccagct    60

<210> SEQ ID NO 239
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 239
cgggtaccga gctcgaattc ttagaagaga gacagaatgc ttcttacccg tgccccagga    60

<210> SEQ ID NO 240
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 240
cgggtaccga gctcgaattc ttagaagaga gacagaatgc ttcttacccg tgccccagac    60

<210> SEQ ID NO 241
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 241
cgggtaccga gctcgaattc ttagaagaga gacagaatgc ttcttacccg tgccccagat    60

<210> SEQ ID NO 242
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 242
cgggtaccga gctcgaattc ttagaagaga gacagaatgc ttcttacccg tgccccagcc    60
```

<210> SEQ ID NO 243
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 243
cgggtaccga gctcgaattc ttagaagaga gacagaatgc ttcttacccg tgccccaggc     60

<210> SEQ ID NO 244
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 244
cgggtaccga gctcgaattc ttagaagaga gacagaatgc ttcttacccg tgccccaggt     60

<210> SEQ ID NO 245
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 245
cgggtaccga gctcgaattc ttagaagaga gacagaatgc ttcttacccg tgccccagtc     60

<210> SEQ ID NO 246
<211> LENGTH: 60
<212> TYPE: DNA
<213> ORGANISM: Artificial Sequence
<220> FEATURE:
<223> OTHER INFORMATION: Laboratory Synthesized

<400> SEQUENCE: 246
cgggtaccga gctcgaattc ttagaagaga gacagaatgc ttcttacccg tgccccagtt     60

<210> SEQ ID NO 247
<211> LENGTH: 24
<212> TYPE: DNA
<213> ORGANISM: Artificial Sequence
<220> FEATURE:
<223> OTHER INFORMATION: Laboratory Synthesized

<400> SEQUENCE: 247
caccgtacat aaaggacact gtga                                            24

<210> SEQ ID NO 248
<211> LENGTH: 24
<212> TYPE: DNA
<213> ORGANISM: Artificial Sequence
<220> FEATURE:
<223> OTHER INFORMATION: Laboratory Synthesized

<400> SEQUENCE: 248
caccgcaatt cagtacaatt aggt                                            24

<210> SEQ ID NO 249
<211> LENGTH: 24
<212> TYPE: DNA
<213> ORGANISM: Artificial Sequence
<220> FEATURE:

<223> OTHER INFORMATION: Laboratory Synthesized

<400> SEQUENCE: 249 caccgattttt ctctaatgtt atta                                             24

<210> SEQ ID NO 250
<211> LENGTH: 24
<212> TYPE: DNA
<213> ORGANISM: Artificial Sequence
<220> FEATURE:
<223> OTHER INFORMATION: Laboratory Synthesized

<400> SEQUENCE: 250
caccgttttt cgagtgattc tatt                                              24

<210> SEQ ID NO 251
<211> LENGTH: 24
<212> TYPE: DNA
<213> ORGANISM: Artificial Sequence
<220> FEATURE:
<223> OTHER INFORMATION: Laboratory Synthesized

<400> SEQUENCE: 251
caccgtttta acaaatgact tgat                                              24

<210> SEQ ID NO 252
<211> LENGTH: 24
<212> TYPE: DNA
<213> ORGANISM: Artificial Sequence
<220> FEATURE:
<223> OTHER INFORMATION: Laboratory Synthesized

<400> SEQUENCE: 252
caccgagaca gttaatatca ctgc                                              24

<210> SEQ ID NO 253
<211> LENGTH: 24
<212> TYPE: DNA
<213> ORGANISM: Artificial Sequence
<220> FEATURE:
<223> OTHER INFORMATION: Laboratory Synthesized

<400> SEQUENCE: 253
caccgttata tcattcttac ataa                                              24

<210> SEQ ID NO 254
<211> LENGTH: 24
<212> TYPE: DNA
<213> ORGANISM: Artificial Sequence
<220> FEATURE:
<223> OTHER INFORMATION: Laboratory Synthesized

<400> SEQUENCE: 254
caccggggat tctcttgctc gctt                                              24

<210> SEQ ID NO 255
<211> LENGTH: 24
<212> TYPE: DNA
<213> ORGANISM: Artificial Sequence
<220> FEATURE:
<223> OTHER INFORMATION: Laboratory Synthesized

<400> SEQUENCE: 255
caccgtggat tcaaacttag gtat                                              24

```
<210> SEQ ID NO 256
<211> LENGTH: 24
<212> TYPE: DNA
<213> ORGANISM: Artificial Sequence
<220> FEATURE:
<223> OTHER INFORMATION: Laboratory Synthesized

<400> SEQUENCE: 256
caccgttaga tcaactggaa tgga                                          24

<210> SEQ ID NO 257
<211> LENGTH: 24
<212> TYPE: DNA
<213> ORGANISM: Artificial Sequence
<220> FEATURE:
<223> OTHER INFORMATION: Laboratory Synthesized

<400> SEQUENCE: 257
caccgatatt tcgcaatgaa agag                                          24

<210> SEQ ID NO 258
<211> LENGTH: 24
<212> TYPE: DNA
<213> ORGANISM: Artificial Sequence
<220> FEATURE:
<223> OTHER INFORMATION: Laboratory Synthesized

<400> SEQUENCE: 258
caccgacaat acgcaacttc caca                                          24

<210> SEQ ID NO 259
<211> LENGTH: 24
<212> TYPE: DNA
<213> ORGANISM: Artificial Sequence
<220> FEATURE:
<223> OTHER INFORMATION: Laboratory Synthesized

<400> SEQUENCE: 259
caccgtatat tctctgttaa caga                                          24

<210> SEQ ID NO 260
<211> LENGTH: 24
<212> TYPE: DNA
<213> ORGANISM: Artificial Sequence
<220> FEATURE:
<223> OTHER INFORMATION: Laboratory Synthesized

<400> SEQUENCE: 260
caccggttct gaggtggacc taat                                          24

<210> SEQ ID NO 261
<211> LENGTH: 24
<212> TYPE: DNA
<213> ORGANISM: Artificial Sequence
<220> FEATURE:
<223> OTHER INFORMATION: Laboratory Synthesized

<400> SEQUENCE: 261
caccggagat tctggggctt caag                                          24

<210> SEQ ID NO 262
<211> LENGTH: 24
<212> TYPE: DNA
<213> ORGANISM: Artificial Sequence
<220> FEATURE:
<223> OTHER INFORMATION: Laboratory Synthesized
```

```
<400> SEQUENCE: 262
caccgtaaat actgcagatt atgt                                              24

<210> SEQ ID NO 263
<211> LENGTH: 24
<212> TYPE: DNA
<213> ORGANISM: Artificial Sequence
<220> FEATURE:
<223> OTHER INFORMATION: Laboratory Synthesized

<400> SEQUENCE: 263
caccgagaaa cgacaaatcc tatt                                              24

<210> SEQ ID NO 264
<211> LENGTH: 24
<212> TYPE: DNA
<213> ORGANISM: Artificial Sequence
<220> FEATURE:
<223> OTHER INFORMATION: Laboratory Synthesized

<400> SEQUENCE: 264
caccgaagga acaaggttta tcaa                                              24

<210> SEQ ID NO 265
<211> LENGTH: 24
<212> TYPE: DNA
<213> ORGANISM: Artificial Sequence
<220> FEATURE:
<223> OTHER INFORMATION: Laboratory Synthesized

<400> SEQUENCE: 265
caccgcatac tgtttgctca caga                                              24

<210> SEQ ID NO 266
<211> LENGTH: 24
<212> TYPE: DNA
<213> ORGANISM: Artificial Sequence
<220> FEATURE:
<223> OTHER INFORMATION: Laboratory Synthesized

<400> SEQUENCE: 266
caccggctac agaattctgt gtgg                                              24

<210> SEQ ID NO 267
<211> LENGTH: 24
<212> TYPE: DNA
<213> ORGANISM: Artificial Sequence
<220> FEATURE:
<223> OTHER INFORMATION: Laboratory Synthesized

<400> SEQUENCE: 267
caccgacaga acatccttgg aagt                                              24

<210> SEQ ID NO 268
<211> LENGTH: 24
<212> TYPE: DNA
<213> ORGANISM: Artificial Sequence
<220> FEATURE:
<223> OTHER INFORMATION: Laboratory Synthesized

<400> SEQUENCE: 268
aaactcacag tgtcctttat gtac                                              24

<210> SEQ ID NO 269
<211> LENGTH: 24
```

<212> TYPE: DNA
<213> ORGANISM: Artificial Sequence
<220> FEATURE:
<223> OTHER INFORMATION: Laboratory Synthesized

<400> SEQUENCE: 269
aaacacctaa ttgtactgaa ttgc                                              24

<210> SEQ ID NO 270
<211> LENGTH: 24
<212> TYPE: DNA
<213> ORGANISM: Artificial Sequence
<220> FEATURE:
<223> OTHER INFORMATION: Laboratory Synthesized

<400> SEQUENCE: 270
aaactaataa cattagagaa aatc                                              24

<210> SEQ ID NO 271
<211> LENGTH: 24
<212> TYPE: DNA
<213> ORGANISM: Artificial Sequence
<220> FEATURE:
<223> OTHER INFORMATION: Laboratory Synthesized

<400> SEQUENCE: 271
aaacaataga atcactcgaa aaac                                              24

<210> SEQ ID NO 272
<211> LENGTH: 24
<212> TYPE: DNA
<213> ORGANISM: Artificial Sequence
<220> FEATURE:
<223> OTHER INFORMATION: Laboratory Synthesized

<400> SEQUENCE: 272
aaacatcaag tcatttgtta aaac                                              24

<210> SEQ ID NO 273
<211> LENGTH: 24
<212> TYPE: DNA
<213> ORGANISM: Artificial Sequence
<220> FEATURE:
<223> OTHER INFORMATION: Laboratory Synthesized

<400> SEQUENCE: 273
aaacgcagtg atattaactg tctc                                              24

<210> SEQ ID NO 274
<211> LENGTH: 24
<212> TYPE: DNA
<213> ORGANISM: Artificial Sequence
<220> FEATURE:
<223> OTHER INFORMATION: Laboratory Synthesized

<400> SEQUENCE: 274
aaacttatgt aagaatgata taac                                              24

<210> SEQ ID NO 275
<211> LENGTH: 24
<212> TYPE: DNA
<213> ORGANISM: Artificial Sequence
<220> FEATURE:
<223> OTHER INFORMATION: Laboratory Synthesized

<400> SEQUENCE: 275
aaacaagcga gcaagagaat cccc                                          24

<210> SEQ ID NO 276
<211> LENGTH: 24
<212> TYPE: DNA
<213> ORGANISM: Artificial Sequence
<220> FEATURE:
<223> OTHER INFORMATION: Laboratory Synthesized

<400> SEQUENCE: 276
aaacatacct aagtttgaat ccac                                          24

<210> SEQ ID NO 277
<211> LENGTH: 24
<212> TYPE: DNA
<213> ORGANISM: Artificial Sequence
<220> FEATURE:
<223> OTHER INFORMATION: Laboratory Synthesized

<400> SEQUENCE: 277
aaactccatt ccagttgatc taac                                          24

<210> SEQ ID NO 278
<211> LENGTH: 24
<212> TYPE: DNA
<213> ORGANISM: Artificial Sequence
<220> FEATURE:
<223> OTHER INFORMATION: Laboratory Synthesized

<400> SEQUENCE: 278
aaacctcttt cattgcgaaa tatc                                          24

<210> SEQ ID NO 279
<211> LENGTH: 24
<212> TYPE: DNA
<213> ORGANISM: Artificial Sequence
<220> FEATURE:
<223> OTHER INFORMATION: Laboratory Synthesized

<400> SEQUENCE: 279
aaactgtgga agttgcgtat tgtc                                          24

<210> SEQ ID NO 280
<211> LENGTH: 24
<212> TYPE: DNA
<213> ORGANISM: Artificial Sequence
<220> FEATURE:
<223> OTHER INFORMATION: Laboratory Synthesized

<400> SEQUENCE: 280
aaactctgtt aacagagaat atac                                          24

<210> SEQ ID NO 281
<211> LENGTH: 24
<212> TYPE: DNA
<213> ORGANISM: Artificial Sequence
<220> FEATURE:
<223> OTHER INFORMATION: Laboratory Synthesized

<400> SEQUENCE: 281
aaacattagg tccacctcag aacc                                          24

<210> SEQ ID NO 282
<211> LENGTH: 24
<212> TYPE: DNA
<213> ORGANISM: Artificial Sequence

```
<220> FEATURE:
<223> OTHER INFORMATION: Laboratory Synthesized

<400> SEQUENCE: 282
aaaccttgaa gccccagaat ctcc                                          24

<210> SEQ ID NO 283
<211> LENGTH: 24
<212> TYPE: DNA
<213> ORGANISM: Artificial Sequence
<220> FEATURE:
<223> OTHER INFORMATION: Laboratory Synthesized

<400> SEQUENCE: 283
aaacacataa tctgcagtat ttac                                          24

<210> SEQ ID NO 284
<211> LENGTH: 24
<212> TYPE: DNA
<213> ORGANISM: Artificial Sequence
<220> FEATURE:
<223> OTHER INFORMATION: Laboratory Synthesized

<400> SEQUENCE: 284
aaacaatagg atttgtcgtt tctc                                          24

<210> SEQ ID NO 285
<211> LENGTH: 24
<212> TYPE: DNA
<213> ORGANISM: Artificial Sequence
<220> FEATURE:
<223> OTHER INFORMATION: Laboratory Synthesized

<400> SEQUENCE: 285
aaacttgata aaccttgttc cttc                                          24

<210> SEQ ID NO 286
<211> LENGTH: 24
<212> TYPE: DNA
<213> ORGANISM: Artificial Sequence
<220> FEATURE:
<223> OTHER INFORMATION: Laboratory Synthesized

<400> SEQUENCE: 286
aaactctgtg agcaaacagt atgc                                          24

<210> SEQ ID NO 287
<211> LENGTH: 24
<212> TYPE: DNA
<213> ORGANISM: Artificial Sequence
<220> FEATURE:
<223> OTHER INFORMATION: Laboratory Synthesized

<400> SEQUENCE: 287
aaacccacac agaattctgt agcc                                          24

<210> SEQ ID NO 288
<211> LENGTH: 24
<212> TYPE: DNA
<213> ORGANISM: Artificial Sequence
<220> FEATURE:
<223> OTHER INFORMATION: Laboratory Synthesized

<400> SEQUENCE: 288
aaacacttcc aaggatgttc tgtc                                          24
```

```
<210> SEQ ID NO 289
<211> LENGTH: 25
<212> TYPE: DNA
<213> ORGANISM: Artificial Sequence
<220> FEATURE:
<223> OTHER INFORMATION: Laboratory Synthesized

<400> SEQUENCE: 289
caccgaactt cgagatacag cagac                                  25

<210> SEQ ID NO 290
<211> LENGTH: 25
<212> TYPE: DNA
<213> ORGANISM: Artificial Sequence
<220> FEATURE:
<223> OTHER INFORMATION: Laboratory Synthesized

<400> SEQUENCE: 290
aaacgtctgc tgtatctcga agttc                                  25

<210> SEQ ID NO 291
<211> LENGTH: 24
<212> TYPE: DNA
<213> ORGANISM: Artificial Sequence
<220> FEATURE:
<223> OTHER INFORMATION: Laboratory Synthesized

<400> SEQUENCE: 291
caccgggcca gctggaggcc gtcg                                   24

<210> SEQ ID NO 292
<211> LENGTH: 24
<212> TYPE: DNA
<213> ORGANISM: Artificial Sequence
<220> FEATURE:
<223> OTHER INFORMATION: Laboratory Synthesized

<400> SEQUENCE: 292
aaaccgacgg cctccagctg gccc                                   24

<210> SEQ ID NO 293
<211> LENGTH: 25
<212> TYPE: DNA
<213> ORGANISM: Artificial Sequence
<220> FEATURE:
<223> OTHER INFORMATION: Laboratory Synthesized

<400> SEQUENCE: 293
caccgagcca ggtgaggcct ggagg                                  25

<210> SEQ ID NO 294
<211> LENGTH: 25
<212> TYPE: DNA
<213> ORGANISM: Artificial Sequence
<220> FEATURE:
<223> OTHER INFORMATION: Laboratory Synthesized

<400> SEQUENCE: 294
aaaccctcca ggcctcacct ggctc                                  25

<210> SEQ ID NO 295
<211> LENGTH: 25
<212> TYPE: DNA
<213> ORGANISM: Artificial Sequence
<220> FEATURE:
<223> OTHER INFORMATION: Laboratory Synthesized
```

<400> SEQUENCE: 295
caccgaatta tggagtatgt gtctg                                           25

<210> SEQ ID NO 296
<211> LENGTH: 25
<212> TYPE: DNA
<213> ORGANISM: Artificial Sequence
<220> FEATURE:
<223> OTHER INFORMATION: Laboratory Synthesized

<400> SEQUENCE: 296
aaaccagaca catactccat aattc                                           25

<210> SEQ ID NO 297
<211> LENGTH: 24
<212> TYPE: DNA
<213> ORGANISM: Artificial Sequence
<220> FEATURE:
<223> OTHER INFORMATION: Laboratory Synthesized

<400> SEQUENCE: 297
caccgatggt gcatctgact cctg                                            24

<210> SEQ ID NO 298
<211> LENGTH: 24
<212> TYPE: DNA
<213> ORGANISM: Artificial Sequence
<220> FEATURE:
<223> OTHER INFORMATION: Laboratory Synthesized

<400> SEQUENCE: 298
aaaccaggag tcagatgcac catc                                            24

<210> SEQ ID NO 299
<211> LENGTH: 24
<212> TYPE: DNA
<213> ORGANISM: Artificial Sequence
<220> FEATURE:
<223> OTHER INFORMATION: Laboratory Synthesized

<400> SEQUENCE: 299
caccgagtcc gagcagaaga agaa                                            24

<210> SEQ ID NO 300
<211> LENGTH: 24
<212> TYPE: DNA
<213> ORGANISM: Artificial Sequence
<220> FEATURE:
<223> OTHER INFORMATION: Laboratory Synthesized

<400> SEQUENCE: 300
aaacttcttc ttctgctcgg actc                                            24

<210> SEQ ID NO 301
<211> LENGTH: 25
<212> TYPE: DNA
<213> ORGANISM: Artificial Sequence
<220> FEATURE:
<223> OTHER INFORMATION: Laboratory Synthesized

<400> SEQUENCE: 301
caccggtcac ctccaatgac taggg                                           25

<210> SEQ ID NO 302

```
<211> LENGTH: 25
<212> TYPE: DNA
<213> ORGANISM: Artificial Sequence
<220> FEATURE:
<223> OTHER INFORMATION: Laboratory Synthesized

<400> SEQUENCE: 302
aaacccctag tcattggagg tgacc                                          25

<210> SEQ ID NO 303
<211> LENGTH: 25
<212> TYPE: DNA
<213> ORGANISM: Artificial Sequence
<220> FEATURE:
<223> OTHER INFORMATION: Laboratory Synthesized

<400> SEQUENCE: 303
caccgcactt ttcgacatag tgtgg                                          25

<210> SEQ ID NO 304
<211> LENGTH: 25
<212> TYPE: DNA
<213> ORGANISM: Artificial Sequence
<220> FEATURE:
<223> OTHER INFORMATION: Laboratory Synthesized

<400> SEQUENCE: 304
aaacccacac tatgtcgaaa agtgc                                          25

<210> SEQ ID NO 305
<211> LENGTH: 25
<212> TYPE: DNA
<213> ORGANISM: Artificial Sequence
<220> FEATURE:
<223> OTHER INFORMATION: Laboratory Synthesized

<400> SEQUENCE: 305
caccgcagca tcagaggact agctc                                          25

<210> SEQ ID NO 306
<211> LENGTH: 25
<212> TYPE: DNA
<213> ORGANISM: Artificial Sequence
<220> FEATURE:
<223> OTHER INFORMATION: Laboratory Synthesized

<400> SEQUENCE: 306
aaacgagcta gtcctctgat gctgc                                          25

<210> SEQ ID NO 307
<211> LENGTH: 25
<212> TYPE: DNA
<213> ORGANISM: Artificial Sequence
<220> FEATURE:
<223> OTHER INFORMATION: Laboratory Synthesized

<400> SEQUENCE: 307
caccgattcc cagcacgctg atgtg                                          25

<210> SEQ ID NO 308
<211> LENGTH: 25
<212> TYPE: DNA
<213> ORGANISM: Artificial Sequence
<220> FEATURE:
<223> OTHER INFORMATION: Laboratory Synthesized

<400> SEQUENCE: 308
```
aaaccacatc agcgtgctgg gaatc                                          25

<210> SEQ ID NO 309
<211> LENGTH: 24
<212> TYPE: DNA
<213> ORGANISM: Artificial Sequence
<220> FEATURE:
<223> OTHER INFORMATION: Laboratory Synthesized

<400> SEQUENCE: 309
caccgataca ttttgtctag acgt                                           24

<210> SEQ ID NO 310
<211> LENGTH: 24
<212> TYPE: DNA
<213> ORGANISM: Artificial Sequence
<220> FEATURE:
<223> OTHER INFORMATION: Laboratory Synthesized

<400> SEQUENCE: 310
aaacacgtct agacaaaatg tatc                                           24

<210> SEQ ID NO 311
<211> LENGTH: 25
<212> TYPE: DNA
<213> ORGANISM: Artificial Sequence
<220> FEATURE:
<223> OTHER INFORMATION: Laboratory Synthesized

<400> SEQUENCE: 311
caccgtttca cttttagata tgata                                          25

<210> SEQ ID NO 312
<211> LENGTH: 25
<212> TYPE: DNA
<213> ORGANISM: Artificial Sequence
<220> FEATURE:
<223> OTHER INFORMATION: Laboratory Synthesized

<400> SEQUENCE: 312
aaactatcat atctaaaagt gaaac                                          25

<210> SEQ ID NO 313
<211> LENGTH: 25
<212> TYPE: DNA
<213> ORGANISM: Artificial Sequence
<220> FEATURE:
<223> OTHER INFORMATION: Laboratory Synthesized

<400> SEQUENCE: 313
caccgaagac tcgagccctc cagcg                                          25

<210> SEQ ID NO 314
<211> LENGTH: 25
<212> TYPE: DNA
<213> ORGANISM: Artificial Sequence
<220> FEATURE:
<223> OTHER INFORMATION: Laboratory Synthesized

<400> SEQUENCE: 314
aaaccgctgg agggctcgag tcttc                                          25

<210> SEQ ID NO 315
<211> LENGTH: 25
<212> TYPE: DNA

```
<213> ORGANISM: Artificial Sequence
<220> FEATURE:
<223> OTHER INFORMATION: Laboratory Synthesized

<400> SEQUENCE: 315
caccgcagcc agtcagcgtc ctcgc                                      25

<210> SEQ ID NO 316
<211> LENGTH: 25
<212> TYPE: DNA
<213> ORGANISM: Artificial Sequence
<220> FEATURE:
<223> OTHER INFORMATION: Laboratory Synthesized

<400> SEQUENCE: 316
aaacgcgagg acgctgactg gctgc                                      25

<210> SEQ ID NO 317
<211> LENGTH: 25
<212> TYPE: DNA
<213> ORGANISM: Artificial Sequence
<220> FEATURE:
<223> OTHER INFORMATION: Laboratory Synthesized

<400> SEQUENCE: 317
caccggtaca acgaatgggt agaac                                      25

<210> SEQ ID NO 318
<211> LENGTH: 25
<212> TYPE: DNA
<213> ORGANISM: Artificial Sequence
<220> FEATURE:
<223> OTHER INFORMATION: Laboratory Synthesized

<400> SEQUENCE: 318
aaacgttcta cccattcgtt gtacc                                      25

<210> SEQ ID NO 319
<211> LENGTH: 27
<212> TYPE: DNA
<213> ORGANISM: Artificial Sequence
<220> FEATURE:
<223> OTHER INFORMATION: Laboratory Synthesized

<400> SEQUENCE: 319
cttctaagaa ttcgagctcg gtacccg                                    27

<210> SEQ ID NO 320
<211> LENGTH: 20
<212> TYPE: DNA
<213> ORGANISM: Artificial Sequence
<220> FEATURE:
<223> OTHER INFORMATION: Laboratory Synthesized

<400> SEQUENCE: 320
ccaatgctta atcagtgagg                                            20
```